US008802827B2

(12) United States Patent
Luo et al.

(10) Patent No.: US 8,802,827 B2
(45) Date of Patent: Aug. 12, 2014

(54) AX1 PCSK9 ANTAGONISTS

(75) Inventors: Peter Peizhi Luo, Lansdale, PA (US); Kevin Caili Wang, Lansdale, PA (US); Pingyu Zhong, Blue Bell, PA (US); Mark Hsieh, Jenkintown, PA (US); Yan Li, San Jose, CA (US); Xinwei Wang, Germantown, MD (US); Feng Dong, Lansdale, PA (US); Andrei Golosov, Cambridge, MA (US); Yan Ni, Westfield, NJ (US); Weirong Wang, Harleysville, PA (US); Laurence B. Peterson, Westfield, NJ (US); Rose Cubbon, Fanwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 103 days.

(21) Appl. No.: 13/503,726

(22) PCT Filed: Oct. 29, 2010

(86) PCT No.: PCT/US2010/054640

§ 371 (c)(1), (2), (4) Date: Apr. 24, 2012

(87) PCT Pub. No.: WO2011/053759

PCT Pub. Date: May 5, 2011

(65) Prior Publication Data

US 2012/0231005 A1 Sep. 13, 2012

Related U.S. Application Data

(60) Provisional application No. 61/256,720, filed on Oct. 30, 2009, provisional application No. 61/323,117, filed on Apr. 12, 2010.

(51) Int. Cl.

| | |
|---|---|
| ***C07K 16/40*** | (2006.01) |
| ***C07K 16/00*** | (2006.01) |
| ***A61K 39/395*** | (2006.01) |

(52) U.S. Cl.

USPC ................ 530/388.26; 530/387.1; 530/388.1; 424/146.1; 424/130.1

(58) Field of Classification Search

CPC .............. A61K 2300/00; A61K 45/06; A61K 39/3955; C07K 16/40; C07K 231/92

See application file for complete search history.

(56) References Cited

U.S. PATENT DOCUMENTS

| | | | |
|---|---|---|---|
| 5,977,322 | A | 11/1999 | Marks et al. |
| 2002/0086014 | A1 | 7/2002 | Korman et al. |
| 2003/0119038 | A1 | 6/2003 | Bingham et al. |
| 2004/0009178 | A1 | 1/2004 | Bowdish et al. |
| 2004/0009553 | A1 | 1/2004 | Glucksmann et al. |
| 2006/0286112 | A1 | 12/2006 | Kellermann et al. |
| 2009/0232795 | A1 | 9/2009 | Condra et al. |

FOREIGN PATENT DOCUMENTS

| | | |
|---|---|---|
| EP | 1 067 182 | 1/2001 |
| EP | 1 440 981 | 7/2004 |
| EP | 1 471 152 | 10/2004 |
| WO | WO 01/031007 | 5/2001 |
| WO | WO 01/034768 | 5/2001 |
| WO | WO 01/057081 | 8/2001 |
| WO | WO 01/077137 | 10/2001 |
| WO | WO 01/098468 | 12/2001 |
| WO | WO 02/014358 | 2/2002 |
| WO | WO 02/046383 | 6/2002 |
| WO | WO 02/090526 | 11/2002 |
| WO | WO 02/102993 | 12/2002 |
| WO | WO 02/102994 | 12/2002 |
| WO | WO 2008/057457 A2 | 5/2008 |
| WO | WO 2009/026558 A1 | 2/2009 |
| WO | WO 2009/055783 A2 | 4/2009 |
| WO | WO 2009/100297 A1 | 8/2009 |

OTHER PUBLICATIONS

Abifadel et al. (2003) Nature Genetics 34(2):154-156 "Mutations in PCSK9 cause autosomal dominant hypercholesterolemia".
Benjannet et al. (2004) *J Biol Chem*. 279(47):48865-75 "NARC-1/PCSK9 and its natural mutants: zymogen cleavage and effects on the low density lipoprotein (LDL) receptor and LDL cholesterol".
Cohen et al. (2006) *N. Engl. J. Med*. 354(12):1264-1272 "Sequence variations in PCSK9, low LDL, and protection against coronary heart disease".
Dubuc et al. (2004) *Arterioscler Thromb Vasc Biol*. 24(8):1454-9 "Statins upregulate PCSK9, the gene encoding the proprotein convertase neural apoptosis-regulated convertase-1 implicated in familial hypercholesterolemia".
Genbank Accession No. NP_777596.2, PRI Aug. 31, 2012 (Sharotri et al.).
Genbank Accession No. AX207686 Pat Aug. 31, 2001 (Chiang).
Genbank Accession No. NP_705793 Rod Nov. 25, 2012 (Fattori et al.).
Genbank Accession No. P59996 Rod Nov. 28, 2012 (Chiang).
Genbank Accession No. PH1492 Rod May 7, 1999 (Giusti and Manser).
Graham et al., (2007) *J. Lipid Res*. 48(4):763-767 "Antisense inhibition of proprotein convertase subtilisin/kexin type 9 reduces serum LDL in hyperlipidemic mice".
Lalanne et al. (2005) *J. Lipid Res*. 46:1312-1319 "Wild-type PCSK9 inhibits LDL clearance but does not affect apoB-containing lipoprotein production in mouse and cultured cells".

(Continued)

*Primary Examiner* — Sharon Wen
(74) *Attorney, Agent, or Firm* — Sheela Mohan-Peterson

(57) ABSTRACT

Antagonists of human proprotein convertase subtilisin-kexin type 9 ("PCSK9") are disclosed. The disclosed antagonists are effective in the inhibition of PCSK9 function and, accordingly, present desirable antagonists for use in the treatment of conditions associated with PCSK9 activity. The present invention also discloses nucleic acid encoding said antagonists, vectors, host cells, and compositions comprising the antagonists. Methods of making PCSK9-specific antagonists as well as methods of using the antagonists for inhibiting or antagonizing PCSK9 function are also disclosed and form important additional aspects of the present disclosure.

9 Claims, 26 Drawing Sheets

(56) References Cited

OTHER PUBLICATIONS

Leren (2004) *Clin. Genet*. 65(5):419-422 "Mutations in the PCSK9 gene in Norwegian subjects with autosomal dominant hypercholesterolemia".

Maxwell et al. (2003) *J Lipid Res*. 44(11):2109-19 "Novel putative SREBP and LXR target genes identified by microarray analysis in liver of cholesterol-fed mice".

Ouguerram et al. (2004) *Arterioscler. Thromb. Vasc. Biol*. 24:1448-1453 "Apolipoprotein B100 metabolism in autosomal-dominant hypercholesterolemia related to mutations in PCSK9".

Park et al. (2004) *J. Biol. Chem*. 279(48):50630-50638 Post-transcriptional regulation of low density lipoprotein receptor "protein by proprotein convertase subtilisin/kexin type 9a in mouse liver".

Rashid et al. (2005) *Proc Natl Acad Sci U S A*. 102(15):5374-9 "Decreased plasma cholesterol and hypersensitivity to statins in mice lacking Pcsk9".

Seidah, et al. (2003) *Proc Natl Acad Sci U S A*. 100(3):928-33 "The secretory proprotein convertase neural apoptosis-regulated convertase 1 (NARC-1): liver regeneration and neuronal differentiation".

Timms et al. (2004) *Hum. Genet*. 114(4):349-353 "A mutation in PCSK9 causing autosomal-dominant hypercholesterolemia in a Utah pedigree".

Chan et al. (2009) *Proc Natl Acad Sci U.S.A.* 106(24):9820-9825 "A proprotein convertase subtilisin/kexin type 9 neutralizing antibody reduces serum cholesterol in mice and nonhuman primates".

Lagace et al. (2006) *J Clin Invest.* 116(11):2995-3005 "Secreted PCSK9 decreases the number Of LDL receptors in hepatocytes and in livers of parabiotic mice".

A

AX9 VK variants

```
AX9     DIQMTQSPSSLSASVGDRVTITCRASQDVSKYLAWYQQKPGKAPKLLIYAASSLQSGVPSRFSGSGSGTDFTLTISSLQPEDFATYYCQQVYGSPWAYVFGGGTKVEIK SEQ53
AX188   DIQMTQSPSSLSASVGDRVTITCRASQSVSRYLAWYQQKPGKAPKLLIYAASSLQSGVPSRFSGSGSGTDFTLTISSLQPEDFATYYCEAYDYSSGPWVFGGGTKVEIK SEQ55
AX189   DIQMTQSPSSLSASVGDRVTITCRASQDVSRYLTWYQQKPGKAPKLLIYAASSLQSGVPSRFSGSGSGTDFTLTISSLQPEDFATYYCQAYDYSLGDYVFGGGTKVEIK SEQ67
AX190   DIQMTQSPSSLSASVGDRVTITCRASQSVSKYLTWYQQKPGKAPKLLIYAASSLQSGVPSRFSGSGSGTDFTLTISSLQPEDFATYYCQSYDYSLSDYVFGGGTKVEIK SEQ56
AX191   DIQMTQSPSSLSASVGDRVTITCRASQDISKYLAWYQQKPGKAPKLLIYAASSLQSGVPSRFSGSGSGTDFTLTISSLQPEDFATYYCQAYDYSSSAYVFGGGTKVEIK SEQ57
AX192   DIQMTQSPSSLSASVGDRVTITCRASQAVSNYLAWYQQKPGKAPKLLIYAASSLQSGVPSRFSGSGSGTDFTLTISSLQPEDFATYYCEAYDYSLGRYVFGGGTKVEIK SEQ58
AX193   DIQMTQSPSSLSASVGDRVTITCRASQAISKYLAWYQQKPGKAPKLLIYAASSLQSGVPSRFSGSGSGTDFTLTISSLQPEDFATYYCESYDYSLGHYVFGGGTKVEIK SEQ59
Ax194   DIQMTQSPSSLSASVGDRVTITCRASQAVSRYLAWYQQKPGKAPKLLIYAASSLQSGVPSRFSGSGSGTDFTLTISSLQPEDFATYYCQAYDYSLGAYVFGGGTKVEIK SEQ60
Ax195   DIQMTQSPSSLSASVGDRVTITCRASQAVSKYLAWYQQKPGKAPKLLIYAASSLQSGVPSRFSGSGSGTDFTLTISSLQPEDFATYYCQAYDYSLSDYVFGGGTKVEIK SEQ61
Ax196   DIQITQSPSSLSASVGDRVTITCRASQDVSRYLAWYQQKPGKAPKLLIYAASSLQSGVPSRFSGSGSGTDFTLTISSLQPEDFATYYCESYDYSLSHYVFGGGTKVEIK SEQ62
Ax197   DIQMTQSPSSLSASVGDRVTITCRASQAISRYLAWYQQKPGKAPKLLIYAASSLQSGVPSRFSGSGSGTDFTLTISSLQPEDFATYYCQAYDYSLGHYVFGGGTKVEIK SEQ63
Ax198   DIQMTQSPSSLSASVGDRVTITCRASQAVSSYLAWYQQKPGKAPKLLIYAASSLQSGVPSRFSGSGSGTDFTLTISSLQPEDFATYYCEAYDYSLNGWVFGGGTKVEIK SEQ64
Ax199   DIQMTQSPSSLSASVGDRVTITCRASQSVSRYLAWYQQKPGKAPKLLIYAASSLQSGVPSRFSGSGSGTDFTLTISSLQPEDFATYYCQAYDYSLGPYVFGGGTKVEIK SEQ65
AX200   DIQMTQSPSSLSASVGDRVTITCRASQDVSRYLAWYQQKPGKAPKLLIYAASSLQSGVPSRFSGSGSGTDFTLTISSLQPEDFATYYCEAYDYSLGHYVFGGGTKVEIK SEQ66
```

B

VK Consensus of AX9 variants

DIQMTQSPSSLSASVGDRVTITCRASQX1X2SX3YLX4WYQQKPGKAPKLLIYAASSLQSGVPSRFSGSGSGTDFTLTISSL
QPEDFATYYCX5X6YDX7SX8X9X10X11VFGGGTKVEIK [SEQ ID NO: 53]

| Bin # | Amino acid residues in the bin |
| --- | --- |
| Bin 2 | 158-ER, 341-TNAQDQPVTLGTLG (SEQ ID NO: 112), 366-EDI, 380-SQS, 421-DVINEAWFPE (SEQ ID NO: 113) |
| Bin 3 | 188-SIQ, 205-FENVPEEDGTR (SEQ ID NO: 114), 219-QASKCD (SEQ ID NO: 115), 251-RVLNCQGKG (SEQ ID NO: 116) |

B
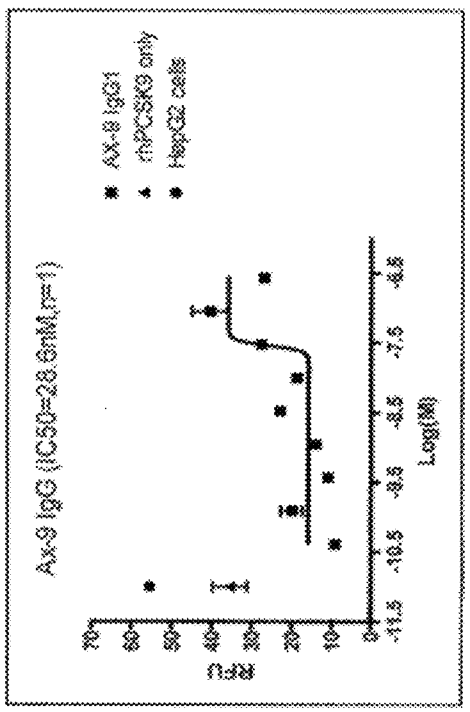
A
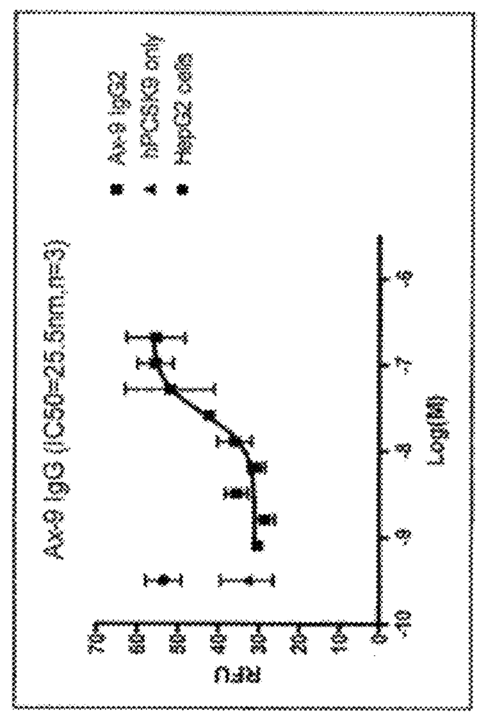
FIG. 14

B
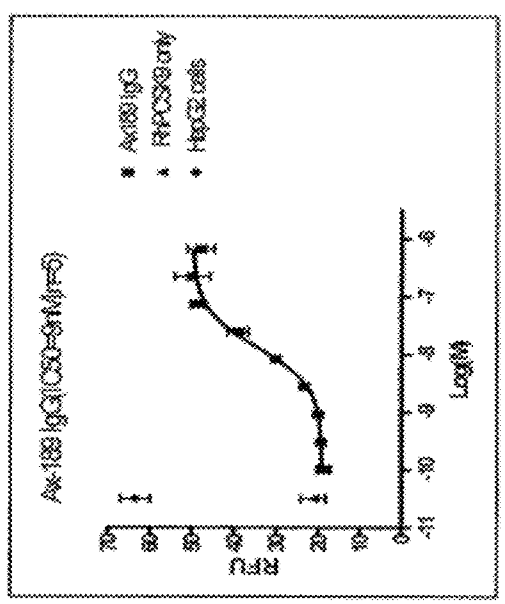
A
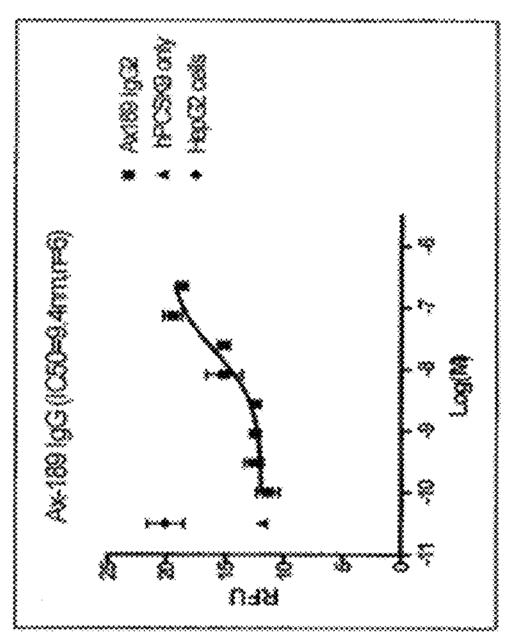
FIG. 15

AX1 PCSK9 ANTAGONISTS

CROSS-REFERENCE TO RELATED APPLICATIONS

This application is a 371 of PCT/US2010/054640, filed Oct. 29, 2010, which claims benefit of U.S. provisional application, U.S. Ser. No. 61/256,720, filed Oct. 30, 2009, and claims benefit of U.S. provisional application, U.S. Ser. No. 61/323,117, filed Apr. 12, 2010.

STATEMENT REGARDING FEDERALLY-SPONSORED R&D

Not Applicable.

REFERENCE TO MICROFICHE APPENDIX

Not Applicable.

BACKGROUND OF THE INVENTION

Proprotein convertase subtilisin-kexin type 9 (hereinafter called "PCSK9"), also known as neural apoptosis-regulated convertase 1 ("NARC-1"), is a proteinase K-like subtilase identified as the $9^{th}$ member of the secretory subtilase family; see Seidah et al., 2003 *PNAS* 100:928-933. The gene for PCSK9 localizes to human chromosome 1p33-p34.3; Seidah et al., supra. PCSK9 is expressed in cells capable of proliferation and differentiation including, for example, hepatocytes, kidney mesenchymal cells, intestinal ileum, and colon epithelia as well as embryonic brain telencephalon neurons; Seidah et al., supra.

Original synthesis of PCSK9 is in the form of an inactive enzyme precursor, or zymogen, of ~72-kDa which undergoes autocatalytic, intramolecular processing in the endoplasmic reticulum ("ER") to activate its functionality. This internal processing event has been reported to occur at the SSVFAQ↓STPWNL$^{158}$ motif (SEQ ID NOs: 103 and 104, respectively); Benjannet et al., 2004 *J. Biol. Chem.* 279: 48865-48875. Such internal processing has been reported as a requirement of exit from the ER; Benjannet et al., supra; Seidah et al., supra. The cleaved and, thereby, activated protein is secreted in association with the cleaved peptide; supra.

The sequence for human PCSK9 (~22-kb long with 12 exons encoding a 692 amino acid protein) can be found in one instance at Deposit No. NP__77596.2. Tillman, mouse and rat PCSK9 nucleic acid sequences have been deposited; see, e.g., GenBank Accession Nos.: AX21327530 (also AX207686), NP__705793 (also Q80W65), and P59996, respectively. PCSK9 possesses several domains found in other proprotein convertases, including an N-terminal signal sequence, a pro domain, a catalytic domain and a cysteine-rich C terminal domain. The PCSK9 catalytic domain shares high sequence similarity with the proteinase K family of subtilases and, notably, a catalytic triad of D186, H226 and S386.

PCSK9 is disclosed and/or claimed in several patent publications including, but not limited to the following: PCT Publication Nos. WO 01/31007, WO 01/57081, WO 02/14358, WO 01/98468, WO 02/102993, WO 02/102994, WO 02/46383, WO 02/90526, WO 01/77137, and WO 01/34768; US Publication Nos. US 2004/0009553 and US2003/0119038, and European Publication Nos. EP 1 440 981, EP 1 067 182, and EP 1 471 152.

PCSK9 has been ascribed a role in the differentiation of hepatic and neuronal cells (Seidah et al., supra.), is highly expressed in embryonic liver, and has been strongly implicated in cholesterol homeostasis. Studies have suggested a specific role for PCSK9 in cholesterol biosynthesis or uptake. In a study of cholesterol-fed rats, Maxwell et al. found that PCSK9 was downregulated in a similar manner to three other genes involved in cholesterol biosynthesis, Maxwell et al, 2003 *J. Lipid Res.* 44:2109-2119. The expression of PCSK9 has, in fact, been shown to be regulated by sterol regulatory element-binding proteins ("SREBP"), as seen with other genes involved in cholesterol metabolism; supra. Later support for these findings came about through a study of PCSK9 transcriptional regulation which demonstrated that such regulation was quite typical of other genes implicated in lipoprotein metabolism; Dubuc et al, 2004 *Arterioscler. Thromb. Vasc. Biol.* 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

Several lines of evidence demonstrate that PCSK9, in particular, lowers the amount of hepatic LDLR protein and thus compromises the liver's ability to remove LDL cholesterol from the circulation. Adenovirus-mediated overexpression of PCSK9 in the livers of mice results in the accumulation of circulating LDL-C due to a dramatic loss of hepatic LDLR protein, with no effect on LDLR mRNA levels; Benjannet et al., 2004 *J. Biol. Chem.* 279:48865-48875; Maxwell & Breslow, 2004 *PNAS* 101:7100-7105; Park et al, 2004 *J. Biol. Chem.* 279:50630-50638; and Lalanne et al, 2005 *J. Lipid Res.* 46:1312-1319. The effect of PCSK9 over-expression on raising circulating LDL-C levels in mice is completely dependent on the expression of LDLR, again, indicating that the regulation of LDL-C by PCSK9 is mediated through downregulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid et al., 2005 *PNAS* 102:5374-5379; and Graham et al., 2007 *J. Lipid Res.* 48(4):763-767. In addition, lowering PCSK9 levels in cultured human hepatocytes by siRNA also results in higher LDLR protein levels and an increased ability to take up LDL-C; Benjannet et al., 2004 *J. Biol. Chem.* 279:48865-48875; and Lalanne et al., 2005 *J Lipid Res.* 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *Nature Genetics* 34:154-156; Timms et al., 2004 *Hum. Genet.* 114:349-353; Leren, 2004 *Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Engl. J. Med.* 354:1264-1272.

The identification of compounds and/or agents effective in the treatment of cardiovascular affliction is highly desirable. In clinical trials, reductions in LDL cholesterol levels have been directly related to the rate of coronary events; Law et al., 2003 *BMJ* 326:1423-1427. More recently, the moderate lifelong reduction in plasma LDL cholesterol levels was found to correlate with a substantial reduction in the incidence of coronary events; Cohen et al., supra. This was the case even in populations with a high prevalence of non-lipid-related cardiovascular risk factors; supra. Accordingly, there is great benefit to be reaped from the managed control of LDL cholesterol levels.

The present invention advances these interests by providing antagonists of PCSK9 of use for inhibiting the activities of PCSK9 and the corresponding role PCSK9 plays in various therapeutic conditions.

SUMMARY OF THE INVENTION

The present invention relates to protein-specific antagonists of PCSK9 and, in particular embodiments, those antagonists that inhibit human PCSK9. Broadly, protein-specific antagonists of PCSK9 (or "PCSK9-specific antagonists" as referred to herein) are PCSK9 protein binding molecules or molecules effective in the selective binding of PCSK9 and inhibition of PCSK9 function. In particular embodiments, the present invention relates to monoclonal antibody variants having high affinity and desired properties from a therapeutic perspective. These molecules are of import in the treatment of conditions associated with or impacted by PCSK9 function, including, but not limited to hypercholesterolemia, coronary heart disease, metabolic syndrome, acute coronary syndrome and related conditions. PCSK9-specific antagonists are characterized by selective recognition and binding to PCSK9, PCSK9-specific antagonists do not show significant binding to proteins other than PCSK9, other than in those specific instances where the antagonist is supplemented or designed to confer an additional, distinct specificity to the PCSK9-specific binding component.

PCSK9-specific antagonists forming particular embodiments hereof comprise (a) a heavy chain variable region comprising a CDR3 domain comprising (in select embodiments, consisting of) a sequence selected from the group consisting of: SEQ ID NOs: 15, 16, 18, 20 and residues 4-15 of the foregoing sequences that are 18 amino acids in length, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%); and/or (b) a light chain variable region comprising a CDR3 domain comprising (in select embodiments, consisting of) a sequence selected from the group consisting of: SEQ ID NOs: 33-35, 37, and 39, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%).

PCSK9-specific antagonists forming additional embodiments hereof comprise (a) a heavy chain variable region comprising a CDR2 domain comprising (in select embodiments, consisting of) a sequence selected from the group consisting of: SEQ ID NOs: 8, 9, 11, 13 and residues 4-20 of the foregoing sequences that are 23 amino acids in length, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%); and/or (b) a light chain variable region comprising a CDR2 domain comprising SEQ ID NO: 31, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%).

In specific embodiments, PCSK9-specific antagonists bind to human PCSK9 with a $K_D$ of $1.2\times10^{-6}$ M or less. In more specific embodiments, PCSK9-specific antagonists bind to human PCSK9 with a $K_D$ of $1\times10^{-7}$ M or less. In additional embodiments, PCSK9-specific antagonists bind to human PCSK9 with a $K_D$ of $1\times10^{-8}$ M or less. In further embodiments, PCSK9-specific antagonists bind to human PCSK9 with a $K_D$ of $5\times10^{-9}$ M or less, or of $1\times10^{-9}$ M or less. In select embodiments, PCSK9-specific antagonists bind to human PCSK9 with a $K_D$ of $1\times10^{-10}$ M or less, a $K_D$ of $1\times10^{-11}$ M or less, or a $K_D$ of $1\times10^{-12}$ M or less. In specific embodiments, PCSK9-specific antagonists do not bind proteins other than PCSK9 at the above levels indicated for binding to PCSK9.

Particular embodiments of the present invention include PCSK9-specific antagonists which exhibit binding to PCSK9 at one of the above prescribed levels and compete for binding to PCSK9 with AX1 and its variants as described herein. AX1 and its disclosed variants, described as any antibody molecules fitting within the descriptions, sequence and/or functional limitations provided throughout the present disclosure, form important PCSK9-specific antagonists hereof.

AX1 antibody molecules are characterized as comprising a (i) heavy chain variable region ("VH") comprising SEQ ID NO: 41; and (ii) a light chain variable region ("VL") comprising SEQ ID NO: 50 or 52 (AXIDG). Said VH and VL regions comprise the full complement of disclosed CDRs 1, 2 and 3 for the VH [SEQ ID NO: 2 (or SEQ ID NO: 4) as CDR1; SEQ ID NO: 9 (or SEQ ID NO: 11) as CDR2; and SEQ ID NO: 16 (or SEQ ID NO: 18) as CDR3] and VL regions [SEQ ID NO: 24 as CDR1; SEQ ID NO: 31 as CDR2; and SEQ ID NO: 35 as CDR3], respectively. Examples of AX1 antibody molecules include without limitation: (i) a Fab which comprises a light chain comprising SEQ ID NO: 73 and an Fd chain comprising amino acids comprising amino acids 1-227 of SEQ ID NO: 69 (or SEQ ID NO: 69); (ii) a full length antibody molecule which comprises a light chain comprising SEQ ID NO: 85 and a heavy chain comprising SEQ ID NO: 79; and (iii) an antibody produced by the expression of SEQ ID NO: 91.

One particular variant disclosed herein, AX9 antibody molecules, are characterized as comprising a (i) heavy chain variable region ("VH") comprising SEQ ID NO: 43; and (ii) a light chain variable region ("VL") comprising SEQ ID NO: 53. Said VH and VL regions comprise the full complement of disclosed CDRs 1, 2 and 3 for the VH [SEQ ID NO: 6 as CDR1; SEQ ID NO: 13 as CDR2; and SEQ ID NO: 20 as CDR3] and VL regions [SEQ ID NO: 26 as CDR1; SEQ ID NO: 31 as CDR2; and SEQ ID NO: 37 as CDR3], respectively. Examples of AX9 antibody molecules include without limitation: (i) a Fab which comprises a light chain comprising SEQ ID NO: 75 and an Fd chain comprising amino acids comprising amino acids 1-229 of SEQ ID NO: 71 (or SEQ ID NO: 71); (ii) a full length antibody molecule which comprises a light chain comprising SEQ ID NO: 87 and a heavy chain comprising SEQ ID NO: 81; and (iii) an antibody produced by the expression of SEQ ID NO: 92.

One particular variant disclosed herein, AX189 antibody molecules, are characterized as comprising a (i) heavy chain variable region ("VH") comprising SEQ ID NO: 43; and (ii) a light chain variable region ("VL") comprising SEQ ID NO: 67. Said VH and VL regions comprise the full complement of disclosed CDRs 1, 2 and 3 for the VH [SEQ ID NO: 6 as CDR1; SEQ ID NO: 13 as CDR2; and SEQ ID NO: 20 as CDR3] and VL regions [SEQ ID NO: 28 as CDR1; SEQ ID NO: 31 as CDR2; and SEQ ID NO: 39 as CDR3], respectively. Examples of AX189 antibody molecules include without limitation: (i) a Fab which comprises a light chain comprising SEQ ID NO: 77 and an Fd chain comprising amino acids comprising amino acids 1-229 of SEQ ID NO: 71 (or SEQ ID NO: 71); (ii) a full length antibody molecule which comprises a light chain comprising SEQ ID NO: 89 and a heavy chain comprising SEQ ID NO: 81 (or SEQ ID NO: 83); and (iii) an antibody produced by the expression of SEQ ID NO: 93.

PCSK9-specific antagonists are effective in counteracting PCSK9-dependent inhibition of cellular LDL-uptake, and particularly human PCSK9-dependent inhibition of cellular LDL uptake. Repeatedly, PCSK9-specific antagonists as described herein have demonstrated dose-dependent inhibition of the effects of PCSK9 on LDL uptake. Accordingly, the disclosed PCSK9-specific antagonists are of import for lowering plasma LDL cholesterol levels. The disclosed antagonists also have utility for various diagnostic purposes, including the detection and quantification of PCSK9.

In particular embodiments, the present invention encompasses antibody molecules comprising the disclosed heavy and/or light chain variable regions, equivalents of said regions having one or more amino acid substitutions that do not substantially impact function, and homologs thereof. Select embodiments comprise isolated PCSK9-specific antagonists that comprise disclosed CDR domains or sets of the heavy and/or light chain CDR domains, and equivalents of such domains characterized as having one or more amino acid substitutions. As will be appreciated by those skilled in the art, fragments of PCSK9-specific antagonists that retain the ability to antagonize PCSK9 may be inserted into various frameworks; see, e.g., U.S. Pat. No. 6,818,418 and references contained therein, the collective disclosures of which are incorporated herein by reference, which discuss various scaffolds which may be used to display antibody loops previously selected on the basis of antigen binding. In the alternative, genes encoding for VL and VH may be joined, using recombinant methods, for example using a synthetic linker that enables them to be made as a single protein chain in which the VL and VH regions pair to form monovalent molecules, otherwise known as single chain Fvs ("ScFVs"); see, e.g., Bird et al., 1988 *Science* 242: 423-426, and Huston et al., 1988 *Proc. Natl. Acad. Sci. USA* 85:5879-5883, the disclosures of which are incorporated herein by reference. In another alternative, the VH and VL may be fused with two interactive domains, and form a Fab-like molecule, see, e.g., ccFv, Wang et al., U.S. Pat. No. 6,833,441 and U.S. Pat. No. 7,429,652.

PCSK-9 specific antagonists and fragments may be in the fowl of various non-antibody-based scaffolds, including but not limited to avimers (Avidia); DARPins (Molecular Partners); Adnectins (Adnexus), Anticalins (Pieris) and Affibodies (Affibody). The use of alternative scaffolds for protein binding is well appreciated in the scientific literature, see, e.g., Binz & Plückthun, 2005 *Curr. Opin. Biotech.* 16:1-11; the disclosure of which is incorporated herein by reference.

Accordingly, any PCSK9-specific antagonist, including antibody molecules and non-antibody-based scaffolds comprising (i) the disclosed heavy and/or light chain variable region CDR3 sequences (heavy chain variable region CDR3 sequence selected from SEQ ID NOs: 15, 16, 18, 20, 169 and residues 4-15 of the foregoing sequences that are 18 amino acids in length; light chain variable region CDR3 sequence selected from SEQ ID NOs: 33, 34, 35, 37 and 39), (ii) the disclosed heavy and/or light chain variable region CDR2 sequences (heavy chain variable region CDR2 sequence selected from SEQ ID NOs: 8, 9, 11, 13, 171 and residues 4-20 of the foregoing sequences that are 23 amino acids in length; light chain variable region CDR2 sequence SEQ ID NO: 31 or SEQ ID NO: 31), (iii) the disclosed heavy and/or light chain variable region CDR1 sequences (heavy chain variable region CDR1 sequence selected from SEQ ID NOs: 1, 2, 4, 6, 169 and residues 4-13 of the foregoing sequences that are 16 amino acids in length; light chain variable region CDR1 sequence selected from SEQ ID NOs: 22, 23, 24, 26 and 28), (iv) the disclosed heavy chain variable CDR1, CDR2 and CDR3 sequences or the disclosed light chain variable CDR1, CDR2 and CDR3 sequences, (v) a full complement (CDRs 1, 2 and 3) of the disclosed heavy and light chain CDRs within a variable region framework of a human heavy and/or light chain sequence, respectively, or (vi) the disclosed heavy and/or light chain variable regions (heavy chain variable sequence selected from SEQ ID NOs: 41, 43 and 45-49; light chain variable sequence selected from SEQ ID NOs: 50, 52, 53, 55-66 and 67) form important embodiments of the present invention; where antagonists, antibody molecules or scaffolds exhibit selectivity for PCSK9 and counteract PCSK9-dependent inhibition of cellular LDL-uptake.

In another aspect, the present invention provides nucleic acid encoding the disclosed PCSK9-specific antagonists and, in particular embodiments, PCSK9-specific antagonists which comprise the disclosed heavy and light chains, the disclosed variable heavy and light regions and select components thereof (including CDRs 1, 2 and/or 3), particularly the disclosed respective CDR3 or CDR2 regions. In another aspect, the present invention provides vectors comprising said nucleic acid. The present invention, additionally, provides isolated cell(s) comprising nucleic acid encoding disclosed PCSK9-specific antagonists. In another aspect, the present invention provides isolated cell(s) comprising a polypeptide or vector of the present invention.

The present invention provides methods for making PCSK9-specific antagonists disclosed herein including but not limited to antibodies, antigen binding fragments, derivatives, chimeric molecules, fusions of any of the foregoing with another polypeptide, or alternative structures/compositions capable of specifically binding PCSK9 which comprise the disclosed sequences. The methods comprise: (i) incubating a cell comprising nucleic acid encoding the PCSK9-specific antagonist(s), or which comprises individual nucleic acids encoding one or more components thereof, said nucleic acids which, when expressed, collectively produce the antagonist(s), under conditions that allow for the expression and/or assembly of the PCSK9-specific antagonist(s), and (ii) isolating said antagonist(s) from the cell. One of skill in the art can obtain PCSK9-specific antagonists disclosed herein using standard recombinant DNA techniques as well.

The present invention provides a method for antagonizing the activity or function of PCSK9 or a noted effect of PCSK9 which comprises contacting a cell, population of cells, or tissue sample of interest expressing PCSK9 (or treated with or having therein human PCSK9) with a PCSK9-specific antagonist disclosed herein under conditions that allow said antagonist to bind to PCSK9. Specific embodiments of the present invention include such methods wherein the cell is a human cell. Additional embodiments are wherein the cell expresses human-derived PCSK9.

In another aspect, the present invention provides a method for antagonizing the activity or function of PCSK9 or a noted effect of PCSK9 in a subject exhibiting a condition associated with PCSK9 activity, or a condition where the functioning of PCSK9 is contraindicated for a particular subject, which comprises administering to the subject a therapeutically effective amount of a PCSK9-specific antagonist of the present invention in a pharmaceutical or other composition.

The present invention, thus, encompasses a method of treating a condition associated with PCSK9 activity, or a condition wherein the functioning of PCSK9 is contraindicated for a particular subject, which comprises administering to the subject a therapeutically effective amount of a PCSK9-specific antagonist of the present invention in a pharmaceutical or other composition. In select embodiments, the condition is hypercholesterolemia, coronary heart disease, metabolic syndrome, acute coronary syndrome or related conditions.

In specific embodiments, the present invention encompasses a method of administering a disclosed PCSK9-specific antagonist to a subject which comprises delivering a therapeutically effective amount of a pharmaceutical or other composition comprising a PCSK9-specific antagonist as disclosed herein.

In another aspect, the present invention provides a pharmaceutical composition or other composition comprising a PCSK9-specific antagonist of the invention characterized as comprising a pharmaceutically acceptable carrier including but not limited to an excipient, diluent, stabilizer, buffer, or alternative designed to facilitate administration of the antagonist in the desired amount to the treated individual.

The following table offers a generalized outline of the sequences discussed in the present application. The Sequence Listing including all notations, sequences and features forms an express part of the disclosure hereof:

TABLE 1

| SEQ ID NO: | DESCRIPTION |
|---|---|
| SEQ ID NOs: 15, 16, 18, 20 and 173 | HEAVY CHAIN CDR3 |
| SEQ ID NOs: 17, 19, 21 and 174 | HEAVY CHAIN CDR3; NUCLEIC ACID |
| SEQ ID NOs: 8, 9, 11, 13 and 171 | HEAVY CHAIN CDR2 |
| SEQ ID NOs: 10, 12, 14 and 172 | HEAVY CHAIN CDR2; NUCLEIC ACID |
| SEQ ID NOs: 1, 2, 4, 6 and 169 | HEAVY CHAIN CDR1 |
| SEQ ID NOs: 3, 5, 7 and 170 | HEAVY CHAIN CDR1; NUCLEIC ACID |
| SEQ ID NOs: 33, 34, 35, 37 and 39 | LIGHT CHAIN CDR3 |
| SEQ ID NOs: 36, 38 and 40 | LIGHT CHAIN CDR3; NUCLEIC ACID |
| SEQ ID NOs: 30-31 | LIGHT CHAIN CDR2 |
| SEQ ID NO: 32 | LIGHT CHAIN CDR2; NUCLEIC ACID |
| SEQ ID NOs: 22, 23, 24, 26 and 28 | LIGHT CHAIN CDR1 |
| SEQ ID NOs: 25, 27 and 29 | LIGHT CHAIN CDR1; NUCLEIC ACID |
| SEQ ID NOs: 41, 43 and 45-49 | VARIABLE HEAVY REGIONS |
| SEQ ID NOs: 42, 44 | VARIABLE HEAVY REGIONS; NUCLEIC ACID |
| SEQ ID NOs: 50, 52, 53, 55-66 and 67 | VARIABLE LIGHT REGIONS |
| SEQ ID NO: 51, 54, 68 | VARIABLE LIGHT REGION; NUCLEIC ACID |

TABLE 1-continued

| SEQ ID NO: | DESCRIPTION |
|---|---|
| SEQ ID NOs: 69, 71 | FAB HEAVY CHAIN |
| SEQ ID NOs: 70, 72 | FAB HEAVY CHAIN; NUCLEIC ACID |
| SEQ ID NO: 73, 75, 77 | FAB LIGHT CHAIN |
| SEQ ID NO: 74, 76, 78 | FAB LIGHT CHAIN; NUCLEIC ACID |
| SEQ ID NOs: 79, 81, 83 | IGG2 HEAVY CHAIN |
| SEQ ID NOs: 80, 82, 84 | IGG2 HEAVY CHAIN; NUCLEIC ACID |
| SEQ ID NOs: 85, 87, 89 | IGG2 LIGHT CHAIN |
| SEQ ID NOs: 86, 88,90 | IGG2 LIGHT CHAIN; NUCLEIC ACID |
| SEQ ID NOs: 91-93 | ANTIBODY EXPRESSION VECTOR SEQUENCE |
| SEQ ID NOs: 94-102 | AX1 AND VARIANT FRAMEWORK REGIONS |
| SEQ ID NO: 103 | FRAGMENT OF PROCESSING SITE |
| SEQ ID NO: 104 | FRAGMENT OF PROCESSING SITE |
| SEQ ID NOs: 105-116 | AX1/AX189 EPITOPES |
| SEQ ID NO: 117 | Constant domain of IgG1 |
| SEQ ID NO: 118 | Constant domain of IgG2 |
| SEQ ID NO: 119 | Constant domain of IgG4 |
| SEQ ID NO: 120 | Constant domain of IgG2m4 |
| SEQ ID NO: 121-165 | FIGURE SEQUENCES |
| SEQ ID NO: 166 | AX1/AX189 EPITOPE |
| SEQ ID NO: 167 | PCSK9 |
| SEQ ID NO: 168 | EGF_AB PEPTIDE |

BRIEF DESCRIPTION OF THE DRAWINGS

FIGS. 2A-B illustrate disclosed variants and amino acid substitutions in VK-CDR regions.

FIGS. 14A-B illustrate Ax-9 IgG's dose-dependent inhibition of human (A) and rhesus (B) PCSK9-dependent loss of cellular LDL-uptake. Ax-9 IgG can inhibit the effect of PCSK9 on cellular LDL uptake. IC50s for Ax-9 IgG are 25.5 nM (n=3) and 28.6 nM for human and rhesus PCSK9 protein, respectively.

FIGS. 15A-B illustrate Ax-189 IgG's dose-dependent inhibition of human (A) and rhesus (B) PCSK9-dependent loss of cellular LDL-uptake. Ax-189 IgG can inhibit the effect of PCSK9 on cellular LDL uptake. IC50s for Ax-189 IgG are 9.4 nM (n=6) and 9 nM (n=5) for human and rhesus PCSK9 protein, respectively.

DETAILED DESCRIPTION OF THE INVENTION

Figure 1:
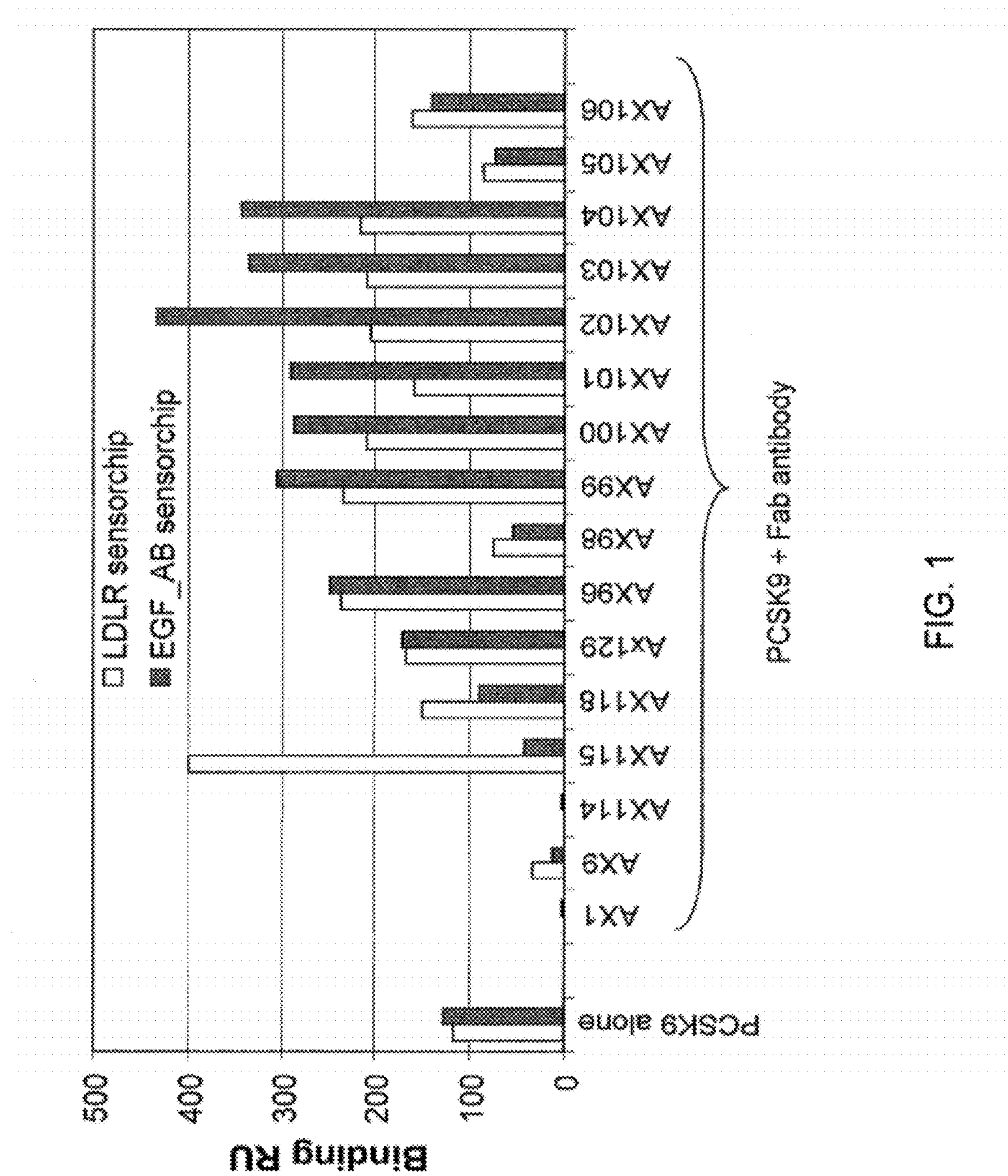
FIG. 1 illustrates the impact of PDL1 Fabs on PCSK9-LDL receptor interaction. This Biacore-based assay shows that binding of AX1, AX9, and AX114 to PCSK9 inhibits the interaction of PCSK9-LDLR and PCSK9-EGF_AB domain. EGF_AB domain in LDLR involves the interaction with PCSK9.

The present invention relates to protein-specific antagonists of PCSK9 and, in particular embodiments, those antagonists that inhibit human PCSK9. Protein-specific antagonists of PCSK9 (or "PCSK9-specific antagonists") in accordance herewith are effective in the selective binding to and inhibition of PCSK9 function and, thus, are of import in the treatment of conditions associated with or impacted by PCSK9 function, including, but not limited to, hypercholesterolemia, coronary heart disease, metabolic syndrome, acute coronary syndrome and related conditions. Use of the term "antagonist" refers to the fact that the subject molecule can antagonize the functioning of PCSK9. Use of the term "antagonizing" or derivatives thereof refers to the act of opposing, counteracting, inhibiting, neutralizing or curtailing one or more functions of PCSK9. Reference herein to PCSK9 function or PCSK9 activity refers to any function or activity that is driven by, requires, or is exacerbated or enhanced by PCSK9. PCSK9-specific antagonists as described herein have proven to be effective for counteracting human PCSK9-dependent inhibition of cellular LDL-uptake.

One important embodiment hereof relates to AX1 antibody molecules and variants thereof. Specific embodiments of the present invention include AX1 antibody molecules characterized as comprising a (i) heavy chain variable region ("VH") comprising or consisting of SEQ ID NO: 41; and (ii) a light chain variable region ("VL") comprising or consisting of SEQ ID NO: 50 or 52 (AX1DG). Said VH and VL regions comprise the full complement of disclosed CDRs 1, 2 and 3 for the VH [SEQ ID NO: 2 (or SEQ ID NO: 4) as CDR1; SEQ ID NO: 9 (or SEQ ID NO: 11) as CDR2; and SEQ ID NO: 16

(or SEQ ID NO: 18) as CDR3] and VL regions [SEQ ID NO: 24 as CDR1; SEQ ID NO: 31 as CDR2; and SEQ ID NO: 35 as CDR3], respectively. Examples of AX1 antibody molecules include without limitation: (i) a Fab which comprises a light chain comprising SEQ ID NO: 73 and an Fd chain comprising amino acids comprising amino acids 1-227 of SEQ ID NO: 69 (or SEQ ID NO: 69); (ii) a full length antibody molecule which comprises a light chain comprising SEQ ID NO: 85 and a heavy chain comprising SEQ ID NO: 79; and (iii) an antibody produced by the expression of SEQ ID NO: 91.

In specific embodiments, PCSK9-specific antagonists disclosed herein comprise in contiguous order for one or both heavy or light chains: (a) framework 1 (FR1) sequence; (b) CDR1 sequence; (c) framework 2 (FR2) sequence; (d) CDR2 sequence; (e) framework 3 (FR3) sequence, (f) CDR3 sequence; and (g) framework 4 (FR4) sequence. In specific embodiments, the heavy chain comprises in contiguous order: (a) FR1 sequence SEQ ID NO: 94; (b) CDR1 sequence selected from the group consisting of SEQ ID NOs: 1, 2, and 6; (c) FR2 sequence SEQ ID NO: 95; (d) CDR2 sequence selected from the group consisting of: SEQ ID NOs: 8, 9 and 13; (e) FR3 sequence SEQ ID NO: 96; (f) CDR3 sequence selected from the group consisting of: SEQ ID NOs: 15, 16 and 20; and (g) FR4 sequence SEQ ID NO: 97. In specific embodiments, the light chain comprises in contiguous order: (a) FR1 sequence SEQ ID NO: 98; (b) CDR1 sequence selected from the group consisting of: SEQ ID NOs: 22, 23, 24, 26 and 28; (c) FR2 sequence SEQ ID NO: 99; (d) CDR2 sequence selected from the group consisting of SEQ ID NOs: 30 and 31; (e) FR3 sequence SEQ ID NO: 100; (f) CDR3 sequence selected from the group consisting of: SEQ ID NOs: 33, 34, 35, 37 and 39; and (g) FR4 sequence SEQ ID NO: 101 or 102. The present invention includes antibody molecules have both heavy and light chains as described above and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%). The select group of AX1 antibodies exemplified demonstrate without limitation that PCSK9-specific antagonists as disclosed herein effectively inhibit human PCSK9.

One particular variant disclosed herein, AX9 antibody molecules, are characterized as comprising a (i) heavy chain variable region ("VH") comprising SEQ ID NO: 43; and (ii) a light chain variable region ("VL") comprising SEQ ID NO: 53. Said VH and VL regions comprise the full complement of disclosed CDRs 1, 2 and 3 for the VH [SEQ ID NO: 6 as CDR1; SEQ ID NO: 13 as CDR2; and SEQ ID NO: 20 as CDR3] and VL regions [SEQ ID NO: 26 as CDR1; SEQ ID NO: 31 as CDR2; and SEQ ID NO: 37 as CDR3], respectively. Examples of AX9 antibody molecules include without limitation: (i) a Fab which comprises a light chain comprising SEQ ID NO: 75 and an Fd chain comprising amino acids comprising amino acids 1-229 of SEQ ID NO: 71 (or SEQ ID NO: 71); (ii) a full length antibody molecule which comprises a light chain comprising SEQ ID NO: 87 and a heavy chain comprising SEQ ID NO: 81; and (iii) an antibody produced by the expression of SEQ ID NO: 92.

One particular variant disclosed herein, AX189 antibody molecules, are characterized as comprising a (i) heavy chain variable region ("VH") comprising SEQ ID NO: 43; and (ii) a light chain variable region ("VL") comprising SEQ ID NO: 67. Said VH and VL regions comprise the full complement of disclosed CDRs 1, 2 and 3 for the VH [SEQ ID NO: 6 as CDR1; SEQ ID NO: 13 as CDR2; and SEQ ID NO: 20 as CDR3] and VL regions [SEQ ID NO: 28 as CDR1; SEQ ID NO: 31 as CDR2; and SEQ ID NO: 39 as CDR3], respectively. Examples of AX189 antibody molecules include without limitation: (i) a Fab which comprises a light chain comprising SEQ ID NO: 77 and an Fd chain comprising amino acids comprising amino acids 1-229 of SEQ ID NO: 71 (or SEQ ID NO: 71); (ii) a full length antibody molecule which comprises a light chain comprising SEQ ID NO: 89 and a heavy chain comprising SEQ ID NO: 81 (or SEQ ID NO: 83); and (iii) an antibody produced by the expression of SEQ ID NO: 93.

The CDR definitions arrived at and disclosed herein were defined using the Abmaxis in-silico program, Luo et al., U.S. Pat. No. 7,117,096 and U.S. Patent Publication No. US2004/0010376 or WO03/099999. Applicants wish to note, however, that various other methods are also available to delineate and define the start and end points of the CDR sequences, including but not limited to Kabat, 1991 *Sequences of Proteins of Immunological Interest*, 5$^{th}$ edit., NIH Publication no. 91-3242 U.S. Department of Health and Human Services; Clothia et al., 1987 *J. Mol. Biol.* 196:901-917; Clothia et al., 1989 *Nature* 342:877-883; Lefranc, 1997 *Immunol. Today,* 18:509; and Chen et al., 1999 *J. Mol. Biol.* 293:865-881. These and other methods have been reviewed and are well within the realm of skills possessed by those in the art; see, e.g., Honegger & Plückthun, 2001 *J. Mol. Biol.* 309:657-670. While the current inventors have employed the Abmaxis program to define the CDRs, the present invention fully encompasses the different definitions around the sequences and the varying CDR delineations arrived at through use of any different analysis software or methods. For example, CDRs may also be defined as the component of the antibody molecules that binds an epitope or which is involved in binding the antigen. The CDR may comprise from 5-20 amino acids. In particular embodiments, the CDRs may further comprise from 2-6 flanking amino acids on each side of the CDR into the framework region. The above methods and resulting CDR definitions based on the presently disclosed sequences are fully within the scope of the present disclosure and anticipated herein.

PCSK9-specific molecules also have utility for various diagnostic purposes in the detection and quantification of PCSK9.

Disclosed PCSK9-specific antagonists are, furthermore, unique in that select embodiments have demonstrated a preferential recognition of processed PCSK9, the active form of PCSK9.

PCSK9-specific antagonists as disclosed herein are desirable molecules for lowering plasma LDL cholesterol levels and are of utility for any primate, mammal or vertebrate of commercial or domestic veterinary importance. PCSK9-specific antagonists are of utility as well to inhibit the activity of PCSK9 in any population of cells or tissues possessing the LDL receptor. The utility of the disclosed antagonists is directly measurable by assays readily available to the skilled artisan. Means for measuring LDL uptake are described in the literature; see, e.g., Barak & Webb, 1981 *J. Cell Biol.* 90:595-604, and Stephan & Yurachek, 1993 *J. Lipid Res.* 34:325330. In addition, means for measuring LDL cholesterol in plasma is well described in the literature; see, e.g., McNamara et al., 2006 *Clinica Chimica Acta* 369:158-167. The particular impact of the disclosed antagonists on cellular LDL uptake may also be measured through a method which comprises providing purified PCSK9 and labeled LDL particles to a cell sample; providing a PCSK9 antagonist to the cell sample; incubating said cell sample for a period of time sufficient to allow LDL particle uptake by the cells; quantifying the amount of label incorporated into the cell; and identifying those antagonists that result in an increase in the amount of quantified label taken up by the cells as compared with that observed when PCSK9 is administered alone. An additional method for measuring the impact of the disclosed antagonists comprises providing purified PCSK9 and labeled LDL particles to a cell sample; providing a PCSK9 antagonist to the cell sample; incubating said cell sample for a period of time sufficient to allow LDL particle uptake by the cells; isolating cells of the cell sample by removing the supernate; reducing non-specific association of labeled LDL particles (whether to the plate, the cells, or anything other than the LDL receptor); lysing the cells; quantifying the amount of label retained within the cell lysate; and identifying those antagonists that result in an increase in the amount of quantified label taken up by the cells as compared with that observed when PCSK9 is administered alone. Antagonists that result in an increase in the amount of quantified label are PCSK9 antagonists.

Any type of cell bearing the LDL receptor can be employed in the above methods including, but not limited to HEK cells, HepG2 cells, and CHO cells. LDL particles derived from any source are of use in the above-described assays. In particular assays, the LDL particles are fresh particles derived from blood. This can be accomplished by any method available to the skilled artisan including, but not limited to, the method of Havel et al., 1955 *J. Clin. Invest.* 34: 1345-1353. The LDL particles may be labeled with fluorescence. The labeled LDL particles may have incorporated therein visible wavelength excited fluorophore 3,3'-dioctadecylindocarbocyanine iodide (dil(3)) to form the highly fluorescent LDL derivative dil(3)-LDL. Any label which enables the skilled artisan to detect LDL in the cellular lysate may be used. An LDL analog may be used that would only become detectable (e.g., become fluorescent or fluoresce at a different wavelength, etc.) when metabolized intracellularly or, for instance, if it were to become associated with (or dissociated from) other molecules in the process of becoming internalized (e.g. a FRET assay, in which an LDL analog would become associated with a secondary fluor, or else be dissociated from a quencher). Any means available in the art for detecting internalization of labeled LDL particles can be employed. The incubation time for the LDL particles and PCSK9 with the cells is an amount of time sufficient to allow LDL particle uptake by the cells. This time may be within the range of 5 minutes to 360 minutes. The concentration of PCSK9 added to the cells may be in the range of 1 nM to 5 μM and, in specific methods, be in the range of 0.1 nM to 3 μM. One specific means by which the skilled artisan can determine a range of concentrations for a particular PCSK9 protein is to develop a dose response curve in the LDL-uptake assay. A concentration of PCSK9 can be selected that promotes close to maximal loss of LDL-uptake and is still in the linear range of the dose response curve. Typically, this concentration is ~5 times the EC-50 of the protein extracted from the dose response curve. The concentrations can vary by protein.

Broadly, PCSK9-specific antagonists as defined herein selectively recognize and specifically bind to PCSK9. An antibody is typically said to specifically bind an antigen when the dissociation constant is ≤1 μM, preferably ≤100 nM and most preferably ≤10 nM. Use of the terms "selective" or "specific" herein, further, refers to the fact that the disclosed antagonists do not show significant binding to proteins other than PCSK9, except in those specific instances where the antagonist is supplemented or designed to confer an additional, distinct specificity to the PCSK9-specific binding portion (as, for example, in bispecific or bifunctional molecules where the molecule is designed to bind two molecules or effect two functions, at least one of which is to specifically bind PCSK9). In specific embodiments, PCSK9-specific antagonists bind to human PCSK9 with a $K_D$ of $1.2\times10^{-6}$ M or less. In more specific embodiments, PCSK9-specific antagonists bind to human PCSK9 with a $K_D$ of $5\times10^{-7}$ M or less, of $2\times10^{-7}$ M or less, or of $1\times10^{-7}$ M or less. In additional embodiments, PCSK9-specific antagonists bind to human PCSK9 with a $K_D$ of $1\times10^{-8}$ M or less. In further embodiments, PCSK9-specific antagonists bind to human PCSK9 with a $K_D$ of $5\times10^{-9}$ M or less, or of $1\times10^{-9}$ M or less. In select embodiments, PCSK9-specific antagonists bind to human PCSK9 with a $K_D$ of $1\times10^{-10}$ M or less, a $K_D$ of $1\times10^{-11}$ M or less, or a $K_D$ of $1\times10^{-12}$ M or less. In specific embodiments, PCSK9-specific antagonists do not bind proteins other than PCSK9 at the above $K_D$s. $K_D$ refers to the dissociation constant obtained from the ratio of $K_d$ (the dissociation rate of a particular binding molecule-target protein interaction) to $K_a$ (the association rate of the particular binding molecule-target protein interaction), or $K_d/K_a$ which is expressed as a molar concentration (M). $K_D$ values can be determined using methods well established in the art. A preferred method for determining the $K_D$ of a binding molecule is by using surface plasmon resonance, for example employing a biosensor system such as a Biacore™ (GE Healthcare Life Sciences) system.

PCSK9-specific antagonists disclosed herein have been shown to dose-dependently inhibit human PCSK9 dependent effects on LDL uptake. Accordingly, PCSK9-specific antagonists as disclosed herein are characterized by their ability to counteract PCSK9-dependent inhibition of LDL uptake into cells. This uptake of LDL into cells by the LDL receptor is referred to herein as "cellular LDL uptake". In specific embodiments, PCSK9-specific antagonists counteract or antagonize human PCSK9-dependent inhibition of LDL uptake into cells, exhibiting an $IC_{50}$ of less than $1.0\times10^{-6}$ M, or, in order of preference, less than $1\times10^{-7}$ M, $1\times10^{-8}$ M, $1\times10^{-9}$ M, $1\times10^{-10}$ M, $1\times10^{-11}$ M and $1\times10^{-12}$ M. The extent of inhibition by any PCSK9-specific antagonist may be measured quantitatively in statistical comparison to a control, or via any alternative method available in the art for assessing a negative effect on, or inhibition of, PCSK9 function (i.e., any method capable of assessing antagonism of PCSK9 function). In specific embodiments, the inhibition is at least about 10% inhibition. In other embodiments, the inhibition is at least 20%, 30%, 40%, 50%, 60%, 70,%, 80%, 90%, or 95%. Accordingly, PCSK9-specific antagonists capable of effecting these levels of inhibition of PCSK9 function form particular embodiments hereof. Specific embodiments provide PCSK9 antagonists as described that, upon administration to a subject, lower LDL by at least 20%, 25%, 30%, 35%, 40%, 45%, 50%, 55%, 60%, 65% and above. In specific embodiments, the PCSK9 antagonists lower LDL by those levels for a period of at least 7 days, 10 days, 15 days, 20 days, 25 days, 30 days, 35 days, 40 days and longer. In particular embodiments, the percent lowering is greater than or equal to 10, 15, 20 and 25 for over 20, 30 or 40 days. Particular embodiments, provide lowering greater than or equal to 25% for over 25 days (see, e.g., Example 20 and FIGS. 24-25). Specific embodiments also provide for PCSK9-specific antagonists that bind to human FcRn at approximately pH 6.0 and dissociate at approximately pH 7.3 (see, e.g., Example 18 and FIGS. 17-20). Particular embodiments are wherein the disclosed PCSK9-specific antagonists exhibit a dissociation of <5% (in specific embodiments, less than 3% or 1%) at neutral pH. Dissociation (or % bound) can be calculated as described in Example 18. Specific embodiments, also provide PCSK-9 specific antagonists as described herein that have a ½ life in mice (or monkeys) of greater than 50, 60, 70, 80, 90, 95, 100, 100, 120, 130 or 140 hours (see, e.g., Example 19 and FIGS. 21-23). In particular embodiments, PCSK9-specific antagonists are provided that have a ½ life in primates of greater than 50, 60, 70, 80, 90, 100, 110, 120, 130, 140 and 145 days (see, e.g., Example 19). The present invention also provides, in specific embodiments, PCSK9-specific antagonists that, after 1 week of stress at 45° C. (under conditions similar to that described in Example 22), in pH 5, 6, 7 or 8 buffers have essentially no increase in oligomers, higher order aggregates and exhibit no clipping (see, e.g., Example 22 and Table 11). In specific embodiments, the above effects are as seen in humans and non-human primates (or where particularly specified, mice). In specific embodiments, the above effects are seen following intravenous or subcutaneous administration.

A PCSK9-specific antagonist in accordance herewith can be any binding molecule that specifically binds human PCSK9 protein including, but not limited to, antibody molecules as defined below, any PCSK9-specific binding structure, any polypeptide or nucleic acid structure that specifically binds PCSK9, and any of the foregoing incorporated into various protein scaffolds; including but not limited to, various non-antibody-based scaffolds, and various structures capable of affording or allowing for selective binding to PCSK9 including but not limited to small modular immunopharmaceuticals (or "SMIPs"; see, Haan & Maggos, 2004 *Biocentury* January 26); Immunity proteins (see, e.g., Chak et al., 1996 *Proc. Natl. Acad. Sci. USA* 93:6437-6442); cytochrome b562 (see Ku and Schultz, 1995 *Proc. Natl. Acad. Sci. USA* 92:6552-6556); the peptide α2p8 (see Barthe et al., 2000 *Protein Sci.* 9:942-955); avimers (Avidia; see Silverman et al., 2005 *Nat. Biotechnol.* 23:1556-1561); DARPins (Molecular Partners; see Binz et al., 2003 *J. Mol. Biol.* 332:489-503; and Forrer et al., 2003 *FEBS Lett.* 539:2-6); Tetranectins (see, Kastrup et al., 1998 *Acta. Crystallogr. D. Biol. Crystallogr.* 54:757-766); Adnectins (Adnexus; see, Xu et al., 2002 *Chem. Biol.* 9:933-942), Anticalins (Pieris; see Vogt & Skerra, 2004 *Chemobiochem.* 5:191-199; Beste et al., 1999 *Proc. Natl. Acad. Sci. USA* 96:1898-1903; Lamla & Erdmann, 2003 *J. Mol. Biol.* 329:381-388; and Lamla & Erdmann, 2004 *Protein Expr. Purif.* 33:39-47); A-domain proteins (see North & Blacklow, 1999 *Biochemistry* 38:3926-3935), Lipocalins (see Schlehuber & Skerra, 2005 *Drug Discov. Today* 10:23-33); Repeat-motif proteins such as Ankyrin repeat proteins (see Sedgwick & Smerdon, 1999 *Trends Biochem. Sci.* 24:311-316; Mosavi et al., 2002 *Proc. Natl. Acad. Sci. USA* 99:16029-16034; and Binz et al., 2004 *Nat. Biotechnol.* 22:575-582); Insect Defensin A (see Zhao et al., 2004 *Peptides* 25:629-635); Kunitz domains (see Roberts et al., 1992 *Proc. Natl. Acad. Sci. USA* 89:2429-2433; Roberts et al., 1992 *Gene* 121:9-15; Dennis & Lazarus, 1994 *J. Biol. Chem.* 269:22129-22136; and Dennis & Lazarus, 1994 *J. Biol. Chem.* 269:22137-22144); PDZ-Domains (see Schneider et al., 1999 *Nat. Biotechnol.* 17:170-175); Scorpion toxins such as Charybdotoxin (see Vita et al., 1998 *Biopolymers* 47:93-100); $10^{th}$ fibronectin type III domain (or IOFn3; see Koide et al., 1998 *J. Mol. Biol.* 284:1141-1151, and Xu et al., 2002 *Chem. Bipl.* 9:933-942); CTLA-4 (extracellular domain; see Nuttall et al., 1999 *Proteins* 36:217-227; and Irving et al., 2001 *J. Immunol. Methods* 248:31-45); Knottins (see Souriau et al., 2005 *Biochemistry* 44:7143-7155 and Lehtio et al., 2000 *Proteins* 41:316-322); Neocarzinostatin (see Heyd et al. 2003 *Biochemistry* 42:5674-5683); carbohydrate binding module 4-2 (CBM4-2; see Cicortas et al., 2004 *Protein Eng. Des. Sel.* 17:213-221); Tendamistat (see McConnell & Hoess, 1995 *J. Mol. Biol.* 250:460-470, and Li et al., 2003 *Protein Eng.* 16:65-72); T cell receptor (see Holler et al., 2000 *Proc. Natl. Acad. Sci. USA* 97:5387-5392; Shusta et al., 2000 *Nat. Biotechnol.* 18:754-759; and Li et al., 2005 *Nat. Biotechnol.* 23:349-354); Affibodies (Affibody; see Nord et al., 1995 *Protein Eng.* 8:601-608; Nord et al., 1997 *Nat. Biotechnol.* 15:772-777; Gunneriusson et al., 1999 *Protein Eng.* 12:873-878); and other selective binding proteins or scaffolds recognized in the literature; see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Antibodies and the use of antigen-binding fragments is well defined and understood in the literature. The use of alternative scaffolds for protein binding is well appreciated in the scientific literature as well, see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Accordingly, non-antibody-based scaffolds or antagonist molecules in accordance herewith exhibiting selectivity for PCSK9 that counteract PCSK9-dependent inhibition of cellular LDL-uptake form important embodiments of the present invention. Aptamers (nucleic acid or peptide molecules capable of selectively binding a target molecule) are one specific example. They can be selected from random sequence pools or identified from natural sources such as riboswitches. Peptide aptamers, nucleic acid aptamers (e.g., structured nucleic acid, including both DNA and RNA-based structures) and nucleic acid decoys can be effective for selectively binding and inhibiting proteins of interest; see, e.g., Hoppe-Seyler & Butz, 2000 *J. Mol. Med.* 78:426-430; Bock et al., 1992 *Nature* 355:564-566; Bunka & Stockley, 2006 *Nat. Rev. Microbiol.* 4:588-596; Martell et al., 2002 *Molec. Ther.* 6:30-34; Jayasena, 1999 *Clin. Chem.* 45:1628-1650; the disclosures of which are incorporated herein by reference.

Given AX1's significant neutralizing activity and the activity of its variants, it is clearly of interest to identify other PCSK9-specific antagonists that bind to PCSK9 in the same manner as AX1 or one of its variants. One means of identifying antagonists and particularly antibodies that bind to the same region or epitope as AX1 or its variants, or an overlapping epitope is through a competition or similar assay where the candidate antibody or binding molecule would have to out-compete AX1 (or variant) for the epitope. Competitive antagonists encompassed herein are molecules that inhibit (i.e., prevent, or interfere with, AX1 (or variant) binding in comparison to a control) or reduce AX1 (or variant) binding by at least 50%, 60%, 70%, and 80% in order of increasing preference (even more preferably, at least 90% and, most preferably, at least 95%) at 1 μM or less with AX1 (or variant) at or below its $K_D$, and in particular those molecules that antagonize (i) PCSK9 binding to the LDL receptor, (ii) PCSK9 internalization into cells, or (iii) both PCSK9 binding to the LDL receptor and PCSK9 internalization into cells. Competition between binding members may be readily assayed in vitro for example using ELISA and/or by monitoring the interaction of the antibodies with PCSK9 in solution. The exact means for conducting the analysis is not critical. PCSK9 may be immobilized to a 96-well plate or may be placed in a homogenous solution. In specific embodiments, the ability of unlabeled candidate antibody(ies) to block the binding of labeled AX1 (or variant) can be measured using radioactive, enzyme or other labels. In the reverse assay, the ability of unlabeled antibodies to interfere with the interaction of labeled AX1 (or variant) with PCSK9 wherein said AX1 (or variant) and PCSK9 are already bound is determined. In specific embodiments, (i) PCSK9 is contacted with labeled AX1 (or variant); (ii) PCSK9 is contacted with the candidate antibody or pool of antibodies; and (iii) antibodies capable of interrupting or preventing complexes between PCSK9 and AX1 (or variant) are identified. The readout in such an example is through measurement of bound label. AX1 (or variant) and the candidate antibody(ies) may be added in any order or at the same time.

Antibodies identified as AX1 (or variant) competitors in the above or other suitable assays may be tested for the ability to antagonize or neutralize (i) PCSK9 binding to the LDL receptor; and/or (ii) PCSK9 internalization into cells. These parameters may be measured through the use of assays similar to that employed or described in the current specification. In specific embodiments, the inhibition demonstrated by the competing antibody is at least about 10% inhibition. In other embodiments, the inhibition is at least 20%, 30%, 40%, 50%, 60%, 70%, 80%, 90% or 95%.

The present invention specifically encompasses PCSK9-specific antagonists and particularly monoclonal antibody molecules (and their corresponding amino acid and nucleic acid sequences) that selectively bind to the same epitope as AX1 (or variant) or an overlapping epitope interfering with AX1 (or variant)'s binding to PCSK9. Monoclonal antibodies that specifically bind to the epitope of AX1 (or variant), or an overlapping epitope antagonize or neutralize (i) PCSK9 binding to the LDL receptor; (ii) PCSK9 internalization into cells, or (iii) both. A monoclonal antibody molecule in accordance herewith may be an intact (complete or full length) antibody, a substantially intact antibody, or a portion or fragment of an antibody comprising an antigen-binding portion, e.g., a Fab fragment, Fab' fragment or $F(ab)_2$ fragment of a murine antibody or of a chimeric antibody or of a humanized antibody or of a human antibody. Monoclonal, as used herein, refers to a homogeneous or substantially homogeneous (or pure) antibody population (i.e., at least about 90%, 91%, 92%, 93%, 94%, 95%, 96%, more preferably at least about 97% or 98%, or most preferably at least 99% of the antibodies in the population are identical and would compete in an ELISA assay for the same antigen or epitope). In specific embodiments of the present invention, the present invention provides monoclonal antibodies that (i) compete for binding to PCSK9 with a AX1 (or variant) antibody molecule, reducing AX1 (or variant) binding by at least 50% at 1 μM or less with AX1 (or variant) at or below its $K_D$, (ii) block PCSK9 binding to the LDL receptor, (iii) inhibit PCSK9 internalization into the cell, and (iv) comprise a specific antigen-binding region, VH, VL, set of CDRs or heavy CDR3, heavy and/or light chain or any variant of these components as described herein.

In any of the above assays for identifying antibodies binding the same or overlapping epitope region as AX1 (or variant), binding of the known binder (i.e., AX1 (or variant) antibody molecule) as compared to the binding of the candidate binder should be distinguishable. This can (but need not) be accomplished through the use of labels on either or both molecules as will be readily appreciated by the skilled artisan. Labels, as used herein, refer to another molecule or agent incorporated into/affixed to the antibody molecule. In one embodiment, the label is a detectable marker, e.g., a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In particular embodiments, the present invention encompasses antagonists as described herein characterized as binding specifically to any epitope sequence selected from the group consisting of SEQ ID NOs: 105-108, 166 and regions therein such as 157-NL-158, SEQ ID NOs: 109-111, and 133-134. In particular embodiments, the present invention encompasses antagonists as described herein characterized as binding specifically to any epitope sequence selected from the group consisting of: SEQ ID NOs: 112-113, 158-ER, 366EDI, and 380-SQS. In specific embodiments, the present invention encompasses antagonists the bind specifically to one or more sequences selected from the group consisting of: 157-NL-158 and SEQ ID NO: 109-111. In particular embodiments, the present invention also encompasses antagonists characterized as binding specifically to one or more epitope sequences selected from the group consisting of: SEQ ID NOs: 114-116 and 188-SIQ. These epitopes are described further in Example 10 and in FIGS. 3, 6, 7 and 8. The numerical numbers provide the starting and/or ending position on human PCSK9.

In specific embodiments, binding of a PCSK9-specific antagonist is significantly reduced or a mutant PCSK9 protein having one or more (e.g., 1, 2, 3, 4, 5 or more) mutations at the following residue positions: 366 and 426, as compared to a wild-type PCSK9 protein (SEQ ID NO: 167). In certain embodiments, binding of a PCSK9-specific antagonist is significantly reduced for a mutant PCSK9 protein having one or more (e.g., 1, 2, 3, 4, 5 or more) of the following mutations: E366K and E426M.

In particular embodiments, binding of a PCSK9-specific antagonist is significantly reduced or a mutant PCSK9 protein having one or more (e.g., 1, 2, 3, 4, 5 or more) mutations at the following residue positions: 201, 202, 206, 207, 247 and 248, as compared to a wild-type PCSK9 protein (SEQ ID NO: 167).

An AX1 or AX189 (or variant) antibody used as the standard for the competition assays may be any antibody molecule described herein. Molecules (peptides, antagonists, antibody molecules, etc.) tested may be from any source or library. In particular embodiments, the molecules are selected from a phage display library. In specific embodiments the molecules are selected using an EGF_AB peptide (293-

DKVCNMARDCRDWSDEPIKECGT-NECLDNNGGCSHVCNDLKIGYECLCPDG-FQLVAQRRCEDIDECQDPDTCSQLCVNLE-372; SEQ ID NO: 168) that competes with AX1 or AX189 (or variant) in a mariner similar to that described in Example 11.

Expression and selection of any of the PCSK9-specific antagonists described in the present application may be achieved using suitable technologies including, but not limited to phage display (see, e.g., International Application Number WO 92/01047, Kay et al., 1996 *Phage Display of Peptides and Proteins: A Laboratory Manual*, San Diego: Academic Press), Wang et al., 2010 *J. Mol Biol.* 395:1088-1101; Wang et al., U.S. Pat. No. 7,175,983; yeast display, bacterial display, T7 display, and ribosome display (see, e.g., Lowe & Jermutus, 2004 *Curr. Pharm. Biotech.* 517-527).

Particular PCSK9-specific antagonists forming part of the present invention are antibody molecules or antibodies. "Antibody molecule" or "Antibody" as described herein refers to an immunoglobulin-derived structure with selective binding to human PCSK9 including, but not limited to, a full length or whole antibody, an antigen binding fragment (a fragment derived, physically or conceptually, from an antibody structure), a derivative of any of the foregoing, a fusion of any of the foregoing with another polypeptide, or any alternative structure/composition which incorporates any of the foregoing for purposes of selectively binding to/inhibiting the function of PCSK9. Antibody molecules can exist, for example, as intact immunoglobulins or as a number of well characterized fragments produced by, for example, digestion with various peptidases. The recognized immunoglobulin genes include the kappa, lambda, alpha, gamma, delta, epsilon and mu constant region genes, as well as a myriad of immunoglobulin variable region genes. Light chains are classified as gamma, mu, alpha, delta, or epsilon, which in turn define the immunoglobulin classes, IgG, IgM, IgA, IgD and IgE, respectively. "Whole" antibodies or "full length" antibodies often refers to proteins that comprise two heavy (H) and two light (L) chains inter-connected by disulfide bonds which comprise: (1) in terms of the heavy chains, a variable region (abbreviated herein as "$V_H$") and a heavy chain constant region which comprises three domains, $C_{H1}$, $C_{H2}$, and $C_{H3}$; and (2) in terms of the light chains, a light chain variable region (abbreviated herein as "$V_L$") and a light chain constant region which comprises one domain, $C_L$. Pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially a Fab with part of the hinge region broken. While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

Antibody fragments and, more specifically, antigen binding fragments are molecules possessing an antibody variable region or segment thereof (which comprises one or more of the disclosed CDR 3 or CDR2 domains, heavy and/or light, within framework regions of heavy and/or light chains, as appropriate), which confers selective binding to PCSK9, and particularly human PCSK9. Antibody fragments containing such an antibody variable region include, but are not limited to the following antibody molecules: a Fab, a $F(ab')_2$, a Fd, a Fv, a scFv, ccFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, an isolated CDR3, a minibody, a 'scAb', a dAb fragment, a diabody, a triabody, a tetrabody, a minibody, and artificial antibodies based upon protein scaffolds, including but not limited to fibronectin type III polypeptide antibodies (see, e.g., U.S. Pat. No. 6,703,199 and International Application Numbers WO 02/32925 and WO 00/34784) or cytochrome B; see, e.g., Nygren et al., 1997 *Curr. Opinion Struct. Biol.* 7:463-469; the disclosures of which are incorporated herein by reference. The antibody portions or binding fragments may be natural, or partly or wholly synthetically produced. Such antibody portions can be prepared by various means known by one of skill in the art, including, but not limited to, conventional techniques, such as papain or pepsin digestion. One of skill in the art will, furthermore, appreciate that any of the above antibody molecules, including full length as well as the various antibody fragments, may be synthesized de novo either chemically or by utilizing recombinant DNA methodology. Thus, the term antibody, as used herein, also includes full length antibodies and antibody fragments either produced by the generation or modification of whole antibodies or those synthesized de novo using recombinant DNA methodologies.

The term "isolated" as used herein in reference to antibody molecules, PCSK9-specific antagonists in general, encoding nucleic acid or other describes a property as it pertains to the disclosed PCSK9-specific antagonists, nucleic acid or other that makes them different from that found in nature. The difference can be, for example, that they are of a different purity than that found in nature, or that they are of a different structure or form part of a different structure than that found in nature. A structure not found in nature, for example, includes recombinant human immunoglobulin structures including, but not limited to, recombinant human immunoglobulin structures with optimized CDRs. Other examples of structures not found in nature are PCSK9-specific antagonists or nucleic acid substantially free of other cellular material. Isolated PCSK9-specific antagonists are generally free of other protein-specific antagonists having different protein specificities (i.e., possess an affinity for other than PCSK9).

In one particular aspect, the present invention provides isolated PCSK9-specific antagonists which antagonize PCSK9 function. In particular embodiments, said PCSK9-specific antagonists inhibit human PCSK9's antagonism of cellular LDL uptake by interfering with PCSK9 binding to the LDL receptor and resultant PCSK9 cell internalization. Disclosed PCSK9-specific antagonists, thus, form desirable molecules for lowering plasma LDL-cholesterol levels; see, e.g., Cohen et al., 2005 *Nat. Genet.* 37:161-165 (wherein significantly lower plasma LDL cholesterol levels were noted in individuals heterozygous for a nonsense mutation in allele PCSK9); Rashid et al., 2005 *Proc. Natl. Acad. Sci. USA* 102:5374-5379 (wherein PCSK9-knockout mice evidenced increased numbers of LDLRs in hepatocytes, accelerated plasma LDL clearance, and significantly lower plasma cholesterol levels); and Cohen et al., 2006 *N. Engl. J. Med.* 354:1264-1272 (wherein humans heterozygous for mutated, loss of function, PCSK9 exhibited a significant reduction in the long-term risk of developing atherosclerotic heart disease).

Through repeat experiments, antibody molecules tested herein dose-dependently inhibited the effects of both human PCSK9 on LDL uptake. In specific embodiments, the present invention, thus, encompasses isolated PCSK9-specific antagonists as described herein, as well as equivalents (characterized as having one or more (in specific embodiments, 1-5 or 1-3) amino acid substitutions that do not degrade the PCSK9-selective property of the disclosed AX1 or variant antibody molecules) or homologs thereof. Particular embodiments comprise isolated PCSK9-specific antagonists that comprise the CDR domains disclosed herein or sets of heavy and/or light chain CDR domains disclosed herein, or equivalents thereof, characterized as having one or more amino acid substitutions.

Use of the terms "domain" or "region" herein simply refers to the respective portion of the antibody molecule wherein the sequence or segment at issue will reside or, in the alternative, currently resides.

In specific embodiments, the present invention provides isolated PCSK9-specific antagonists and, in more specific embodiments, antibody molecules that comprise (i) a heavy chain variable region selected from the group consisting of: SEQ ID NOs: 41, 43, and 45-49 and/or (ii) a light chain variable region selected from the group consisting of: SEQ ID NOs: 50, 52, 53, 55-66 and 67; equivalents thereof characterized as having one or more (in particular embodiments, 1-5 or 1-3) amino acid substitutions, and homologs thereof. The disclosed antagonists should counteract or inhibit human PCSK9-dependent inhibition of cellular LDL uptake. In specific embodiments, the present invention provides homologs of the disclosed antagonists characterized as comprising a heavy chain variable and/or a light chain variable region being at least 90% (or in specific embodiments, at least 95%, 97% or 99%) identical in sequence to either or both, respectively, of (i) a heavy chain variable region selected from the group consisting of: SEQ ID NOs: 41, 43, and 45-49 and/or (ii) a light chain variable region selected from the group consisting of: SEQ ID NOs: 50, 52, 53, 55-66 and 67; said antagonists which inhibit human PCSK9-dependent inhibition of cellular LDL uptake by at least 10%.

In particular embodiments, the present invention provides isolated PCSK9-specific antagonists and, in more specific embodiments, PCSK9 antibody molecules that comprise (i) variable heavy CDR3 sequence selected from the group consisting of SEQ ID NOs: 15, 16, 18, 20, 173 and residues 4-15 of SEQ ID NOs: 15, 16 and 20 and/or (ii) variable light CDR3 sequence selected from the group consisting of: SEQ ID NOs: 33, 34, 35, 37 and 39; and equivalents thereof characterized as having one or more (in particular embodiments, 1-5 or 1-3) amino acid substitutions; specific embodiments of which inhibit human PCSK9-dependent inhibition of cellular LDL uptake by at least 10%. Specific embodiments provide isolated antagonists which additionally comprise in the heavy and/or light chain variable regions CDR1 and/or CDR2 sequences as described herein; or equivalents thereof characterized as having one or more (in specific embodiments, 1-5 or 1-3) amino acid substitutions in any one or more of the CDR sequences. In specific embodiments, the present invention provides homologs of the disclosed antagonists characterized as being at least 90% (in specific embodiments, 95%, 97%, or 99%) identical to the CDR3 sequences or within each of the CDR1, CDR2 and CDR3 sequences; said antagonists which inhibit human PCSK9-dependent inhibition of cellular LDL uptake by at least 10%.

In particular embodiments, the present invention provides isolated PCSK9-specific antagonists and, in more specific embodiments, PCSK9 antibody molecules that comprise (i) variable heavy CDR2 sequence selected from the group consisting of: SEQ ID NOs: 8, 9, 11, 13, 171 and residues 4-20 of SEQ ID NOs: 8, 9 and 13 and/or (ii) variable light CDR2 sequence selected from the group consisting of SEQ ID NOs: 30-31; and equivalents thereof characterized as having one or more (in particular embodiments, 1-5 or 1-3) amino acid substitutions; specific embodiments of which inhibit human PCSK9-dependent inhibition of cellular LDL uptake by at least 10%. Specific embodiments provide isolated antagonists which additionally comprise heavy and/or light chain variable regions CDR1 and/or CDR3 sequences as described herein; or equivalents thereof characterized as having one or more (in specific embodiments, 1-5 or 1-3) amino acid substitutions in any one or more of the CDR sequences. In specific embodiments, the present invention provides homologs of the disclosed antagonists characterized as being at least 90% (in specific embodiments, 95%, 97%, or 99%) identical to the CDR2 sequences or within each of the CDR1, CDR2 and CDR3 sequences; said antagonists which inhibit human PCSK9-dependent inhibition of cellular LDL uptake by at least 10%.

Select variable heavy CDR1 regions comprise sequence selected from the group consisting of: 1, 2, 4, 6, 169 and residues 4-13 of SEQ ID NOs: 1, 2 and 6; and equivalents thereof characterized as having one or more (in particular embodiments, 1-5 or 1-3) amino acid substitutions.

Select variable light CDR1 regions comprise sequence selected from the group consisting of: SEQ ID NOs: 22, 23, 24, 26 and 28; and equivalents thereof characterized as having one or more (in particular embodiments, 1-5 or 1-3) amino acid substitutions.

Specific embodiments provide isolated PCSK9-specific antagonists and, in more specific embodiments, antibody molecules which comprise one or more (in particular embodiments, one of each CDR1, 2, and 3 regions) heavy chain variable region CDR1, CDR2, and CDR3 sequences and light chain variable region CDR1, CDR2, and CDR3 sequences as disclosed herein; and equivalents thereof characterized as having one or more (in particular embodiments, 1-5 or 1-3) amino acid substitutions in any one or more of the CDR sequences; specific embodiments of which inhibit human PCSK9-dependent inhibition of cellular LDL uptake by at least 10%. In specific embodiments, the present invention provides homologs of the disclosed antagonists characterized as being at least 90% (in specific embodiments, 95%, 97%, or 99%) identical over the disclosed heavy and light chain variable region CDR1, CDR2 and CDR3 sequences, respectively; said antagonists which inhibit human PCSK9-dependent inhibition of cellular LDL uptake by at least 10%.

One particular aspect of the present invention encompasses isolated PCSK9-specific antagonists and, in more specific embodiments, antibody molecules which are variants of that disclosed above which inhibit human PCSK9-dependent inhibition of cellular LDL uptake by at least 10%.

Additional distinct embodiments encompass isolated PCSK9-specific antagonists which comprise: (a) a heavy chain variable region comprising CDR1, CDR2 and CDR3 sequence, wherein (i) the CDR1 sequence is selected from the group consisting of: SEQ ID NOs: 1, 2, 4, 6 and 169, and residues 4-13 of SEQ ID NOs: 1, 2 and 6; (ii) the CDR2 sequence is selected from the group consisting of: SEQ ID NOs: 8, 9, 11, 13, 171 and residues 4-20 of SEQ ID NOs: 8, 9 and 13; and (iii) the CDR3 sequence is selected from the group consisting of: SEQ ID NOs: 15, 16, 18, 20, 173, and residues 4-15 of SEQ ID NOs: 1, 2 and 6 and/or (b) a light chain variable region comprising CDR1, CDR2 and CDR3 sequence, wherein (i) the CDR1 sequence is selected from the group consisting of: SEQ ID NOs: 22, 23, 24, 26 and 28; (ii) the CDR2 sequence is selected from the group consisting of:

SEQ ID NOs: 30-31; and (iii) the CDR3 sequence is selected from the group consisting of: SEQ ID NOs: 33, 34, 35, 37 and 39; and equivalents thereof characterized as having one or more (in particular embodiments, 1-5 or 1-3) amino acid substitutions; specific embodiments of which inhibit human PCSK9-dependent inhibition of cellular LDL uptake by at least 10%.

In specific embodiments herein the CDRs are in place of the corresponding regions of AX132 (or disclosed variants) or alternative antagonist, antibody molecule or scaffold structure with or without amino acid substitutions (in specific embodiments, 1-5 or 1-3); specific embodiments of which inhibit human PCSK9-dependent inhibition of cellular LDL uptake by at least 10%.

Particular embodiments are isolated PCSK9-specific antagonists which comprise the above-described VH and VL regions in a full length antibody. Specific embodiments herein further comprise a series of amino acids selected from the group consisting of: SEQ ID NO: 117 (IgG1), SEQ ID NO: 118 (IgG2), SEQ ID NO: 119 (IgG4) and SEQ ID NO: 120 (IgG2m4).

Amino acid substitutions encompassed herein may be conservative or non-conservative amino acid substitutions. Amino acid substitutions, as one of ordinary skill in the art will appreciate, are substitutions that replace an amino acid residue with one imparting similar or better (for the intended purpose) functional and/or chemical characteristics. Antagonists bearing amino acid substitutions can be tested for retained or better activity using functional assays available in the art or described herein. PCSK9-specific antagonists possessing one or more amino acid substitutions which retain the ability to selectively bind to human PCSK9 and antagonize PCSK9 functioning at a level the same or better than AX132 (or variant) antibody molecules as described herein are referred to herein as "functional equivalents" of the disclosed antagonists and form specific embodiments of the present invention. Conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Modifications as described above may or may not be designed to significantly alter the binding or functional inhibition characteristics of the PCSK9-specific antagonist, and may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis as discussed in, for example, MacLennan et al., 1998 *Acta Physiol. Scand Suppl.* 643:55-67, and Sasaki et al., 1998 *Adv. Biophys.* 35:1-24.

In one specific embodiment of the present invention, a CDR disclosed herein is altered so as to generate a more stable variant or a variant that is recombinantly expressed at higher levels. For example, if Asn-Gly or Asp-Gly is in a CDR, the invention encompasses variants wherein the Asp or Asn is changed to Glu or Ala or wherein the Gly is changed to Ala. A benefit of such a change is removal of the potential for isoaspartate formation. Also, if a Met is in a CDR in an exposed position, the scope of the present invention includes variants wherein the Met is changed to Lys, Leu, Ala, or Phe. A benefit of such a change is removal of the potential for methionine oxidation. If an Asn is in a CDR of the invention, the scope of the present invention includes variants wherein Asn is changed to Gln or Ala. A benefit of such a change is removal of the potential for deamidation. Furthermore, if an Asn-Pro is in a CDR of the present invention, the present invention includes variants wherein Asn is changed to Gln or Ala or wherein Pro is changed to Ala. A benefit of such a change is removal of a possible scissile Asn-Pro peptide bond. The scope of the invention includes embodiments wherein the heavy or light chain CDRs of any of the disclosed antibody molecules are independently changed in one or more places as described above.

In another aspect, the present invention provides isolated PCSK9-specific antagonists and, in more specific embodiments, antibody molecules which comprise heavy and/or light chain variable regions comprising amino acid sequences that are homologous to the corresponding amino acid sequences of the disclosed antibodies, wherein the antibody molecules inhibit PCSK9-dependent inhibition of cellular LDL uptake. Specific embodiments are antagonists which comprise heavy and/or light chain variable regions which are at least 90% identical to disclosed heavy and/or light chain variable regions (or heavy and/or light chains), respectively. Reference to "at least 90% identical" includes at least 90, 91, 92, 93, 94, 95, 96, 97, 98, 99 and 100% identical sequences along the full length of the molecule disclosed herein.

PCSK9-specific antagonists with amino acid sequences homologous to the amino acid sequences of antagonists described herein are typically produced to improve one or more of the properties of the antagonist without negatively impacting its specificity for PCSK9. One method of obtaining such sequences, which is not the only method available to the skilled artisan, is to mutate sequence encoding the PCSK9-specific antagonist or specificity-determining region(s) thereof, express an antagonist comprising the mutated sequence(s), and test the encoded antagonist for retained function using available functional assays including those described herein. Mutation may be by site-directed or random mutagenesis. As one of skill in the art will appreciate, however, other methods of mutagenesis can readily bring about the same effect. For example, in certain methods, the spectrum of mutants are constrained by non-randomly targeting amino acid substitutions based on either amino acid chemical or structural characteristics, or else by protein structural considerations. In affinity maturation experiments, several such mutations may be found in a single selected molecule, whether they are randomly or non-randomly selected. There are also various structure-based approaches toward affinity maturation as demonstrated in, e.g., U.S. Pat. No. 7,117,096, PCT Pub. Nos.: WO 02/084277 and WO 03/099999; the disclosures of which are incorporated herein by reference.

As used herein, the percent homology between two amino acid or nucleic acid sequences is equivalent to the percent identity between the two sequences, and these two terms will be used interchangeably throughout. As used herein, % identity of two nucleic acid or amino acid sequences is determined using the algorithm of Karlin and Altschul (Proc. Natl. Acad. Sci. USA 90:5873-5877, 1993). Such an algorithm is incorporated into the NBLAST and XBLAST programs of Altschul et al., 1990 *J. Mol. Biol.* 215:403-410. BLAST nucleotide searches are performed with the NBLAST program, score=100, wordlength=12, to obtain nucleic acid sequences homologous to a nucleic acid molecule of the invention. BLAST protein searches are performed with the XBLAST program, score=50, wordlength-3, to obtain amino acid sequences homologous to an amino acid sequence disclosed herein. To obtain gapped alignments for comparison purposes, Gapped BLAST is utilized as described in Altschul et al., 1997 *Nucleic Acids Res.* 25:3389-3402. When utilizing BLAST and Gapped BLAST programs, the default parameters of the respective programs (e.g., XBLAST and NBLAST) are used.

Utilization of components of one or more disclosed PCSK9-specific molecules to produce other binding molecules with similar or better specificity is well within the realm of one skilled in the art. This can be accomplished, for example, using techniques of recombinant DNA technology. One specific example of this involves the introduction of DNA encoding the immunoglobulin variable region, or one or more of the CDRs, of an antibody to the variable region, constant region, or constant region plus framework regions, as appropriate, of a different immunoglobulin. Such molecules form important aspects of the present invention. Specific immunoglobulins or the corresponding sequences, into which particular disclosed sequences may be inserted or, in the alternative, form the essential part of, include but are not limited to the following antibody molecules which form particular embodiments of the present invention: a Fab (monovalent fragment with variable light (VL), variable heavy (VH), constant light (CL) and constant heavy 1 (CH1) domains), a $F(ab')_2$ (bivalent fragment comprising two Fab fragments linked by a disulfide bridge or alternative at the hinge region), a Fd (VH and CH1 domains), a Fv (VL and VH domains), a scFv (a single chain Fv where VL and VH are joined by a linker, e.g., a peptide linker, see, e.g., Bird et al., 1988 *Science* 242:423-426, Huston et al., 1988 *PNAS USA* 85:5879-5883), a bispecific antibody molecule (an antibody molecule comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer (see, e.g., PCT/US92/09965), an isolated CDR3, a minibody (single chain-CH3 fusion that self assembles into a bivalent dimer of about 80 kDa), a 'scAb' (an antibody fragment containing VH and VL as well as either CL or CHI), a dAb fragment (VH domain, see, e.g., Ward et al., 1989 *Nature* 341:544-546, and McCafferty et al., 1990 *Nature* 348:552-554; or VL domain; Holt et al., 2003 *Trends in Biotechnology* 21:484-489), a diabody (see, e.g., Holliger et al., 1993 *PNAS USA* 90:6444-6448 and International Application Number WO 94/13804), a triabody, a tetrabody, a minibody (a scFv joined to a CH3; see, e.g., Hu et al., 1996 *Cancer Res.* 56:3055-3061), IgG, IgG1, IgG2, IgG3, IgG4, IgM, IgD, IgA, IgE or any derivatives thereof, and artificial antibodies based upon protein scaffolds, including but not limited to fibronectin type III polypeptide antibodies (see, e.g., U.S. Pat. No. 6,703,199 and International Application Number WO 02/32925) or cytochrome B; see, e.g., Koide et al., 1998 *J. Molec. Biol.* 284:1141-1151, and Nygren et al., 1997 *Current Opinion in Structural Biology* 7:463-469; the disclosures of which are incorporated herein by reference. Certain antibody molecules including, but not limited to, Fv, scFv, diabody molecules or domain antibodies (Domantis) may be stabilized by incorporating disulfide bridges to line the VH and VL domains, see, e.g., Reiter et al., 1996 *Nature Biotech.* 14:1239-1245; the disclosure of which is incorporated herein by reference. Bispecific antibodies may be produced using conventional technologies (see, e.g., Holliger & Winter, 1993 *Current Opinion Biotechnol.* 4:446-449, specific methods of which include production chemically, or from hybrid hybridomas) and other technologies including, but not limited to, the BiTE™ technology (molecules possessing antigen binding regions of different specificity with a peptide linker) and knobs-into-holes engineering (see, e.g., Ridgeway et al., 1996 *Protein Eng.* 9:616-621; the disclosure of which is incorporated herein by reference). Bispecific diabodies may be produced in *E. coli*, and these molecules as other PCSK9-specific antagonists, as one of skill in the art will appreciate, may be selected using phage display in the appropriate libraries (see, e.g., International Application Number WO 94/13804; the disclosure of which is incorporated herein by reference).

Variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992 *Bio/Technology* 10:779-783; the disclosure of which is incorporated herein by reference. A variable heavy domain may be paired with a variable light domain to provide an antigen binding site. In addition, independent regions (e.g., a variable heavy domain alone) may be used to bind antigen. The artisan is well aware, as well, that two domains of an Fv fragment, VL and VH, while perhaps coded by separate genes, may be joined, using recombinant methods, by a synthetic linker that enables them to be made as a single protein chain in which the VL and VH regions pair to form monovalent molecules (scFvs).

Specific embodiments provide the CDR(s) in germline framework regions. Framework regions, including but not limited to human framework regions, are known to those of skill in the art (e.g., a human or non-human framework). The framework regions may be naturally occurring or consensus framework regions. In one aspect, the framework region of an antibody of the invention is human (see, e.g., Clothia et al., 1998 *J. Mol. Biol.* 278:457-479 for a listing of human framework regions; said disclosure of which is incorporated herein by reference in its entirety). Specific embodiments herein provide the disclosed heavy and/or light chain variable CDR3 sequences into VH3 or VK3, respectively, in place of the relevant CDR. Specific embodiments herein provide the disclosed heavy and/or light chain variable CDR1, CDR2 and/or CDR3 sequences into VH3 or VK3, respectively, in place of the relevant CDRs.

The present invention encompasses antibody molecules that are human, humanized, deimmunized, chimeric and primatized. The invention also encompasses antibody molecules produced by the process of veneering; see, e.g., Mark et al., 1994 Handbook of Experimental Pharmacology, vol. 113: The pharmacology of monoclonal Antibodies, Springer-Verlag, pp. 105-134; the disclosure of which is incorporated herein by reference. "Human" in reference to the disclosed antibody molecules specifically refers to antibody molecules having variable and/or constant regions derived from human germline immunoglobulin sequences, wherein said sequences may, but need not, be modified/altered to have certain amino acid substitutions or residues that are not encoded by human germline immunoglobulin sequence.

Such mutations can be introduced by methods including, but not limited to, random or site-specific mutagenesis in vitro, or by somatic mutation in viva. Specific examples of mutation techniques discussed in the literature are that disclosed in Gram et al., 1992 *PNAS USA* 89:3576-3580; Barbas et al., 1994 *PNAS USA* 91:3809-3813, and Schier et al., 1996 *J. Mol. Biol.* 263:551-567; the disclosures of which are incorporated herein by reference. These are only specific examples and do not represent the only available techniques. There are a plethora of mutation techniques in the scientific literature which are available to, and widely appreciated by, the skilled artisan. "Humanized" in reference to the disclosed antibody molecules refers specifically to antibody molecules wherein CDR sequences derived from another mammalian species, such as a mouse, are grafted onto human framework sequences. "Primatized" in reference to the disclosed antibody molecules refers to antibody molecules wherein CDR sequences of a non-primate are inserted into primate framework sequences, see, e.g., WO 93/02108 and WO 99/55369; the disclosures of which are incorporated herein by reference.

Specific antibodies of the present invention are monoclonal antibodies and, in particular embodiments, are in one of the following antibody formats: IgD, IgA, IgE, IgM, IgG1, IgG2, IgG3, IgG4 or any derivative of any of the foregoing. The language "derivatives thereof" or "derivatives" in this respect includes, inter alia, (i) antibodies and antibody molecules with amino acid modifications in one or both variable regions (i.e., VH and/or VL), (ii) antibodies and antibody molecules with manipulations in the constant regions of the heavy and/or light chains, and/or (iii) antibodies and antibody molecules that contain additional chemical moieties which are not normally a part of the immunoglobulin molecule (e.g., pegylation).

Manipulations of the variable regions can be within one or more of the VH and/or VL CDR regions. Site-directed mutagenesis, random mutagenesis or other method for generating sequence or molecule diversity can be utilized to create mutants which can subsequently be tested for a particular functional property of interest in available in vitro or in vivo assays including those described herein.

Antibodies of the present invention also include those in which modifications have been made to the framework residues within VH and/or VL to improve one or more properties of the antibody of interest. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al; the disclosure of which is incorporated herein by reference.

In addition or alternative to modifications made within the framework or CDR regions, antibodies of the invention may be engineered to include modifications within the Fc or constant regions, where present, typically to alter one or more functional properties of the antibody, such as serum half-life, complement fixation, Fc receptor binding, and/or antigen-dependent cellular cytotoxicity.

The concept of generating "hybrids" or "combinatorial" IgG forms comprising various antibody isotypes to hone in on desired effector functionality has generally been described; see, e.g., Tao et al., 1991 *J. Exp. Med.* 173:1025-1028. A specific embodiment of the present invention encompasses antibody molecules that possess specific manipulations in the Fc region which have been found to result in reduced or altered binding to FcγR receptors, C1q or FcRn on the part of the antibody. The present invention, therefore, encompasses antibodies in accordance with the present description that do not provoke (or provoke to a lesser extent) antibody-dependent cellular cytotoxicity ("ADCC"), complement-mediated cytotoxicity ("CMC"), or form immune complexes, while retaining normal pharmacokinetic ("PK") properties. Specific embodiments of the present invention provide an antibody molecule as defined in accordance with the present invention which comprises, as part of its immunoglobulin structure, SEQ ID NO: 120 and, in particular embodiments, residues 107-326 of SEQ ID NO: 120 as part of the immunoglobulin structure. The present invention encompasses antibody molecules which comprise: (i) a light chain variable region selected from the group consisting of: SEQ ID NOs: 50, 52, 53, 55-66 and 67, and (ii) a heavy chain variable region selected from the group consisting of SEQ ID NOs: 41, 43, and 45-49 in sequence with (adjacent to) or followed by a series of amino acids selected from the group consisting of: SEQ ID NO: 117 (IgG1), SEQ ID NO: 118 (IgG2), SEQ ID NO: 119 (IgG4) and SEQ ID NO: 120 (IgG2m4). In particular embodiments, the light chain and heavy chain pairings of (i) and (ii) above are (a) SEQ ID NOs: 50 (or 52) and 41; or (b) SEQ ID NOs: 53 (or 67) and 43.

Specific PCSK9-specific antagonists may carry a detectable label, or may be conjugated to a toxin (e.g., a cytotoxin), a radioactive isotope, a radionuclide, a liposome, a targeting moiety, a biosensor, a cationic tail, or an enzyme (e.g., via a peptidyl bond or linker). Such PCSK9-specific antagonist compositions form an additional aspect of the present invention.

In another aspect, the present invention provides isolated nucleic acid encoding disclosed PCSK9-specific antagonists. "Isolated" as mentioned prior refers to the property of the thing referred to that makes them different from that found in nature. The difference can be, for example, that they are of a different purity than that found in nature, or that they are of a different structure or form part of a different structure than that found in nature. An example of nucleic acid not found in nature is, for example, nucleic acid substantially free of other cellular material. The nucleic acid may be present in whole cells, in a cell lysate, or in a partially purified or substantially pure form. In specific instances, a nucleic acid may be isolated when purified away from other cellular components or other contaminants, e.g., other cellular nucleic acids or proteins, for example, using standard techniques, including without limitation, alkaline/SDS treatment, CsCl banding, column chromatography, agarose gel electrophoresis and other suitable methods known in the art. The nucleic acid may include DNA (inclusive of cDNA) and/or RNA. Nucleic acids of the present invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

The present invention encompasses isolated nucleic acid encoding disclosed variable heavy and/or light chains and select components thereof, particularly the disclosed variable or respective CDR regions. In specific embodiments hereof, the CDR(s) are provided within antibody framework regions and, in particular embodiments, human framework regions. Specific embodiments provide isolated nucleic acid encoding the CDR(s) into germline framework regions including, but not limited to, human germline framework regions. Specific embodiments herein provide isolated nucleic acid encoding heavy chain CDR3 sequence selected from the group consisting of: SEQ ID NOs: 15, 16, 18, 20, 173 and residues 4-15 of SEQ ID NOs: 15, 16, and 20 (in specific embodiments, said nucleic acid of which comprises a sequence selected from the group consisting of: SEQ ID NOs: 17, 19, 21 and 174). Specific embodiments herein provide isolated nucleic acid encoding heavy chain CDR2 sequence selected from the group consisting of: SEQ ID NOs: 8, 9, 11, 13, 171 and residues 4-20 of SEQ ID NOs: 8, 9 and 13 (in specific embodiments, said nucleic acid of which comprises a sequence selected from the group consisting of: SEQ ID NOs: 10, 12, 14 and 172). Specific embodiments herein provide isolated nucleic acid encoding heavy chain CDR1 sequence selected from the group consisting of: SEQ ID NOs: 1, 2, 4, 6, 169 and residues 4-13 of SEQ ID NOs: 1, 2 and 6 (in specific embodiments, said nucleic acid of which comprises a sequence selected from the group consisting of: SEQ ID NOs: 3, 5, 7 and 170). Specific embodiments herein provide nucleic acid encoding the disclosed heavy chain variable CDR1, CDR2 and/or CDR3 sequences into VH3 in place of the relevant CDRs. Specific embodiments herein provide isolated nucleic acid encoding light chain CDR3 sequence selected from the group consisting of: SEQ ID NOs: 33, 34, 35, 37 and 39 (in specific embodiments, said nucleic acid of which comprises a sequence selected from the group consisting of: SEQ ID NOs: 36, 38 and 40). Specific embodiments herein provide isolated nucleic acid encoding light chain CDR2 sequence selected from the group consisting of: SEQ ID NOs: 30 and 31 (in specific embodiments, said nucleic acid of which comprises SEQ ID NOs: 32). Specific embodiments herein provide isolated nucleic acid encoding light chain CDR1 sequence selected from the group consisting of: SEQ ID NOs: 22, 23, 24, 26 and 28 (in specific embodiments, said nucleic acid of which comprises a sequence selected from the group consisting of: SEQ ID NOs: 25, 27 and 29). Specific embodiments herein provide nucleic acid encoding the disclosed light chain variable CDR1, CDR2 and/or CDR3 sequences into VK3 in place of the relevant CDRs. Specific embodiments provide both the heavy and light chain CDRs (1, 2 and 3) or some combination of one or more thereof.

The isolated nucleic acid encoding the variable regions can be provided within any desired antibody molecule format including, but not limited to, the following: $F(ab')_2$, a Fab, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, a minibody, a dAb fragment, diabody, triabody or tetrabody, a minibody, IgG, IgG1, IgG2, IgG3, IgG4, IgM, IgD, IgA, IgE or any derivatives thereof.

Specific embodiments provide isolated nucleic acid which encodes PCSK9-specific antagonists and, in more specific embodiments, antibody molecules comprising (i) a heavy chain variable domain selected from the group consisting of SEQ ID NOs: 41, 43 and 45-49; specific embodiments of which comprise nucleic acid sequence SEQ ID NO: 42 or SEQ ID NO: 44; and/or (ii) a light chain variable domain selected from the group consisting of: SEQ ID NOs: 50, 52, 53, 55-66 and 67; specific embodiments of which comprise nucleic acid sequence selected from the group consisting of SEQ ID NOs: 51, 54, 68. The present invention further provides in specific embodiments, homologs of the antagonists disclosed above, characterized as being at least 90% (in specific embodiments, 95%, 97% or 99%) identical through the heavy and/or light chain variable regions.

Additional embodiments provide isolated nucleic acid encoding PCSK9-specific antagonists and, in more specific embodiments, antibody molecules which comprise (i) a light chain selected from the group consisting of SEQ ID NOs: 73, 75, 77, 85, 87 and 89 (specific embodiments of which comprise nucleic acid selected from the group consisting of: SEQ ID NOs: 74, 76, 78, 86, 88 and 90); and/or (ii) a heavy chain or Fd chain selected from the group consisting of: SEQ ID NOs: 69, 71, 79, 81, 83, amino acids 1-227 of SEQ ID NO: 69 and amino acids 1-229 of SEQ ID NO: 71 (specific embodiments of which comprise nucleic acid selected from the group consisting of: SEQ ID NOs: 70, 72, 80, 82, 84 and nucleotides 1-663 of SEQ ID NOs: 70 and 72. The present invention further provides in specific embodiments, homologs of the antagonists disclosed above, characterized as being at least 90% identical over the heavy and/or light chains.

Specific embodiments of the present invention encompass nucleic acid encoding antibody molecules that possess manipulations in the Fc region which result in reduced or altered binding to FcγR receptors, C1q or FcRn on the part of the antibody. One specific embodiment of the present invention is isolated nucleic acid which encodes for antibody molecules comprising as part of their immunoglobulin structure SEQ ID NO: 120 and, in particular embodiments, residues 107-326 of SEQ ID NO: 120. In specific embodiments, synthetic PCSK9-specific antagonists can be produced by expression from nucleic acid generated from oligonucleotides synthesized and assembled within suitable expression vectors; see, e.g., Knappick et al., 2000 *J. Mol. Biol.* 296:57-86, and Krebs et al., 2001 *J. Immunol. Methods* 254:67-84.

The present invention encompasses nucleic acid encoding antibody molecules which comprise: (i) the disclosed nucleic acid encoding the light chain variable region and constant region, and (ii) the disclosed nucleic acid encoding the heavy chain variable region, followed in sequence by (adjacent to) a set of nucleotides encoding for a set of amino acids selected from the group consisting of: SEQ ID NO: 117 (IgG1), SEQ ID NO: 118 (IgG2), SEQ ID NO: 119 (IgG4) and SEQ ID NO: 120 (IgG2m4). Plasmid sequence comprising heavy and light chain AX1 anti-PCSK9 antibody molecule sequence can be found as SEQ ID NO: 91. Plasmid sequence comprising heavy and light chain AX9 anti-PCSK9 antibody molecule sequence can be found as SEQ ID NO: 92. Plasmid sequence comprising heavy and light chain AX189 anti-PCSK9 antibody molecule sequence can be found as SEQ ID NO: 93. Nucleic acid encoding such antibody molecules form important embodiments hereof. Additional plasmid sequences can be obtained by substituting the altered region for that present in the disclosed plasmid sequences.

Also included within the present invention are isolated nucleic acids comprising nucleotide sequences which are at least about 90% identical and more preferably at least about 95% identical to the full length of the nucleotide sequences described herein, and which nucleotide sequences encode PCSK9-specific antagonists which inhibit PCSK9-dependent inhibition of cellular LDL uptake by at least 10%.

Reference to "at least about 90% identical" throughout the application includes at least about 90, 91, 92, 93, 94, 95, 96, 97, 98, 99 or 100% identical.

The invention further provides isolated nucleic acid at least a portion of which hybridizes to the complement of nucleic acid encoding any one of the variable heavy, variable light, heavy chain, and light chain regions disclosed herein under stringent hybridization conditions, said nucleic acid of which confers upon antibody molecules the ability to specifically bind PCSK9 and antagonize PCSK9 function, and PCSK9-specific antagonists expressed employing said nucleic acid. Methods for hybridizing nucleic acids are well-known in the art; see, e.g., Ausubel, *Current Protocols in Molecular Biology*, John Wiley & Sons, N.Y., 6.3.1-6.3.6, 1989. Stringent hybridization conditions involve hybridizing at 68° C. in 5×SSC/5×Denhardt's solution (or equivalent)/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. The skilled artisan can manipulate various hybridization and/or washing conditions to specifically target nucleic acid in the hybridizing portion that is at least 80, 85, 90, 95, 98, or 99% identical to the variable heavy, variable light, heavy chain and/or light chain regions disclosed herein. Basic parameters affecting the choice of hybridization conditions and guidance for devising suitable conditions are set forth by Sambrook et al., *Molecular Cloning: A Laboratory Manual*, Cold Spring Harbor Laboratory Press, Cold Spring Harbor, N.Y., chapters 9 and 11, 1989 and Ausubel et al. (eds), *Current Protocols in Molecular Biology*, John Wiley & Sons, Inc., sections 2.10 and 6.3-6.4, 1995 (the disclosures of which are incorporated herein by reference), and can be readily determined by those having ordinary skill in the art. PCSK9 antagonists having one or more regions comprising nucleic acid which hybridizes to the disclosed heavy chain, light chain, variable heavy or variable light regions under stringent hybridization conditions should be effective in antagonizing one or more functions of PCSK9. Said antagonists and encoding nucleic acid, thus, form important embodiments of the present invention.

In another aspect, the present invention provides vectors comprising the nucleic acid disclosed herein. Vectors in accordance with the present invention include, but are not limited to, plasmids and other expression constructs (e.g., phage or phagemid, as appropriate) suitable for the expression of the desired antibody molecule at the appropriate level for the intended purpose; see, e.g., Sambrook & Russell, *Molecular Cloning: A Laboratory Manual*: 3rd Edition, Cold Spring Harbor Laboratory Press; the disclosure of which is incorporated herein by reference. For most cloning purposes, DNA vectors may be used. Typical vectors include plasmids, modified viruses, bacteriophage, cosmids, yeast artificial chromosomes, bacterial artificial chromosomes, and other forms of episomal or integrated DNA. It is well within the purview of the skilled artisan to determine an appropriate vector for a particular gene transfer, generation of a recombinant PCSK9-specific antagonist, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, and/or other sequences as appropriate and the potential for high copy number. Examples of expression vectors for the production of protein-specific antagonists are well known in the art; see, e.g., Persic et al., 1997 *Gene* 187:9-18; Boel et al., 2000 *J. Immunol. Methods* 239:153-166, and Liang et al., 2001 *J. Immunol. Methods* 247:119-130; the disclosures of which are incorporated herein by reference. If desired, nucleic acid encoding the antagonist may be integrated into the host chromosome using techniques well known in the art; see, e.g., Ausubel, *Current Protocols in Molecular Biology*, John Wiley & Sons, 1999, and Marks et al., International Application Number WO 95/17516. Nucleic acid may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10. Specifically with regards to antibody molecules, the antibody light chain gene and the antibody heavy chain gene can be inserted into separate vectors or, more typically, both genes may be inserted into the same expression vector. Nucleic acid encoding any PCSK9-specific antagonist or component thereof can be inserted into an expression vector using standard methods (e.g., ligation of complementary restriction sites on the nucleic acid fragment and vector, or blunt end ligation if no restriction sites are present). Another specific example of how this may be carried out is through use of recombinational methods, e.g. the Clontech "InFusion" system, or Invitrogen "TOPO" system (both in vitro), or intracellularly (e.g. the Cre-Lox system). Specifically with regards to antibody molecules, the light and heavy chain variable regions can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector comprising nucleic acid encoding a PCSK9-specific antagonist can encode a signal peptide that facilitates secretion of the antagonist from a host cell. The nucleic acid can be cloned into the vector such that the nucleic acid encoding a signal peptide is linked in-frame adjacent to the PCSK9-specific antagonist-encoding nucleic acid. The signal peptide may be an immunoglobulin or a non-immunoglobulin signal peptide. Any technique available to the skilled artisan may be employed to introduce the nucleic acid into the host cell; see, e.g., Morrison, 1985 *Science*, 229:1202. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The PCSK9-specific antagonist so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) comprising nucleic acid encoding disclosed PCSK9-specific antagonists. A variety of different cell lines are contemplated herein and can be used for the recombinant production of PCSK9-specific antagonists, including but not limited to those from prokaryotic organisms (e.g., *E. coli*, *Bacillus*, and *Streptomyces*) and from eukaryotic (e.g., yeast, Baculovirus, and mammalian); see, e.g., Breitling et al., Recombinant antibodies, John Wiley & Sons, Inc. and Spektrum Akademischer Verlag, 1999; the disclosure of which is incorporated herein by reference. Plant cells, including transgenic plants, and animal cells, including transgenic animals (other than humans), comprising the nucleic acid or antagonists disclosed herein are also contemplated as part of the present invention. Suitable mammalian cells or cell lines including, but not limited to, those derived from Chinese Hamster Ovary (CHO cells, including but not limited to DHFR-CHO cells (described in Urlaub and Chasin, 1980 *Proc. Natl. Acad. Sci. USA* 77:4216-4220) used, for example, with a DHFR selectable marker (e.g., as described in Kaufman and Sharp, 1982 *Mol. Biol.* 159:601-621), NS0 myeloma cells (where a GS expression system as described in WO 87/04462, WO 89/01036, and EP 338,841 may be used), COS cells, SP2 cells, HeLa cells, baby hamster kidney cells, YB2/0 rat myeloma cells, human embryonic kidney cells, human embryonic retina cells, and others comprising the nucleic acid or antagonists disclosed herein form additional embodiments of the present invention; the preceding cited disclosures of which are incorporated herein by reference. Specific embodiments of the present invention comprising nucleic acid encoding disclosed PCSK9-specific antagonists include, but are not limited to, *E. coli*; see, e.g., Plückthun, 1991 *Bio/Technology* 9:545-551, or yeast, such as *Pichia*, and recombinant derivatives thereof (see, e.g., Li et al., 2006 *Nat. Biotechnol.* 24:210-215); the preceding disclosures of which are incorporated herein by reference. Specific embodiments of the present invention relate to eukaryotic cells comprising nucleic acid encoding the disclosed PCSK9-specific antagonists, see, Chadd & Chamow, 2001 *Current Opinion in Biotechnology* 12:188-194, Andersen & Krummen, 2002 *Current Opinion in Biotechnology* 13:117, Larrick & Thomas, 2001 *Current Opinion in Biotechnology* 12:411-418; the disclosures of which are incorporated herein by reference. Specific embodiments of the present invention relate to mammalian cells comprising nucleic acid encoding the disclosed PCSK9-specific antagonists which are able to produce PCSK9-specific antagonists with proper post translational modifications. Post translational modifications include, but are by no means limited to, disulfide bond formation and glycosylation. Another type of post translational modification is signal peptide cleavage. Preferred embodiments herein have the appropriate glycosylation; see, e., Yoo et al., 2002 *J. Immunol. Methods* 261:1-20; the disclosure of which is incorporated herein by reference. Naturally occurring antibodies contain at least one N-linked carbohydrate attached to a heavy chain. Id. Different types of mammalian host cells can be used to provide for efficient post-translational modifications. Examples of such host cells include Chinese Hamster Ovary (CHO), HeLa, C6, PC12, and myeloma cells; see, Yoo et al., 2002 *J. Immunol. Methods* 261:1-20, and Persic et al., 1997 *Gene* 187:9-18; the disclosures of which are incorporated herein by reference.

In another aspect, the present invention provides isolated cell(s) comprising a polypeptide of the present invention.

In another aspect, the present invention provides a method of making a PCSK9-specific antagonist of the present invention, which comprises incubating a cell comprising nucleic acid encoding the PCSK9-specific antagonist, or a heavy and/or light chain or a fragment thereof (e.g., VH and/or VL, or one or more of the disclosed heavy and/or light chain variable region CDRs) of a desired PCSK9-specific antagonist (dictated by the desired antagonist) with specificity for human PCSK9 under conditions that allow the expression of the PCSK9-specific antagonist, or the expression and assembly of said heavy and/or light chains or fragment into a PCSK9-specific antagonist, and isolating said PCSK9-specific antagonist from the cell. One example by which to generate particular desired heavy and/or light chain sequence or fragment is to first amplify (and modify) the germline heavy and/or light chain variable sequences or fragment using PCR. Germline sequence for human heavy and/or light variable regions are readily available to the skilled artisan, see, e.g., the "Vbase" human germline sequence database, and Kabat, E. A. et al., 1991 *Sequences of Proteins of Immunological Interest*, Fifth Edition, U.S. Department of Health and Human Services, NIH Publication No. 91-3242; Tomlinson, I. M. et al., 1992 "The Repertoire of Human Germline VH Sequences Reveals about Fifty Groups of VH Segments with Different Hypervariable Loops" *J. Mol. Biol.* 227:776-798; and Cox, J. P. L. et al., 1994 "A Directory of Human Germ-line Vκ Segments Reveals a Strong Bias in their Usage" *Eur. J. Immunol.* 24:827-836; the disclosures of which are incorporated herein by reference. Mutagenesis of germline sequences may be carried out using standard methods, e.g., PCR-mediated mutagenesis where the mutations are incorporated into PCR primers, or site-directed mutagenesis. If full-length antibodies are desired, sequence is available for the human heavy chain constant region genes; see, e.g., Kabat. E. A. et al., 1991 *Sequences of Proteins of Immunological Interest*, Fifth Edition, U.S. Department of Health and Human Services, NIH Publication No. 91-3242. Fragments containing these regions may be obtained, for example, by standard PCR amplification. Alternatively, the skilled artisan can avail him/herself of vectors already encoding heavy and/or light chain constant regions.

Fab expression and purification may be achieved in a number of ways. One common way is to perform papain digestion of whole IgG1s to release two equivalents of Fab and one equivalent of Fc region. However, for phage displayed libraries, which also needs to be expressed in *E. coli*, Fab is typically displayed via covalent linkage to a protein and also to a hexahistidine tag (His-tag). In a typical fashion, induction by IPTG is followed by intracellular expression of the Fab. Subsequently, whole cells are lysed and the desired Fab is purified using a nickel affinity column. Depending on the specific case, this can yield high background in analytical SE-HPLC, presumably from misfolded, partially folded, disulfide scrambled or proteolyzed Fabs containing the His-tag since His-tag does not discriminate between these and the correctly folded Fab. Thus, in specific embodiments, expression of Fabs is carried out as follows: the periplasmic transport signal from phage, such as pIII and pVIII coat protein leader sequences, are utilized in the expression vector to localize the Fab polypeptides into the oxidizing environment of the periplasmic space. There, chaperone-like enzymes can facilitate correct Fab folding and thus allow formation of correct disulfide bonds. The initial overnight growth phase may be set at 30° C. Subsequently, the bacterial culture can be induced into Fab production, using lower concentration of IPTG (1 mM, 0.5 mM, or 0.1 mM) to induce the lac operon and start translation of the Fab genes. The temperature can be lowered to 22-23° C. Both the low IPTG and low temperature slow the *E. coli* protein synthesis in order to avoid overloading the periplasmic folding machinery. Cells may then be harvested by low speed centrifugation (~4000 g) and undergo periplasmic extraction. Periplasmic extraction is a gentle osmotic release process that primarily aims to make the outer bacterial cell wall leaky via mild osmotic shock, allowing Fabs to escape the periplasm into the surrounding media. After extraction, the cells can then be centrifuged at high speed (>15000 g) and the supernatant, containing released soluble Fab is saved for affinity chromatography.

In the specific embodiment above, affinity chromatography can be as follows: Affinity purification using protein G resin selectively binds folded constant region of the Fab at neutral pH (typically, using PBS or HBS at ~7.0-7.4). The bound Fab can be released under acidic pH (typically with glycine-HCl, pH 2.7-4.0) and eluted into a tube containing 1M Tris base at pH 9 to minimize exposure of the Fab to acidic pH. Alternatively, because the extract from the periplasmic extraction is relatively clean compared to a whole cell lysate, a nickel affinity column may be used to purify a Fab with a His-tag. In both cases, the eluted Fabs are buffer exchanged (e.g., by dialysis or centrifugal filtration using 30 kD MW cutoff filters) into the storage buffer, typically P135 or any preferred formulation buffer. The sample can be analyzed using analytical size exclusion (SE) HPLC generally show single peak consisting of >95% desired product. Additional polishing may be performed, if desired, using orthogonal methods, such as cation (CEX) or anion exchange (AEX) or hydrophobic interaction (HIC) chromatography.

Accordingly, in specific embodiments, the expression vector used for expression of the disclosed PCSK9-specific antagonists comprises sequence for phage coat protein pill or pVIII leaders sequence or other export leader sequence to export the expressed antagonist into the bacterial periplasm. In specific embodiments, this is for the expression of Fab. In specific embodiments, the invention comprises a method for producing a PCSK9-specific antagonist which comprises: (a) inserting a vector as described herein into a cell (in particular embodiments, the vector encodes a Fab); wherein the vector comprises a phage coat protein PIII or pVIII leader sequence; (b) culturing the cell under conditions appropriate for production of the PCSK9-specific antagonist; and (c) isolating the PCSK9-specific antagonist produced by periplasmic extraction using gentle lysis conditions to disrupt primarily the outer cell wall to release periplasmic contents and minimize contamination by intracellular contents. In specific embodiments, this may further comprise purifying the PCSK9-specific antagonist by: (1) affinity of the constant domain to protein G to purify correctly folded PCSK9-specific antagonists (such as Fabs); (ii) affinity of the His-tag to a nickel affinity column; or (iii) other suitable purification technique. This may then be followed by analyzing the buffer-exchanged Fab or isolated PCSK9-specific antagonist using SDS-PAGE, analytical SE-HPLC, or mass spectrometry to QC the final product.

Available techniques exist to recombinantly produce other antibody molecules which retain the specificity of an original antibody. A specific example of this is where DNA encoding the immunoglobulin variable region or the CDRs is introduced into the constant regions, or constant regions and framework regions, or simply the framework regions, of another antibody molecule; see, e.g., EP-184,187, GB 2188638, and EP-239400; the disclosures of which are incorporated herein by reference. Cloning and expression of antibody molecules, including chimeric antibodies, are described in the literature; see, e.g., EP 0120694 and EP 0125023; the disclosures of which are incorporated herein by reference.

Antibody molecules in accordance with the present invention may, in one instance, be raised and then screened for characteristics identified herein using known techniques. Basic techniques for the preparation of monoclonal antibodies are described in the literature, see, e.g., Kohler and Milstein (1975, *Nature* 256:495-497); the disclosure of which is incorporated herein by reference. Fully human monoclonal antibodies can be produced by available methods. These methods include, but are by no means limited to, the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, full human monoclonal antibodies. This technology is well known in the art and is fully detailed in various publications, including but not limited to U.S. Pat. Nos. 5,545,806; 5,569,825; 5,625,126; 5,633,425; 5,789,650; 5,877,397; 5,661,016; 5,814,318; 5,874,299; 5,770,249 (assigned to GenPharm International and available through Medarex, under the umbrella of the "UltraMab Human Antibody Development System"); as well as U.S. Pat. Nos. 5,939, 598; 6,075,181; 6,114,598; 6,150,584 and related family members (assigned to Abgenix, disclosing their XenoMouse® technology); the disclosures of which are incorporated herein by reference. See also reviews from Kellerman and Green, 2002 *Curr. Opinion in Biotechnology* 13:593-597, and Kontermann & Stefan, 2001 *Antibody Engineering*, Springer Laboratory Manuals; the disclosures of which are incorporated herein by reference.

Alternatively, a library having potential PCSK9-specific antagonists or any library of antibody molecules may be brought into contact with PCSK9, and ones able to demonstrate specific binding selected. Functional studies can then be carried out to ensure proper functionality, e.g., inhibition of PCSK9-dependent inhibition of cellular LDL uptake. There are various techniques available to the skilled artisan for the selection of protein-specific molecules from libraries using enrichment technologies including, but not limited to, phage display (e.g., see technology from Abmaxis disclosed in U.S. Pat. Nos. 7,175,983 and 7,117,096, WO 03/099999, and Wang et al., 2010 *J. Mol. Biol.* 395:1088-1101 and Cambridge Antibody Technology ("CAT") disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or applications which rely on priority filing GB 9206318, filed May 24, 1992; see also Vaughn et al., 1996, *Nature Biotechnology* 14:309-314), ribosome display (see, e.g., Hanes and Pluckthün, 1997 *Proc. Natl. Acad. Sci.* 94:4937-4942), bacterial display (see, e.g., Georgiou, et al., 1997 *Nature Biotechnology* 15:29-34) and/or yeast display (see, e.g., Kieke, et al., 1997 *Protein Engineering* 10:1303-1310, and Wang et al., 2010 *J. Immunol. Methods* 354:11-19); the preceding disclosures of which are incorporated herein by reference. A library, for example, can be displayed on the surface of bacteriophage particles, with nucleic acid encoding the PCSK9-specific antagonist or fragment thereof expressed and displayed on its surface. Nucleic acid may then be isolated from bacteriophage particles exhibiting the desired level of activity and the nucleic acid used in the development of desired antagonist. Phage display has been thoroughly described in the literature; see, e.g., Wang et al., 2010 *J. Mol. Biol.* 395:1088-1101, Kontermann & Stefan, supra, and International Application Number WO 92/01047; the disclosures of which are incorporated herein by reference. Specifically with regard to antibody molecules, individual heavy or light chain clones in accordance with the present invention may also be used to screen for complementary heavy or light chains, respectively, capable of interaction therewith to form a molecule of the combined heavy and light chains; see, e.g., International Application Number WO 92/01047. Any method of panning which is available to the skilled artisan may be used to identify PCSK9-specific antagonists. Another specific method for accomplishing this is to pan against the target antigen in solution, e.g. biotinylated, soluble PCSK9, and then capture the PCSK9-specific antagonist-phage complexes on streptavidin-coated magnetic beads, which are then washed to remove nonspecifically-bound phage. The captured phage can then be recovered from the beads in the same way they would be recovered from the surface of a plate, as described herein.

PCSK9-specific antagonists may be purified by techniques available to one of skill in the art. Titers of the relevant antagonist preparation, ascites, hybridoma culture fluids, or relevant sample may be determined by various serological or immunological assays which include, but are not limited to, precipitation, passive agglutination, enzyme-linked immunosorbent antibody ("ELISA") techniques and radioimmunoassay ("RIA") techniques.

The present invention relates in part to methods employing PCSK9-specific antagonists described herein for antagonizing PCSK9 function; said methods of which are further described below. Use of the term "antagonizing" throughout the present application refers to the act of opposing, inhibiting, counteracting, neutralizing or curtailing one or more functions of PCSK9. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. Specific embodiments of the present invention include such methods wherein the cell is a human cell.

In another aspect, the present invention provides a method for antagonizing the activity of PCSK9 in a subject, which comprises administering to the subject a therapeutically effective amount of a PCSK9-specific antagonist of the present invention. In specific embodiments, the methods for antagonizing PCSK9 function are for the treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated for a particular subject. In select embodiments, the condition may be hypercholesterolemia, coronary heart disease, metabolic syndrome, acute coronary syndrome or related conditions.

The present invention, thus, contemplates the use of PCSK9-specific antagonists described herein in various methods of treatment where antagonizing PCSK9 function is desirable. The method of treatment can be prophylactic or therapeutic in nature. In specific embodiments, the present invention relates to a method of treatment for a condition associated with/attributed to PCSK9 activity, or a condition where the functioning of PCSK9 is contraindicated for a particular subject, which comprises administering to the subject a therapeutically effective amount of a PCSK9-specific antagonist of the present invention. In select embodiments, the condition may be hypercholesterolemia, coronary heart disease, metabolic syndrome, acute coronary syndrome or related conditions.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic/prophylactic effect for the period of time desired. The desired effect may be, for example, amelioration of at least one symptom associated with the treated condition. These amounts will vary, as the skilled artisan will appreciate, according to various factors, including but not limited to the disease state, age, sex and weight of the individual, and the ability of the PCSK9-specific antagonist to elicit the desired effect in the individual. The response may be documented by in vitro assay, in vivo non-human animal studies, and/or further supported from clinical trials.

The present invention provides methods for treating or preventing disorders of cholesterol or lipid homeostasis and disorders and complications associated therewith, e.g., hypercholesterolemia, hyperlipidemia, hypertriglyceridaemia, sitosterolemia, atherosclerosis, arteriosclerosis, coronary heart disease, metabolic syndrome, acute coronary syndrome, vascular inflammation, xanthoma and related conditions.

The present invention also provides methods for improving blood cholesterol markers associated with increased risk of heart disease. These markers include, but are not limited to, high total cholesterol, high LDL, high total cholesterol to HDL ratio and high LDL to HDL ratio.

In general, a total cholesterol of less than 200 mg/dL is considered desirable, 200-239 mg/dL is considered borderline high and 240 mg/dL and above is considered high. For example, the present invention comprises methods for reducing total cholesterol, e.g., to less than or equal to about 200 mg/dL by administering a therapeutically effective amount of a PCSK9-specific antagonist of the present invention.

In general, a blood LDL level of less than 100 mg/dL is considered optimal; 100-129 mg/dL is considered near optimal/above optimal, 130-159 mg/dL is considered borderline high, 160-189 mg/dL is considered high and 190 mg/dL and above is considered very high. For example, the present invention comprises methods for reducing LDL, e.g., to less than about 100 mg/dL by administering a therapeutically effective amount of a PCSK9-specific antagonist of the present invention.

In general, HDL levels considered normal are at least 35-40 mg/dL. For example, the present invention comprises methods for increasing HDL, e.g., to greater than or equal to about 35-40 mg/dL by administering a therapeutically effective amount of anti-PCSK9 antibody or antigen binding fragment thereof of the present invention.

Another indicator of heart disease risk is the ratio of total cholesterol to HDL. In general, a very low risk of heart disease correlates with a ratio of <3.4 (men) or <3.3 (women); a low risk is associated with a ratio of 4.0 (men) or 3.8 (women), an average risk is associated with a ratio of 5.0 (men) or 4.5 (women), a moderate risk is associated with a ratio of 9.5 (men) or 7.0 (women) and a high risk is associated with a ratio of >23 (men) or >11 (women). For example, the present invention comprises methods for reducing the ratio of total cholesterol to HDL, e.g., to less than about 4.5 or 5.0 by administering a therapeutically effective amount of a PCSK9-specific antagonist of the present invention.

A further indicator of heart disease risk is the ratio of LDL to I-IDL. In general, a very low risk is associated with a ratio of 1 (men) or 1.5 (women), an average risk is associated with a ratio of 3.6 (men) or 3.2 (women), a moderate risk is associated with a ratio of 6.3 (men) or 5.0 (women) and a high risk is associated with a ratio of 8 (men) or 6.1 (women). For example, the present invention comprises methods for the ratio of LDL to HDL, e.g., to less than or equal to about 3.2 or 3.6 by administering a therapeutically effective amount of a PCSK9-specific antagonist of the present invention.

The PCSK9-specific antagonist may be administered as a pharmaceutical composition. The present invention, thus, provides a pharmaceutically acceptable composition comprising a PCSK9-specific antagonist of the invention and a pharmaceutically acceptable carrier including but not limited to an excipient, diluent, stabilizer, buffer, or alternative designed to facilitate administration of the antagonist in the desired format and amount to the treated individual.

The pharmaceutical composition may be formulated by any number of strategies known in the art, see, e.g., McGoff and Scher, 2000 *Solution Formulation of Proteins/Peptides*: In—McNally, E. J., ed. Protein Formulation and Delivery. New York, N.Y.: Marcel Dekker; pp. 139-158; Akers & Defilippis, 2000, *Peptides and Proteins as Parenteral Solutions*. In—Pharmaceutical Formulation Development of Peptides and Proteins. Philadelphia, Pa.: Taylor and Francis; pp. 145-177; Akers et al., 2002, *Pharm. Biotechnol.* 14:47-127. A pharmaceutically acceptable composition suitable for patient administration will contain an effective amount of the PCSK9-specific antagonist in a formulation which both retains biological activity while also promoting maximal stability during storage within an acceptable temperature range.

The antagonist-based pharmaceutically acceptable composition may, in particular embodiments, be in liquid or solid form, or in the form of gas particles or aerosolized particles. Any technique for production of liquid or solid formulations may be utilized. Such techniques are well within the realm of the abilities of the skilled artisan. Solid formulations may be produced by any available method including, but not limited to, lyophilization, spray drying, or drying by supercritical fluid technology. Solid formulations for oral administration may be in any form rendering the antagonist accessible to the patient in the prescribed amount and within the prescribed period of time. The oral formulation can take the form of a number of solid formulations including, but not limited to, a tablet, capsule, or powder. Solid formulations may alternatively be lyophilized and brought into solution prior to administration for either single or multiple dosing according to methods well known to the skilled artisan. Antagonist compositions should generally be formulated within a biologically relevant pH range and may be buffered to maintain a proper pH range during storage. Both liquid and solid formulations generally require storage at lower temperatures (e.g., 2-8° C.) in order to retain stability for longer periods. Formulated antagonist compositions, especially liquid formulations, may contain a bacteriostat to prevent or minimize proteolysis during storage, including but not limited to effective concentrations (e.g., ≤1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antagonist formulation, including but not limited to sugars as a cryoprotectant (including but not limited to polyhydroxy hydrocarbons such as sorbitol, mannitol, glycerol, and dulcitol and/or disaccharides such as sucrose, lactose, maltose, or trehalose) and, in some instances, a relevant salt (including but not limited to NaCl, KCl, or LiCl). Such antagonist formulations, especially liquid formulations slated for long term storage, will rely on a useful range of total osmolarity to both promote long term stability at temperatures of, for example, 2-8° C. or higher, while also making the formulation useful for parenteral injection. As appropriate, preservatives, stabilizers, buffers, antioxidants and/or other additives may be included. The formulations may contain a divalent cation (including but not limited to MgCl2, CaCl2, and MnCl2); and/or a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)). Any combination of such components form specific embodiments of the present invention.

Pharmaceutical compositions in liquid format may include a liquid carrier, e.g., water, petroleum, animal oil, vegetable oil, mineral oil, or synthetic oil. The liquid format may also include physiological saline solution, dextrose or other saccharide solution or glycols, such as ethylene glycol, propylene glycol or polyethylene glycol.

Preferably, the pharmaceutical composition may be in the form of a parenterally acceptable aqueous solution that is pyrogen-free with suitable pH, tonicity, and stability. Pharmaceutical compositions may be formulated for administration after dilution in isotonic vehicles, for example, Sodium Chloride Injection, Ringer's Injection, or Lactated Ringer's Injection.

One aspect of the present invention is a pharmaceutical composition which comprises: (i) about 50 to about 200 mg/mL of the PCSK9-specific antagonists described herein; (ii) a polyhydroxy hydrocarbon (including but not limited to sorbitol, mannitol, glycerol and dulcitol) and/or a disaccharide (including but not limited to sucrose, lactose, maltose and trehalose); the total of said polyhydroxy hydrocarbon and/or disaccharide being about 1% to about 6% weight per volume ("w/v") of the formulation; (iii) about 5 mM to about 200 mM of histidine, imidazole, phosphate or acetic acid which serves as a buffering agent to prevent pH drift over the shelf life of the pharmaceutical composition and as a tonicity modifier; (iv) about 5 mM to about 200 mM of arginine, proline, phenylalanine, alanine, glycine, lysine, glutamic acid, aspartic acid or methionine to counteract aggregation; (v) about 0.01M to about 0.1M of hydrochloric acid ("HCl") in an amount sufficient to achieve a pH in the range of about 5.5 to about 7.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.5 to about 7.5; and wherein said pharmaceutical composition optionally comprises about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

HCl may be added as free acid, Histidine-HCl or Arginine-HCl. Where supplied as Histidine-HCl or Arginine-HCl, the total amounts of Histidine or Arginine in the HCl form should be that specified above. Accordingly, some or all of the HCl depending on the amounts of Histidine and/or Arginine may be supplied as Histidine-HCl and/or Arginine-HCl; as appropriate. Use of the term "about" with respect to amounts disclosed in the specification means within 10% of the specified numbers provided. A range provided as, for example" in "about 50 to about 200" expressly includes as distinct embodiments each number within said range. As such in the above example, embodiments including but not limited to those having 50, 100, 125, 150 and 200 form specific embodiments herein. Pharmaceutical compositions as disclosed herein have general applicability despite the mode of administration. In specific embodiments, the disclosed pharmaceutical compositions are useful for subcutaneous administration as a liquid or upon reconstitution of a lyophilized form. Proteins that can be employed in the disclosed formulations include any polymeric protein or polypeptide characterized as comprising covalently linked amino acid residues delivered for purposes of effecting a therapeutic benefit. Proteins of use in the present compositions include but are not limited to any antibody molecules as defined herein or any non-antibody or non-immunoglobulin proteins, peptides, pegylated proteins and fusion proteins.

Specific aspects of the present invention relate to the above disclosed pharmaceutical compositions which comprise: (i) about 50 to about 200 mg/mL of the PCSK9-specific antagonists described herein; (ii) about 1% to about 6% (in particular embodiments from about 2% to about 6%) w/v mannitol, trehalose or sucrose; (iii) about 10 mM to about 100 mM of histidine; (iv) about 25 mM to about 100 mM of arginine or proline; (v) about 0.02 M to about 0.05M of hydrochloric acid ("HCl") in an amount sufficient to achieve a pH in the range of about 5.8 to about 7; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 7; and wherein said pharmaceutical composition optionally comprising about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

Specific embodiments provide pharmaceutical compositions which comprise: (i) 50 to 200 mg/mL of the PCSK9-specific antagonists described herein; (ii) about 1% to about 6% (in particular embodiments from about 2% to about 6%) w/v mannitol, trehalose or sucrose; (iii) about 10 mM to about 150 mM of histidine; (iv) about 10 mM to about 150 mM of arginine or proline; (v) about 0.03 M to about 0.05 M of hydrochloric acid ("HCl") in an amount sufficient to achieve a pH in the range of about 5.8 to about 6.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 6.5; and wherein said pharmaceutical composition optionally comprising about 0.01% to about 1% w/v of Polysorbate-80 (Tween 80™) or Polysorbate-20 (Tween 20™).

Specific embodiments herein provide pharmaceutical compositions which comprise: (i) 50 to 200 mg/mL of the PCSK9-specific antagonists described herein; (ii) about 1% to about 6% (in particular embodiments from about 2% to about 6%) w/v sucrose; (iii) about 25 mM to about 100 mM of histidine; (iv) about 25 mM to about 100 mM of arginine; (v) about 0.040 M to about 0.045 M of hydrochloric acid ("HCl") in an amount sufficient to achieve a pH of about 6; and (vi) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). In specific embodiments thereof, the levels of histidine and arginine are within 25 mM of each other and, in other embodiments are the same.

Specific embodiments herein provide pharmaceutical compositions which comprise (i) 50 to 200 mg/mL of the PCSK9-specific antagonists described herein; (ii) sucrose, histidine and arginine in one of the following amounts: (a) about 1% w/v sucrose, about 10 mM histidine and about 25 mM arginine; (b) about 2% w/v sucrose, about 25 mM histidine and about 25 mM arginine; (c) about 3% w/v sucrose, about 50 mM histidine and about 50 mM arginine; or (d) about 6% w/v sucrose, about 100 mM histidine and about 100 mM arginine; (iii) about 0.04 mol or, alternatively, about 1.46 g of HCl; and (iv) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). Specific embodiments herein are wherein the amounts of sucrose, histidine and arginine in (ii) above are that described in (c) or (d). Specific embodiments employing pharmaceutical formulations as described above wherein the amounts of sucrose, histidine and arginine are that specified in (ii) (c) were found to provide an osmolality similar to the physiological value of 300 mOsm and provided stability in both the liquid and lyophilized form.

Specific embodiments herein provide pharmaceutical compositions as described which comprise 50 to 200 mg/ml of any one of the various PCSK9-specific antagonists described herein. For purposes of exemplification of one distinct embodiment thereof, and not to be construed as a limitation, is the following: a pharmaceutical formulation as described above which comprises: a PCSK9-specific antagonist which comprises: (a) a light chain comprising SEQ ID NO: 85; and (b) a heavy chain comprising SEQ ID NO: 79; wherein said PCSK9-specific antagonist is an antibody molecule that antagonizes PCSK9's inhibition of cellular LDL uptake. An additional embodiment is a pharmaceutical formulation as described above which comprises: a PCSK9-specific antagonist which comprises: (a) a light chain comprising SEQ ID NO: 87; and (b) a heavy chain comprising SEQ ID NO: 81; wherein said PCSK9-specific antagonist is an antibody molecule that antagonizes PCSK9's inhibition of cellular LDL uptake. An additional embodiment is a pharmaceutical formulation as described above which comprises: a PCSK9-specific antagonist which comprises: (a) a light chain comprising SEQ ID NO: 89; and (b) a heavy chain comprising SEQ ID NO: 83; wherein said PCSK9-specific antagonist is an antibody molecule that antagonizes PCSK9's inhibition of cellular LDL uptake.

Particular embodiments herein are pharmaceutical compositions according to the above description which are lyophilized and reconstituted. In specific embodiments, said protein concentration in said lyophilized and reconstituted solution is up to 2-fold higher than in the pre-lyophilized composition. In specific embodiments, the protein or PCSK9-specific antagonist concentration in the lyophilized and/or reconstituted pharmaceutical composition is in the range of about 50 mg/mL to about 300 mg/mL. Diluents useful for reconstituting the lyophilized pharmaceutical compositions include but are not limited to sterile water, bacteriostatic water for injection ("BWFI"), phosphate-buffered saline, a sterile saline solution, physiological saline solution, Ringer's solution or dextrose solution and may in specific embodiments contain 0.01-1% (w/v) of Polysorbate-80 (Tween 80™) or Polysorbate-20 (Tween 26™). In specific embodiments, lyophilized powder can be reconstituted with 1/60.2× original volume (or 0.167 mL) up to 1× (1 mL).

Exemplary embodiments of the present invention are pharmaceutical compositions as described herein which are stable. Other embodiments of the present invention are pharmaceutical compositions as described herein which are stable to lyophilization and reconstitution. Various methods are available to the skilled artisan to prepare lyophilized compositions; see, e.g., Martin & Mo, 2007 "Stability Considerations for Lyophilized Biologics" Amer. Pharm. Rev. "Stable" as used herein refers to the property of the protein or PCSK9-specific antagonist to retain its physical or chemical stability, conformational integrity, or its ability to exhibit less denaturation, protein clipping, aggregation, fragmentation, acidic variant formation or loss of biological activity compared with a control sample at a temperature in the range of 4-37° C. for at least about 30 days. Other embodiments remain stable for up to 3 months, 6 months, 12 months, 2 years or longer periods at the above temperatures. In specific embodiments the formulation exhibits no significant changes at 2-8° C. for at least 6 months, and preferably 12 months, 2 years or longer, in order of preference. Specific embodiments experience less than 10% or, in particular embodiments, less than 5% of denaturation, protein clipping, aggregation, fragmentation, acidic variant formation or loss of biological activity compared with a control sample at a temperature in the range of 25-45° C. (or alternatively 2-8° C.) for at least about 30 days, 3 months, 6 months, 12 months, 2 years or longer. Stability of the formulations can be tested via several means known to the skilled artisan including, but not limited to Size Exclusion Chromatography (SEC-HPLC) to measure aggregation and fragmentation, Dynamic Light Scattering (DLS) to measure particle size of concentrated samples, capillary SDS-PAGE to measure fragmentation and capillary iso-electric focusing (cIEF) or cation exchange chromatography ("CEX") to measure acidic variants formation. Techniques suitable for the analysis of protein stability are well understood by those of skill in the art: see review in *Peptide and Protein Drug Delivery,* 247-301, Vincent Lee Ed., Marcel Dekker, Inc., New York, N.Y., Pubs. (1991) and Jones, 1993 *Adv. Drug Delivery Rev.* 10:29-90.

Pharmaceutical compositions as described herein should be sterile. There are various techniques available to the skilled artisan to accomplish this including, but not limited to, filtration through sterile filtration membranes. In specific embodiments, employing lyophilized and reconstituted compositions, this may be done prior to or following lyophilization and reconstitution.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors including but not limited to the particular PCSK9-specific antagonist utilized, the patient being treated, the condition of the patient, the area being treated, the route of administration, and the treatment desired. A physician or veterinarian of ordinary skill can readily determine and prescribe the effective therapeutic amount of the antagonist. Dosage ranges may be from about 0.01 to 100 mg/kg, and more usually 0.05 to 25 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. For purposes of illustration, and not limitation, in specific embodiments, a dose of 5 mg to 2.0 g may be utilized to deliver the antagonist systemically. In specific embodiments, the concentration of the dose provided will be in the range of about 8 mg/mL to about 200 mg/mL. In other embodiments, a dose contemplated for use in the present invention is from about 50 mg/mL to about 150 mg/mL. In specific embodiments, the dose will be from about 0.1 mL to about 1.5 mL and in specific embodiments is 1 mL. Optimal precision in achieving concentrations of antagonist within a range that yields efficacy without toxicity requires a regimen based on the kinetics of the drug's availability to the target site(s). This involves a consideration of the distribution, equilibrium, and elimination of the PCSK9-specific antagonist. Antagonists described herein may be used alone at appropriate dosages. Alternatively, co-administration or sequential administration of other agents may be desirable. It will be possible to present a therapeutic dosing regime for the PCSK9-specific antagonists of the present invention in conjunction with alternative treatment regimes. For example, PCSK9-specific antagonists may be used in combination or in conjunction with other drugs (therapeutic and/or prophylactic). In specific embodiments, the PCSK9-specific antagonists are used in combination or in conjunction with cholesterol-lowering drugs, for example, cholesterol absorption inhibitors (e.g., Zetia®) and cholesterol synthesis inhibitors (e.g., Zocor® and Vytorin®). The present invention contemplates such combinations and they form an important embodiment hereof. Accordingly, the present invention relates to methods of treatment as described above where the PCSK9-specific antagonist is administered/delivered simultaneously with, following or prior to another drug or drugs (therapeutic and/or prophylactic), including but not limited to cholesterol-lowering drugs, including cholesterol absorption inhibitors.

Individuals (subjects) capable of treatment as described herein include primates, human and non-human, and include any non-human mammal or vertebrate of commercial or domestic veterinary importance.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), or administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment. Treatment may be provided on a daily, weekly, biweekly, or monthly basis, or any other regimen that delivers the appropriate amount of PCSK9-specific antagonist to the individual at the prescribed times such that the desired treatment is effected and maintained. The formulations may be administered in a single dose or in more than one dose at separate times.

Also contemplated are methods of using the disclosed antagonists in the manufacture of a medicament for treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated for a particular subject. In select embodiments, the condition may be hypercholesterolemia, coronary heart disease, metabolic syndrome, acute coronary syndrome or related conditions.

PCSK9-specific antagonists disclosed herein may also be used as a method of diagnosis of PCSK9. In select embodiments, the present invention encompasses methods of identifying or quantifying the level of PCSK9 present in a sample (including but not limited to a biological sample, e.g., serum or blood) which comprises contacting the sample with a PCSK9-specific antagonist described herein and detecting or quantifying, respectively, binding to PCSK9. The PCSK9-specific antagonist may be used in various assay formats known to the skilled artisan and may form part of a kit (the general features of a kit of which are further described below).

The present invention further provides for the administration of disclosed anti-PCSK9 antagonists for purposes of gene therapy. Through such methods, cells of a subject are transformed with nucleic acid encoding a PCSK9-specific antagonist of the invention. Subjects comprising the nucleic acids then produce the PCSK9-specific antagonists endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, supra, may be easily adapted for the introduction of nucleic acids encoding an anti-PCSK9 antibody of the invention to a subject.

Nucleic acids encoding any PCSK9-specific antagonist may be introduced to a subject.

The nucleic acids may be introduced to the cells of a subject by any means known in the art. In preferred embodiments, the nucleic acids are introduced as part of a viral vector. Examples of preferred viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genova, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). Preferably, the viral vectors are replication defective, that is, they are unable to replicate autonomously, and thus are not infectious, in the target cell. Preferably, the replication defective virus is a minimal virus, i.e., it retains only the sequences of its genome which are necessary for encapsidating the genome to produce viral particles. Defective viruses, which entirely or almost entirely lack viral genes, are preferred. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro Onc.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (PCT Publication Nos. WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio.* 489:45-57, 2001; PCT Publication Nos. WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.,* 62:1120, 1988; EP 453242 and EP178220. The retroviruses are integrating viruses which infect dividing cells.

Lentiviral vectors can be used as agents for the direct delivery and sustained expression of nucleic acids encoding a PCSK9-specific antagonist of the invention in several tissue types, including brain, retina, muscle, liver and blood. The vectors can efficiently transduce dividing and nondividing cells in these tissues, and maintain long-term expression of the PCSK9-specific antagonist. For a review, see Zufferey et al, *J. Virol.* 72:9873-80, 1998 and Kafiri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.,* 58:491-562, 1994; Bredenbeek et al, *J. Virol.,* 67:6439-6446, 1993; Ijima et al, *Int J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in PCT Publication Nos. WO 95/18863 and WO 96/17823, and in U.S. Pat. No. 5,459,127.

It is also possible to introduce the vector in vivo as a naked DNA plasmid. Naked DNA vectors for gene therapy can be introduced into desired host cells by methods known in the art, e.g., electroporation, microinjection, cell fusion, DEAE dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Other reagents commonly used for transfection of plasmids include, but are by no means limited to, FuGene, Lipofectin, and Lipofectamine. Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, Bioelectrochemistry 53:1-10, 2001; PCT Publication Nos. WO 99/01157, WO 99/01158 and WO 99/01175).

Pharmaceutical compositions suitable for such gene therapy approaches and comprising nucleic acids encoding an anti-PCSK9 antagonist of the present invention are included within the scope of the present invention.

In another aspect, the present invention provides a method for identifying, isolating, quantifying or antagonizing PCSK9 in a sample of interest using a PCSK9-specific antagonist of the present invention. The PCSK9-specific antagonists may be utilized as research tools in immunochemical assays, such as Western blots, ELISAs, radioimmunoassay, immunohistochemical assays, immunoprecipitations, or other immunochemical assays known in the art (see, e.g., Immunological Techniques Laboratory Manual, ed. Goers, J. 1993, Academic Press) or various purification protocols. The antagonists may have a label incorporated therein or affixed thereto to facilitate ready identification or measurement of the activities associated therewith. One skilled in the art is readily familiar with the various types of detectable labels (e.g., enzymes, dyes, or other suitable molecules which are either readily detectable or cause some activity/result that is readily detectable) which are or may be useful in the above protocols.

An additional aspect of the present invention is kits comprising PCSK9-specific antagonists or pharmaceutical compositions disclosed herein and instructions for use, Kits typically but need not include a label indicating the intended use of the contents of the kit. The term label includes any writing, or recorded material supplied on or with the kit, or which otherwise accompanies the kit. In specific embodiments wherein the pharmaceutical composition is provided lyophilized, the kit may include sterile water or saline for reconstitution of the formulation into liquid form. In specific embodiments, the amount of water or saline is from about 0.1 ml to 1.0 ml.

The following examples are provided to illustrate the present invention without limiting the same hereto:

Example 1

Abmaxis PDL1 Phage Library Panning Against PCSK9 Protein

A synthetic human Fab library was panned against human PCSK9. Antigen protein PCSK9 was coated on Maxisorp well stripe (Nuns-Immuno Modules) at a concentration of 1-10 μg/ml for overnight at 4° C. Multiple wells of antigen were prepared for each library. 5% milk in PBS was used to block the coated wells at room temperature for 1-2 hours. After a wash with PBS, 100 μl of phage library solution/well (usually $1\text{-}5\times10^{12}$ in 2% milk-PBS) was added into 4 parallel wells, and incubated for designed length of time (usually 1-2 hours). After several washings with PBST and PBS, the bound phages were eluted from the wells with fresh-prepared 1.4% triethylamine in ddH2O (10 minutes incubation at room temperature), followed immediately with neutralization by adding 50 μl of 1M Tris-HCl (pH 6.8).

The eluted, enriched phage pool was further amplified through the following steps: First, TG1 cells were infected with eluted phages at 37° C. for 1 hour, then plated out on 2YT agar plates with 2% glucose and 100 μg/ml carbenicillin for overnight culture. Thus TG1 cells harboring enriched phagemid library were harvested from the plates, and infected with helper phage GMCT for 1 hour. The Fab-display phages were then generated from those TG1 cells harboring both library phagemids and GMCT helper phage genome by overnight growth in 2xYT/carbenicillin/Kanamycin at 22° C. The phagemid particles were purified from overnight culture supernatants by precipitation with PEG/NaCl, and re-suspended in PBS. The PEG-precipitation was repeated once. The phage concentration was determined by $OD_{268}$ measurement.

With amplified first round phages, the panning process as described above was repeated twice for further enrichment of PCSK9-binding phages. The eluted phages from the third round panning were used to infect TG1 cells. The TG1 cells harboring phagemids from third round panning were picked from 2YT agar plates for Fab ELISA screening assay.

Example 2

Fab ELISA Screening for PCSK9 Binders

Over 10,000 clones from third round panning were picked by MegaPix Picking Robot (Genetix), and inoculated into 384-well plates with 60 μl of 2YT/2% Glucose/carbenicillin for overnight culture at 30° C. with 450 rpm shaking. The duplicated plates were made by transferring ~1-3 μl overnight culture from each well into new plates with 50 μl/well of 2YT/0.1% Glucose/carbenicillin. The duplicated plates were incubated in a shaker at 30° C. for 6 hours, then 10 Owen of IPTG was added for a final concentration of 1 mM. After overnight culture at 22° C., the soluble Fab in IPTG-induction plates were released by adding lysozyme into each well.

To detect the antigen binding activity of soluble Fabs generated from the above experiment, the antigen plates were generated by overnight coating of 5 μg/ml human PCSK9 antigen. After blocking with 5% milk-PBS and a wash with PBST, 15-20 μl of Fab samples from IPTG-induction plates was transferred into antigen plates for 1-2 hours incubation at room temperature. The plates were washed 5 times with PBS-T, and added with 1:2000 diluted goat anti-human Kappa-HRP (SouthernBiotech Cat. No. 2060-05) or 1:10,000 diluted goat anti-human Fab-HRP in 5% MPBS for 1 hour incubation. After washing away unbound HRP-conjugates with PBST, the substrate solution QuantaBlu WS (Pierce 15169) was then added to each well and incubated for 5-15 minutes. The relative fluorescence units (RFU) of each well was measured to determine the Fab binding activity by using excitation wavelength 330 nm and emission detection wavelength 410 nm.

The ELISA results showed 30 to 80% clones from third round panning of individual PDL1 sub-libraries bound to antigen PCSK9. The positive clones were then sent out for DNA sequencing. A total of 128 unique Fab sequences were identified from the PDL1

Example 3

Fab Protein Expression and Purification from TG1 Cells 50 ml of overnight cultures for individual clones in 2YT/2% glucose/Carbenicillin 100 μg/ml were grown in 37° C. shaker incubator. In the second day, 750 mL to 1 L of 2YT/0.1% glucose/100 μg/mL Carbenicillin was inoculated for each clone by transferring 5-10 ml of the overnight culture. The cultures were grown at 30° C. with shaking for approximately 3-4 hours until OD600~1. IPTG was added to the culture to reach the final concentration of 0.1-0.5 mM. After overnight IPTG induction at 22° C., the cells pellets were collected by centrifugation at 10,000 rpm for 10-15 minutes, to proceed for periplasmic preparation.

Soluble Fabs were extracted from cell periplasm. The periplasmic preparation was performed as follows. The TG1 pellet was re-suspended in 20 mL pre-chilled PPB buffer (20% Sucrose+2 mM EDTA+30 mM Tris, pH=8), and incubated on ice for 1 hour. The supernatant with soluble Fab was collected by centrifugation. Subsequently, the cell pellet was further re-suspended in 20 mL pre-chilled 5 mM magnesium sulfate with 1 hour incubation on ice. Two supernatants were combined for further Fab purification.

The soluble Fab from the periplasmic extraction was purified using a HiTrap Protein G HP column (GE Healthcare). The column was initially equilibrated with equilibration buffer (PBS or Tris, pH 7.3). The supernatant from periplasmic preparation was loaded onto a 1-ml or 5-mL protein-G column (HiTrap, GE healthcare). After wash with 10 column volumes (CVs) of equilibration buffer, Fab protein was eluted with 8 CVs of elution buffer (0.3 M acetic acid, pH3). The eluted fractions were collected, and neutralized with 0.5 volume of 1M Tris, pH 9 buffer. The Fab samples were buffer-exchanged into PBS using Amicon centrifugal filters with 10 kD molecular weight cutoff. The quality of purified Fab was analyzed using size exclusion HPLC (SE-HPLC). Purified Fab was also used for ELISA assay and Biacore assay (below). Overall, the summary of Fab yields is ~1-2 mg/L with high degree of variability, from less than 1 mg/L to well over 10 mg/L. All Fabs show single main peak by SE-HPLC. The ELISA assay results confirmed all Fabs isolated from PDL1 library bound to human PCSK9 antigen.

Example 4

Biacore-Based PCSP9-LDL Receptor Interaction Assay

The LDL-Receptor (LDLR) and EG_FAB domain of LDLR (this domain involves the interaction with PCSK9) were immobilized on two different flow cells in the same CM5 chips by coupling of amine groups of LDLR or EGF_AB domain onto carboxylated surfaces of sensor chips according to the instruction of Amine Coupling Kit (GE/Biacore). Briefly, LDLR and EGF_AB were diluted to 20 μg/ml in pH 4.5 10 mM Acetate buffer and injected to two flow cells on the same CM5 chip to achieve an immobilization level of ~1500RU. 100 nM human PCSK9 alone in running buffer (1×HBSP with 0.1 mM $CaCl_2$) was injected into the flow cells (at 20 μl/min for 2.5 minutes) to measure the interaction of PSK9 with LDLR and EGF_AB domain. After injection, the flow cells were regenerated by 10 mM HCl.

To determine the impact of the binding of Fab antibody to PCSK9, each purified Fab sample (1 μM in the running buffer) was incubated with human PCSK9 at the concentration of 100 nM for 30 minutes at room temperature. The prepared PCSK9/Fab samples were injected into the CM5 chip, and binding of PCSK9/Fab complex was measured.

As shown in FIG. 1, human PCSK9 alone bound to both LDLR and EGF_AB domain. When the binding of Fab antibody did not inhibit the PCSK9-LDLR interaction, the binding of PCSK9/Fab complex to LDLR or EGF_AB resulted in higher binding RU then PCSK9 alone. Among the Fab antibodies tested, AX1, AX9 and AX114 Fabs showed significant inhibition on PCSK9 binding to LDLR or EGFAB domain.

The PCSK9 antagonists AX1 and AX9 sequences are listed below.

```
Amino acid sequence of AX1_VH (SEQ ID NO: 41):
EVQLLESGGGLVQPGGSLRLSCKASGFTFTSYYMHWVRQAPGKGLEWIGRINPDSGSTK

YNEKFKGRATISRDNSKNTLYLQMNSLRAEDTAVYYCARGGRLSWDFDVWGQGTLVT

VSS

DNA sequence of AX1_VH (SEQ ID NO: 42):
GAAGTGCAGCTGCTGGAATCTGGTGGTGGTCTGGTGCAGCCAGGTGGTTCTCTGCGT

CTGTCTTGCAAGGCCTCTGGTTTCACCTTCACTTCTTACTACATGCACTGGGTGCGTC
```

-continued

AGGCACCAGGTAAGGGTCTGGAATGGATCGGTCGGATCAACCCAGATTCTGGTAGT

ACTAAGTACAACGAGAAGTTCAAGGGTCGTGCCACCATCTCTAGAGACAACTCTAA

GAACACCCTGTACTTGCAGATGAACTCTCTGCGTGCCGAGGACACTGCAGTGTACTA

CTGCGCCCGTGGTGGTCGTTTATCCTGGGACTTCGACGTCTGGGGTCAGGGTACGCT

GGTGACTGTCTCGAGC

Amino acid sequence of AX1_VK (SEQ ID NO: 50):
DIQMTQSPSSLSASVGDRVTITCRASQDISRYLAWYQQKPGKAPKLLIYAASSLQSGVPS

RFSGSGSGTDFTLTISSLQPEDFATYYCAAYDYSLGGYVFGDGTKVEIK

DNA sequence of AX1_VK (SEQ ID NO: 51):
GACATCCAGATGACCCAGTCTCCATCTTCTCTGTCTGCCTCTGTGGGCGACCGGGTG

ACCATCACCTGCCGTGCCTCTCAGGATATCTCTAGGTATCTGGCCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCGCGGCTTACGACTATTCTTTGG

GCGGTTACGTGTTCGGTGATGGTACCAAAGTGGAGATCAAA

Amino acid sequence of AX1 fd chain (Fab molecule)
(SEQ ID NO: 69)
EVQLLESGGGLVQPGGSLRLSCKASGFTFTSYYMHWVRQAPGKGLEWIGRINPDSGSTK

YNEKFKGRATISRDNSKNTLYLQMNSLRAEDTAVYYCARGGRLSWDFDVWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHT

DNA sequence of AX1 fd chain (Fab molecule)
(SEQ ID NO: 70)
GAAGTGCAGCTGCTGGAATCTGGTGGTGGTCTGGTGCAGCCAGGTGGTTCTCTGCGT

CTGTCTTGCAAGGCCTCTGGTTTCACCTTCACTTCTTACTACATGCACTGGGTGCGTC

AGGCACCAGGTAAGGGTCTGGAATGGATCGGTCGGATCAACCCAGATTCTGGTAGT

ACTAAGTACAACGAGAAGTTCAAGGGTCGTGCCACCATCTCTAGAGACAACTCTAA

GAACACCCTGTACTTGCAGATGAACTCTCTGCGTGCCGAGGACACTGCAGTGTACTA

CTGCGCCCGTGGTGGTCGTTTATCCTGGGACTTCGACGTCTGGGGTCAGGGTACGCT

GGTGACTGTCTCGAGCGCAAGCACCAAAGGCCCATCGGTATTCCCCCTGGCACCCTC

CTCCAAGAGCACCTCTGGGGGCACAGCGGCCCTGGGCTGCCTGGTCAAGGACTACT

TCCCCGAGCCGGTGACGGTGTCGTGGAACTCAGGCGCTCTGACCAGCGGCGTGCAC

ACCTTCCCGGCTGTCCTACAGTCCTCAGGACTCTACTCCCTCAGCAGCGTGGTGACT

GTGCCCTCCAGCAGCTTGGGCACCCAGACCTACATCTGCAACGTGAATCACAAGCCC

AGCAACACTAAGGTGGACAAGAAAGTTGAGCCCAAATCTTGTGACAAAACTCACAC

A

Amino acid sequence of AX1 light chain (Fab molecule)
(SEQ ID NO: 73)
DIQMTQSPSSLSASVGDRVTITCRASQDISRYLAWYQQKPGKAPKLLIYAASSLQSGVPS

RFSGSGSGTDFTLTISSLQPEDFATYYCAAYDYSLGGYVFGDGTKVEIKRTVAAPSVFIFP

PSDEQLKSGTASVVCLLNNFYPREAKVQWKVDNALQSGNSQESVTEQDSKDSTYSLSST

LTLSKADYEKHKVYACEVTHQGLSSPVTKSFNRGEC

DNA sequence of AX1 light chain (Fab molecule)
(SEQ ID NO: 74)
GACATCCAGATGACCCAGTCTCCATCTTCTCTGTCTGCCTCTGTGGGCGACCGGGTG -continued

ACCATCACCTGCCGTGCCTCTCAGGATATCTCTAGGTATCTGGCCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCGCGGCTTACGACTATTCTTTGG

GCGGTTACGTGTTCGGTGATGGTACCAAAGTGGAGATCAAACGTACGGTGGCTGCA

CCATCTGTCTTCATCTTCCCGCCATCTGATGAGCAGTTGAAATCTGGAACTGCCTCTG

TTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCGTCACAA

AGAGCTTCAACAGGGGAGAGTGT

AX1_IgG2 sequences are listed below.

Amino acid sequence of AX1_IgG2 heavy chain (SEQ ID NO: 79)

EVQLLESGGGLVQPGGSLRLSCKASGFTFTSYYMHWVRQAPGKGLEWIGRINPDSGSTK

YNEKFKGRATISRDNSKNTLYLQMNSLRAEDTAVYYCARGGRLSWDFDVWGQGTLVT

VSSASTKGPSVFPLAPCSRSTSESTAALGCLVKIDYFPEPVTVSWNSGALTSGVHTFPAVL

QSSGLYSLSSVVTVPSSNFGTQTYTCNVDHKPSNTKVDKTVERKCCVECPPCPAPPVAG

PSVFLFPPKPKDTLMISRTPEVTCVVVDVSHEDPEVQFNWYVDGVEVHNAKTKPREEQF

NSTFRVVSVLTVVHQDWLNGKEYKCKVSNKGLPAPIEKTISKTKGQPREPQVYTLPPSRE

EMTKNQVSLTCLVKGFYPSDIAVEWESNGQPENNYKTTPPMLDSDGSFFLYSKLTVDKS

RWQQGNVESCSVMHEALHNHYTQKSLSLSPGK

DNA sequence of AX1_IgG2 heavy chain (SEQ ID NO: 80)

GAAGTGCAGCTGCTGGAATCTGGTGGTGGTCTGGTGCAGCCAGGTGGTTCTCTGCGT

CTGTCTTGCAAGGCCTCTGGTTTCACCTTCACTTCTTACTACATGCACTGGGTGCGTC

AGGCACCAGGTAAGGGTCTGGAATGGATCGGTCGGATCAACCCAGATTCTGGTAGT

ACTAAGTACAACGAGAAGTTCAAGGGTCGTGCCACCATCTCTAGAGACAACTCTAA

GAACACCCTGTACTTGCAGATGAACTCTCTGCGTGCCGAGGACACTGCAGTGTACTA

CTGCGCCCGTGGTGGTCGTTTATCCTGGGACTTCGACGTCTGGGGTCAGGGTACGCT

GGTGACTGTCTCGAGCGCATCCACCAAGGGCCCATCCGTCTTCCCCCTGGCGCCCTG

CTCCAGGAGCACCTCCGAGAGCACAGCCGCCCTGGGCTGCCTGGTCAAGGACTACT

TCCCCGAACCGGTGACGGTGTCCTGGAACTCTGGCGCCCTGACCTCTGGCGTGCACA

CCTTCCCTGCTGTGCTGCAATCCTCTGGCCTGTACTCCCTGTCCTCTGTGGTGACAGT

GCCATCCTCCAACTTCGGCACCCAGACCTACACATGCAATGTGGACCACAAGCCATC

CAACACCAAGGTGGACAAGACAGTGGAGCGGAAGTGCTGTGTGGAGTGCCCCCCAT

GCCCTGCCCCCCCTGTGGCTGGCCCATCTGTGTTCCTGTTCCCCCCCAAGCCCAAGG

ACACCCTGATGATCTCCCGGACCCCTGAGGTGACCTGTGTGGTGGTGGACGTGTCCC

ATGAGGACCCTGAGGTGCAGTTCAACTGGTATGTGGATGGCGTGGAGGTGCACAAT

GCCAAGACCAAGCCCCGGGAGGAGCAGTTCAACTCCACCTTCCGGGTGGTGTCTGT

GCTGACAGTGGTGCACCAGGACTGGCTGAATGGCAAGGAGTACAAGTGCAAGGTGT

CCAACAAGGGCCTGCCTGCCCCCATCGAGAAGACCATCTCCAAGACCAAGGGCCAG

-continued

CCCCGGGAGCCCCAGGTGTACACCCTGCCCCCATCCCGGGAGGAGATGACCAAGAA

CCAGGTGTCCCTGACCTGCCTGGTGAAGGGCTTCTACCCATCCGACATTGCTGTGGA

GTGGGAGTCCAATGGCCAGCCTGAGAACAACTACAAGACCACCCCCCCCATGCTGG

ACTCTGATGGCTCCTTCTTCCTGTACTCCAAGCTGACAGTGGACAAGTCCCGGTGGC

AGCAGGGCAATGTGTTCTCCTGCTCTGTGATGCATGAGGCCCTGCACAACCACTACA

CCCAGAAGTCCCTGTCCCTGTCCCCTGGCAAG

Amino acid sequence of AX1_IgG2 light chain (SEQ ID NO: 85)

DIQMTQSPSSLSASVGDRVTITCRASQDISRYLAWYQQKPGKAPKLLIYAASSLQSGVPS

RFSGSGSGTDFTLTISSLQPEDFATYYCAAYDYSLGGYVFGDGTKVEIKRTVAAPSVFIFP

PSDEQLKSGTASVVCLLNNFYPREAKVQWKVDNALQSGNSQESVTEQDSKDSTYSLSST

LTLSKADYEKHKVYACEVTHQGLSSPVTKSFNRGEC

DNA sequence of AX1_IgG2 light chain (SEQ ID NO: 86)

GACATCCAGATGACCCAGTCTCCATCTTCTCTGTCTGCCTCTGTGGGCGACCGGGTG

ACCATCACCTGCCGTGCCTCTCAGGATATCTCTAGGTATCTGGCCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCGCGGCTTACGACTATTCTTTGG

GCGGTTACGTGTTCGGTGATGGTACCAAAGTGGAGATCAAACGTACGGTGGCTGCA

CCATCTGTCTTCATCTTCCCGCCATCTGATGAGCAGTTGAAATCTGGAACTGCCTCTG

TTGTGTGCCTGCTGAATAACTTCTATCCCAGAGAGGCCAAAGTACAGTGGAAGGTGG

ATAACGCCCTCCAATCGGGTAACTCCCAGGAGAGTOTCACAGAGCAGGACAGCAAG

GACAGCACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCGTCACAA

AGAGCTTCAACAGGGGAGAGTGT

AX1_Fab display vector sequence (SEQ ID NO: 91):

GCGCAACGCAATTAATGTGAGTTAGCTCACTCATTAGGCACCCCAGGCTTTACACTT

TATGCTTCCGGCTCGTATGTTGTGTGGAATTGTGAGCGGATAACAATTTACCGGTTCT

TGTAAGGAGGAATTAAAAAATGAAAAAGTCTTTAGTCCTCAAAGCCTCCGTAGCCG

TTGCTACCCTCGTTCCGATGCTAAGCTTCGCTGACATCCAGATGACCCAGTCTCCATC

TTCTCTGTCTGCCTCTGTGGGCGACCGGGTGACCATCACCTGCCGTGCCTCTCAGGA

TATCTCTAGGTATCTGGCCTGGTATCAGCAGAAGCCAGGTAAGGCGCCAAAGCTGCT

GATCTACGCCGCCTCTTCTTTGCAGTCTGGTGTGCCATCTCGTTTCTCTGGTTCTGGT

TCTGGCACCGACTTCACCCTGACCATCTCTTCTTTGCAGCCAGAAGACTTCGCCACCT

ACTACTGCGCGGCTTACGACTATTCTTTGGGCGGTTACGTGTTCGGTGATGGTACCA

AAGTGGAGATCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCA

CCCTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGTTG

ATAAGGCGCGCCACAATTTCACAGTAAGGAGGTTTAACTTATGAAAAAATTATTATT

-continued

CGCAATTCCTTTAGTTGTTCCTTTCTATTCTCACTCCGCTGGATCCGAAGTGCAGCTG

CTGGAATCTGGTGGTGGTCTGGTGCAGCCAGGTGGTTCTCTGCGTCTGTCTTGCAAG

GCCTCTGGTTTCACCTTCACTTCTTACTACATGCACTGGGTGCGTCAGGCACCAGGT

AAGGGTCTGGAATGGATCGGTCGGATCAACCCAGATTCTGGTAGTACTAAGTACAA

CGAGAAGTTCAAGGGTCGTGCCACCATCTCTAGAGACAACTCTAAGAACACCCTGT

ACTTGCAGATGAACTCTCTGCGTGCCGAGGACACTGCAGTGTACTACTGCGCCCGTG

GTGGTCGTTTATCCTGGGACTTCGACGTCTGGGGTCAGGGTACGCTGGTGACTGTCT

CGAGCGCAAGCACCAAAGGCCCATCGGTATTCCCCCTGGCACCCTCCTCCAAGAGC

ACCTCTGGGGGCACAGCGGCCCTGGGCTGCCTGGTCAAGGACTACTTCCCCGAGCC

GGTGACGGTGTCGTGGAACTCAGGCGCTCTGACCAGCGGCGTGCACACCTTCCCGG

CTGTCCTACAGTCCTCAGGACTCTACTCCCTCAGCAGCGTGGTGACTGTGCCCTCCA

GCAGCTTGGGCACCCAGACCTACATCTGCAACGTGAATCACAAGCCCAGCAACACT

AAGGTGGACAAGAAAGTTGAGCCCAAATCTTGTGACAAAACTCACACAGCGGCCGC

TTATCCATACGACGTACCAGACTACGCAGGAGGTCATCACCATCATCACCATGTCGA

CAGATCTGGAGGAGGTGAGGAGAAGTCCCGGCTGTTGGAGAAGGAGAACCGTGAA

CTGGAAAAGATCATTGCTGAGAAAGAGGAGCGTGTCTCTGAACTGCGCCATCAACT

CCAGTCTGTAGGAGGTTGTTAATAAGTCGACGTTTAAACGGTCTCCAGCTTGGCTGT

TTTGGCGGATGAGAGAAGATTTTCAGCCTGATACAGATTAAATCAGAACGCAGAAG

CGGTCTGATAAAACAGAATTTGCCTGGCGGCAGTAGCGCGGTGGTCCCACCTGACCC

CATGCCGAACTCAGAAGTGAAACGCCGTAGCGCCGATGGTAGTGTGGGGTCTCCCC

ATGCGAGAGTAGGGAACTGCCAGGCATCAAATAAAACGAAAGGCTCAGTCGAAAG

ACTGGGCCTTTACGCGCTCACTGGCCGTCGTTTTACAACGTCGTGACTGGGAAAACC

CTGGCGTTACCCAACTTAATCGCCTTGCAGCACATCCCCCTTTCGCCAGCTGGCGTA

ATAGCGAAGAGGCCCGCACCGATCGCCCTTCCCAACAGTTGCGCAGCCTGAATGGC

GAATGGGACGCGCCCTGTAGCGGCGCATTAAGCGCGGCGGGTGTGGTGGTTACGCG

CAGCGTGACCGCTACACTTGCCAGCGCCCTAGCGCCCGCTCCTTTCGCTTTCTTCCCT

TCCTTTCTCGCCACGTTCGCCGGCTTTCCCCGTCAAGCTCTAAATCGGGGGCTCCCTT

TAGGGTTCCGATTTAGTGCTTTACGGCACCTCGACCCCAAAAAACTTGATTAGGGTG

ATGGTTCACGTAGTGGGCCATCGCCCTGATAGACGGTTTTTCGCCCTTTGACGTTGG

AGTCCACGTTCTTTAATAGTGGACTCTTGTTCCAAACTGGAACAACACTCAACCCTA

TCTCGGTCTATTCTTTTGATTTATAAGGGATTTTGCCGATTTCGGCCTATTGGTTAAA

AAATGAGCTGATTTAACAAAAATTTAACGCGAATTTTAACAAAATATTAACGCTTAC

AATTTAGGTGGCACTTTTCGGGGAAATGTGCGCGGAACCCCTATTTGTTTATTTTTCT

AAATACATTCAAATATGTATCCGCTCATGAGACAATAACCCTGATAAATGCTTCAAT

AATATTGAAAAAGGAAGAGTATGAGTATTCAACATTTCCGTGTCGCCCTTATTCCCT

TTTTTGCGGCATTTTGCCTTCCTGTTTTTGCTCACCCAGAAACGCTGGTGAAAGTAAA

AGATGCTGAAGATCAGTTGGGTGCACGAGTGGGTTACATCGAACTGGATCTCAACA

GCGGTAAGATCCTTGAGAGTTTTCGCCCCGAAGAACGTTTTCCAATGATGAGCACTT

TTAAAGTTCTGCTATGTGGCGCGGTATTATCCCGTATTGACGCCGGGCAAGAGCAAC

TCGGTCGCCGCATACACTATTCTCAGAATGACTTGGTTGAGTACTCACCAGTCACAG

-continued

AAAAGCATCTTACGGATGGCATGACAGTAAGAGAATTATGCAGTGCTGCCATAACC

ATGAGTGATAACACTGCGGCCAACTTACTTCTGACAACGATCGGAGGACCGAAGGA

GCTAACCGCTTTTTTGCACAACATGGGGGATCATGTAACTCGCCTTGATCGTTGGGA

ACCGGAGCTGAATGAAGCCATACCAAACGACGAGCGTGACACCACGATGCCTGTAG

CAATGGCAACAACGTTGCGCAAACTATTAACTGGCGAACTACTTACTCTAGCTTCCC

GGCAACAATTAATAGACTGGATGGAGGCGGATAAAGTTGCAGGACCACTTCTGCGC

TCGGCCCTTCCGGCTGGCTGGTTTATTGCTGATAAATCTGGAGCCGGTGAGCGTGGG

TCTCGCGGTATCATTGCAGCACTGGGGCCAGATGGTAAGCCCTCCCGTATCGTAGTT

ATCTACACGACGGGGAGTCAGGCAACTATGGATGAACGAAATAGACAGATCGCTGA

GATAGGTGCCTCACTGATTAAGCATTGGTAACTGTCAGACCAAGTTTACTCATATAT

ACTTTAGATTGATTTAAAACTTCATTTTTAATTTAAAAGGATCTAGGTGAAGATCCTT

TTTGATAATCTCATGACCAAAATCCCTTAACGTGAGTTTTCGTTCCACTGAGCGTCAG

ACCCCGTAGAAAAGATCAAAGGATCTTCTTGAGATCCTTTTTTTCTGCGCGTAATCT

GCTGCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAATA

CTGTCCTTCTAGTGTAGCCGTAGTTAGGCCACCACTTCAAGAACTCTGTAGCACCGC

CTACATACCTCGCTCTGCTAATCCTGTTACCAGTGGCTGCTGCCAGTGGCGATAAGT

CGTGTCTTACCGGGTTGGACTCAAGACGATAGTTACCGGATAAGGCGCAGCGGTCG

GGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAA

AGGCGGACAGGTATCCGGTAAGCGGCAGGGTCGGAACAGGAGAGCGCACGAGGGA

GCTTCCAGGGGGAAACGCCTGGTATCTTTATAGTCCTGTCGGGTTTCGCCACCTCTG

ACTTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTG

ATACCGCTCGCCGCAGCCGAACGACCGAGCGCAGCGAGTCAGTGAGCGAGGAAGCG

GAAGAGCGCCCAATACGCAAACCGCCTCTCCCCGCGCGTTGGCCGATTCATTAATGC

AGCTGGCACGACAGGTTTCCCGACTGGAAAGCGGGCAGTGA

Amino acid sequence of AX9_VH (SEQ ID NO: 43):
EVQLLESGGGLVQPGGSLRLSCKASGYTFSSYWMHWVRQAPGKGLEWIGRIDPYNGGT

KYNEKFKGKATISRDNSKNTLYLQMNSLRAEDTAVYYCARYGYYLGSYAMDYWGQG

TLVTVSS

DNA sequence of AX9_VH (SEQ ID NO: 44):
GAAGTGCAGCTGTTGGAATCTGGTGGTGGTCTGGTGCAGCCAGGTGGTTCTCTGCGT

CTGTCTTGCAAGGCCTCTGGTTACACCTTCTCTTCTTACTGGATGCACTGGGTGCGTC

AGGCACCAGGTAAGGGTCTGGAATGGATCGGTCGTATCGACCCATATAACGGTGGC

ACCAAGTACAACGAGAAGTTCAAGGGTAAGGCCACCATCTCTAGAGACAACTCTAA

GAACACCCTGTACTTGCAGATGAACTCTCTGCGTGCCGAGGACACTGCAGTGTACTA

CTGCGCCCGTTATGGTTACTACCTTGGCTCTTACGCCATGGACTACTGGGGTCAGGG

TACGCTGGTGACTGTCTCGAGC

Amino acid sequence of AX9_VK (SEQ ID NO: 53):
DIQMTQSPSSLSASVGDRVTITCRASQDVSKYLAWYQQKPGKAPKLLIYAASSLQSGVPS -continued

RFSGSGSGTDFTLTISSLQPEDFATYYCQVYDSSPNAYVFGGGTKVEIK

DNA sequence of AX9_VK (SEQ ID NO: 54):
GACATCCAGATGACCCAGTCTCCATCTTCTCTGTCTGCCTCTGTGGGCGACCGGGTG

ACCATCACCTGCCGTGCCTCTCAGGATGTCTCTAAGTATCTGGCCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCCAGGTATACGACAGCTCTCCAA

ACGCTTATGTGTTCGGTGGTGGTACCAAAGTGGAGATCAAA

Amino acid sequence of AX9 fd chain (Fab molecule)
(SEQ ID NO: 71)
EVQLLESGGGLVQPGGSLRLSCKASGYTFSSYWMHWVRQAPGKGLEWIGRIDPYNGGT

KYNEKFKGKATISRDNSKNTLYLQMNSLRAEDTAVYYCARYGYYLGSYAMDYWGQG

TLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHT

DNA sequence of AX9 fd chain (Fab molecule)
(SEQ ID NO: 72)
GAAGTGCAGCTGTTGGAATCTGGTGGTGGTCTGGTGCAGCCAGGTGGTTCTCTGCGT

CTGTCTTGCAAGGCCTCTGGTTACACCTTCTCTTCTTACTGGATGCACTGGGTGCGTC

AGGCACCAGGTAAGGGTCTGGAATGGATCGGTCGTATCGACCCATATAACGGTGGC

ACCAAGTACAACGAGAAGTTCAAGGGTAAGGCCACCATCTCTAGAGACAACTCTAA

GAACACCCTGTACTTGCAGATGAACTCTCTGCGTGCCGAGGACACTGCAGTGTACTA

CTGCGCCCGTTATGGTTACTACCTTGGCTCTTACGCCATGGACTACTGGGGTCAGGG

TACGCTGGTGACTGTCTCGAGCGCAAGCACCAAAGGCCCATCGGTATTCCCCCTGGC

ACCCTCCTCCAAGAGCACCTCTGGGGGCACAGCGGCCCTGGGCTGCCTGGTCAAGG

ACTACTTCCCCGAGCCGGTGACGGTGTCGTGGAACTCAGGCGCTCTGACCAGCGGC

GTGCACACCTTCCCGGCTGTCCTACAGTCCTCAGGACTCTACTCCCTCAGCAGCGTG

GTGACTGTGCCCTCCAGCAGCTTGGGCACCCAGACCTACATCTGCAACGTGAATCAC

AAGCCCAGCAACACTAAGGTGGACAAGAAAGTTGAGCCCAAATCTTGTGACAAAAC

TCACACA

Amino acid sequence of AX9 light chain (Fab molecule)
(SEQ ID NO: 75)
DIQMTQSPSSLSASVGDRVTITCRASQDVSKYLAWYQQKPGKAPKLLIYAASSLQSGVPS

RFSGSGSGTDFTLTISSLQPEDFATYYCQVYDSSPNAYVFGGGTKVEIKRTVAAPSVFIFP

PSDEQLKSGTASVVCLLNNFYPREAKVQWKVDNALQSGNSQESVTEQDSKDSTYSLSST

LTLSKADYEKHKVYACEVTHQGLSSPVTKSFNRGEC

DNA sequence of AX9 light chain (Fab molecule)
(SEQ ID NO: 76)
GACATCCAGATGACCCAGTCTCCATCTTCTCTGTCTGCCTCTGTGGGCGACCGGGTG

ACCATCACCTGCCGTGCCTCTCAGGATGTCTCTAAGTATCTGGCCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCCAGGTATACGACAGCTCTCCAA

ACGCTTATGTGTTCGGTGGTGGTACCAAAGTGGAGATCAAACGTACGGTGGCTGCAC

CATCTGTCTTCATCTTCCCGCCATCTGATGAGCAGTTGAAATCTGGAACTGCCTCTGT

TGTGTGCCTGCTGAATAACTTCTATCCCAGAGAGGCCAAAGTACAGTGGAAGGTGG

-continued

```
ATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCGTCACAA

AGAGCTTCAACAGGGGAGAGTGT
```

AX9_IgG2 sequences are listed below.

```
Amino acid sequence of AX9_IgG2 heavy chain
                                                (SEQ ID NO: 81)
EVQLLESGGGLVQPGGSLRLSCKASGYTFSSYWMHWVRQAPGKGLEWIGRIDPYNGGT

KYNEKFKGKATISRDNSKNTLYLQMNSLRAEDTAVYYCARYGYYLGSYAMDYWGQG

TLVTVSSASTKGPSVFPLAPCSRSTSESTAALGCLVKDYFPEPVTVSWNSGALTSGVHTF

PAVLQSSGLYSLSSVVTVPSSNFGTQTYTCNVDHKPSNTKVDKTVERKCCVECPPCPAPP

VAGPSVFLFPPKPKDTLMISRTPEVTCVVVDVSHEDPEVQFNWYVDGVEVHNAKTKPRE

EQFNSTFRVVSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDGSFFLYSKLT

VDKSRWQQGNVFSCSVMHEALHNHYTQKSLSLSPGK

DNA sequence of AX9_IgG2 heavy chain
                                                (SEQ ID NO: 82)
GAAGTGCAGCTGTTGGAATCTGGTGGTGGTCTGGTGCAGCCAGGTGGTTCTCTGCGT

CTGTCTTGCAAGGCCTCTGGTTACACCTTCTCTTCTTACTGGATGCACTGGGTGCGTC

AGGCACCAGGTAAGGGTCTGGAATGGATCGGTCGTATCGACCCATATAACGGTGGC

ACCAAGTACAACGAGAAGTTCAAGGGTAAGGCCACCATCTCTAGAGACAACTCTAA

GAACACCCTGTACTTGCAGATGAACTCTCTGCGTGCCGAGGACACTGCAGTGTACTA

CTGCGCCCGTTATGGTTACTACCTTGGCTCTTACGCCATGGACTACTGGGGTCAGGG

TACGCTGGTGACTGTCTCGAGCGCATCCACCAAGGGCCCATCCGTCTTCCCCCTGGC

GCCCTGCTCCAGGAGCACCTCCGAGAGCACAGCCGCCCTGGGCTGCCTGGTCAAGG

ACTACTTCCCCGAACCGGTGACGGTGTCCTGGAACTCTGGCGCCCTGACCTCTGGCG

TGCACACCTTCCCTGCTGTGCTGCAATCCTCTGGCCTGTACTCCCTGTCCTCTGTGGT

GACAGTGCCATCCTCCAACTTCGGCACCCAGACCTACACATGCAATGTGGACCACA

AGCCATCCAACACCAAGGTGGACAAGACAGTGGAGCGGAAGTGCTGTGTGGAGTGC

CCCCCATGCCCTGCCCCCCCTGTGGCTGGCCCATCTGTGTTCCTGTTCCCCCCCAAGC

CCAAGGACACCCTGATGATCTCCCGGACCCCTGAGGTGACCTGTGTGGTGGTGGACG

TGTCCCATGAGGACCCTGAGGTGCAGTTCAACTGGTATGTGGATGGCGTGGAGGTGC

ACAATGCCAAGACCAAGCCCCGGGAGGAGCAGTTCAACTCCACCTTCCGGGTGGTG

TCTGTGCTGACAGTGGTGCACCAGGACTGGCTGAATGGCAAGGAGTACAAGTGCAA

GGTGTCCAACAAGGGCCTGCCTGCCCCCATCGAGAAGACCATCTCCAAGACCAAGG

GCCAGCCCCGGGAGCCCCAGGTGTACACCCTGCCCCCATCCCGGGAGGAGATGACC

AAGAACCAGGTGTCCCTGACCTGCCTGGTGAAGGGCTTCTACCCATCCGACATTGCT

GTGGAGTGGGAGTCCAATGGCCAGCCTGAGAACAACTACAAGACCACCCCCCCCAT

GCTGGACTCTGATGGCTCCTTCTTCCTGTACTCCAAGCTGACAGTGGACAAGTCCCG

GTGGCAGCAGGGCAATGTGTTCTCCTGCTCTGTGATGCATGAGGCCCTGCACAACCA

CTACACCCAGAAGTCCCTGTCCCTGTCCCCTGGCAAG

Amino acid sequence of AX9_IgG2 light chain
```

-continued (SEQ ID NO: 87)
DIQMTQSPSSLSASVGDRVTITCRASQDVSKYLAWYQQKPGKAPKLLIYAASSLQSGVPS

RFSGSGSGTDFTLTISSLQPEDFATYYCQVYDSSPNAYVFGGGTKVEIKRTVAAPSVFIFP

PSDEQLKSGTASVVCLLNNFYPREAKVQWKVDNALQSGNSQESVTEQDSKDSTYSLSST

LTLSKADYEKHKVYACEVTHQGLSSPVTKSFNRGEC

DNA sequence of AX9_IgG2 light chain (SEQ ID NO: 88)
GACATCCAGATGACCCAGTCTCCATCTTCTCTGTCTGCCTCTGTGGGCGACCGGGTG

ACCATCACCTGCCGTGCCTCTCAGGATGTCTCTAAGTATCTGGCCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCCAGGTATACGACAGCTCTCCAA

ACGCTTATGTGTTCGGTGGTGGTACCAAAGTGGAGATCAAACGTACGGTGGCTGCAC

CATCTGTCTTCATCTTCCCGCCATCTGATGAGCAGTTGAAATCTGGAACTGCCTCTGT

TGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCGTCACAA

AGAGCTTCAACAGGGGAGAGTGT

AX9_Fab display vector sequence (SEQ ID NO: 92):
GCGCAACGCAATTAATGTGAGTTAGCTCACTCATTAGGCACCCCAGGCTTTACACTT

TATGCTTCCGGCTCGTATGTTGTGTGGAATTGTGAGCGGATAACAATTTACCGGTTCT

TGTAAGGAGGAATTAAAAAATGAAAAAGTCTTTAGTCCTCAAAGCCTCCGTAGCCG

TTGCTACCCTCGTTCCGATGCTAAGCTTCGCTGACATCCAGATGACCCAGTCTCCATC

TTCTCTGTCTGCCTCTGTGGGCGACCGGGTGACCATCACCTGCCGTGCCTCTCAGGA

TGTCTCTAAGTATCTGGCCTGGTATCAGCAGAAGCCAGGTAAGGCGCCAAAGCTGCT

GATCTACGCCGCCTCTTCTTTGCAGTCTGGTGTGCCATCTCGTTTCTCTGGTTCTGGT

TCTGGCACCGACTTCACCCTGACCATCTCTTCTTTGCAGCCAGAAGACTTCGCCACCT

ACTACTGCCAGGTATACGACAGCTCTCCAAACGCTTATGTGTTCGGTGGTGGTACCA

AAGTGGAGATCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCA

CCCTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGTTG

ATAAGGCGCGCCACAATTTCACAGTAAGGAGGTTTAACTTATGAAAAAATTATTATT

CGCAATTCCTTTAGTTGTTCCTTTCTATTCTCACTCCGCTGGATCCGAAGTGCAGCTG

TTGGAATCTGGTGGTGGTCTGGTGCAGCCAGGTGGTTCTCTGCGTCTGTCTTGCAAG

GCCTCTGGTTACACCTTCTCTTCTTACTGGATGCACTGGGTGCGTCAGGCACCAGGT

AAGGGTCTGGAATGGATCGGTCGTATCGACCCATATAACGGTGGCACCAAGTACAA

CGAGAAGTTCAAGGGTAAGGCCACCATCTCTAGAGACAACTCTAAGAACACCCTGT

ACTTGCAGATGAACTCTCTGCGTGCCGAGGACACTGCAGTGTACTACTGCGCCCGTT

ATGGTTACTACCTTGGCTCTTACGCCATGGACTACTGGGGTCAGGGTACGCTGGTGA

-continued

CTGTCTCGAGCGCAAGCACCAAAGGCCCATCGGTATTCCCCCTGGCACCCTCCTCCA

AGAGCACCTCTGGGGGCACAGCGGCCCTGGGCTGCCTGGTCAAGGACTACTTCCCC

GAGCCGGTGACGGTGTCGTGGAACTCAGGCGCTCTGACCAGCGGCGTGCACACCTT

CCCGGCTGTCCTACAGTCCTCAGGACTCTACTCCCTCAGCAGCGTGGTGACTGTGCC

CTCCAGCAGCTTGGGCACCCAGACCTACATCTGCAACGTGAATCACAAGCCCAGCA

ACACTAAGGTGGACAAGAAAGTTGAGCCCAAATCTTGTGACAAAACTCACACAGCG

GCCGCTTATCCATACGACGTACCAGACTACGCAGGAGGTCATCACCATCATCACCAT

GTCGACAGATCTGGAGGAGGTGAGGAGAAGTCCCGGCTGTTGGAGAAGGAGAACC

GTGAACTGGAAAAGATCATTGCTGAGAAAGAGGAGCGTGTCTCTGAACTGCGCCAT

CAACTCCAGTCTGTAGGAGGTTGTTAATAAGTCGACGTTTAAACGGTCTCCAGCTTG

GCTGTTTTGGCGGATGAGAGAAGATTTTCAGCCTGATACAGATTAAATCAGAACGCA

GAAGCGGTCTGATAAAACAGAATTTGCCTGGCGGCAGTAGCGCGGTGGTCCCACCT

GACCCCATGCCGAACTCAGAAGTGAAACGCCGTAGCGCCGATGGTAGTGTGGGGTC

TCCCCATGCGAGAGTAGGGAACTGCCAGGCATCAAATAAAACGAAAGGCTCAGTCG

AAAGACTGGGCCTTTACGCGCTCACTGGCCGTCGTTTTACAACGTCGTGACTGGGAA

AACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAA

TGGCGAATGGGACGCGCCCTGTAGCGGCGCATTAAGCGCGGCGGGTGTGGTGGTTA

CGCGCAGCGTGACCGCTACACTTGCCAGCGCCCTAGCGCCCGCTCCTTTCGCTTTCTT

CCCTTCCTTTCTCGCCACGTTCGCCGGCTTTCCCCGTCAAGCTCTAAATCGGGGGCTC

CCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACG

TTGGAGTCCACGTTCTTTAATAGTGGACTCTTGTTCCAAACTGGAACAACACTCAAC

CCTATCTCGGTCTATTCTTTTGATTTATAAGGGATTTTGCCGATTTCGGCCTATTGGTT

AAAAAATGAGCTGATTTAACAAAAATTTAACGCGAATTTTAACAAAATATTAACGCT

TACAATTTAGGTGGCACTTTTCGGGGAAATGTGCGCGGAACCCCTATTTGTTTATTTT

TCTAAATACATTCAAATATGTATCCGCTCATGAGACAATAACCCTGATAAATGCTTC

AATAATATTGAAAAAGGAAGAGTATGAGTATTCAACATTTCCGTGTCGCCCTTATTC

CCTTTTTTGCGGCATTTTGCCTTCCTGTTTTTGCTCACCCAGAAACGCTGGTGAAAGT

AAAAGATGCTGAAGATCAGTTGGGTGCACGAGTGGGTTACATCGAACTGGATCTCA

ACAGCGGTAAGATCCTTGAGAGTTTTCGCCCCGAAGAACGTTTTCCAATGATGAGCA

CTTTTAAAGTTCTGCTATGTGGCGCGGTATTATCCCGTATTGACGCCGGGCAAGAGC

AACTCGGTCGCCGCATACACTATTCTCAGAATGACTTGGTTGAGTACTCACCAGTCA

CAGAAAAGCATCTTACGGATGGCATGACAGTAAGAGAATTATGCAGTGCTGCCATA

ACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTG

GGAACCGGAGCTGAATGAAGCCATACCAAACGACGAGCGTGACACCACGATGCCTG

TAGCAATGGCAACAACGTTGCGCAAACTATTAACTGGCGAACTACTTACTCTAGCTT

CCCGGCAACAATTAATAGACTGGATGGAGGCGGATAAAGTTGCAGGACCACTTCTG

CGCTCGGCCCTTCCGGCTGGCTGGTTTATTGCTGATAAATCTGGAGCCGGTGAGCGT

-continued

```
GGGTCTCGCGGTATCATTGCAGCACTGGGGCCAGATGGTAAGCCCTCCCGTATCGTA

GTTATCTACACGACGGGGAGTCAGGCAACTATGGATGAACGAAATAGACAGATCGC

TGAGATAGGTGCCTCACTGATTAAGCATTGGTAACTGTCAGACCAAGTTTACTCATA

TATACTTTAGATTGATTTAAAACTTCATTTTTAATTTAAAAGGATCTAGGTGAAGATC

CTTTTTGATAATCTCATGACCAAAATCCCTTAACGTGAGTTTTCGTTCCACTGAGCGT

CAGACCCCGTAGAAAAGATCAAAGGATCTTCTTGAGATCCTTTTTTTCTGCGCGTAA

TCTGCTGCTTGCAAACAAAAAAACCACCGCTACCAGCGGTGGTTTGTTTGCCGGATC

AAGAGCTACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCTGTAGCAC

CGCCTACATACCTCGCTCTGCTAATCCTGTTACCAGTGGCTGCTGCCAGTGGCGATA

AGTCGTGTCTTACCGGGTTGGACTCAAGACGATAGTTACCGGATAAGGCGCAGCGG

TCGGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAG

GGAGCTTCCAGGGGGAAACGCCTGGTATCTTTATAGTCCTGTCGGGTTTCGCCACCT

CTGACTTGAGCGTCGATTTTTGTGATGCTCGTCAGGGGGGCGGAGCCTATGGAAAAA

CGCCAGCAACGCGGCCTTTTTACGGTTCCTGGCCTTTTGCTGGCCTTTTGCTCACATG

TTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAA

GCGGAAGAGCGCCCAATACGCAAACCGCCTCTCCCCGCGCGTTGGCCGATTCATTA

ATGCAGCTGGCACGACAGGTTTCCCGACTGGAAAGCGGGCAGTGA
```

Example 5

Biacore-Based Competition Assay for Binding Epitope Binning

Human PCSK9 protein was immobilized on CM5 chip by coupling primary amine groups of PCSK9 onto carboxylated surfaces of sensor chips according to the instruction of Amine Coupling Kit (GE/Biacore). Briefly, hPCSK9 protein was diluted to 50 μg/ml in pH 5.5/10 mM Acetate solution, and was injected onto the NHS/EDC activated surface to achieve an immobilization level of 1000-2000 RU, followed with surface inactivation by injection of Ethanolamine. The Fab or IgG protein (1 μM in HBS-P buffer) was then injected for 3 minutes binding, followed with 5 minutes dissociation. In the binding epitope binning assay, two flow cells were immobilized with same amount of hPCSK9 protein to detect the binding competition between antibody 1 and antibody 2. On the flow cell 1, antibody 1 was injected twice to occupy its binding epitope, antibody 2 was then injected for binding. The flow cell 2 was setup as a reference, only antibody 2 was injected onto it for binding. To determine whether there was competition between antibody 1 and antibody 2, the sensorgrams of antibody 2 from both flow cells were overplayed. When two antibodies compete, pre-occupation of antibody 1 could significantly or totally inhibit the antibody 2 binding. Cross competition for 19 antibodies from PDL1 library was completed, and 3 independent epitope bins on human PCSK9 were identified, see table 2. Ax1 and Ax9 competed to PCSK9 binding, and shared the epitope bin B.

TABLE 2

Three epitope bins for PCSK9 antibodies

| Bin A binder | Bin B binder | Bin C binder |
|---|---|---|
| AX114 | AX1 | AX116 |
| AX132 | AX9 | |
| AX139 | AX40 | |
| AX212 | AX56 | |
| AX213 | AX115 | |
| AX210 | AX118 | |
| AX211 | AX119 | |
| | AX188 | |
| | AX189 | |
| | AX191 | |

Example 6

AX1 Engineering

VK_FR4 of antibody was engineered from FGDGTKVEIK to FGGGTKVEIK in the IgG2 expression vector, and resulted in AX1 variant AX1DG.

Amino acid sequence of AX1DG_VH1 (SEQ ID NO: 41):
EVQLLESGGGLVQPGGSLRLSCKASGFTFTSYYMHWVRQAPGKGLEWIGRINPDSGSTK

YNEKFKGRATISRANSKNTLYLQMNSLRAEDTAVYYCARGGLSWDFDVWGQGTLVT

VSS

Amino acid sequence of AX1DG_VK (SEQ ID NO: 52):
DIQMTQSPSSLSASVGDRVTITCRASQDISRYLAWYQQKPGKAPKLLIYAASSLQSGVPS

RFSGSGSGTDFTLTISSLQPEDFATYYCAAYDYSLGGYVFGGGTKVEIK

The AX1DG maintained the binding affinity to human and rhesus PCSK9 proteins, shown in table 3.

TABLE 3

| affinity to PCSK9 | | | |
|---|---|---|---|
| Molecule | Format | Human PCSK9 $K_D$ (M) | Rhesus PCSK9 $K_D$ (M) |
| AX1 | IgG2 | 5.75E−09 | 8.61E−09 |
| AX1-DG | IgG2 | 4.61E−09 | 8.10E−09 |

Example 7

Optimization of AX9

An AX9 light chain library was constructed using the adapter-directed phage display technology as described by Wang et al., Journal of Molecular Biology 2010, 395:1088-1101. Phage developed from the library were processed for panning against PCSK9 as described in Example 2. PCSK9 positive clones were sequenced, and 13 unique Vk variants including AX189 were discovered. The VK sequences of AX9 variants are illustrated in FIG. 2A. A consensus of the VK variants was illustrated in FIG. 2B as well.

The sequences of one variant AX189 are listed below.

Amino acid sequence of AX189_VH (SEQ ID NO: 43):
EVQLLESGGGLVQPGGSLRLSCKASGYTFSSYWMHWVRQAPGKGLEWIGRIDPYNGGT

KYNEKFKGKATISRDNSKNTLYLQMNSLRAEDTAVYYCARYGYYLGSYAMDYWGQG

TLVTVSS

DNA sequence of AX189_VH (SEQ ID NO: 44):
GAAGTGCAGCTGTTGGAATCTGGTGGTGGTCTGGTGCAGCCAGGTGGTTCTCTGCGT

CTGTCTTGCAAGGCCTCTGGTTACACCTTCTCTTCTTACTGGATGCACTGGGTGCGTC

AGGCACCAGGTAAGGGTCTGGAATGGATCGGTCGTATCGACCCATATAACGGTGGC

ACCAAGTACAACGAGAAGTTCAAGGGTAAGGCCACCATCTCTAGAGACAACTCTAA

GAACACCCTGTACTTGCAGATGAACTCTCTGCGTGCCGAGGACACTGCAGTGTACTA

CTGCGCCCGTTATGGTTACTACCTTGGCTCTTACGCCATGGACTACTGGGGTCAGGG

TACGCTGGTGACTGTCTCGAGC

Amino acid sequence of AX189_VK (SEQ ID NO: 67):
DIQMTQSPSSLSASVGDRVTITCRASQDVSRYLTWYQQKPGKAPKLLIYAASSLQSGVPS

RFSGSGSGTDFTLTISSLQPEDFATYYCQAYDYSLSGYVFGGGTKVEIK

DNA sequence of AX189_VK (SEQ ID NO: 68):
GACATCCAGATGACCCAGTCTCCATCTTCTCTGTCTGCCTCTGTGGGCGACCGGGTG

ACCATCACCTGCCGTGCCTCTCAGGATGTCTCTAGGTATCTGACCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCCAGGCTTACGACTATTCTTTGA

GCGGTTACGTGTTCGGTGGTGGTACCAAAGTGGAGATCAAA

Amino acid sequence of AX189 fd chain (Fab molecule)
(SEQ ID NO: 71)
EVQLLESGGGLVQPGGSLRLSCKASGYTFSSYWMHWVRQAPGKGLEWIGRIDPYNGGT

KYNEKFKGKATISRDNSKNTLYLQMNSLRAEDTAVYYCARYGYYLGSYAMDYWGQG

TLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHT

-continued

DNA sequence of AX189 fd chain (Fab molecule
(SEQ ID NO: 72))

GAAGTGCAGCTGTTGGAATCTGGTGGTGGTCTGGTGCAGCCAGGTGGTTCTCTGCGT

CTGTCTTGCAAGGCCTCTGGTTACACCTTCTCTTCTTACTGGATGCACTGGGTGCGTC

AGGCACCAGGTAAGGGTCTGGAATGGATCGGTCGTATCGACCCATATAACGGTGGC

ACCAAGTACAACGAGAAGTTCAAGGGTAAGGCCACCATCTCTAGAGACAACTCTAA

GAACACCCTGTACTTGCAGATGAACTCTCTGCGTGCCGAGGACACTGCAGTGTACTA

CTGCGCCCGTTATGGTTACTACCTTGGCTCTTACGCCATGGACTACTGGGGTCAGGG

TACGCTGGTGACTGTCTCGAGCGCAAGCACCAAAGGCCCATCGGTATTCCCCCTGGC

ACCCTCCTCCAAGAGCACCTCTGGGGGCACAGCGGCCCTGGGCTGCCTGGTCAAGG

ACTACTTCCCCGAGCCGGTGACGGTGTCGTGGAACTCAGGCGCTCTGACCAGCGGC

GTGCACACCTTCCCGGCTGTCCTACAGTCCTCAGGACTCTACTCCCTCAGCAGCGTG

GTGACTGTGCCCTCCAGCAGCTTGGGCACCCAGACCTACATCTGCAACGTGAATCAC

AAGCCCAGCAACACTAAGGTGGACAAGAAAGTTGAGCCCAAATCTTGTGACAAAAC

TCACACA

Amino acid sequence of AX189 light chain (Fab molecule)
(SEQ ID NO: 77)

DIQMTQSPSSLSASVGDRVTITCRASQDVSRYLTWYQQKPGKAPKLLIYAASSLQSGVPS

RFSGSGSGTDFTLTISSLQPEDFATYYCQAYDYSLSGYVFGGGTKVEIKRTVAAPSVFIFP

PSDEQLKSGTASVVCLLNNFYPREAKVQWKVDNALQSGNSQESVTEQDSKDSTYSLSST

LTLSKADYEKHKVYACEVTHQGLSSPVTKSENRGEC

DNA sequence of AX189 light chain (Fab molecule)
(SEQ ID NO: 78)

GACATCCAGATGACCCAGTCTCCATCTTCTCTGTCTGCCTCTGTGGGCGACCGGGTG

ACCATCACCTGCCGTGCCTCTCAGGATGTCTCTAGGTATCTGACCTGGTATCAGCAG

AAGCCAGGTAAGGCGCCAAAGCTGCTGATCTACGCCGCCTCTTCTTTGCAGTCTGGT

GTGCCATCTCGTTTCTCTGGTTCTGGTTCTGGCACCGACTTCACCCTGACCATCTCTT

CTTTGCAGCCAGAAGACTTCGCCACCTACTACTGCCAGGCTTACGACTATTCTTTGA

GCGGTTACGTGTTCGGTGGTGGTACCAAAGTGGAGATCAAACGTACGGTGGCTGCA

CCATCTGTATTCATCTTCCCGCCATCTGATGAGCAGTTGAAATCTGGAACTGCCTCTG

TTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCGTCACAA

AGAGCTTCAACAGGGGAGAGTGT

AX189_IgG2 sequences are listed below.

Amino acid sequence of AX189_IgG2 heavy chain
including leader sequence
(SEQ ID NO: 83)

MGWSLILLFLVAVATRVLSEVQLLESGGGLVQPGGSLRLSCKASGYTFSSYWMHWVRQ

APGKGLEWIGRIDPYNGGTKYNEKFKGKATISRDNSKNTLYLQMNSLRAEDTAVYYCA

RYGYYLGSYAMDYWGQGTLVTVSSASTKGPSVFPLAPCSRSTSESTAALGCLVKDYFPE

PVTVSWNSGALTSGVHTFPAVLQSSGLYSLSSVVTVPSSNFGTQTYTCNVDHKPSNTKV

DKTVERKCCVECPPCPAPPVAGPSVFLFPPKPKDTLMISRTPEVTCVVVDVSHEDPEVQF

-continued

NWYVDGVEVHNAKTKPREEQFNSTFRVVSVLTVVHQDWLNGKEYKCKVSNKGLPAPI

EKTISKTKGQPREPQVYTLPPSREEMTKNQVSLTCLVKGFYPSDIAVEWESNGQPENNY

KTTPPMLDSDGSFFLYSKLTVDKSRWQQGNVFSCSVMHEALHNHYTQKSLSLSPGK

DNA sequence of AX189_IgG2 heavy chain (SEQ ID NO: 84)

ATGGGCTGGTCCCTGATTCTGCTGTTCCTGGTGGCTGTGGCTACCAGGGTGCTGTCTG

AGGTCCAACTTTTGGAGTCTGGAGGAGGACTGGTCCAACCTGGAGGCTCCCTGAGA

CTGTCCTGTAAGGCATCTGGCTACACCTTCTCCTCCTACTGGATGCACTGGGTGAGA

CAGGCTCCTGGCAAGGGATTGGAGTGGATTGGCAGGATTGACCCATACAATGGAGG

CACCAAATACAATGAGAAGTTCAAGGGCAAGGCTACCATCAGCAGGGACAACAGCA

AGAACACCCTCTACCTCCAAATGAACTCCCTGAGGGCTGAGGACACAGCAGTCTAC

TACTGTGCCAGATATGGCTACTACCTGGGCTCCTATGCTATGGACTACTGGGGACAA

GGCACCCTGGTGACAGTGTCCTCTGCTAGCACCAAGGGCCCATCGGTCTTCCCCCTG

GCGCCCTGCTCCAGGAGCACCTCCGAGAGCACAGCGGCCCTGGGCTGCCTGGTCAA

GGACTACTTCCCCGAACCGGTGACGGTGTCGTGGAACTCAGGCGCTCTGACCAGCG

GCGTGCACACCTTCCCGGCTGTCCTACAGTCCTCAGGACTCTACTCCCTCAGCAGCG

TGGTGACCGTGCCCTCCAGCAACTTCGGCACCCAGACCTACACCTGCAACGTAGATC

ACAAGCCCAGCAACACCAAGGTGGACAAGACAGTTGAGCGCAAATGTTGTGTCGAG

TGCCCACCGTGCCCAGCACCACCTGTGGCAGGACCGTCAGTCTTCCTCTTCCCCCCA

AAACCCAAGGACACCCTCATGATCTCCCGGACCCCTGAGGTCACGTGCGTGGTGGT

GGACGTGAGCCACGAAGACCCCGAGGTCCAGTTCAACTGGTACGTGGACGGCGTGG

AGGTGCATAATGCCAAGACAAAGCCACGGGAGGAGCAGTTCAACAGCACGTTCCGT

GTGGTCAGCGTCCTCACCGTCGTGCACCAGGACTGGCTGAACGGCAAGGAGTACAA

GTGCAAGGTCTCCAACAAAGGCCTCCCAGCCCCCATCGAGAAAACCATCTCCAAAA

CCAAAGGGCAGCCCCGAGAACCACAGGTGTACACCCTGCCCCCATCCCGGGAGGAG

ATGACCAAGAACCAGGTCAGCCTGACCTGCCTGGTCAAAGGCTTCTACCCCAGCGA

CATCGCCGTGGAGTGGGAGAGCAATGGGCAGCCGGAGAACAACTACAAGACCACA

CCTCCCATGCTGGACTCCGACGGCTCCTTCTTCCTCTACAGCAAGCTCACCGTGGAC

AAGAGCAGGTGGCAGCAGGGGAACGTCTTCTCATGCTCCGTGATGCATGAGGCTCT

GCACAACCACTACACACAGAAGAGCCTCTCCCTGTCTCCGGGTAAA

Amino acid sequence of AX189_IgG2 light chain including leader sequence (SEQ ID NO: 89)

MGWSCIILFLVATATGVHSDIQMTQSPSSLSASVGDRVTITCRASQDVSRYLTWYQQKP

GKAPKLLIYAASSLQSGVPSRFSGSGSGTDFTLTISSLQPEDFATYYCQAYDYSLSGYVFG

GGTKVEIKRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNRGEC

DNA sequence of AX189_IgG2 light chain (SEQ ID NO: 90)

ATGGGCTGGTCCTGTATCATCCTGTTCCTGGTGGCTACAGCCACAGGAGTGCATTCT

GACATCCAGATGACCCAGAGCCCATCCTCCCTGTCTGCCTCTGTGGGAGACAGGGTG

ACCATCACTTGTAGGGCAAGCCAGGATGTGAGCAGATACCTGACCTGGTATCAACA

GAAGCCTGGCAAGGCTCCAAAACTGCTGATTTATGCTGCCTCCTCCCTCCAATCTGG

AGTGCCAAGCAGGTTCTCTGGCTCTGGCTCTGGCACAGACTTCACCCTGACCATCTC

-continued

CTCCCTCCAACCTGAGGACTTTGCCACCTACTACTGTCAGGCTTATGACTACTCCCTG

TCTGGCTATGTGTTTGGAGGAGGCACCAAGGTGGAGATTAAGCGTACGGTGGCTGC

ACCATCTGTCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGACAGCAA

GGACAGCACCTACAGCCTCAGCAGCACCCTGACGCTGAGCAAAGCAGACTACGAGA

AACACAAAGTCTACGCCTGCGAAGTCACCCATCAGGGCCTGAGCTCGCCCGTCACA

AAGAGCTTCAACAGGGGAGAGTGT

AX189_Fab display vector sequence (SEQ ID NO: 93):
GCGCAACGCAATTAATGTGAGTTAGCTCACTCATTAGGCACCCCAGGCTTTACACTT

TATGCTTCCGGCTCGTATGTTGTGTGGAATTGTGAGCGGATAACAATTTACCGGTTCT

TGTAAGGAGGAATTAAAAAATGAAAAAGTCTTTAGTCCTCAAAGCCTCCGTAGCCG

TTGCTACCCTCGTTCCGATGCTAAGCTTCGCTGACATCCAGATGACCCAGTCTCCATC

TTCTCTGTCTGCCTCTGTGGGCGACCGGGTGACCATCACCTGCCGTGCCTCTCAGGA

TGTCTCTAGGTATCTGACCTGGTATCAGCAGAAGCCAGGTAAGGCGCCAAAGCTGCT

GATCTACGCCGCCTCTTCTTTGCAGTCTGGTGTGCCATCTCGTTTCTCTGGTTCTGGT

TCTGGCACCGACTTCACCCTGACCATCTCTTCTTTGCAGCCAGAAGACTTCGCCACCT

ACTACTGCCAGGCTTACGACTATTCTTTGAGCGGTTACGTGTTCGGTGGTGGTACCA

AAGTGGAGATCAAACGTACGGTGGCTGCACCATCTGTATTCATCTTCCCGCCATCTG

ATGAGCAGTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCA

CCCTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGTTA

ATGATGTACCGGCGCGCCACAATTTCACAGTAAGGAGGTTTAACTTATGAAAAAATT

ATTATTCGCAATTCCTTTAGTTGTTCCTTTCTATTCTCACTCCGCTGGATCCGAAGTG

CAGCTGTTGGAATCTGGTGGTGGTCTGGTGCAGCCAGGTGGTTCTCTGCGTCTGTCTT

GCAAGGCCTCTGGTTACACCTTCTCTTCTTACTGGATGCACTGGGTGCGTCAGGCAC

CAGGTAAGGGTCTGGAATGGATCGGTCGTATCGACCCATATAACGGTGGCACCAAG

TACAACGAGAAGTTCAAGGGTAAGGCCACCATCTCTAGAGACAACTCTAAGAACAC

CCTGTACTTGCAGATGAACTCTCTGCGTGCCGAGGACACTGCAGTGTACTACTGCGC

CCGTTATGGTTACTACCTTGGCTCTTACGCCATGGACTACTGGGGTCAGGGTACGCT

GGTGACTGTCTCGAGCGCAAGCACCAAAGGCCCATCGGTATTCCCCCTGGCACCCTC

CTCCAAGAGCACCTCTGGGGGCACAGCGGCCCTGGGCTGCCTGGTCAAGGACTACT

TCCCCGAGCCGGTGACGGTGTCGTGGAACTCAGGCGCTCTGACCAGCGGCGTGCAC

ACCTTCCCGGCTGTCCTACAGTCCTCAGGACTCTACTCCCTCAGCAGCGTGGTGACT

GTGCCCTCCAGCAGCTTGGGCACCCAGACCTACATCTGCAACGTGAATCACAAGCCC

AGCAACACTAAGGTGGACAAGAAAGTTGAGCCCAAATCTTGTGACAAAACTCACAC

AGCGGCCGCTTATCCATACGACGTACCAGACTACGCAGGAGGTCATCACCATCATC

ACCATTAGAGATCTGGAGGAGGTGAGGAGAAGTCCCGGCTGTTGGAGAAGGAGAAC

CGTGAACTGGAAAAGATCATTGCTGAGAAAGAGGAGCGTGTCTCTGAACTGCGCCA

-continued

TCAACTCCAGTCTGTAGGAGGTTGTTAATAAGTCGACCTCGACCAATTCGCCCTATA

GTGAGTCGTATTACGCGCGCTCACTGGCCGTCGTTTTACAACGTCGTGACTGGGAAA

ACCCTGGCGTTACCCAACTTAATCGCCTTGCAGCACATCCCCCTTTCGCCAGCTGGC

GTAATAGCGAAGAGGCCCGCACCGATCGCCCTTCCCAACAGTTGCGCAGCCTGAAT

GGCGAATGGGACGCGCCCTGTAGCGGCGCATTAAGCGCGGCGGGTGTGGTGGTTAC

GCGCAGCGTGACCGCTACACTTGCCAGCGCCCTAGCGCCCGCTCCTTTCGCTTTCTTC

CCTTCCTTTCTCGCCACGTTCGCCGGCTTTCCCCGTCAAGCTCTAAATCGGGGGCTCC

CTTTAGGGTTCCGATTTAGTGCTTTACGGCACCTCGACCCCAAAAAACTTGATTAGG

GTGATGGTTCACGTAGTGGGCCATCGCCCTGATAGACGGTTTTTCGCCCTTTGACGTT

GGAGTCCACGTTCTTTAATAGTGGACTCTTGTTCCAAACTGGAACAACACTCAACCC

TATCTCGGTCTATTCTTTTGATTTATAAGGGATTTTGCCGATTTCGGCCTATTGGTTA

AAAAATGAGCTGATTTAACAAAAATTTAACGCGAATTTTAACAAAATATTAACGCTT

ACAATTTAGGTGGCACTTTTCGGGGAAATGTGCGCGGAACCCCTATTTGTTTATTTTT

CTAAATACATTCAAATATGTATCCGCTCATGAGACAATAACCCTGATAAATGCTTCA

ATAATATTGAAAAAGGAAGAGTATGAGTATTCAACATTTCCGTGTCGCCCTTATTCC

CTTTTTTGCGGCATTTTGCCTTCCTGTTTTTGCTCACCCAGAAACGCTGGTGAAAGTA

AAAGATGCTGAAGATCAGTTGGGTGCACGAGTGGGTTACATCGAACTGGATCTCAA

CAGCGGTAAGATCCTTGAGAGTTTTCGCCCCGAAGAACGTTTTCCAATGATGAGCAC

TTTTAAAGTTCTGCTATGTGGCGCGGTATTATCCCGTATTGACGCCGGGCAAGAGCA

ACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAA

CCATGAGTGATAACACTGCGGCCAACTTACTTCTGACAACGATCGGAGGACCGAAG

GAGCTAACCGCTTTTTTGCACAACATGGGGGATCATGTAACTCGCCTTGATCGTTGG

GAACCGGAGCTGAATGAAGCCATACCAAACGACGAGCGTGACACCACGATGCCTGT

AGCAATGGCAACAACGTTGCGCAAACTATTAACTGGCGAACTACTTACTCTAGCTTC

CCGGCAACAATTAATAGACTGGATGGAGGCGGATAAAGTTGCAGGACCACTTCTGC

GCTCGGCCCTTCCGGCTGGCTGGTTTATTGCTGATAAATCTGGAGCCGGTGAGCGTG

GGTCTCGCGGTATCATTGCAGCACTGGGGCCAGATGGTAAGCCCTCCCGTATCGTAG

TTATCTACACGACGGGGAGTCAGGCAACTATGGATGAACGAAATAGACAGATCGCT

GAGATAGGTGCCTCACTGATTAAGCATTGGTAACTGTCAGACCAAGTTTACTCATAT

ATACTTTAGATTGATTTAAAACTTCATTTTTAATTTAAAAGGATCTAGGTGAAGATCC

TTTTTGATAATCTCATGACCAAAATCCCTTAACGTGAGTTTTCGTTCCACTGAGCGTC

AGACCCCGTAGAAAAGATCAAAGGATCTTCTTGAGATCCTTTTTTTCTGCGCGTAAT

CTGCTGCTTGCAAACAAAAAAACCACCGCTACCAGCGGTGGTTTGTTTGCCGGATCA

AGAGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAA

GTCGTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACACCG

AACTGAGATACCTACAGCGTGAGCTATGAGAAAGCGCCACGCTTCCCGAAGGGAGA

-continued

AAGGCGGACAGGTATCCGGTAAGCGGCAGGGTCGGAACAGGAGAGCGCACGAGGG

AGCTTCCAGGGGGAAACGCCTGGTATCTTTATAGTCCTGTCGGGTTTCGCCACCTCT

GACTTGAGCGTCGATTTTTGTGATGCTCGTCAGGGGGGCGGAGCCTATGGAAAAAC

GCCAGCAACGCGGCCTTTTTACGGTTCCTGGCCTTTTGCTGGCCTTTTGCTCACATGT

TCTTTCCTGCGTTATCCCCTGATTCTGTGGATAACCGTATTACCGCCTTTGAGTGAGC

TGATACCGCTCGCCGCAGCCGAACGACCGAGCGCAGCGAGTCAGTGAGCGAGGAAG

CGGAAGAGCGCCCAATACGCAAACCGCCTCTCCCCGCGCGTTGGCCGATTCATTAAT

GCAGCTGGCACGACAGGTTTCCCGACTGGAAAGCGGGCAGTGA

The following are sequences, both consensus and variant sequences, that were determined for the CDRs:

SEQ ID NO: 1
CONSENSUS VH CDR1
XASGXXFXXYXXXWVR

Wherein X at position 1 is K or A; X at position 5 is Y or F; X at position 6 is T or D; X at position 8 is S or T; X at position 9 is S or D; X at position 11 is W, Y, T or D; X at position 12 is M, F, Y or I; and X at position 13 is H, S or N.

SEQ ID NO: 2
AXI VH CDR1
KASGFTFTSYYMHWVR

SEQ ID NO: 3
AX1 VH CDR1 NT
AAGGCCTCTGGTTTCACCTTCACTTCTTACTACATGCACTGGGTGCGT

SEQ ID NO 4: AX1 VH CDR1
GFTFTSYYMH

SEQ ID NO 5: AX1 VH CDR1 NT
GGTTTCACCTTCACTTCTTACTACATGCAC

SEQ ID NO: 6
AX9/AX189 VH CDR1
KASGYTFSSYWMHWVR

SEQ ID NO: 7
AX9/AX189 VH CDR1 NT
AAGGCCTCTGGTTACACCTTCTCTTCTTACTGGATGCACTGGGTGCGT

SEQ ID NO: 169
AX9/AX189 VH CDR1
GYTFSSYWMH

SEQ ID NO: 170
AX9/AX189 VH CDR1 NT
GGTTACACCTTCTCTTCTTACTGGATGCAC

SEQ ID NO: 8 -
CONSENSUS VH CDR2
WXXXIXPXXXXTKYNEKRXXXXT

Wherein X at position 2 is 1 or V; X at position 3 is G or S; X at position 4 is R or Y; X at position 6 is D, Y, E or N; X at position 8 is Y or D; X at position 9 is N, S or T; X at position 10 is G, E or T; X at position 11 is G, Y, D or S; X at position 19 is K, A or D; X at position 20 is G, S or D; X at position 21 is K or R; and X at position 22 is A or F.

SEQ ID NO: 9
AX1 VH CDR2
WIGRINPDSGSTKYNEKFKGRAT

-continued

SEQ ID NO: 10
AX1 VH CDR2 NT
TGGAATGGATCGGTCGGATCAACCCAGATTCTGGTAGTACTAAGTACAAC

GAGAAGTTCAAGGGTCGTGCCACC

SEQ ID NO 11: AX1 VH CDR2
RINPDSGSTKYNEKFKG

SEQ ID NO 12: AX1 VH CDR2 NT
CGGATCAACCCAGATTCTGGTAGTACTAAGTACAACGAGAAGTTCAAGGG

T

SEQ ID NO: 13
AX9/189 VH CDR2
WIGRIDPYNGGTKYNEKFKGKAT

SEQ ID NO: 14
AX9/AX189 VH CDR2 NT
TGGATCGGTCGTATCGACCCATATAACGGTGGCACCAAGTACAACGAGAA

GTTCAAGGGTAAGGCCACC

SEQ ID NO: 171
AX9/189 VH CDR2
RIDPYNGGTKYNEKFKG

SEQ ID NO: 172
AX9/AX189 VH CDR2 NT
CGTATCGACCCATATAACGGTGGCACCAAGTACAACGAGAAGTTCAACAC

C

SEQ ID NO: 15
CONSENSUS VH CDR3
CARXXYYXXXYAXDYWGQ

Wherein X at position 4 is Y, S, D or E; X at position 5 is G, T or R; X at position 8 is L, E, D, G or S; X at position 9 is G, D or E; X at position 10 is S, Y or F; and X at position 13 is M, F, Y, L or E.

SEQ ID NO: 16
AX1 VH CDR3
CARGGRLSWDFDVWGQ

SEQ ID NO: 17
AX1 VH CDR3 NT
TGCGCCCGTGGTGGTCGTTTATCCTGGGACTTCGACGTCTGGGGTCAG

SEQ ID NO 18: AX1 VH CDR3
GGRLSWDFDV

SEQ ID NO 19: AX1 VH CDR3 NT
GGTGGTCGTTTATCCTGGGACTTCGACGTC

SEQ ID NO: 20
AX9/189 VH CDR3
CARYGYYLGSYAMDYWGQ

-continued

SEQ ID NO: 21
AX9/189 VH CDR3 NT
TGCGCCCGTTATGGTTACTACCTTGGCTCTTACGCCATGGACTACTGGGG

TCAG

SEQ ID NO: 173
AX9/189 VH CDR3
YGYYLGSYAMDY

SEQ ID NO: 174
AX9/189 VH CDR3 NT
TATGGTTACTACCTTGGCTCTTACGCCATGGACTAC

SEQ ID NO: 22
CONSENSUS VL CDR1
XASQXXSXYLX

Wherein X at position 1 is R or K; X at position 5 is D or S; X at position 6 is V or I; X at position 8 is R, K, T or N; and X at position 11 is T, A or S.

SEQ ID NO: 23
CONSENSUS VL CDR1
RASQXXSXYLX

Wherein X at position 5 is A, D or S; X at position 6 is V or I; X at position 8 is R, K, N or S; X at position 11 is A, T, N or H.

SEQ ID NO: 24
AX1 VL CDR1
RASQDISRYLA

SEQ ID NO: 25
AX1 VL CDR1 NT
CGTGCCTCTCAGGATATCTCTAGGTATCTGGCC

SEQ ID NO: 26
AX9 VL CDR1
RASQDVSKYLA

SEQ ID NO: 27
AX9 VL CDR1 NT
CGTGCCTCTCAGGATGTCTCTAAGTATCTGGCC

SEQ ID NO: 28
AX189 VL CDR1
RASQDVSRYLT

SEQ ID NO: 29
AX189 VL CDR1 NT
CGTGCCTCTCAGGATGTCTCTAGGTATCTGACC

SEQ ID NO: 30
CONSENSUS VL CDR2
XAXXLXX

Wherein X at position 1 is A or R; X at position 3 is S, E or T; X at position 4 is S, E, D or T; X at position 6 is Q, R, K, Y or E; and X at position 7 is S, T or A.

SEQ ID NO: 31
AX1/9/189 VL CDR2
AASSLQS

SEQ ID NO: 32
AX1/9/189 VL CDR2 NT
GCCGCCTCTTCTTTGCAGTCT

SEQ ID NO: 33
CONSENSUS VL CDR3
XXXDXXXXXXV

Wherein X at position 1 is Q, E, Y or A; X at position 2 is A, V or S; X at position 3 is Y, E or W; X at position 5 is Y, S or K; X at position 6 is S or E; X at position 7 is L, S, P, G, D or T; X at position 8 is S, D, N, E, G or A; X at position 9 is G, A, D, R, S or H; and X at position 10 is Y or V.

SEQ ID NO: 34
CONSENSUS VL CDR3
XXYDXSXXXXV

Wherein X at position 1 is Q or E; X at position 2 is A, S or V; X at position 5 is Y or 5; X at position 7 is L, S or P; X at position 8 is G, 5 or N; X at position 9 is A, H, P, R, G or D; and X at position 10 is Y or W.

SEQ ID NO: 35
AX1 VL CDR3
AAYDYSLGGYV

SEQ ID NO: 36
AX1 VL CDR3 NT
GCGGCTTACGACTATTCTTTGGGCGGTTACGTG

SEQ ID NO: 37
AX9 VL CDR3
QVYDSSPNAYV

SEQ ID NO: 38
AX9 VL CDR3 NT
CAGGTATACGACAGCTCTCCAAACGCTTATGTG

SEQ ID NO: 39
AX189 VL CDR3
QAYDYSLSGYV

SEQ ID NO: 40
AX189 VL CDR3 NT
CAGGCTTACGACTATTCTTTGAGCGGTTACGTG

Example 8

Engineered AX189 Variants with the Removal of Deamidation Sites

To remove a potential deamidation site in the VH_CDR2 of Ax189, five mutants of AX189_VH were generated, with the changes of 56G to E (AX421), 55N to S (Ax422), 56G to T (AX423), 55N to T (AX424) and 55N to D (AX425). Affinity measurements showed that those changes still maintained PCSK9 binding activity (see Table 7 in Example 15).

Amino acid sequence of AX421_VH (SEQ ID NO: 45):
EVQLLESGGGLVQPGGSLRLSCKASGYTFSSYWMHWVRQAPGKGLEWIGRIDPYNEGT

KYNEKFKGKATISRDNSKNTLYLQMNSLRAEDTAVYYCARYGYYLGSYAMDYWGQG

TLVTVSS

Amino acid sequence of AX422_VH (SEQ ID NO: 46):
EVQLLESGGGLVQPGGSLRLSCKASGYTFSSYWMHWVRQAPGKGLEWIGRIDPYSGGT -continued

```
KYNEKFKGKATISRDNSKNTLYLQMNSLRAEDTAVYYCARYGYYLGSYAMDYWGQG

TLVTVSS

Amino acid sequence of AX423_VH (SEQ ID NO: 47):
EVQLLESGGGLVQPGGSLRLSCKASGYTFSSYWMHWVRQAPGKGLEWIGRIDPYNTGT

KYNEKFKGKATISRDNSKNTLYLQMNSLRAEDTAVYYCARYGYYLGSYAMDYWGQG

TLVTVSS

Amino acid sequence of AX424_VH (SEQ ID NO: 48):
EVQLLESGGGLVQPGGSLRLSCKASGYTFSSYWMHWVRQAPGKGLEWIGRIDPYTGGT

KYNEKFKGKATISRDNSKNTLYLQMNSLRAEDTAVYYCARYGYYLGSYAMDYWGQG

TLVTVSS

Amino acid sequence of AX425_VH (SEQ ID NO: 49):
EVQLLESGGGLVQPGGSLRLSCKASGYTFSSYWMHWVRQAPGKGLEWIGRIDPYDGGT

KYNEKFKGKATISRDNSKNTLYLQMNSLRAEDTAVYYCARYGYYLGSYAMDYWGQG

TLVTVSS

Amino acid sequence of VK for AX421 AX422, AX423,
AX424 and AX425 (SEQ ID NO: 67):
DIQMTQSPSSLSASVGDRVTITCRASQDVSRYLTWYQQKPGKAPKLLIYAASSLQSGVPS

RFSGSGSGTDFTLTISSLQPEDFATYYCQAYDYSLSGYVFGGGTKVEIK
```

The IgG2s of the two AX1.89 mutants, AX422 (55N to S) and AX424 (55N to T), were generated in HEK-239 cells. Their affinity to human and rhesus PCSK9 were measured by Biacore. The results (table 8 in example 15) showed that these mutants maintained the affinity to both human and rhesus PCSK9, with similar Kon, Koff as the wild type AX189. AX422 and AX424 also maintained its in-vitro FcRn binding profile as well. Furthermore, the AX422 and AX424 variants have equivalent or better IC50 in cell based Exopolar assays (see table 10 in example 17).

Example 9

Computational Docking and PCSK9 Mutagenesis for AX1 and AX189 Epitope Mapping

Definitions: Given residue on PCSK9 is counted as in contact with a given antibody, if Cα atom (see, e.g., "Introduction to Protein Structure" by Carl Branden & John Tooze, 2nd edition, 1999 Garland publishing) of PCSK9 residue is within 10 Angstroms ("Å") from CA of that antibody. For X-ray structure, the residues in contact define the epitope. For docking poses within a given epitope bin, the residues in the contacts with frequency higher than threshold (>50-75%) define the epitope. Two proteins (e.g. AX1 with a control Fab that binds PCSK9 EGFA binding area) defined as compete based on their structural model if the distance between any CA atoms of these proteins is shorter than 5 Å.

To determine epitope for AX1 and AX189, the global docking has been performed with FTDOCK program (Gabb et al. J Mol Biol 1997; 272:106-120). The generated poses have been filtered first to make sure they do not compete (see for definition above) with the control antibody, then to make sure that there are heavy (i.e. not hydrogen) atoms of antibodies that are not more than 5 Å from heavy atoms of residues which are different in human and mouse. The remaining poses were filtered further to make sure that they compete with EGF-AB. The filtered poses have been clustered and analysed for contacts to determine epitopes.

Figure 3:
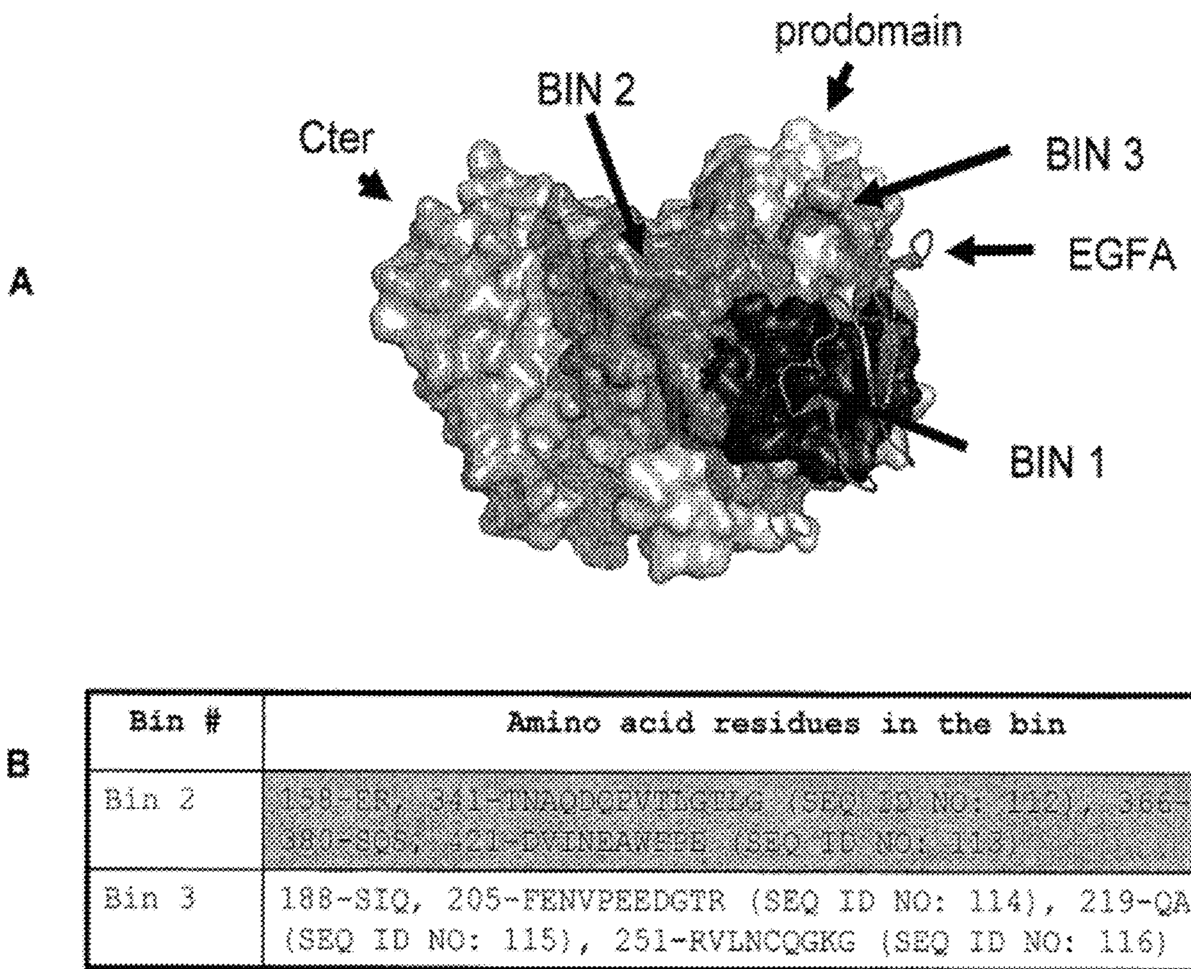
FIGS. 3A-B illustrate the three possible binding bins proposed by computational docking program for the PCSK9 antagonist antibodies isolated from PDL1 library. The bin #2 or #3 is predicted to be the binding regions for AX1 and/or AX189. The surface amino acid residues in each bin are provided (3B).

Based on computational docking studies, three bins have been determined, as shown in FIG. 3.

Table 4 shows the antibody binding differentiation between human and rat PCSK9.

TABLE 4 affinities of antibodies to PCSK9

| Molecule | Format | Human PCSK9 $K_D$ (M) | Rhesus PCSK9 $K_D$ (M) | Mouse PCSK9 9 $K_D$ (M) | rat PCSK9 $K_D$ (M) |
|---|---|---|---|---|---|
| AX1 | IgG2 | 5.75E−09 | 8.61E−09 | no binding | no binding |
| AX1-DG | IgG2 | 4.61E−09 | 8.10E−09 | no binding | no binding |
| AX9 | IgG2 | 2.06E−08 | 8.82E−09 | no binding | no binding |
| AX189 | IgG2 | 1.84E−09 | 1.24E−09 | no binding | no binding |
| AX114 | IgG2 | 2.40E−08 | 1.16E−08 | 1.12E−08 | N/A |
| AX132 | IgG2 | 6.16E−09 | 2.59E−09 | 2.76E−09 | 1E−07 |

Based on the affinity differentiation, human PCSK9 Chimeric mutations to rat PCSK9 residues have been selected to differentiate and test epitope bins. A total of 6 chimeric mutants have been designed. Each mutant represents a patch on PCSK9, see table 5. Mutant #1 is in bin 1, Mutant #2 (from bin 2) or mutant 3 (from bin 3) are expected to abrogate binding of other antibodies such as AX1/AX1DG and AX189. The remaining mutants were selected based on difference between human and rat PCSK9 sequences and partitioned based on their spatial proximity. Several residues were skipped because they are facing pro-domain/buried/not in rPCSK9.

TABLE 5 human PCSK9 mutants with residues of rat PCSK9

| Mutants | residues of rat PCSK9 |
|---|---|
| Mutant #1 | 192, 379 |
| Mutant #2 | 366, 426 |
| Mutant #3 | 201, 202, 206, 207, 247, 248 |

TABLE 5-continued

| human PCSK9 mutants with residues of rat PCSK9 | |
|---|---|
| Mutants | residues of rat PCSK9 |
| Mutant #4 | 245, 396, 405, 420, 440, 443 |
| Mutant #5 | 177, 179, 277, 280 |
| Mutant #6 | 162, 173 |

The human PCSK9 mutant proteins were produced from HEK293 cells. Briefly, the gene of a full-length human PCSK9 inside a mammalian expression vector with His-tag was modified by site-directed mutagenesis to induce the corresponding mutations based on table 5. Then the vectors of PCSK9 mutants were transiently transfected into human HEK293 cells for 7 to 10 days culture at 37° C. The His-tagged PCSK9 mutant proteins were purified from the culture supernatants by NTA columns (GE Healthcare, Pittsburgh, Pa.). The quality of PCSK9 proteins were analyzed using 10% SDS-PAGE.

ELISA assays were performed to study the bindings of PCSK9 mutants to anti-PCSK9 antibodies including AX1DG and AX189. Briefly, the PCSK9 mutant proteins were diluted with PBS to the concentration of 5 μg/ml, and coated to a 96-well ELISA plate with 100 μl/each well for overnight at 4° C. After blocking with 5% milk-PBS, antibody samples (in 5% milk-PBS with 1:2 serial dilution at start concentration of 4 nM) were added to the wells coated with individual PCSK9 mutants, and incubated for 1 hour at room temperature. After PBS wash, the anti-human K antibody conjugated with HRP was added and incubated for another hour. The TMB substrate solution (Thermo Scientific) was then added into PBS-washed plate for 10-20 minutes of development. After adding stop solution, the plates were measured for the absorbance at 450 nM.

Figure 4:
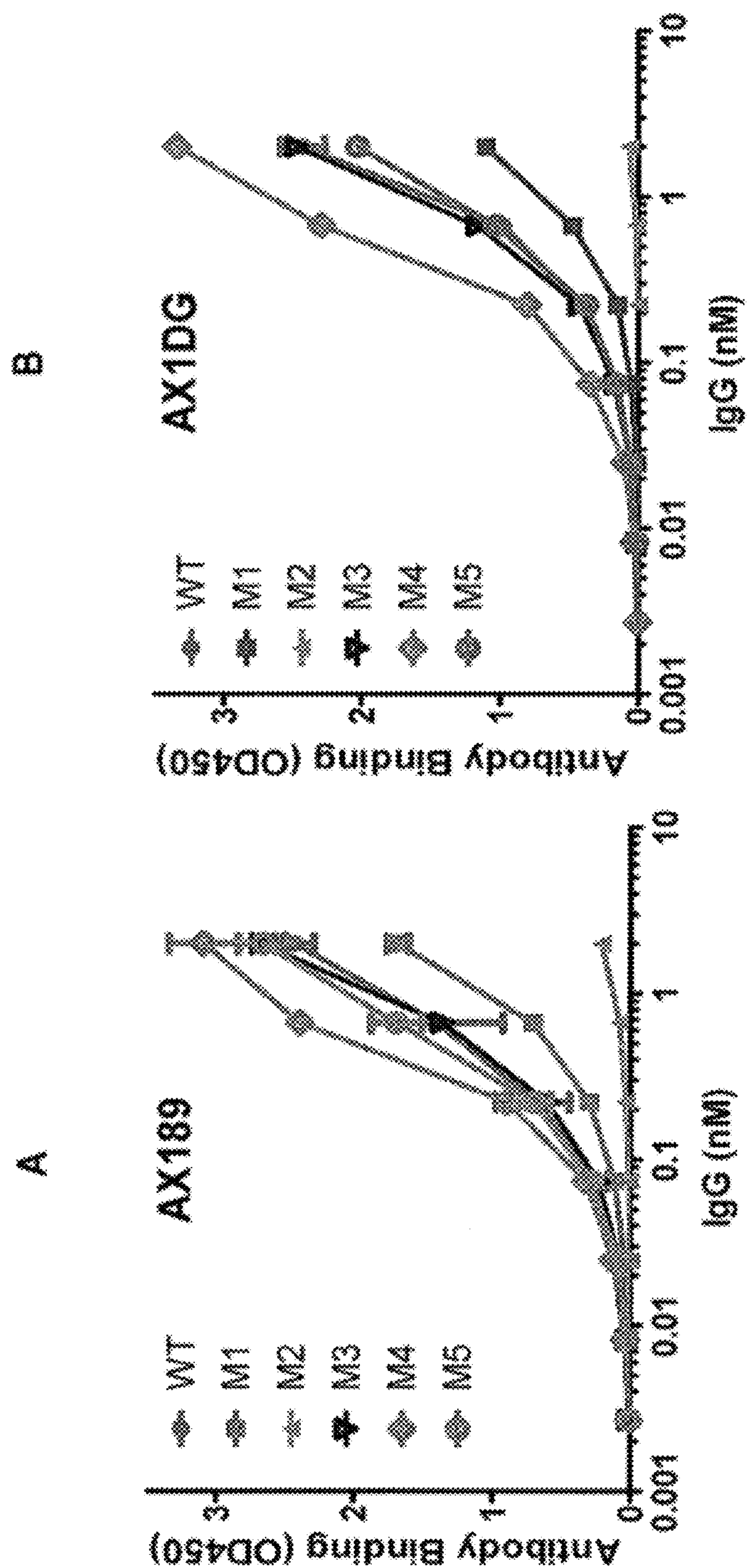
FIGS. 4A-B illustrate ELISA results that indicate the binding of AX1DG(B) and AX189 (A) to the Bin #2. E366K and E426M substitutions in human PCSK9 cause significant loss of binding activity to AX1 and AX189 antibody.
Figure 5:
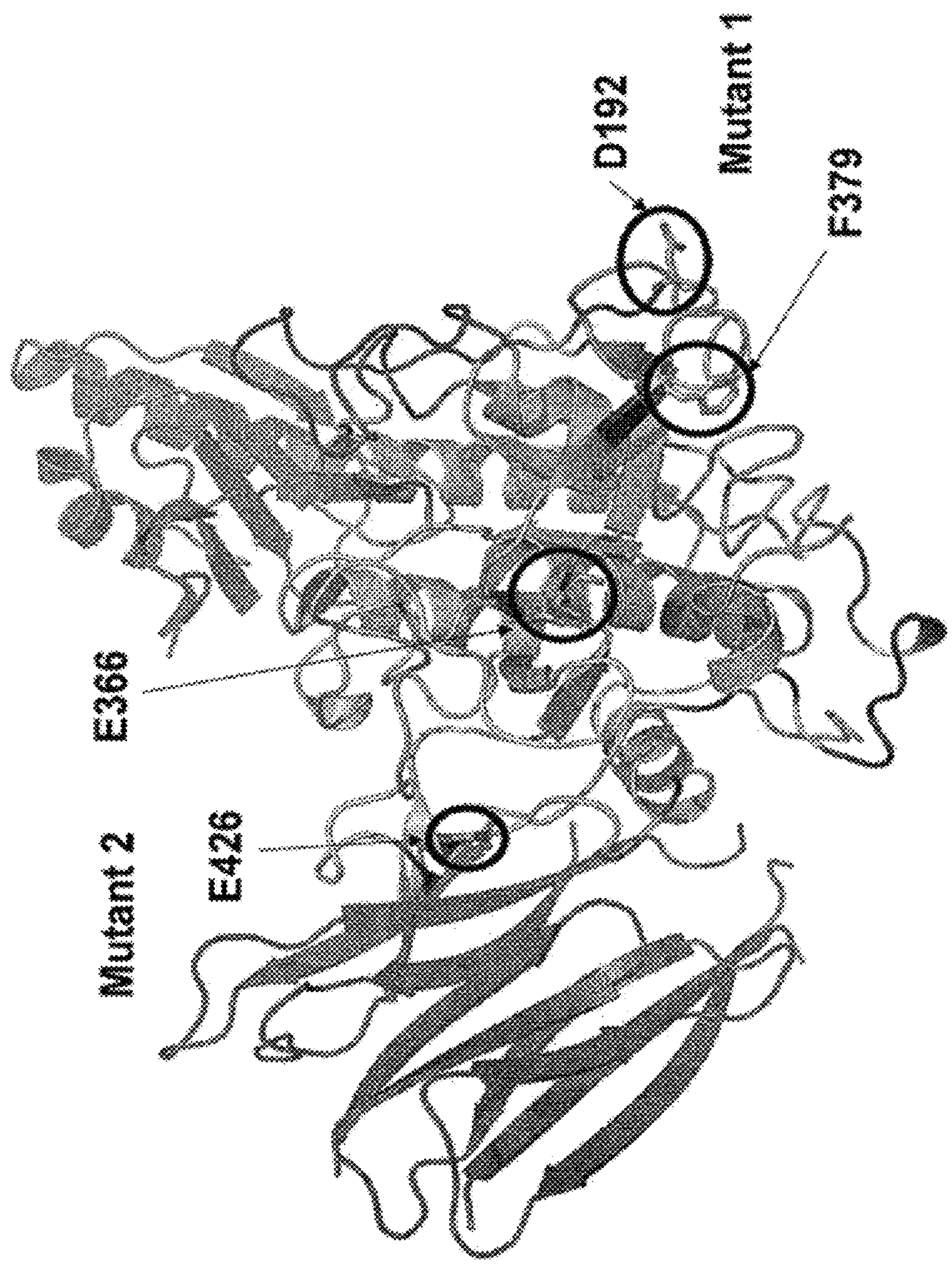
FIG. 5 illustrates the structure of human PCSK9 chimeric mutant #1 with D192G and F379Y substitutions and chimeric mutant #1 with E366K and E426M substitutions.

The ELISA results shown in FIG. 4 indicate the significant loss of binding of PCSk9 mutant #2 to antibody AX1DG and AX189, suggesting that AX1DG and AX189 bind to the epitope Bin 2. PCSK9 mutant #2 has the amino acid substitutions of E366K and E426M (FIG. 5).

Example 10

Epitope Mapping by Hydrogen-Deuterium Exchange Mass Spectrometry (DXMS)

In order to identify the various epitope regions of PCSK9 recognized by anti-PCSK9 antibodies, hydrogen deuterium exchange applied to PCSK9, followed by peptide digestion and mass spectrometry based on protocol of Wood and Hamuro (2001) and further developed and automated (Hamuro et al., 2003 *J. Biomolec. Tech.* 14:171-182; Coales et al., 2009 *Rapid Comm. Mass Spect.* 23:639-647. The multi-steps procedure is described in the following.

Antibody affinity column preparation: Antibody was immobilized by overnight incubation with cyanogen bromide activated Poros AL resin followed by washing with PBS using a filter funnel. The reaction was capped by resuspending the dried resin in ethanolamine solution for 2 hours followed washing with PBS using a filter funnel. The resin was resuspended in PBS then packed into a column. Column was equilibrated with PBS with 2 mM NaCl pH 7 in exchange buffer H at 3° C. All column injections and incubations were done using a syringe pump.

On-solution and off-column deuterium exchange: Exchange H buffer was prepared as PBS in water. Exchange D buffer was prepared as PBS in D2O. Exchange HD buffer was prepared as PBS in 50% D2O. All exchange steps were conducted at 3° C. The mAb column was cleaned with 0.8% formic acid and washed and equilibrated with exchange HD buffer. On-solution exchange of deuterons was initiated by mixing PCSK9 sample 1:1 with exchange D buffer and incubated for predetermined times. The mixture was then injected into mAb column and washed with exchange HD buffer. Off-column exchange was initiated by washing with exchange H buffer and incubating for predetermined times. Off-column exchange was quenched and PCSK9 was eluted using 0.8% formic acid. Fractions were collected and analyzed.

On- and off-column deuterium exchange: All exchange steps were conducted at 3° C. The mAb column was cleaned with 0.8% formic acid and washed and equilibrated with exchange HD buffer. PCSK9 in exchange H buffer was loaded onto the mAb column and washed with exchange H buffer. On-column exchange of deuterons was initiated by the injection of exchange HD buffer and incubating for predetermined times. Off-column exchange was performed and quenched as above. Fractions were collected and analyzed.

Full deuteration of PCSK9: PCSK9 was equilibrated in PBS prepared in D2O and incubated at 60° C. for 3 hours. This was cooled to room temperature and stored on ice. Fully deuterated PCSK9 was loaded onto an antibody affinity column in HD exchange buffer and washed in same buffer. Elution and analysis were same as above.

Peptide Analysis by Mass Spectrometry: Eluted PCSK9 was injected into an immobilized pepsin column for and then onto a C18 reversed-phase LC-MS to identify fragments. PCSK9 from eluted fractions was denatured and reduced in 2M urea, 1M TCEP, pH3, 0° C. for 2 minutes. The sample was then passed over immobilized pepsin column in buffer A (0.05% TFA in water). The peptic fragments were loaded onto a reversed phase trap column and desalted in buffer A. Peptic fragments were separated by a C18 column with a linear gradient of 13-40% Buffer B (95% acetonitrile, 5% water, 0.0025% TFA) in 23 minutes. Peptides were detected by mass spectrometry.

The shift in the masses of known peptic fragments detected by MS is used to determine the HD exchange level. The percent exchange is determined from ratio HD exchange of bound vs. unbound PCSK9 and indicates degree of epitope protection by the antibody. Percent deuteration change is cutoff at 5% as threshold to remove noise.

Figure 6:
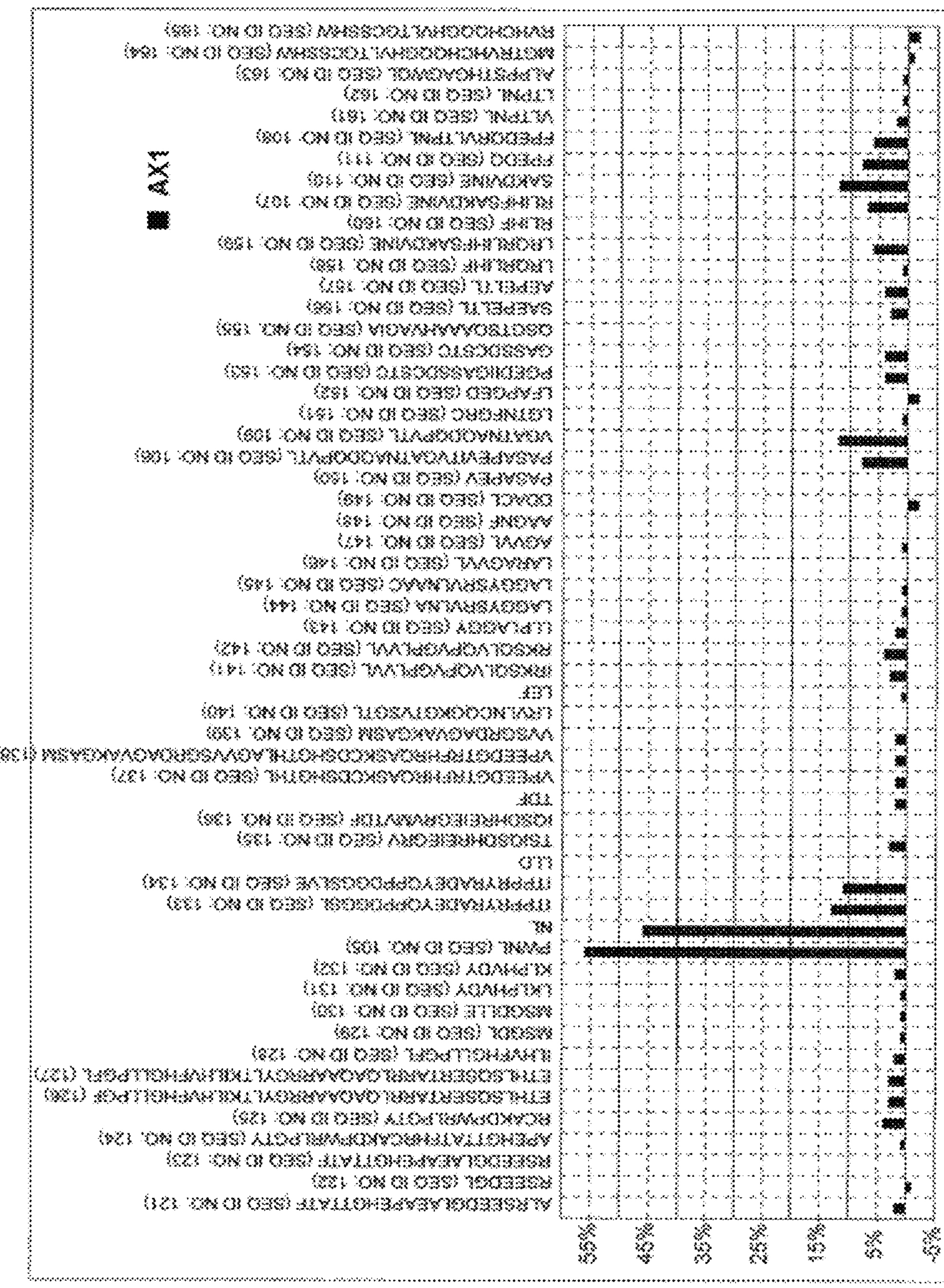
FIG. 6 illustrates the HD exchange profile for AX1 antibody. The PCSK9 peptic fragments that exhibit the greatest deuteration difference upon AX1 binding are 155-PWNL-158 (SEQ ID NO: 105), 327-PASAPEVITVGATNAQDQPVTL-348 (SEQ ID NO: 106), 414-RLIHFSAKDVINE-426 (SEQ ID NO: 107), and 429-FPEDQRVLTPNL-440 (SEQ ID NO: 108), where subfragments 157-NL-158, 336-VGATNAQDQPVTL-348 (SEQ ID NO: 109), 419-SAKDVINE-426 (SEQ ID NO: 110), and 429-FPEDQ-433 (SEQ ID NO: 111) appear to contain the epitope. There may be other weakly interacting sites but these are below the cutoff threshold (5%) and are likely due to indirect or local structural perturbations.
Figure 7:
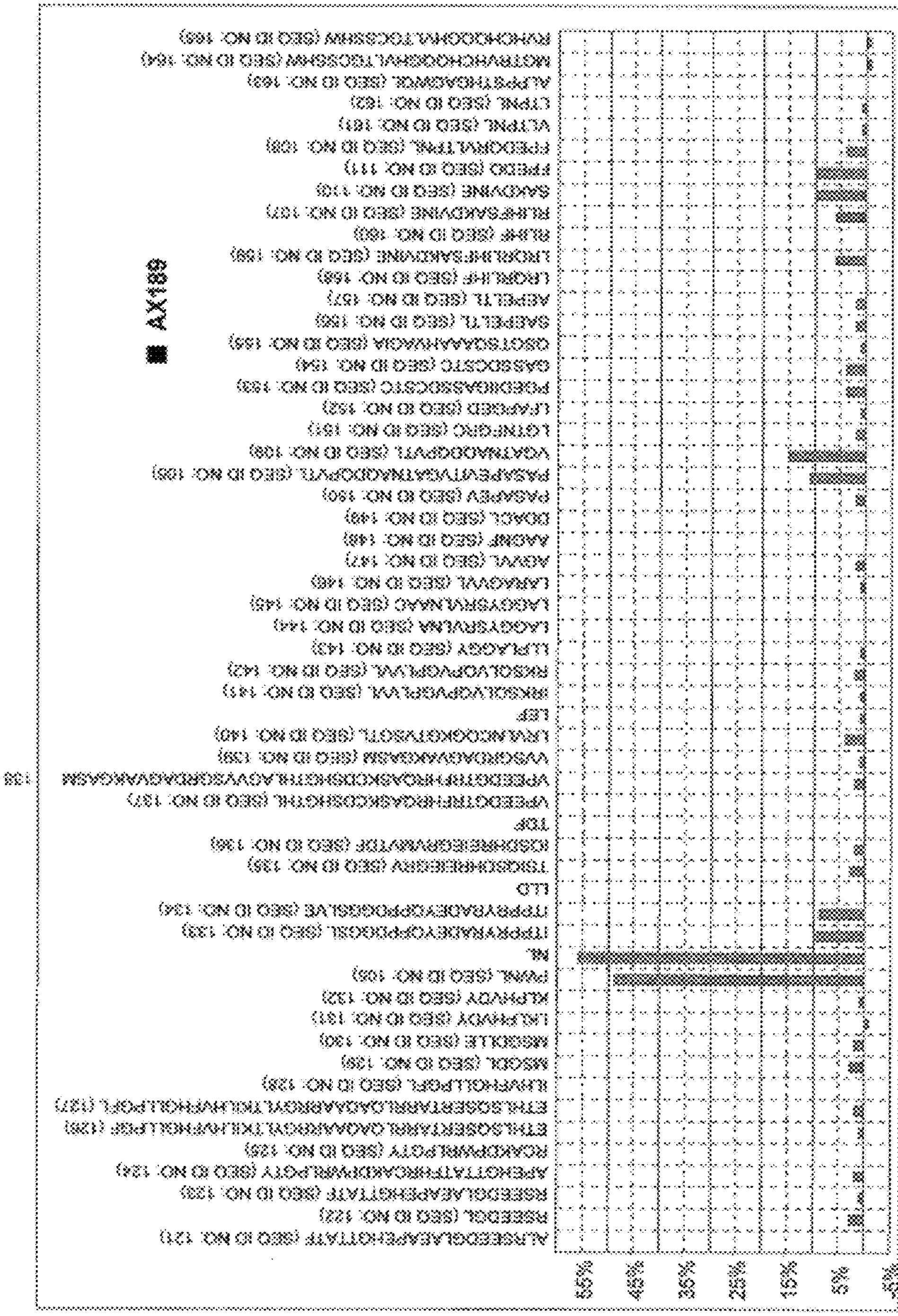
FIG. 7 illustrates the HD exchange profile for AX189 antibody. The PCSK9 peptic fragments that exhibit the greatest deuteration difference upon AX189 binding are 155-PWNL-158 (SEQ ID NO: 105), 327-PASAPEVITVGATNAQDQPVTL-348 (SEQ ID NO: 106), 414-RLIHFSAKDVINE-426 (SEQ ID NO: 107), and 429-FPEDQRVLTPNL- 440 (SEQ ID NO: 108), where subfragments 157-NL-158, 336-VGATNAQDQPVTL-348 (SEQ ID NO: 109), 419-SAKDVINE-426 (SEQ ID NO: 110), and 429-FPEDQ-433 (SEQ ID NO: 111) appear to contain the epitope. There may be other weakly interacting sites but these are below the cutoff threshold (5%) and are likely due to indirect or local structural perturbations.

As shown in FIG. 6 and FIG. 7, the PCSK9 peptic fragments that exhibit the greatest deuteration difference upon AX1 and AX189 binding are very similar. The fragments are 155-PWNL-158 (SEQ ID NO: 105), 327-PASAPEVITVGATNAQDQPVTL-348 (SEQ ID NO: 106), 414-RLIHFSAKDVINE-426 (SEQ ID NO: 107), and 429-FPEDQRVLTPNL-440 (SEQ ID NO: 108), where subfragments 157-NL-158, 336-VGATNAQDQPVTL-348 (SEQ ID NO: 109), 419-SAKDVINE-426 (SEQ ID NO: 110), and 429-FPEDQ-433 (SEQ ID NO: 111) appear to contain the epitope. There may be other weakly interacting sites but these are below the cutoff threshold (5%) and are likely due to indirect or local structural perturbations.

Figure 8:
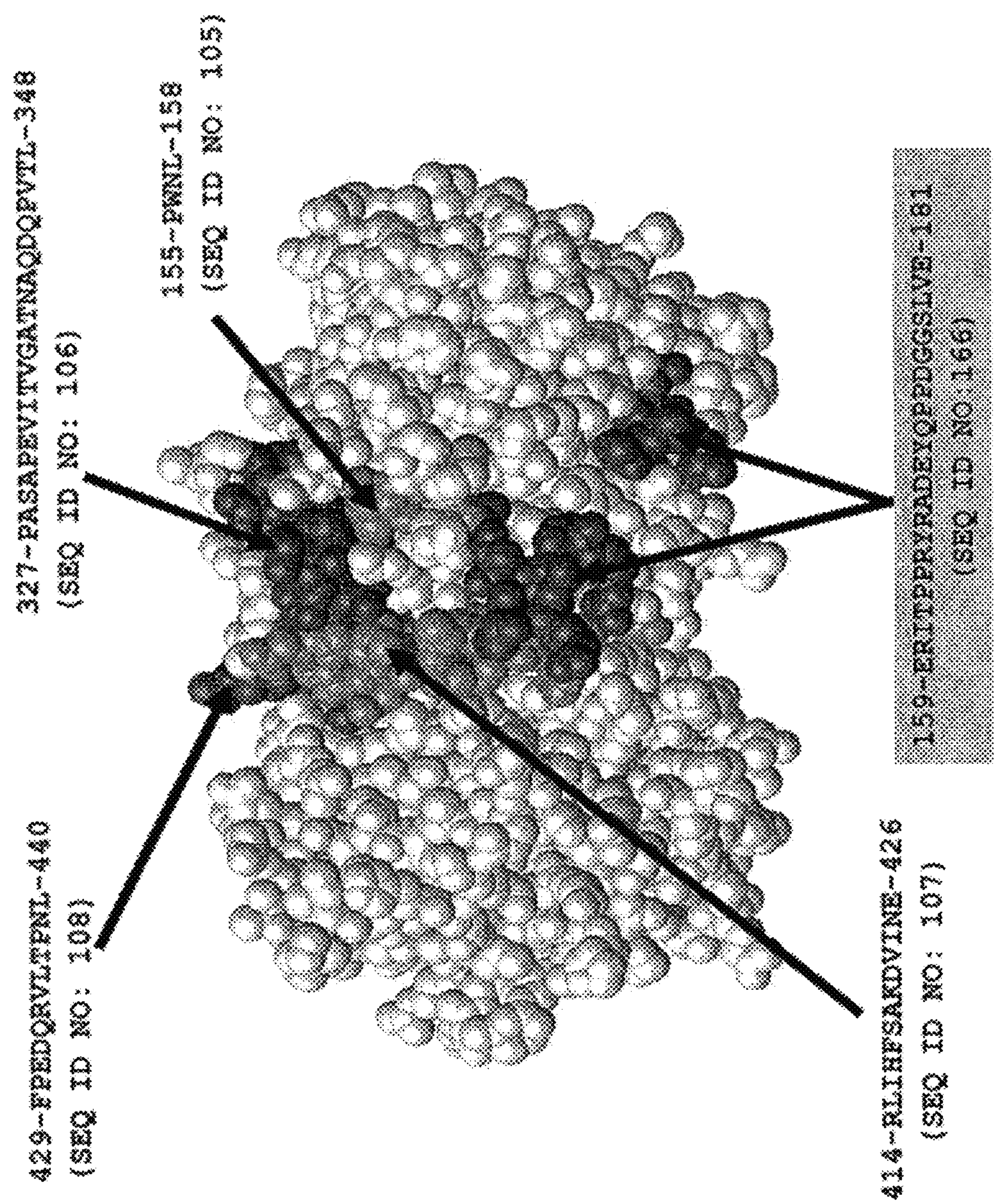
FIG. 8 shows PCSK9 (PDB: 2PMW) with the peptic fragments containing the AX1 and AX189 epitope highlighted. These fragments are: 155-PWNL-158 (SEQ ID NO: 105), 327-PASAPEVITVGATNAQDQPVTL-348 (SEQ ID NO: 106), 414-RLIHFSAKDVINE-426 (SEQ ID NO: 107), 429-FPEDQRVLTPNL-440 (SEQ ID NO: 108) and 159-ERITPPRYRADEYQPPDGGSLVE-181 (SEQ ID NO: 166).

FIG. 8 shows PCSK9 (PDB: 2PMW) with the peptic fragments containing the AX1 and AX189 epitope highlighted. These fragments are: 155-PWNL-158 (SEQ ID NO: 105), 327-PASAPEVITVGATNAQDQPVTL-348 (SEQ ID NO: 106), 414-RLIHFSAKDVINE-426 (SEQ ID NO: 107), 429-FPEDQRVLTPNL-440 (SEQ ID NO: 108) and 159-ERITPPRYRADEYQPPDGGSLVE-181 (SEQ ID NO: 166).

The HD exchange results are consistent with the data from computational docking and PCSK9 mutagenesis study in Example 9. The peptic fragments that exhibit the greatest deuteration difference are largely overlapped with the predicted bin2 fragments in Example 9.

Example 11

Fab Domain Thermostability

Thermostabilities of Fabs and Fab domains were determined from DSC experiments by analysis and deconvolution of excess heat capacity function in Origin 5.0. The melting transition temperatures (Tm) for Fabs or Fab domains are indicated in Table 6. The Tm of various Fabs and Fab domains range from 72 to 78° C. for AX1, AX9, AX189 and variant antibodies, which is consistent with well folded antibody Fab region.

TABLE 6

Thermostabilities of antibodies

| Fab/IgG | Fab Domain Tm, ° C. |
|---|---|
| AX1 | 77.0 |
| AX1-DG | 77.6 |
| AX9 | 73.7 |
| AX188 | 74.9 |
| AX189 | 76.3 |
| AX191 | 80.3 |
| AX192 | 75.7 |
| AX422 | 76.2 |
| AX424 | 76.4 |

Example 12

Selection of Antibodies Binding to AX1/AX189 Epitope on PCSK9

The antibodies with AX1/AX189 binding epitope can also be selected out from a phage display antibody library using EGF_AB peptide that compete with AX1/AX189 for binding. After binding of phage library to human PCSK9 coated on plate, the EGF_AB protein can be added to elute the binding phages. The individual clones from the EGF_AB eluted phage pool can then be screened against human PCSK9 and PCSK9 mutant #2. As shown in example 9, AX1/AX189 bind to human PCSK9 with high affinity, but very low binding to human PCSK9 mutant #2. The Fabs that bind to human PCSK9 can be subjected to a binding screening assay against PCSK9 mutant #2 protein, and the Fab with strong binding to human PCSK9 but weak or no binding to PCSK9 mutant #2 will share the AX1/AX189 binding epitope.

Example 13

Anti-PCSK9 Monoclonal Antibodies Expression and Purification from Mammalian Cells The DNA sequence encoding the Vk1 light chain variable region was amplified by polymerase chain reaction from plasmid template. The product of this amplification was cloned into plasmid pVUNSAGS-FB-LCK that had been previously digested with Fspl and Bmtl, using the InFusion cloning system (Clontech). The resulting plasmid was verified by DNA sequencing across the variable region. Endotoxin-free plasmid preparations were made using the Qiagen Endo-Free plasmid maxiprep kit. The DNA sequence encoding the heavy chain variable region of VH3 was amplified by polymerase chain reaction, and the amplified product was cloned into plasmid pV1 JNSA-BF-HCG2M4 that had been previously digested with Fspl and Bmtl. The resulting plasmid was verified by DNA sequencing across the variable region. Endotoxin-free plasmid preparations were made using the Qiagen Endo-Free plasmid maxiprep kit.

The plasmid DNA for heavy and light chain was mixed at 1:3, and co-tranfected into HEK293 cells. After 5-7 days culture, the supernatant was harvested and proceeded for Protein-A column purification. Briefly, the cell free supernatant was loaded on to protein-A column pre-equilibrated with three column volume of 20 mM Tris-HCl pH7.0 at a flow rate of 5.0 mL/min. The column was washed with three column volumes of the 20 mM Tris-HCl pH7.0 followed by a five column volume wash with 20 mM Tris-HCl pH7.0 containing 1M NaCl to remove the host cell proteins. The anti-PCSK9 antibody was eluted with five column volume of 100 mM Glycine, 100 mM Arginine pH 3.0 and immediately neutralized with 1M Tris-HCl pH8.0.

Example 14

Anti-PCSK9 Monoclonal Antibodies Expression and Purification from Glycoengineered *Pichia pastoris*

Anti-PCSK9 IgG2 monoclonal antibodies were expressed in glyco-engineered *Pichia pastoris* GET 5.0 host YGLY8316, which is capable of transferring terminal galactose at its complex N-linked glycan. Anti-PCSK9 heavy and light chains were codon optimized and expressed under methanol tightly inducible promoter AOX1 using *Saccharomyces cerevisiae* alpha mating factor presequence as secretion signal sequence. Anti-PCSK9 antibody from *Pichia pastoris* GFI 5.0 host YGLY8316 was captured from cell free supernatant media by affinity chromatography using MabSelect™ medium from GE Healthcare (Cat. #17-5199-01). The cell free supernatant was loaded on to Mabselect column (XK 16/20, 1.6 cm×10.0 cm) pre-equilibrated with three column volume of 20 mM Tris-HCl pH7.0 at a flow rate of 5.0 mL/min. The column was washed with three column volumes of the 20 mM Tris-HCl pH7.0 followed by a five column volume wash with 20 mM Tris-HCl pH7.0 containing 1M NaCl to remove the host cell proteins. The anti-PCSK9 antibody was eluted with five column volume of 100 mM Glycine, 100 mM Arginine pH 3.0 and immediately neutralized with 1M Tris-HCl pH8.0. AX1 and AX1DG antibody were well expressed in *Pichia*, yielding ca. 100-250 mg/L of protein in a ~40 hours induction process. For AX189, the expression yield reached to 450 mg/L in an engineered *Pichia* strain.

Strong Cation Exchange Chromatography employing Source 30S resin from GE Healthcare (Cat #17-1273-02) was used as the second step purification to remove the clipped species and aggregates. Mabselect pool of the anti-PCSK9 antibody was 5× diluted with 25 mM Sodium acetate pH5.0 and loaded on to the Source 30S column pre-equilibrated with three column volume of 25 mM Sodium acetate pH5.0. After loading, the column was washed with three column volume of the 25 mM Sodium acetate pH5.0 and elution was performed by developing a linear gradient over ten column volume ranging from 100 mM to 150 mM Sodium chloride in 25 mM Sodium acetate pH5.0. The fractions containing good assembled anti-PCSK9 antibody was pooled together. The Source 30S pooled fractions that contained the anti-PCSK9 antibody was buffer exchanged into the formulation buffer containing 6% Surcose, 100 mM Arginine, 100 mM Histidine pH6.0 (HyClone® Cat # RR10804.02) and sterile filtered using 0.2 μm PES (PolyEtherSulfone) membrane filter and stored @4° C. until release.

Example 15

Biacore Assay for Affinity Measurement

To determine the binding affinity of Fab to PCSK9, Fab capture-based Biacore assay was developed. First, goat anti-Fab IgGs were immobilized onto CM5 chip by amine coupling as described above. The anti-Fab IgGs were diluted to 200 μg/ml in pH 5/10 mM Acetate solution, and injected onto the NHS/EDC activated surface to achieve an immobilization level of ~10,000 RU, followed with surface inactivation by injection of Ethanolamine. Then Fab samples at concentration of 2 μg/ml in HBS-P running buffer were injected for 3 minutes at flow speed of 20 μl/min, followed with K-injection (3 minutes injection for association and 6 minutes for dissociation) of PCSK9 at concentration of 10 to 100 nM. The sensor chip surface was regenerated by 30 second injection of 100 mM phosphoric acid. The binding sensorgrams were fitted with 1:1 Langmuir binding model to determine the binding affinity. The Fab affinities of AX1, Ax189 and other variants are shown in table 7.

TABLE 7

Fab affinity against human PCSK9

| Fabs | Kon | koff | Kd (nM) |
|---|---|---|---|
| AX1 | 7.27E+04 | 4.36E−04 | 6.0 |
| AX9 | 8.71E+04 | 2.08E−03 | 23.9 |
| AX188 | 7.48E+04 | 1.91E−04 | 2.6 |
| AX189 | 8.86E+04 | 5.55E−04 | 6.3 |
| AX191 | 3.23E+04 | 1.67E−04 | 5.2 |
| AX193 | 1.76E+05 | 1.23E−03 | 7.0 |
| AX194 | 1.37E+05 | 8.39E−04 | 6.1 |
| AX195 | 5.21E+04 | 5.13E−04 | 9.9 |
| AX196 | 1.07E+05 | 1.96E−03 | 18.3 |
| AX197 | 6.55E+04 | 3.64E−04 | 5.6 |
| AX198 | 1.28E+05 | 5.47E−04 | 4.3 |
| AX199 | 3.26E+04 | 8.54E−04 | 26.2 |
| AX200 | 6.36E+04 | 6.08E−04 | 9.6 |
| AX421 | 4.39E+04 | 2.94E−04 | 6.7 |
| AX422 | 7.58E+04 | 3.14E−04 | 4.1 |
| AX423 | 3.77E+04 | 1.24E−03 | 32.8 |
| AX424 | 6.96E+04 | 2.95E−04 | 4.2 |
| AX425 | 2.70E+04 | 4.76E−04 | 17.6 |

The Fabs which showed functional efficacy in the cell-base assays were converted into IgG molecules. The affinities of those IgG molecules were also measured by Biacore assay. Briefly, anti-human IgG monoclonal antibody form Human Antibody Capture Kit provided by Biacore was immobilized on CM5 chips at a level of 8000 to 10000 RU. The IgG samples at concentration of ~0.4 μg/ml was injected onto sensor chip for 2 minutes at a flow rate of 20 μl/min, then PCSK9 proteins at 5 concentrations (3.75 to 60 nM) were injected onto IgG captured flow cell for binding kinetic analysis. After each round injection, the sensor chip surface was regenerated by 30 second injection of 3M Magnesium Chloride. The affinities of AX1, AX189 and other variants are shown in table 8.

TABLE 8

IgG Affinity against PCSK9

| IgG/antigen | Kon | koff | Kd (M) |
|---|---|---|---|
| AX1-IgG2 to human PCSK9 | 6.63E+04 | 3.81E−04 | 5.75E−09 |
| AX1-IgG2 to rhesus PCSK9 | 1.26E+05 | 5.30E−04 | 4.20E−09 |
| AX1-DG-IgG2 to human PCSK9 | 6.40E+04 | 2.95E−04 | 4.61E−09 |
| AX1-DG-IgG2 to rhesus PCSK9 | 1.01E+05 | 3.65E−04 | 3.60E−09 |
| AX9-IgG2 to human PCSK9 | 1.66E+05 | 3.42E−03 | 2.06E−08 |
| AX9-IgG2 to rhesus PCSK9 | 3.35E+05 | 2.95E−03 | 8.82E−09 |
| AX188-IgG2 to human PCSK9 | 2.65E+05 | 2.32E−04 | 8.73E−10 |
| AX188-IgG2 to rhesus PCSK9 | 2.96E+05 | 1.35E−04 | 4.54E−10 |
| AX189-IgG2 to human PCSK9 | 3.29E+05 | 6.04E−04 | 1.84E−09 |
| AX189-IgG2 to rhesus PCSK9 | 3.96E+05 | 4.90E−04 | 1.24E−09 |
| AX191-IgG2 to rhesus PCSK9 | 1.85E+05 | 1.16E−04 | 6.25E−10 |
| AX191-IgG2 to human PCSK9 | 1.87E+05 | 1.58E−04 | 8.46E−10 |
| AX422-IgG2 to human PCSK9 | 2.60E+05 | 5.50E−04 | 2.12E−09 |
| AX424-IgG2 to human PCSK9 | 2.37E+05 | 5.11E−04 | 2.16E−09 |
| AX422-IgG2 to rhesus PCSK9 | 2.46E+05 | 4.84E−04 | 1.96E−09 |
| AX424-IgG2 to rhesus PCSK9 | 1.68E+05 | 3.96E−04 | 2.36E−09 |

Example 16

PCSK9-LDLR TR-FRET Assay

This assay is a variant of the one described in Fisher et al., 2007 *J. Biol. Chem.* 282:20502-20512. AlexaFluor647-labeled PCSK9 (final concentration 10 nM) was combined with varying amounts of antibody and to this was added Eu(8044)-labeled LDLR ectodomain to a final concentration of ~4 nM (sufficient to give ~20,000 counts at $Fl_{620}$ nM on the Rubystar) in 10 mM HEPES (pH 7.4), 150 mM NaCl, 0.1 mM $CaCl_2$, 0.05% (w/v) BSA in a total volume of 50 μl using 96 well black Dynatech U bottom plates. After at least 90 minutes of equilibration, samples were read in a Rubystar reader (BMG Corp.) using 20 flashes per well, a 50 μsec integration delay, and a 200 μsec total integration time. Data were expressed as the ratio of ($Fl_{665}/Fl_{620}\times10000$) and an $IC_{50}$ for each antibody was determined from the inflection point of a sigmoidal dose-response curve using a standard four parameter fit.

Figure 9:
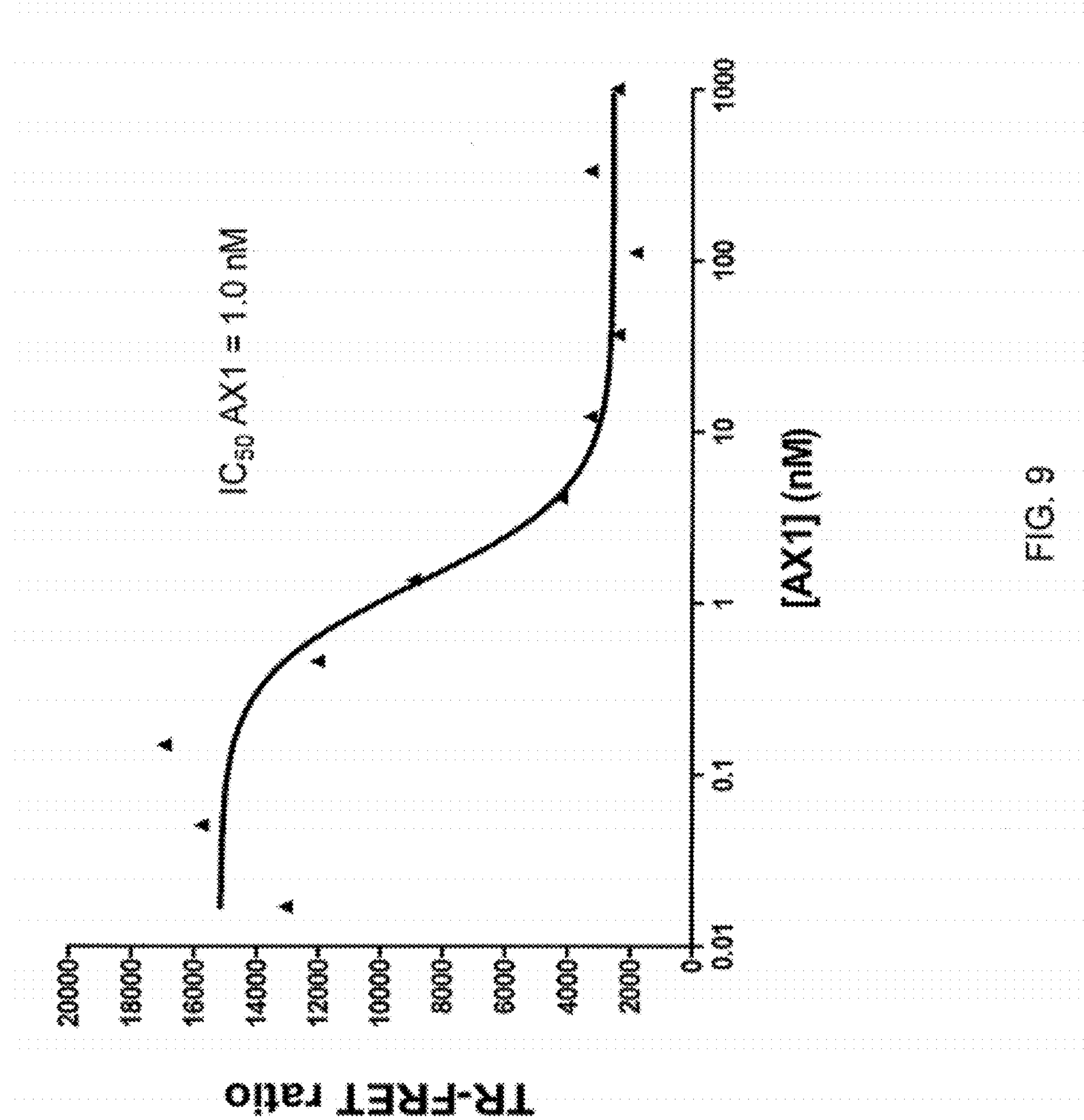
FIG. 9. Monoclonal antibody AX1 IgG2 was tested in a TR-FRET format for inhibition of the interaction of AF647 labeled wild type human PCSK9 and Eu8044 labeled LDL receptor.

FIG. 9 illustrates the result of AX1 antibody. Monoclonal antibody AX1 IgG2 was tested in a TR-FRET format for inhibition of the interaction of AF647 labeled wild type human PCSK9 and Eu8044 labeled LDL receptor. IC50 for AX1 is 1.0 nM.

Figure 10:
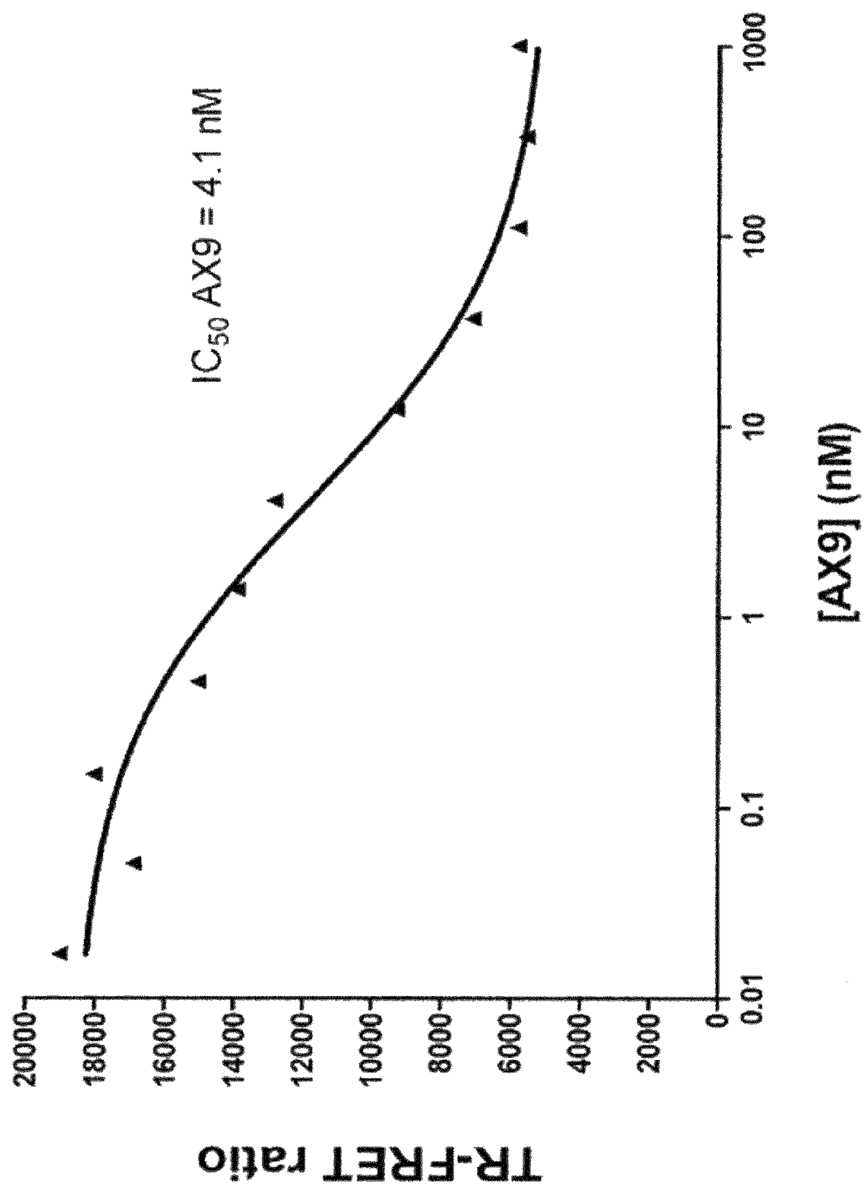
FIG. 10. Monoclonal antibody AX9 IgG2 was tested in a TR-FRET format for inhibition of the interaction of AF647 labeled wild type human PCSK9 and Eu8044 labeled LDL receptor.

FIG. 10 illustrates the result of AX9 antibody. Monoclonal antibody AX9 IgG2 was tested in a TR-FRET format for inhibition of the interaction of AF647 labeled wild type human PCSK9 and Eu8044 labeled LDL receptor. IC50 for AX9 is 4.1 nM.

Figure 11:
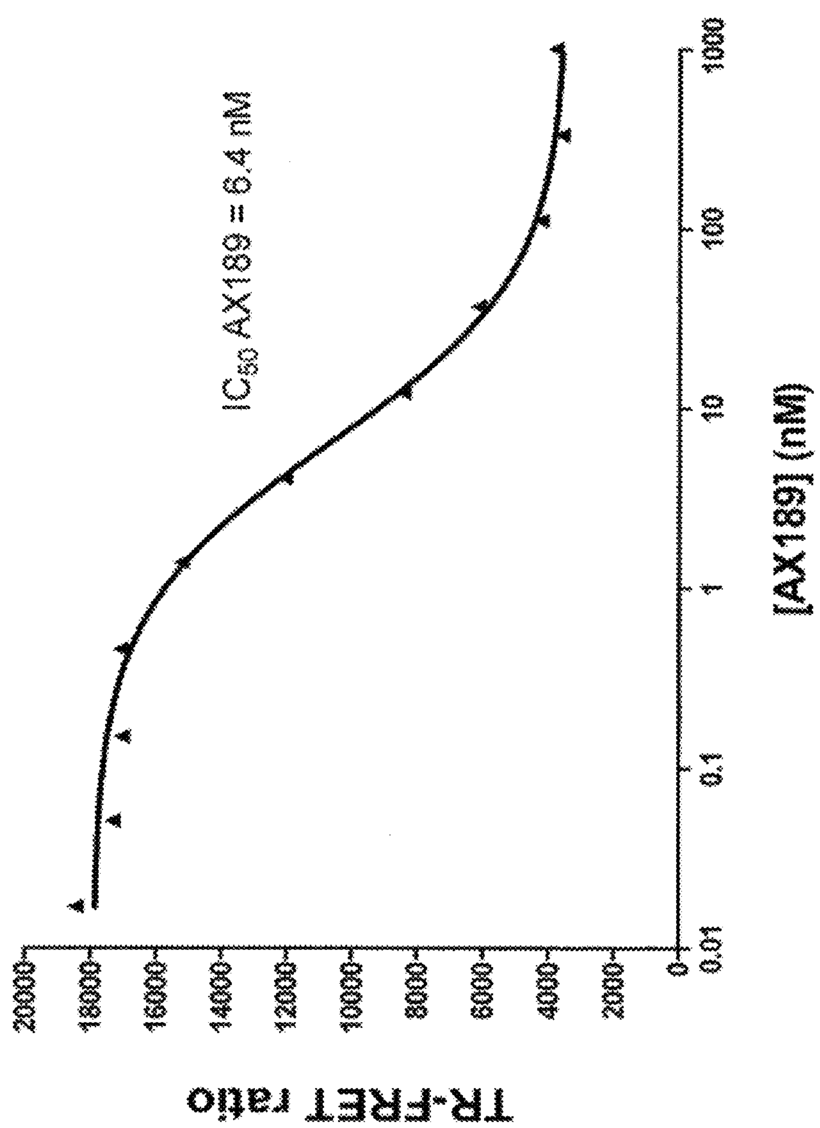
FIG. 11. Monoclonal antibody AX189 IgG2 was tested in a TR-FRET format for inhibition of the interaction of AF647 labeled wild type human PCSK9 and Eu8044 labeled LDL receptor.

FIG. 11 illustrates the result of AX189 antibody. Monoclonal antibody AX189 IgG2 was tested in a TR-FRET format for inhibition of the interaction of AF647 labeled wild type human PCSK9 and Eu8044 labeled LDL receptor. IC50 for AX189 is 6.4 nM.

Figure 12:
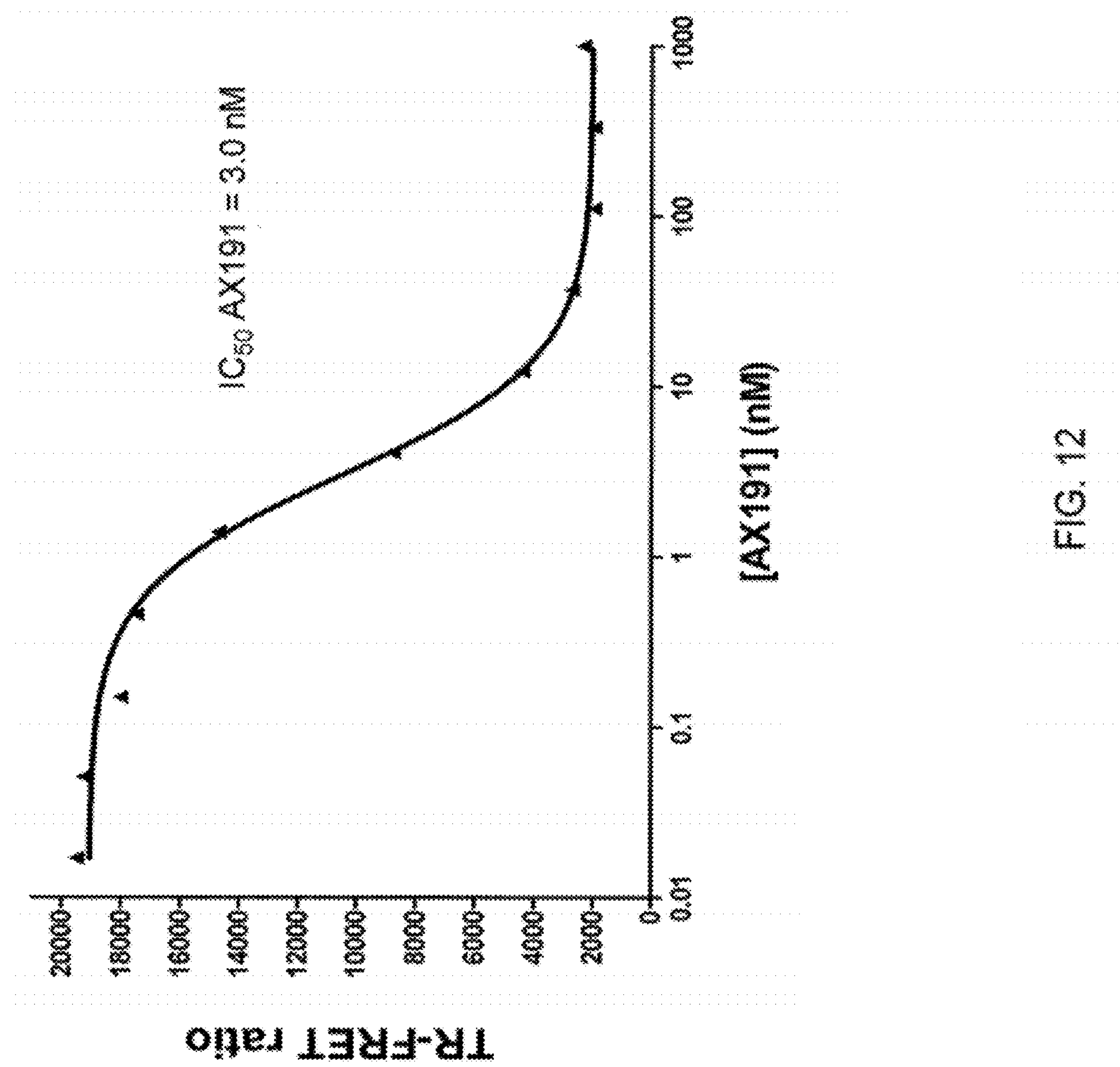
FIG. 12. Monoclonal antibody AX191 IgG2 was tested in a TR-FRET format for inhibition of the interaction of AF647 labeled wild type human PCSK9 and Eu8044 labeled LDL receptor.

FIG. 12 illustrates the result of AX191 antibody. Monoclonal antibody AX191 IgG2 was tested in a TR-FRET format for inhibition of the interaction of AF647 labeled wild type human PCSK9 and Eu8044 labeled LDL receptor. IC50 for AX191 is 3.0 nM.

Example 17

Exopolar Assay

Effects of Exogenous PCSK9 on Cellular LDL Uptake

On day 1, 30,000 HepG2 or HEK cells/well were plated in a 96 well polyD-lysine coated plate. On day 2, the media was switched to no-serum containing DMEM media. On day 3, the media was removed and the cells were washed with Opti-MEM. Purified PCSK9 was added in 100 μl of DMEM media containing LPDS and dI-LDL. The plates were incubated at 37° C. for 6.5 hours. The cells were washed quickly in TBS containing 2 mg/ml BSA; then washed in TBS-BSA for 2 minutes; and then washed twice (but quickly) with TBS. The cells were lysed in 100 μl RIPA buffer. Fluorescence was then measured in the plate using an Ex 520, Em 580 nm. The total cellular protein in each well was measured using a BCA Protein Assay and the fluorescence units were then normalized to total protein.

The Exopolar Assay is effective for characterizing variant effects on LDL uptake; see Table 9 below illustrating how the potencies of PCSK9 mutants correlate with plasma LDL-cholesterol in the Exopolar Assay.

TABLE 9

| Mutation | Gain/Loss | LDL-C (mg/dI) | EC-50 (nM) Exopolar |
|---|---|---|---|
| S127R | Gain | 277 | 14 |
| D374Y | Gain | 388 | 1.3 |
| Wild-type | | 140 | 51 |
| R46L | Loss | 116 | 78 |

AX1, Ax189 and their variants in table 10 inhibited the effect of PCSK9 on LDL uptake in a dose-dependent way, with IC50 (human PCSK9) ranged from 5~25.5 nM.

TABLE 10

Inhibition of PCSK9 on LDL uptake by Fabs and IgGs

| | | | IgG IC50 (nM) | |
|---|---|---|---|---|
| Fabs | Fab IC50 (nM) human PCSK9 | IgGs | human PCSK9 | rhesus PCSK9 |
| AX1 | 146.0 | Ax1-IgG2 | 7 | 11.2 |
| AX1DG | | Ax1DG-IgG2 | 7.4 | |
| AX9 | 287.4 | AX9 IgG1 | 10.7 | 30.3 |
| AX9 | | AX9 IgG2 | 25.5 | 28.6 |
| AX188 | 15.8 | AX188 IgG2 | 24.8 | 18.7 |
| AX189 | 31.0 | AX189 IgG2 | 9.4 | 9 |
| AX191 | 13.0 | AX191 IgG2 | 8.7 | 6.6 |
| AX422 | N/A | AX189 IgG2 | 5.0 | N/A |
| AX424 | N/A | AX191 IgG2 | 6.0 | N/A |

Figure 13:
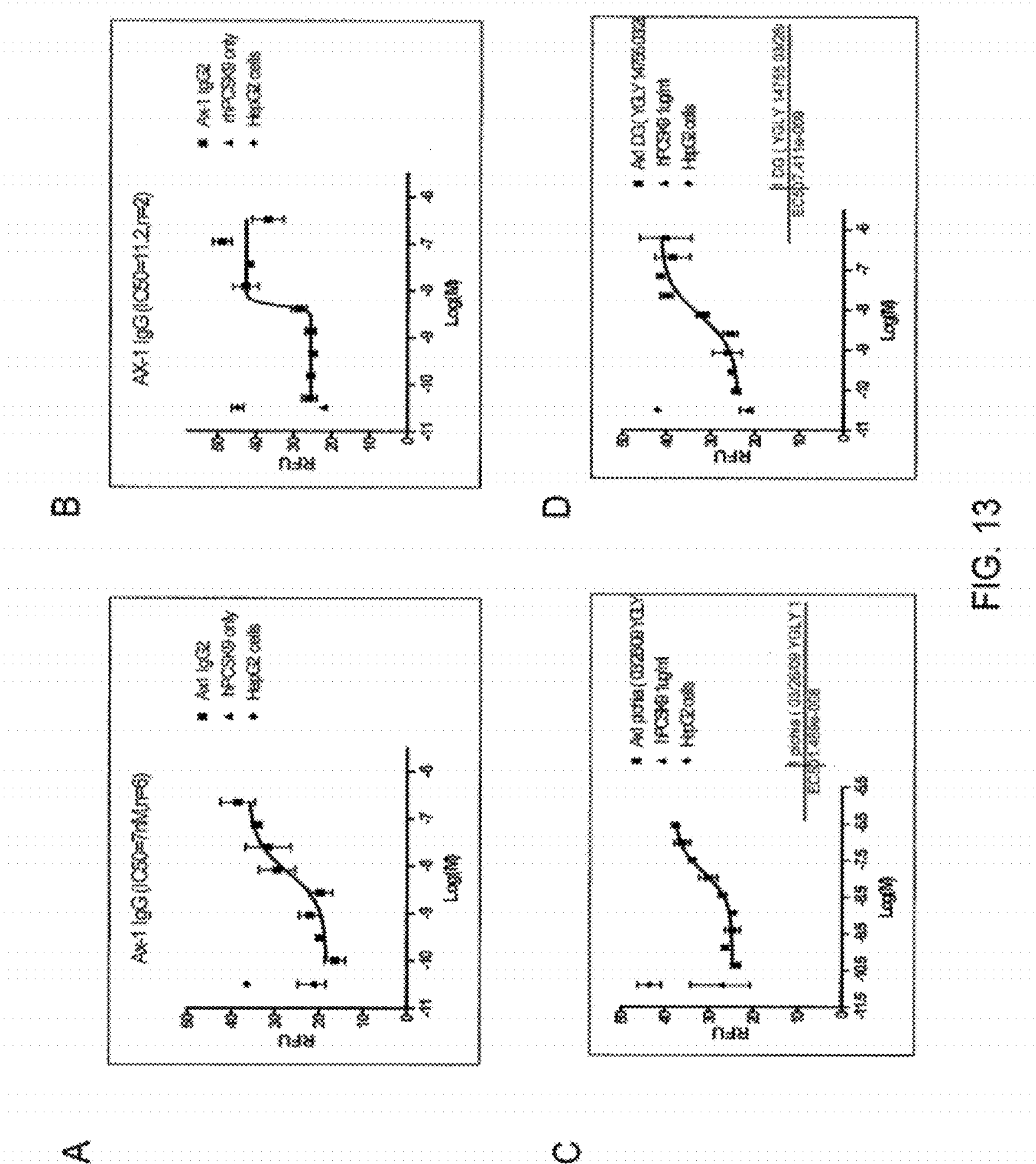
FIGS. 13A-D show antibody IgG (A and B: Ax-1 IgG from HEK cells, C and D: AX-1 IgG from *Pichia*) dose-dependent inhibition of human (A, C and D) and rhesus (B) PCSK9-dependent loss of cellular LDL-uptake. Ax-1 IgG can inhibit the effect of PCSK9 on cellular LDL uptake. IC50s for Ax-1 IgG are 7 nM (n=6) and 11.2 nM (n=2) for human and rhesus PCSK9 protein, respectively.

FIG. 13 shows antibody IgG's (A and B: Ax-1 IgG from HEK cells, C and D: AX-1 IgG from *Pichia*) dose-dependent inhibition of human (A, C and D) and rhesus (B) PCSK9-dependent loss of cellular LDL-uptake. Each experiment had two controls: (i) a cell only control, showing the basal level of cellular LDL uptake, and (ii) a PCSK9 (1 μg/ml) control which shows the level of PCSK9-dependent loss of LDL-uptake. The titration experiments which contain Ax-1 IgG and PCSK9 were done at a fixed concentration of PCSK9 (1 μg/ml) and increasing concentrations of antibodies shown in the graphs. As shown, Ax-1 IgG inhibited the effect of PCSK9 on cellular LDL uptake. IC50s for Ax-1 IgG are 7 nM (n=6) and 11.2 nM (n=2) for human and rhesus PCSK9 protein, respectively.

FIG. 14 illustrates Ax-9 IgG's dose-dependent inhibition of human (A) and rhesus (B) PCSK9-dependent loss of cellular LDL-uptake. Ax-9 IgG cross-reacts with human and rhesus PCSK9. Each experiment had two controls: (i) a cell only control, showing the basal level of cellular LDL uptake, and (ii) a PCSK9 (1 μg/ml) control which shows the level of PCSK9-dependent loss of LDL-uptake. The titration experiments which contain Ax-9IgG and PCSK9 were done at a fixed concentration of PCSK9 (1 μg/ml) and increasing concentrations of antibodies shown in the graphs. As shown, Ax-9 IgG inhibited the effect of PCSK9 on cellular LDL uptake. IC50s for Ax-9 IgG are 25.5 nM (n=3) and 28.6 nM for human and rhesus PCSK9 protein, respectively.

FIG. 15 illustrates Ax-189 IgG's dose-dependent inhibition of human (A) and rhesus (B) PCSK9-dependent loss of cellular LDL-uptake. Ax-189 IgG cross-reacts with human and rhesus PCSK9. Each experiment had two controls: (i) a cell only control, showing the basal level of cellular LDL uptake, and (ii) a PCSK9 (1 μg/ml) control which shows the level of PCSK9-dependent loss of LDL-uptake. The titration experiments which contain Ax-189 IgG and PCSK9 were done at a fixed concentration of PCSK9 (1 μg/ml) and increasing concentrations of antibodies shown in the graphs. As shown, Ax-189 IgG inhibited the effect of PCSK9 on cellular LDL uptake. IC50s for Ax-189 IgG are 9.4 nM (n=6) and 9 nM (n=5) for human and rhesus PCSK9 protein, respectively.

Figure 16:
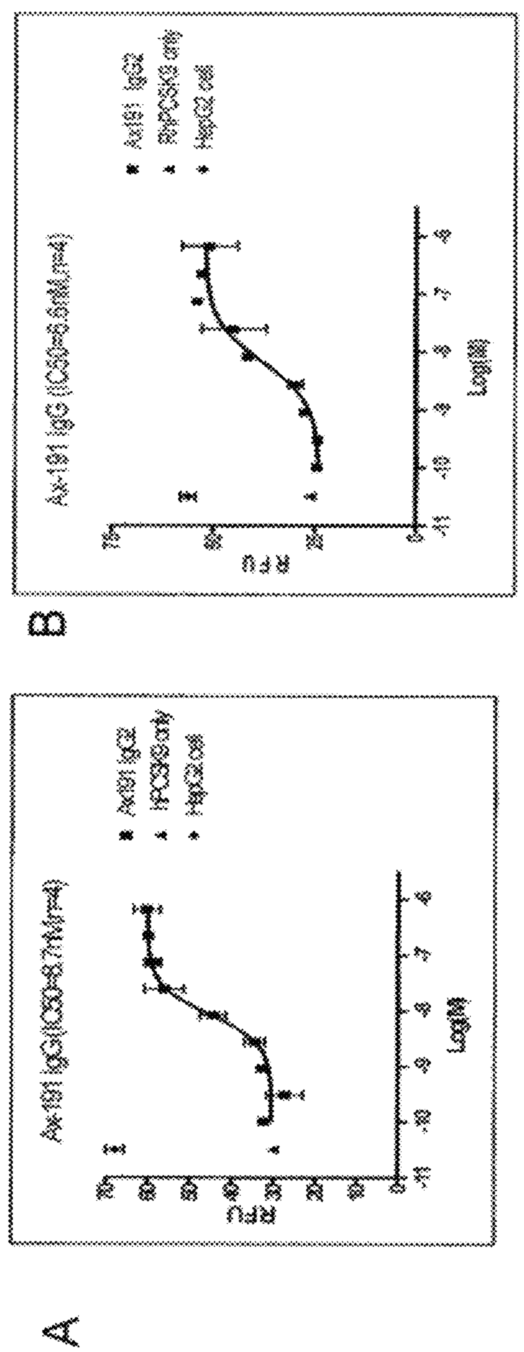
FIGS. 16A-B illustrates Ax-191 IgG's dose-dependent inhibition of human (A) and rhesus (B) PCSK9-dependent loss of cellular LDL-uptake. Ax-191 IgG can inhibit the effect of PCSK9 on cellular LDL uptake. IC50s for Ax-191 IgG are 8.7 nM (n=4) and 6.6 nM (n=4) for human and rhesus PCSK9 protein, respectively.
Figure 17:
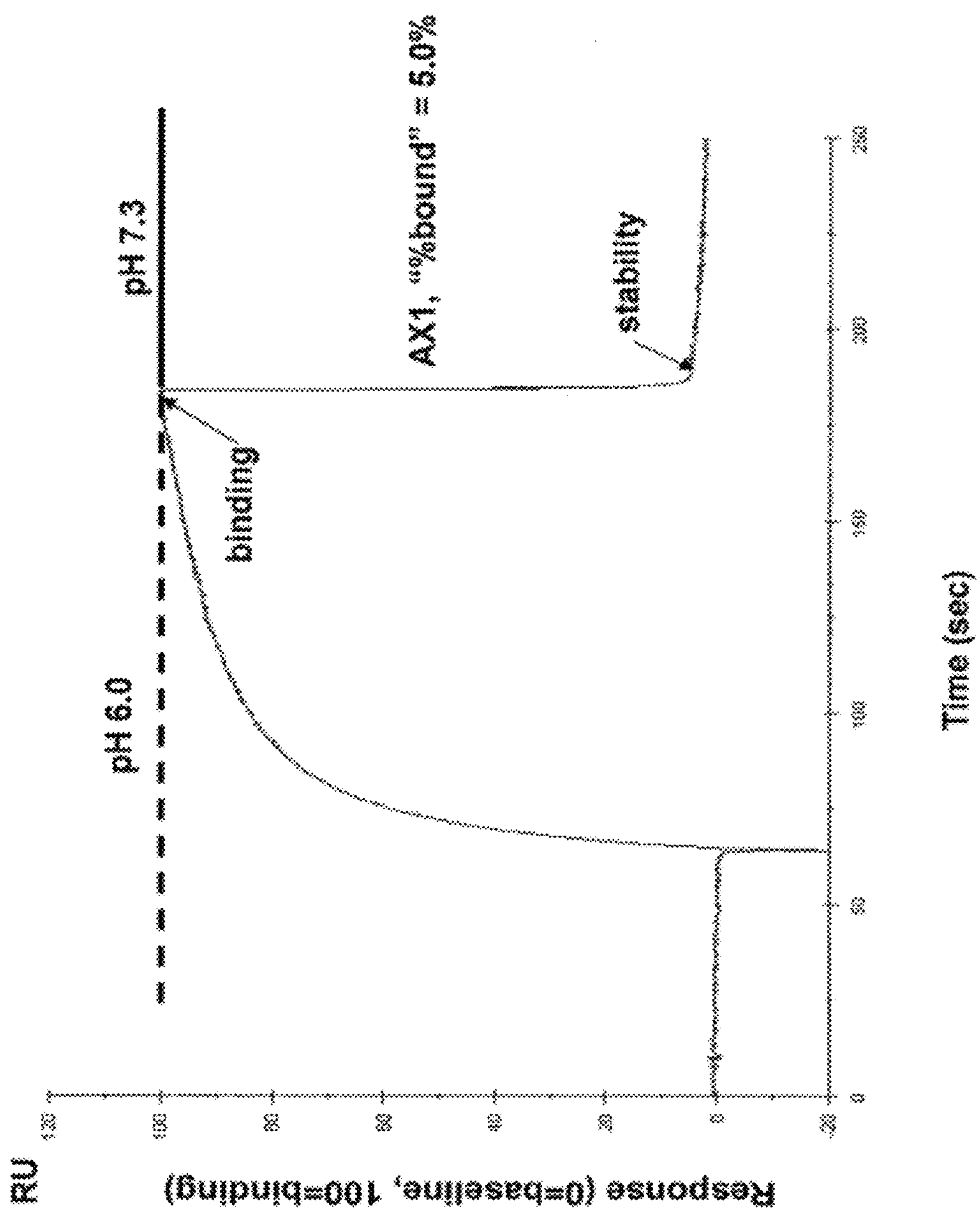
FIG. 17 illustrates binding of AX1 to immobilized human FcRn with Biacore. The sensorgram shows both binding at pH 6.0 and dissociation at pH 7.3. A report point (Stability) was inserted at 5 seconds after the end of pH 6.0 binding and 5% bound was calculated as RUStability/RUBinding (%)
Figure 18:
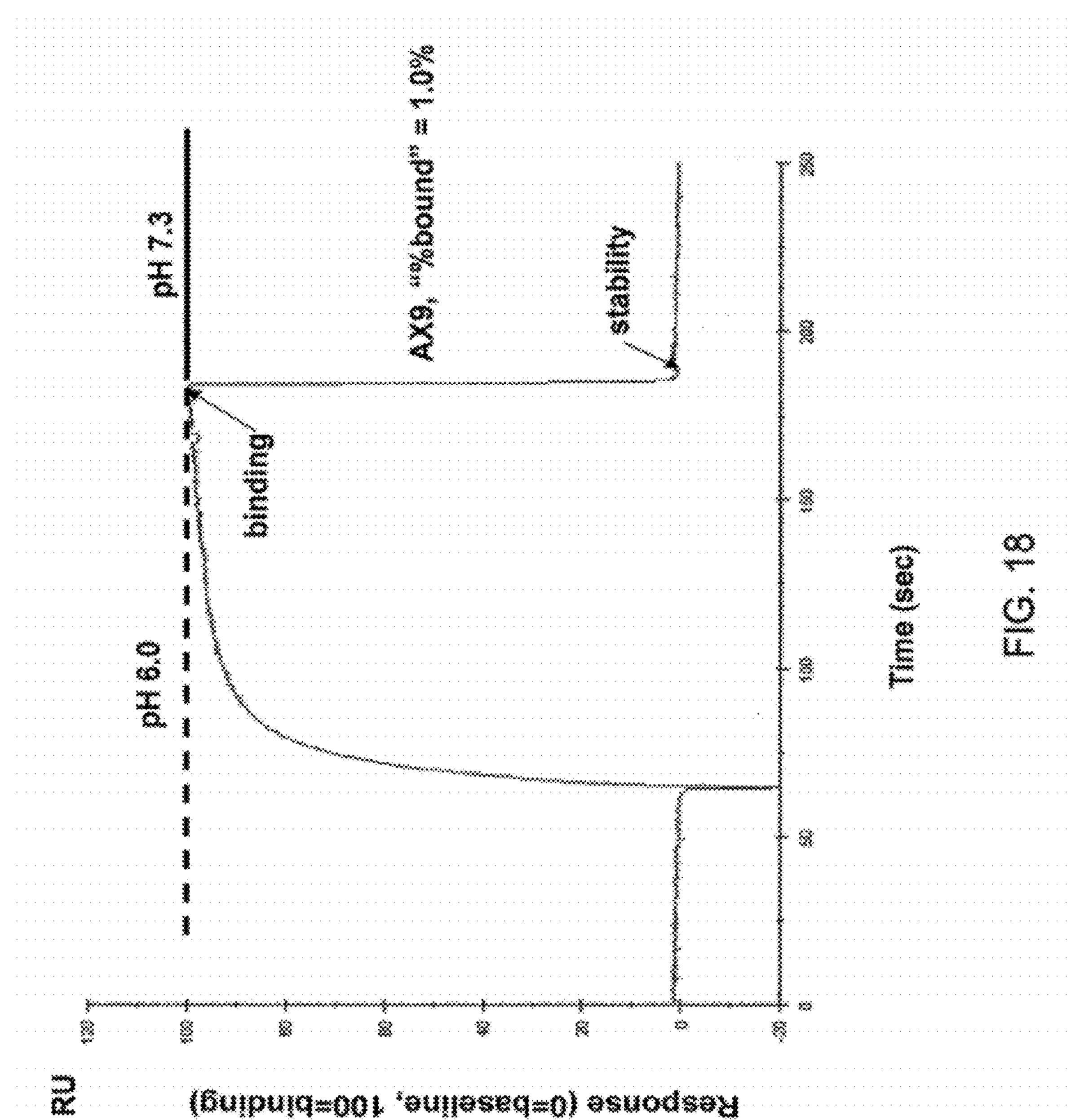
FIG. 18 illustrates binding of AX9 to immobilized human FcRn with Biacore. The sensorgram shows both binding at pH 6.0 and dissociation at pH 7.3. A report point (Stability) was inserted at 5 seconds after the end of pH 6.0 binding and 1% bound was calculated as RUStability/RUBinding (%)
Figure 19:
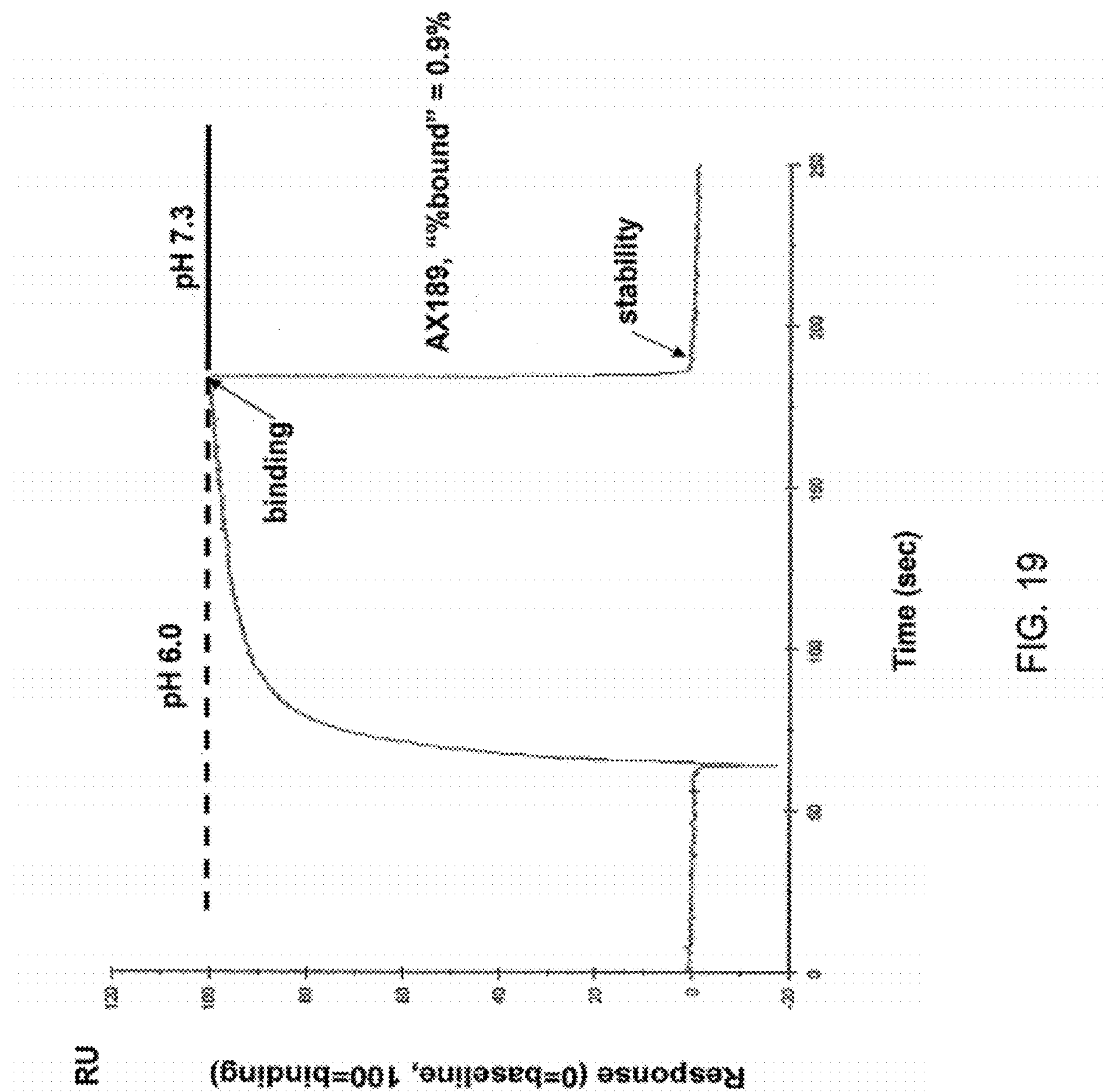
FIG. 19 illustrates binding of AX189 to immobilized human FcRn with Biacore. The sensorgram shows both binding at pH 6.0 and dissociation at pH 7.3. A report point (Stability) was inserted at 5 seconds after the end of pH 6.0 binding and 0.9% bound was calculated as RUStability/RU-Binding (%)
Figure 20:
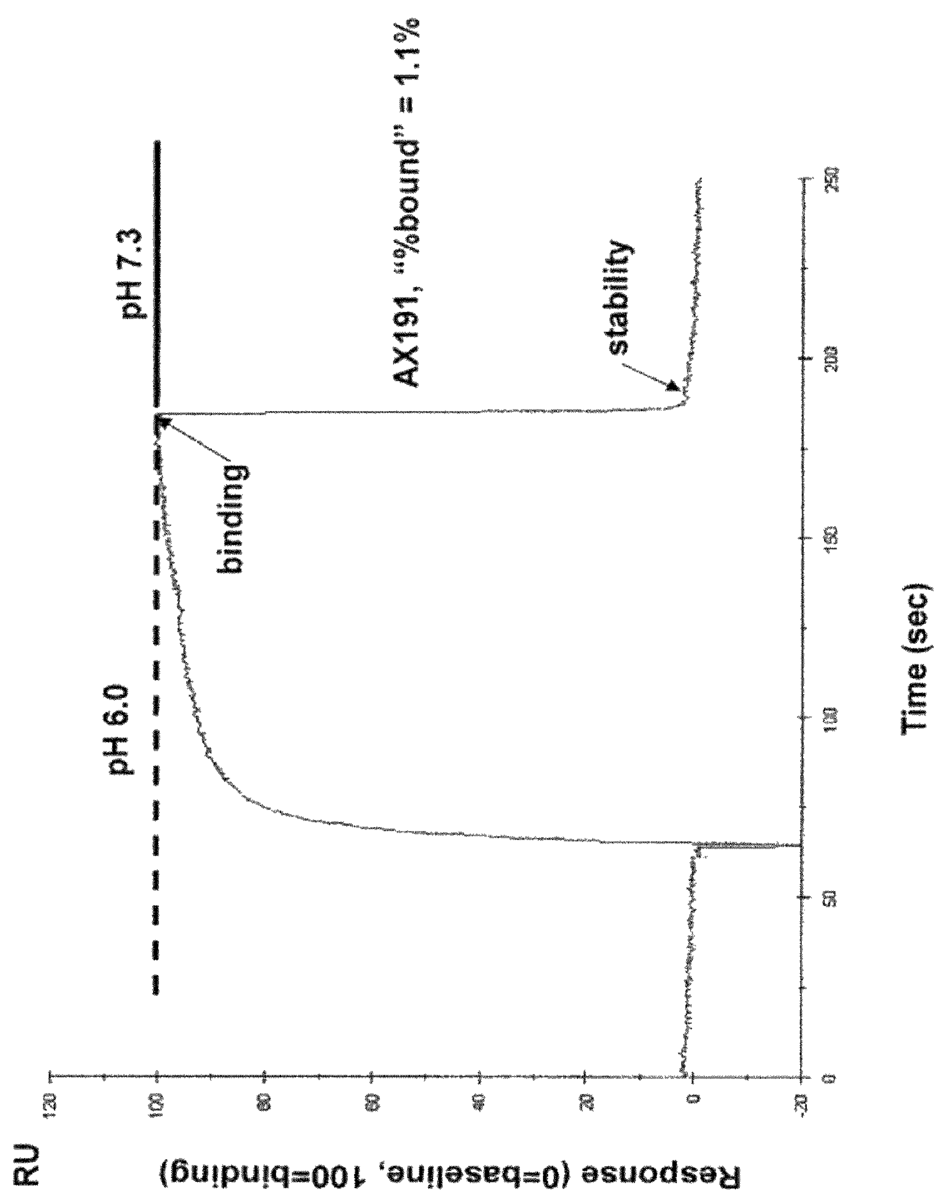
FIG. 20 illustrates binding of AX191 to immobilized human FcRn with Biacore. The sensorgram shows both binding at pH 6.0 and dissociation at pH 7.3. A report point (Stability) was inserted at 5 seconds after the end of pH 6.0 binding and 1.1% bound was calculated as RUStability/RU-Binding (%)

FIG. 16 illustrates Ax-191 IgG's dose-dependent inhibition of human (A) and rhesus (B) PCSK9-dependent loss of cellular LDL-uptake Ax-191 IgG cross-reacts with human and rhesus PCSK9. Each experiment had two controls: (i) a cell only control, showing the basal level of cellular LDL uptake, and (ii) a PCSK9 (1 μg/ml) control which shows the level of PCSK9-dependent loss of LDL-uptake. The titration experiments which contain Ax-191 IgG and PCSK9 were done at a fixed concentration of PCSK9 (1 μg/ml) and increasing concentrations of antibodies shown in the graphs. As shown, Ax-191 IgG inhibited the effect of PCSK9 on cellular LDL uptake. IC50s for Ax-191 IgG are 8.7 nM (n=4) and 6.6 nM (n=4) for human and rhesus PCSK9 protein, respectively.

Example 18

In Vitro FcRn Dissociation Assay

Our internal data showed that monoclonal antibodies with identical Fc sequences but different Fab domains can bind FcRn with considerable differences. Moreover, an apparent correlation between dissociation at neutral pH and in vivo pharmacokinetics was observed: mAbs with slow dissociation (i.e. >5% "% bound" tend to show shorter terminal half life (t½) in vivo). This feature was used as an in vitro screening tool for antibody pharmacokinetics.

The neutral pH dissociation of mAbs from human FcRn was measured by SPR using a Biacore T-100 instrument. Briefly, purified FcRn protein was immobilized onto a Biacore CM5 biosensor chip and PBSP (50 mM NaPO4, 150 mM NaCl and 0.05% (v/v) Surfactant 20) pH 7.3 was used as running buffer. The mAbs were diluted with PBSP pH 6.0 to 100 nM, allowed to bind FcRn for 3 minutes to reach equilibrium and followed by 1 minute of dissociation in pH 7.3 running buffer. A report point (Stability) was inserted at 5 seconds after the end of mAb binding and the "% bound" was calculated as RUStability/RUBinding (%).

FIGS. 17-20 illustrate binding of AX1, AX9, AX189 and AX191 to immobilized human FcRn with Biacore. The "% bound" calculated as $RU_{stability}/RU_{Binding}$(%) are ranged from 0.9% to 5%.

Example 19

Pharmacokinetics Study in Human FcRn Mice

The interaction between IgG and FcRn is species-specific. Human FcRn mice have recently been suggested as a valuable surrogate system for evaluating mAb pharmacokinetics; Petkova et al., 2006 *Int. Immunol.* 12:1759-69. The human FcRn mice (heterozygous Tg276) used in this study were obtained from Jackson Laboratory (Bar Harbor, ME). It is deficient in mouse FcRn-α chain and carries a human FcRn-α chain gene. Id. Our internal data showed that unlike mouse or rat FcRn, this "hybrid" FcRn had comparable human IgG binding characteristics as that of human and monkey FcRn. In addition, good terminal half life correlation between this human FcRn mice and non-human primate was observed.

For pharmacokinetics studies, each animal (2-3/group) received a single intravenous injection of mAb at 10 mg/kg via tail vein. Series of 10 μL of blood was collected at specified time points. A validated anti-human IgG immunoassay was used to determine all mAb levels.

Figure 21:
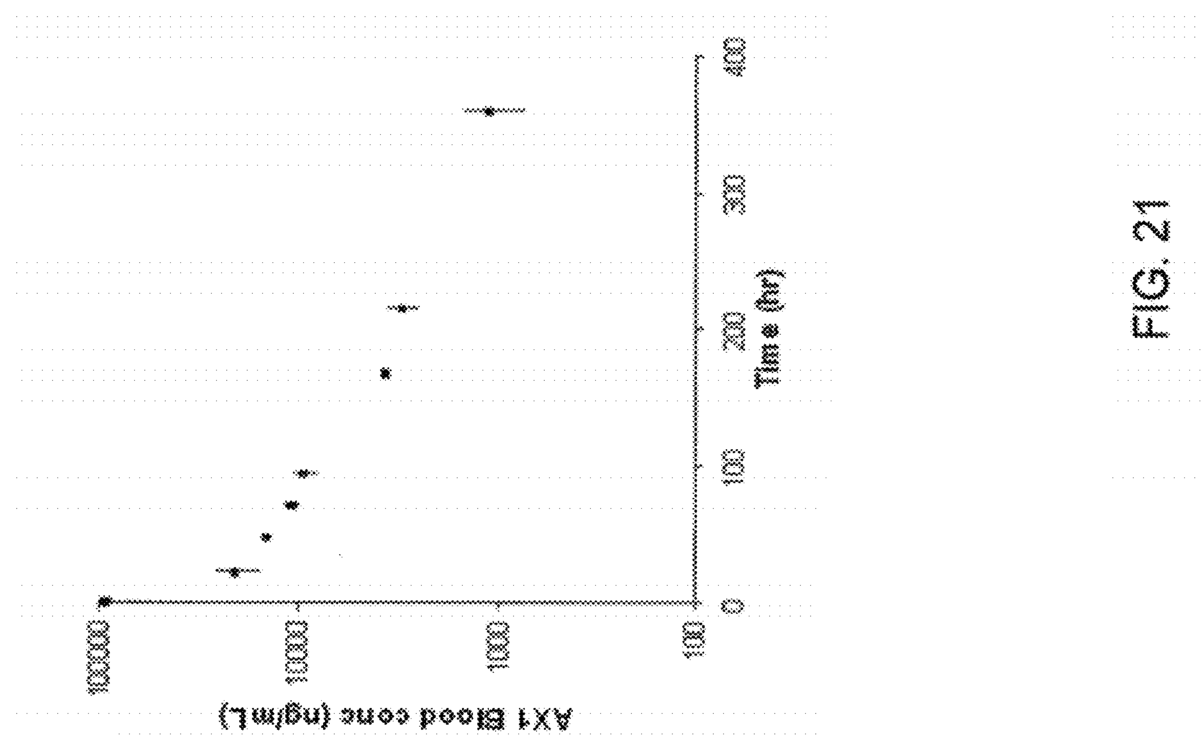
FIG. 21 illustrates the pharmacokinetic profile of AX1 in human FcRn mice following a single 10 mg/kg IV administration. Plotted is the blood drug levels at time points indicated. The half-life of AX1 is 92.5 hr.
Figure 22:
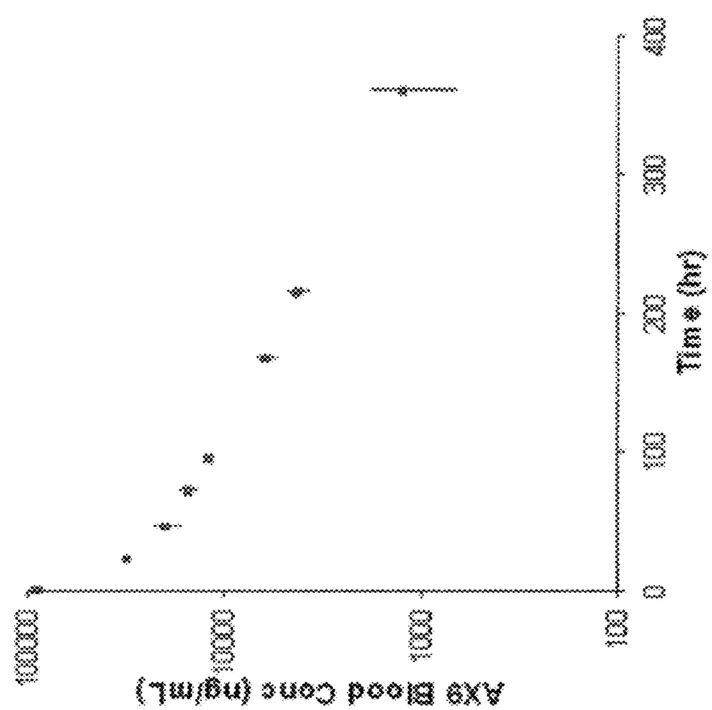
FIG. 22 illustrates the pharmacokinetic profile of AX9 in human FcRn mice following a single 10 mg/kg IV administration. Plotted is the blood drug levels at time points indicated. The half-life of AX9 is 77.5 hr.
Figure 23:
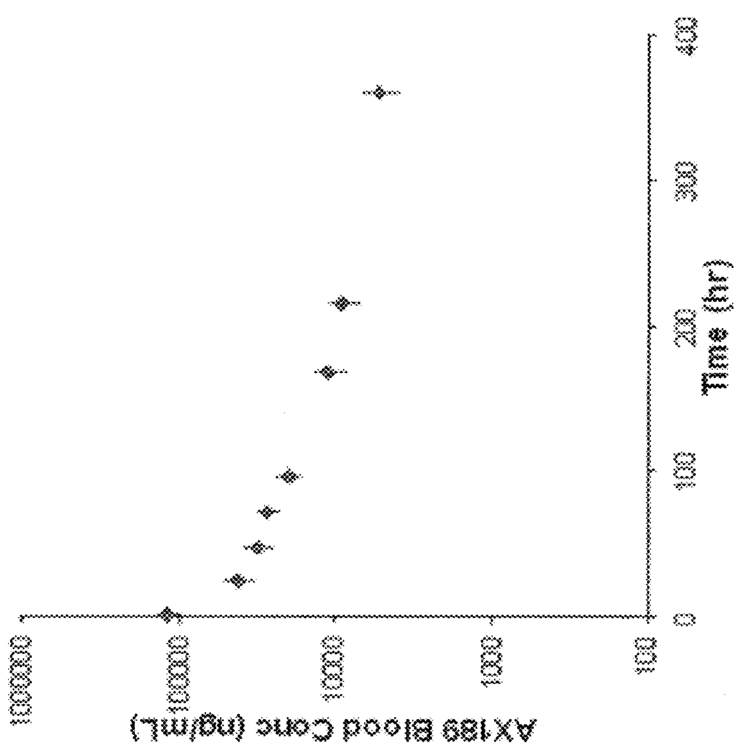
FIG. 23 illustrates the pharmacokinetic profile of AX189 in human FcRn mice following a single 10 mg/kg IV administration. Plotted is the blood drug levels at time points indicated. The half-life of AX189 is 140 hr.

The pharmacokinetic profile of AX1, AX9, AX189 and AX191 were determined in human FcRn mice following a single 10 mg/kg IV administration. FIG. 21-23 illustrate that the half-life of AX1, AX9 and AX189 determined to be 92, 77 and 140 hours, respectively.

The pharmacokinetic profile of AX1 and AX189 were also determined in rhesus monkey following a single 10 mg/kg IV administration. The half-life of AX1 and AX89 were determined to be 112 and 139 hours.

Example 20

Rhesus Pharmacodynamics Study

To characterize pharmacokinetics, pharmacodynamics and target engagement of antibodies, single dose studies were conducted in 3 or 6 Rhesus monkeys at 10 mg/kg with IV route of administration, or 1 mg/kg with subcutaneous route of administration. All Rhesus monkeys used in the study were naive to biologics. Blood samples were collected from the saphenous/femoral vessel at designated time points post dosing and the resulting plasma/serum was stored at −70° C. until analysis.

To generate lipoprotein profiles, plasma or serum was fractionated by chromatography over Superose-6 size exclusion column (GE LifeSciences, Inc.). Total cholesterol levels in the column effluent were continuously measured via in-line mixture with a commercially available enzymatic colorimetric cholesterol detection reagent (Total Cholesterol E, Wako USA) followed by downstream spectrophotometric detection of the reaction products at 600 nm absorbance. The first peak of cholesterol eluted from the column was attributed to VLDL, the second peak to LDL and the third to HDL; the area under each peak was calculated using software provided with the HPLC. To calculate the cholesterol concentration for each lipoprotein fraction, the ratio of the corresponding peak area to total peak area was multiplied by the total cholesterol concentration measured in the sample.

The lipoprotein analysis of the serum samples were carried out as described above. An anti-human IgG ELISA using commercially available reagents was used to quantify Ax1, AX189 levels respectively.

Figure 24:
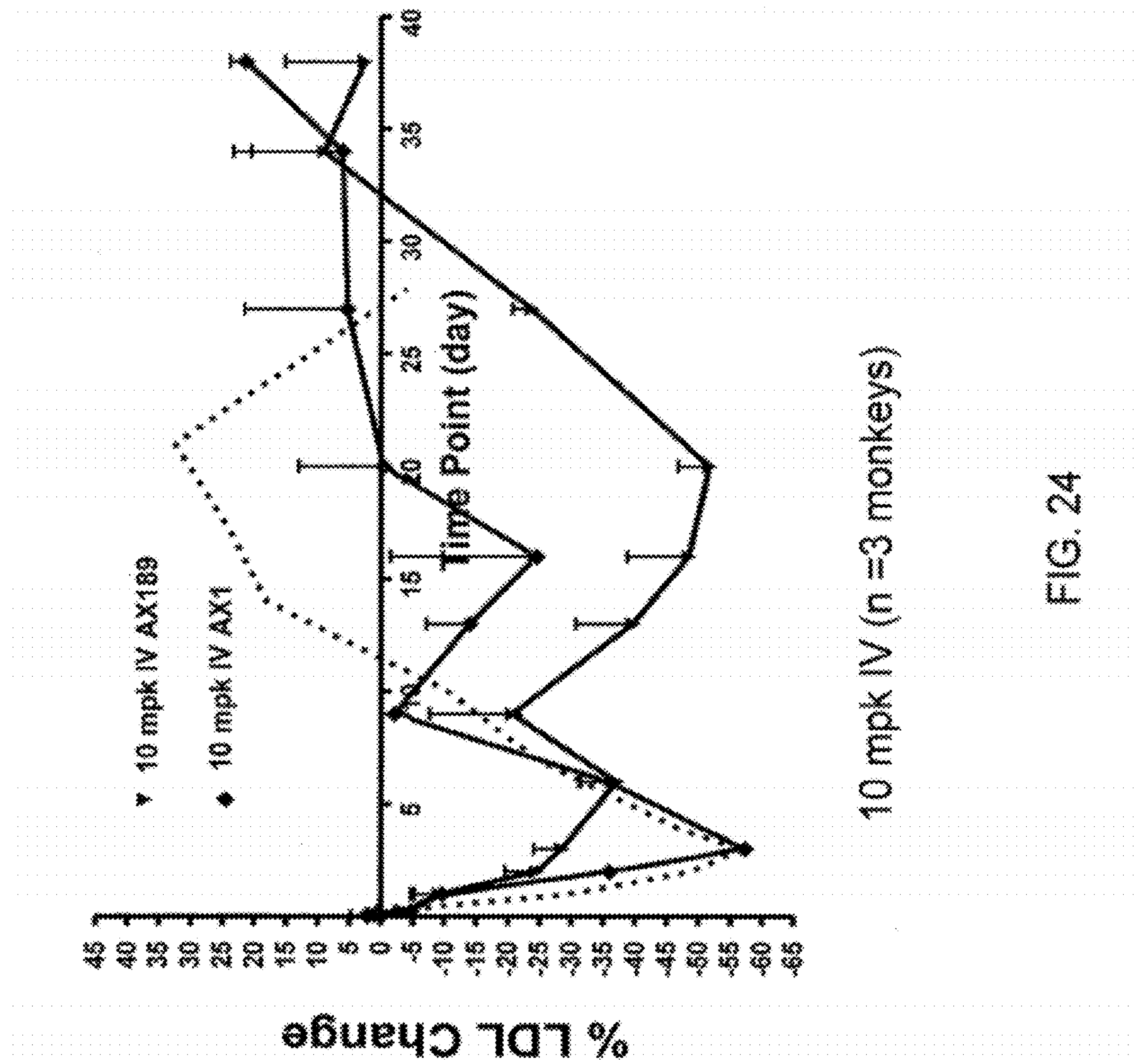
FIG. 24 illustrates the results of pharmacodynamics study in rhesus monkeys at the 10 mpk IV administration. AX1 lowered LDL-C by ≥50% following a single dose and ≥25% LDL-C lowering was observed for ≥10 days. AX189 lowered LDL-C by ≥50% following a single dose and ≥25% LDL-C lowering was observed for ≥25 days
Figure 25:
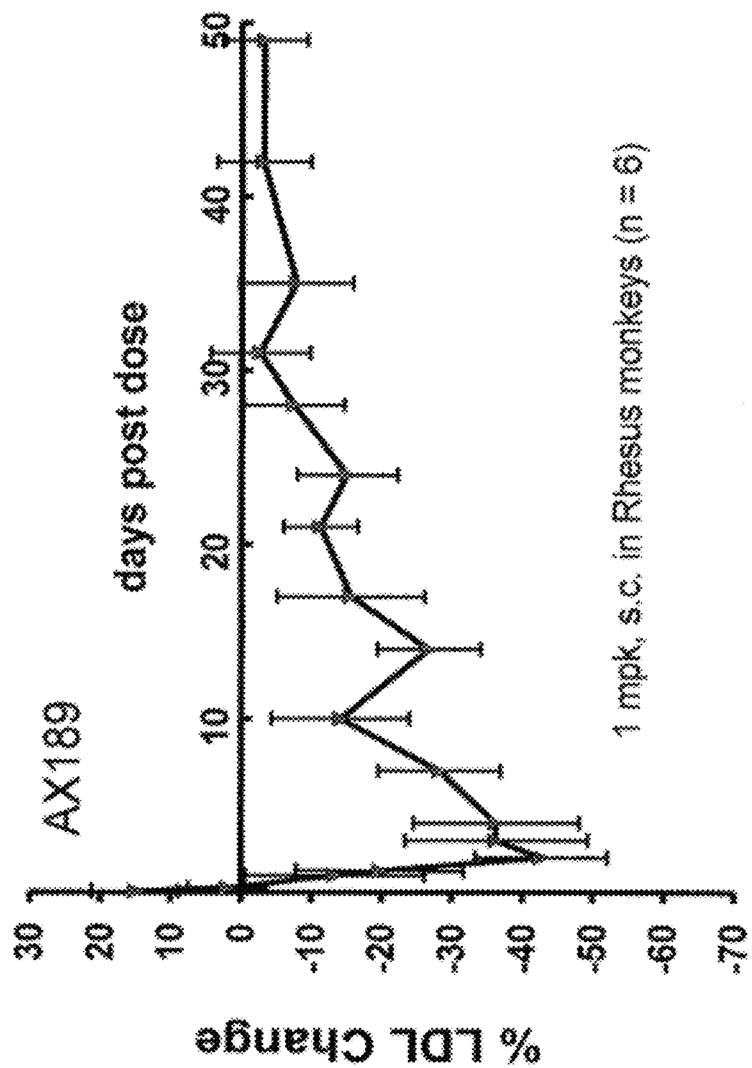
FIG. 25 illustrates the results of pharmacodynamics study in rhesus monkeys at the 1 mpk SC administration. AX189 lowered LDL cholesterol by ≥40%, following a single dose and ≥15% LDL-C lowering was observed for ≥25 days

As shown in FIG. 24, AX1 lowered LDL-C by ≥50% at the 10 mpk dose and ≥25% LDL-C lowering was observed for ≥10 days. AX189 lowered LDL-C by ≥50% at the 10 mpk dose and ≥25% LDL-C lowering was observed for ≥25 days As shown in FIG. 25, AX189 lowered LDL cholesterol following a single dose of 1 mg/kg SC administration, with a maximum mean reduction ≥40%, and ≥15% LDL-C lowering for ≥25 days.

Example 21

Pharmacokinetics Study in Human FcRn Mice

The interaction between IgG and FcRn is species-specific. Human FcRn mice have recently been suggested as a valuable surrogate system for evaluating mAb pharmacokinetics (Petkova et al., 2006 *Int Immunol.* 18(12):1759-69). The human FcRn mice (heterozygous Tg276) used in this study were obtained from Jackson Laboratory (Bar Harbor, Me.). It is deficient in mouse FcRn-α chain and carries a human FcRn-α chain gene. Id. Our internal data showed that unlike mouse or rat FcRn, this "hybrid" FcRn had comparable human IgG binding characteristics as that of human and monkey FcRn. In addition, good terminal half life correlation between this human FcRn mice and non-human primate was observed.

For pharmacokinetics studies, each animal (2-3/group) received a single intravenous injection of mAb at 10 mg/kg via tail vein. Series of 10 μL of blood was collected at specified time points. A validated anti-human IgG immunoassay was used to determine all mAb levels.

The pharmacokinetic profiles of AX1 and AX189 in human FcRn mice following a single 10 mg/kg IV administration were obtained; data not shown. The half-lives of AX1 and AX189 were 92.5 hours and 140.5 hours, respectively.

Example 22

Analytical Size Exclusion Chromatography

High Performance—Size Exclusion Chromatography (HP-SEC) is an analytical method used to separate proteins based on order of decreasing size. This method was used to quantitate the level of aggregation and/or fragmentation of proteins after process and purification (time zero) and after accelerated stability studies. Size Exclusion Chromatography was performed with a Waters 2690 Separations Module/996 Photodiode Array Detector. Material was separated using a TSKgel G3000$SW_{XL}$ (4.6×300 mm) column with a Phenomenex pre-filter GFC 4000 (4×3 mm). The column was loaded with 10 μg of material and eluted with a 25 mM sodium phosphate 300 mM sodium chloride pH 7.0 mobile phase at a flow rate of 0.5 ml/min for 30 minutes. Data was acquired from 200-500 nm and 220 nm profiles were reported.

Figure 26:
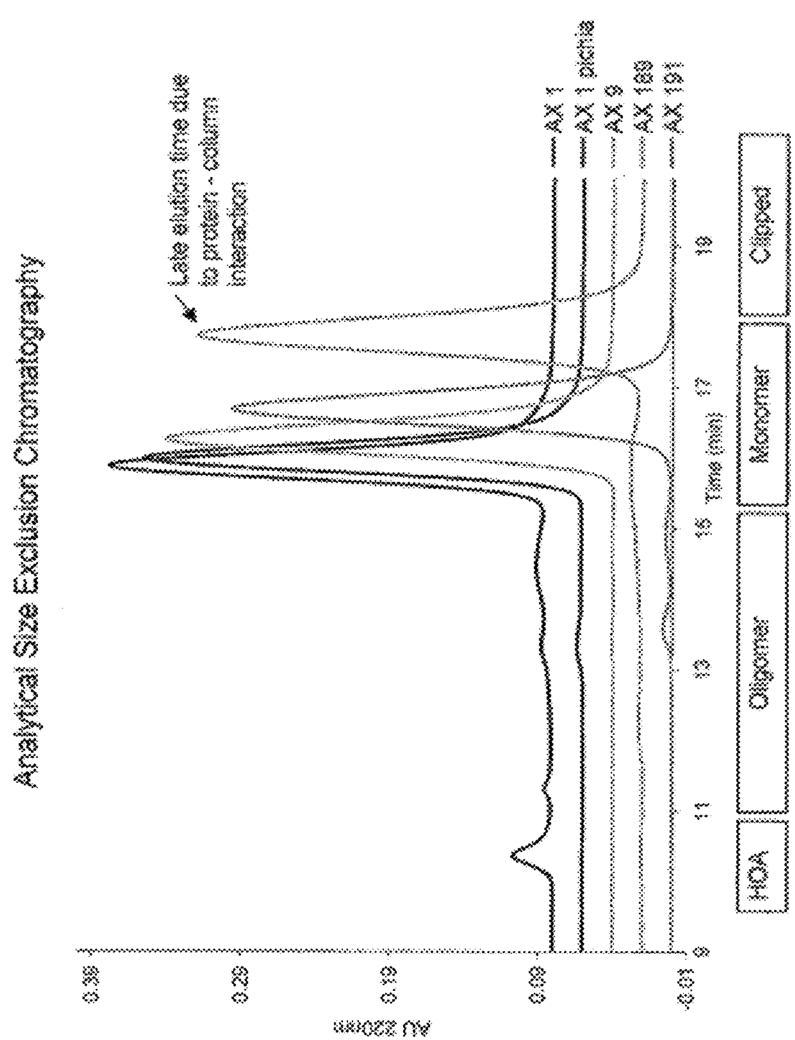
FIG. 26: Size-Exclusion Chromatography for time zero products of mAbs in AX1/AX189 epitope bin

Monoclonal antibodies were formulated at 0.5 mg/ml in pH 5, 6, 7, and 8 buffers. The buffers contained 150 mM sodium chloride and 10 mM acetate, histidine, phosphate, and TRIS for pH 5, 6, 7, and 8 respectively. HP-SEC was used to characterize material purity at time zero and after one weak at 45° C. Stability results are summarized in Table 11 below. FIG. 26 shows time zero SEC profiles. The boxed labels in the figures define the approximate elution times of higher order aggregates (HOAs), oligomer, monomer, and clipped protein.

TABLE 11

| Physical Stability data at time zero and after thermal stress (1 week 45 C.) | | | | | | | | | | | | |
|---|---|---|---|---|---|---|---|---|---|---|---|---|
| | | | | T0 | | | | 1 week stress at 45 C. in pH 5, 6, 7, and 8 buffers | | | |
| mAb[1] | Cell line | Theoretical pI | Elution time (min) | Pre Mon[2] Peak | Olig[3] | HOA[4] | Clip[5] | Inc in Pre Mon[2] Peak | Inc in Olig[3] | Inc in HOA[4] | Inc in Clip[5] |
| AX 1 | *Pichia* | 7.9483 | 15.9 | no | <5% | no | no | na | no | no | no |
| AX 1 | HEK 293 | 7.9483 | 16.0 | no | ≈15% | ≈5% | no | na | no | no | no |
| AX 9 | HEK 293 | 8.0501 | 16.3 | no | No | no | no | na | no | no | no |
| AX 189 | HEK 293 | 8.0494 | 17.8 | no | <5% | no | no | na | no | no | no |
| AX 191 | HEK 293 | 8.0492 | 16.7 | no | <5% | no | no | na | no | no | no |

[1]mAb: monoclonal antibody
[2]Mon: monomer
[3]Olig: Oligomer
[4]HOA: higher order aggregate
[5]Clip: Clipped protein

What is claimed is:

1. An isolated PCSK9-specific antagonist which comprises:

(a) a heavy chain variable region comprising CDR1, CDR2 and CDR3 sequence, wherein (i) the CDR1 sequence is selected from the group consisting of: SEQ ID NO: 2 and residues 4-13 of SEQ ID NO: 2;

(ii) the CDR2 sequence is selected from the group consisting of: SEQ ID NO: 9 and residues 4-20 of SEQ ID NO: 9; and (iii) the CDR3 sequence is selected from the group consisting of SEQ ID NO: 16 and residues 4-15 of SEQ ID NO: 16 and (b) a light chain variable region comprising CDR1, CDR2 and CDR3 sequence, wherein (i) the CDR1 sequence is SEQ ID NO: 24;

(ii) the CDR2 sequence is SEQ ID NO: 31; and (iii) the CDR3 sequence is SEQ ID NO: 35;

said antagonist which inhibits human PCSK9-dependent inhibition of cellular LDL uptake by at least 10%.

2. The PCSK9-specific antagonist of claim 1 which comprises heavy and light chain regions having, in contiguous order, sequences for framework (FR) 1, CDR1, FR2, CDR2, FR3, CDR3, FR4 comprising:

(a) heavy chain framework (FR) sequences 1, 2, 3 and 4 of SEQ ID NOs: 94, 95, 96 and 97, respectively; and (b) light chain FR sequences 1, 2, 3 and 4 of SEQ ID NOs: 98, 99, 100 and 101 (or 102), respectively.

3. The PCSK9-specific antagonist of claim 1 which comprises:

(a) a heavy chain variable region comprising sequence of SEQ ID NO: 41 and (b) a light chain variable region comprising SEQ ID NO: 50 or 52.

4. The PCSK9-specific antagonist of claim 1 which comprises:

(a) a heavy chain comprising sequence selected from the group consisting of: SEQ ID NOs: 69, 71, 79, 81 and 83; and (b) a light chain comprising sequence selected from the group consisting of: SEQ ID NOs: 73, 75, 77, 85, 87 and 89.

5. The PCSK9-specific antagonist of claim 1 that binds to human PCSK9 with a $K_D$ of less than 5 nM.

6. The PCSK9-specific antagonist of claim 1 that antagonizes PCSK9's inhibition of cellular LDL uptake at an $IC_{50}$ of less than 100 nM.

7. The PCSK9-specific antagonist of claim 1 that antagonizes PCSK9's inhibition of cellular uptake by at least 50%.

8. The PCSK9-specific antagonist of claim 1 which is an antibody molecule.

9. A composition comprising the PCSK9-specific antagonist of claim 1 and a pharmaceutically acceptable carrier.

* * * * *

SEQUENCE LISTING

```
<160> NUMBER OF SEQ ID NOS: 174

<210> SEQ ID NO 1
<211> LENGTH: 16
<212> TYPE: PRT
<213> ORGANISM: Artificial Sequence
<220> FEATURE:
<223> OTHER INFORMATION: Consensus VH CDR1 Antibody Sequence
<221> NAME/KEY: VARIANT
<222> LOCATION: (1)...(1)
<223> OTHER INFORMATION: Xaa = K or A
<221> NAME/KEY: VARIANT
<222> LOCATION: (5)...(5)
<223> OTHER INFORMATION: Xaa = Y or F
<221> NAME/KEY: VARIANT
<222> LOCATION: (6)...(6)
<223> OTHER INFORMATION: Xaa = T or D
<221> NAME/KEY: VARIANT
<222> LOCATION: (8)...(8)
<223> OTHER INFORMATION: Xaa = S or T
<221> NAME/KEY: VARIANT
<222> LOCATION: (9)...(9)
<223> OTHER INFORMATION: Xaa = S or D
<221> NAME/KEY: VARIANT
<222> LOCATION: (11)...(11)
<223> OTHER INFORMATION: Xaa = W, Y, T or D
<221> NAME/KEY: VARIANT
<222> LOCATION: (12)...(12)
<223> OTHER INFORMATION: Xaa = M, F, Y or I
<221> NAME/KEY: VARIANT
<222> LOCATION: (13)...(13)
<223> OTHER INFORMATION: Xaa = H, S or N

<400> SEQUENCE: 1

Xaa Ala Ser Gly Xaa Xaa Phe Xaa Xaa Tyr Xaa Xaa Xaa Trp Val Arg
1               5                   10                  15


<210> SEQ ID NO 2
<211> LENGTH: 16
<212> TYPE: PRT
<213> ORGANISM: Artificial Sequence
<220> FEATURE:
<223> OTHER INFORMATION: AX1 VH CDR1 Antibody Sequence

<400> SEQUENCE: 2

Lys Ala Ser Gly Phe Thr Phe Thr Ser Tyr Tyr Met His Trp Val Arg
1               5                   10                  15


<210> SEQ ID NO 3
```

<211> LENGTH: 48
<212> TYPE: DNA
<213> ORGANISM: Artificial Sequence
<220> FEATURE:
<223> OTHER INFORMATION: AX1 VH CDR1 Antibody Sequence

<400> SEQUENCE: 3
aaggcctctg gtttcacctt cacttcttac tacatgcact gggtgcgt 48

<210> SEQ ID NO 4
<211> LENGTH: 10
<212> TYPE: PRT
<213> ORGANISM: Artificial Sequence
<220> FEATURE:
<223> OTHER INFORMATION: AX1 VH CDR1 Antibody Sequence

<400> SEQUENCE: 4

Gly Phe Thr Phe Thr Ser Tyr Tyr Met His
1 5 10

<210> SEQ ID NO 5
<211> LENGTH: 30
<212> TYPE: DNA
<213> ORGANISM: Artificial Sequence
<220> FEATURE:
<223> OTHER INFORMATION: AX1 VH CDR1 Antibody Sequence

<400> SEQUENCE: 5
ggtttcacct tcacttctta ctacatgcac 30

<210> SEQ ID NO 6
<211> LENGTH: 16
<212> TYPE: PRT
<213> ORGANISM: Artificial Sequence
<220> FEATURE:
<223> OTHER INFORMATION: AX9 AX189 VH CDR1 Antibody Sequence

<400> SEQUENCE: 6

Lys Ala Ser Gly Tyr Thr Phe Ser Ser Tyr Trp Met His Trp Val Arg
1 5 10 15

<210> SEQ ID NO 7
<211> LENGTH: 48
<212> TYPE: DNA
<213> ORGANISM: Artificial Sequence
<220> FEATURE:
<223> OTHER INFORMATION: AX9 AX189 VH CDR1 Antibody Sequence

<400> SEQUENCE: 7
aaggcctctg gttacacctt ctcttcttac tggatgcact gggtgcgt 48

<210> SEQ ID NO 8
<211> LENGTH: 23
<212> TYPE: PRT
<213> ORGANISM: Artificial Sequence
<220> FEATURE:
<223> OTHER INFORMATION: Consensus VH CDR2 Antibody Sequence
<221> NAME/KEY: VARIANT
<222> LOCATION: (2)...(2)
<223> OTHER INFORMATION: Xaa = I or V
<221> NAME/KEY: VARIANT
<222> LOCATION: (3)...(3)
<223> OTHER INFORMATION: Xaa = G or S
<221> NAME/KEY: VARIANT
<222> LOCATION: (4)...(4)
<223> OTHER INFORMATION: Xaa = R or Y
<221> NAME/KEY: VARIANT
<222> LOCATION: (6)...(6)
<223> OTHER INFORMATION: Xaa = D, Y, E or N
<221> NAME/KEY: VARIANT
<222> LOCATION: (8)...(8)
<223> OTHER INFORMATION: Xaa = Y or D
<221> NAME/KEY: VARIANT
<222> LOCATION: (9)...(9)
<223> OTHER INFORMATION: Xaa = N, S or T
<221> NAME/KEY: VARIANT
<222> LOCATION: (10)...(10)
<223> OTHER INFORMATION: Xaa = G, E or T
<221> NAME/KEY: VARIANT
<222> LOCATION: (11)...(11)
<223> OTHER INFORMATION: Xaa = G, Y, D or S
<221> NAME/KEY: VARIANT
<222> LOCATION: (19)...(19)
<223> OTHER INFORMATION: Xaa = K, A or D
<221> NAME/KEY: VARIANT
<222> LOCATION: (20)...(20)
<223> OTHER INFORMATION: Xaa = G, S or D
<221> NAME/KEY: VARIANT
<222> LOCATION: (21)...(21)
<223> OTHER INFORMATION: Xaa = K or R
<221> NAME/KEY: VARIANT
<222> LOCATION: (22)...(22)
<223> OTHER INFORMATION: Xaa = A or F

<400> SEQUENCE: 8

Trp Xaa Xaa Xaa Ile Xaa Pro Xaa Xaa Xaa Xaa Thr Lys Tyr Asn Glu
1               5                   10                  15

Lys Arg Xaa Xaa Xaa Xaa Thr
            20

<210> SEQ ID NO 9
<211> LENGTH: 23
<212> TYPE: PRT
<213> ORGANISM: Artificial Sequence
<220> FEATURE:
<223> OTHER INFORMATION: AX1 VH CDR2 Antibody Sequence

<400> SEQUENCE: 9

Trp Ile Gly Arg Ile Asn Pro Asp Ser Gly Ser Thr Lys Tyr Asn Glu
1               5                   10                  15

Lys Phe Lys Gly Arg Ala Thr
            20

<210> SEQ ID NO 10
<211> LENGTH: 74
<212> TYPE: DNA
<213> ORGANISM: Artificial Sequence
<220> FEATURE:
<223> OTHER INFORMATION: AX1 VH CDR2 Antibody Sequence

<400> SEQUENCE: 10
tggaatggat cggtcggatc aacccagatt ctggtagtac taagtacaac gagaagttca     60
agggtcgtgc cacc                                                       74

<210> SEQ ID NO 11
<211> LENGTH: 17
<212> TYPE: PRT
<213> ORGANISM: Artificial Sequence
<220> FEATURE:
<223> OTHER INFORMATION: AX1 VH CDR2 Antibody Sequence

<400> SEQUENCE: 11

Arg Ile Asn Pro Asp Ser Gly Ser Thr Lys Tyr Asn Glu Lys Phe Lys
1               5                   10                  15

Gly

<210> SEQ ID NO 12
<211> LENGTH: 51
<212> TYPE: DNA
<213> ORGANISM: Artificial Sequence
<220> FEATURE:
<223> OTHER INFORMATION: AX1 VH CDR2 Antibody Sequence

<400> SEQUENCE: 12
cggatcaacc cagattctgg tagtactaag tacaacgaga agttcaaggg t 51

<210> SEQ ID NO 13
<211> LENGTH: 23
<212> TYPE: PRT
<213> ORGANISM: Artificial Sequence
<220> FEATURE:
<223> OTHER INFORMATION: AX9 AX189 VH CDR2 Antibody Sequence

<400> SEQUENCE: 13

Trp Ile Gly Arg Ile Asp Pro Tyr Asn Gly Gly Thr Lys Tyr Asn Glu
1               5                   10                  15

Lys Phe Lys Gly Lys Ala Thr
            20

<210> SEQ ID NO 14
<211> LENGTH: 69
<212> TYPE: DNA
<213> ORGANISM: Artificial Sequence
<220> FEATURE:
<223> OTHER INFORMATION: AX9 AX189 VH CDR2 Antibody Sequence

<400> SEQUENCE: 14
tggatcggtc gtatcgaccc atataacggt ggcaccaagt acaacgagaa gttcaagggt 60
aaggccacc 69

<210> SEQ ID NO 15
<211> LENGTH: 18
<212> TYPE: PRT
<213> ORGANISM: Artificial Sequence
<220> FEATURE:
<223> OTHER INFORMATION: Consensus VH CDR3 Antibody Sequence
<221> NAME/KEY: VARIANT
<222> LOCATION: (4)...(4)
<223> OTHER INFORMATION: Xaa = Y, S, D or E
<221> NAME/KEY: VARIANT
<222> LOCATION: (5)...(5)
<223> OTHER INFORMATION: Xaa = G, T or R
<221> NAME/KEY: VARIANT
<222> LOCATION: (8)...(8)
<223> OTHER INFORMATION: Xaa = L, E, D, G or S
<221> NAME/KEY: VARIANT
<222> LOCATION: (9)...(9)
<223> OTHER INFORMATION: Xaa = G, D or E
<221> NAME/KEY: VARIANT
<222> LOCATION: (10)...(10)
<223> OTHER INFORMATION: Xaa = S, Y or F
<221> NAME/KEY: VARIANT
<222> LOCATION: (13)...(13)
<223> OTHER INFORMATION: Xaa = M, F, Y, L or E

<400> SEQUENCE: 15

Cys Ala Arg Xaa Xaa Tyr Tyr Xaa Xaa Xaa Tyr Ala Xaa Asp Tyr Trp
1               5                   10                  15

Gly Gln

<210> SEQ ID NO 16
<211> LENGTH: 16
<212> TYPE: PRT
<213> ORGANISM: Artificial Sequence
<220> FEATURE:
<223> OTHER INFORMATION: AX1 VH CDR3 Antibody Sequence

<400> SEQUENCE: 16

Cys Ala Arg Gly Gly Arg Leu Ser Trp Asp Phe Asp Val Trp Gly Gln
1 5 10 15

<210> SEQ ID NO 17
<211> LENGTH: 48
<212> TYPE: DNA
<213> ORGANISM: Artificial Sequence
<220> FEATURE:
<223> OTHER INFORMATION: AX1 VH CDR3 Antibody Sequence

<400> SEQUENCE: 17
tgcgcccgtg gtggtcgttt atcctgggac ttcgacgtct ggggtcag 48

<210> SEQ ID NO 18
<211> LENGTH: 10
<212> TYPE: PRT
<213> ORGANISM: Artificial Sequence
<220> FEATURE:
<223> OTHER INFORMATION: AX1 VH CDR3 Antibody Sequence

<400> SEQUENCE: 18

Gly Gly Arg Leu Ser Trp Asp Phe Asp Val
1 5 10

<210> SEQ ID NO 19
<211> LENGTH: 30
<212> TYPE: DNA
<213> ORGANISM: Artificial Sequence
<220> FEATURE:
<223> OTHER INFORMATION: AX1 VH CDR3 Antibody Sequence

<400> SEQUENCE: 19
ggtggtcgtt tatcctggga cttcgacgtc 30

<210> SEQ ID NO 20
<211> LENGTH: 18
<212> TYPE: PRT
<213> ORGANISM: Artificial Sequence
<220> FEATURE:
<223> OTHER INFORMATION: AX9 AX189 VH CDR3 Antibody Sequence

<400> SEQUENCE: 20

Cys Ala Arg Tyr Gly Tyr Tyr Leu Gly Ser Tyr Ala Met Asp Tyr Trp
1 5 10 15

Gly Gln

<210> SEQ ID NO 21
<211> LENGTH: 54
<212> TYPE: DNA
<213> ORGANISM: Artificial Sequence
<220> FEATURE:
<223> OTHER INFORMATION: AX9 AX189 VH CDR3 Antibody Sequence

<400> SEQUENCE: 21
tgcgcccgtt atggttacta ccttggctct tacgccatgg actactgggg tcag 54

<210> SEQ ID NO 22
<211> LENGTH: 11
<212> TYPE: PRT
<213> ORGANISM: Artificial Sequence
<220> FEATURE:
<223> OTHER INFORMATION: Consensus VL CDR1 Antibody Sequence
<221> NAME/KEY: VARIANT
<222> LOCATION: (1)...(1)
<223> OTHER INFORMATION: Xaa = R or K
<221> NAME/KEY: VARIANT
<222> LOCATION: (5)...(5)
<223> OTHER INFORMATION: Xaa = D or S
<221> NAME/KEY: VARIANT
<222> LOCATION: (6)...(6)
<223> OTHER INFORMATION: Xaa = V or I
<221> NAME/KEY: VARIANT
<222> LOCATION: (8)...(8)
<223> OTHER INFORMATION: Xaa = R, K, T or N
<221> NAME/KEY: VARIANT
<222> LOCATION: (11)...(11)
<223> OTHER INFORMATION: Xaa = T, A or S

<400> SEQUENCE: 22

Xaa Ala Ser Gln Xaa Xaa Ser Xaa Tyr Leu Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Consensus VL CDR1 Antibody Sequence
<221> NAME/KEY: VARIANT
<222> LOCATION: (5)...(5)
<223> OTHER INFORMATION: Xaa = A, D or S
<221> NAME/KEY: VARIANT
<222> LOCATION: (6)...(6)
<223> OTHER INFORMATION: Xaa = V or I
<221> NAME/KEY: VARIANT
<222> LOCATION: (8)...(8)
<223> OTHER INFORMATION: Xaa = R, K, N or S
<221> NAME/KEY: VARIANT
<222> LOCATION: (11)...(11)
<223> OTHER INFORMATION: Xaa = A, T, N or H

<400> SEQUENCE: 23

Arg Ala Ser Gln Xaa Xaa Ser Xaa Tyr Leu Xaa
1               5                   10

<210> SEQ ID NO 24
<211> LENGTH: 11
<212> TYPE: PRT
<213> ORGANISM: Artificial Sequence
<220> FEATURE:
<223> OTHER INFORMATION: AX1 VL CDR1 Antibody Sequence

<400> SEQUENCE: 24

Arg Ala Ser Gln Asp Ile Ser Arg Tyr Leu Ala
1               5                   10

<210> SEQ ID NO 25
<211> LENGTH: 33
<212> TYPE: DNA
<213> ORGANISM: Artificial Sequence
<220> FEATURE:
<223> OTHER INFORMATION: AX1 VL CDR1 Antibody Sequence

<400> SEQUENCE: 25
cgtgcctctc aggatatctc taggtatctg gcc                                 33

<210> SEQ ID NO 26
<211> LENGTH: 11
<212> TYPE: PRT
<213> ORGANISM: Artificial Sequence
<220> FEATURE:
<223> OTHER INFORMATION: AX9 VL CDR1 Antibody Sequence

<400> SEQUENCE: 26

Arg Ala Ser Gln Asp Val Ser Lys Tyr Leu Ala
1 5 10

<210> SEQ ID NO 27
<211> LENGTH: 33
<212> TYPE: DNA
<213> ORGANISM: Artificial Sequence
<220> FEATURE:
<223> OTHER INFORMATION: AX9 VL CDR1 Antibody Sequence

<400> SEQUENCE: 27
cgtgcctctc aggatgtctc taagtatctg gcc 33

<210> SEQ ID NO 28
<211> LENGTH: 11
<212> TYPE: PRT
<213> ORGANISM: Artificial Sequence
<220> FEATURE:
<223> OTHER INFORMATION: AX189 VL CDR1 Antibody Sequence

<400> SEQUENCE: 28

Arg Ala Ser Gln Asp Val Ser Arg Tyr Leu Thr
1 5 10

<210> SEQ ID NO 29
<211> LENGTH: 33
<212> TYPE: DNA
<213> ORGANISM: Artificial Sequence
<220> FEATURE:
<223> OTHER INFORMATION: AX189 VL CDR1 Antibody Sequence

<400> SEQUENCE: 29
cgtgcctctc aggatgtctc taggtatctg acc 33

<210> SEQ ID NO 30
<211> LENGTH: 7
<212> TYPE: PRT
<213> ORGANISM: Artificial Sequence
<220> FEATURE:
<223> OTHER INFORMATION: Consensus VL CDR2 Antibody Sequence
<221> NAME/KEY: VARIANT
<222> LOCATION: (1)...(1)
<223> OTHER INFORMATION: Xaa = A or R
<221> NAME/KEY: VARIANT
<222> LOCATION: (3)...(3)
<223> OTHER INFORMATION: Xaa = S, E or T
<221> NAME/KEY: VARIANT
<222> LOCATION: (4)...(4)
<223> OTHER INFORMATION: Xaa = S, E, D or T
<221> NAME/KEY: VARIANT
<222> LOCATION: (6)...(6)
<223> OTHER INFORMATION: Xaa = Q, R, K, Y or E
<221> NAME/KEY: VARIANT
<222> LOCATION: (7)...(7)
<223> OTHER INFORMATION: Xaa = S, T or A

<400> SEQUENCE: 30

Xaa Ala Xaa Xaa Leu Xaa Xaa
1 5

<210> SEQ ID NO 31
<211> LENGTH: 7
<212> TYPE: PRT
<213> ORGANISM: Artificial Sequence
<220> FEATURE:
<223> OTHER INFORMATION: AX1 AX9 AX189 VL CDR2 Antibody Sequence

<400> SEQUENCE: 31

Ala Ala Ser Ser Leu Gln Ser
1 5

<210> SEQ ID NO 32
<211> LENGTH: 21
<212> TYPE: DNA
<213> ORGANISM: Artificial Sequence
<220> FEATURE:
<223> OTHER INFORMATION: AX1 AX9 AX189 VL CDR2 Antibody Sequence

<400> SEQUENCE: 32
gccgcctctt ctttgcagtc t 21

<210> SEQ ID NO 33
<211> LENGTH: 11
<212> TYPE: PRT
<213> ORGANISM: Artificial Sequence
<220> FEATURE:
<223> OTHER INFORMATION: Consensus VL CDR3 Antibody Sequence
<221> NAME/KEY: VARIANT
<222> LOCATION: (1)...(1)
<223> OTHER INFORMATION: Xaa = Q, E, Y or A
<221> NAME/KEY: VARIANT
<222> LOCATION: (2)...(2)
<223> OTHER INFORMATION: Xaa = A, V or S
<221> NAME/KEY: VARIANT
<222> LOCATION: (3)...(3)
<223> OTHER INFORMATION: Xaa = Y, E or W
<221> NAME/KEY: VARIANT
<222> LOCATION: (5)...(5)
<223> OTHER INFORMATION: Xaa = Y, S or K
<221> NAME/KEY: VARIANT
<222> LOCATION: (6)...(6)
<223> OTHER INFORMATION: Xaa = S or E
<221> NAME/KEY: VARIANT
<222> LOCATION: (7)...(7)
<223> OTHER INFORMATION: Xaa = L, S, P, G, D or T
<221> NAME/KEY: VARIANT
<222> LOCATION: (8)...(8)
<223> OTHER INFORMATION: Xaa = S, D, N, E, G or A
<221> NAME/KEY: VARIANT
<222> LOCATION: (9)...(9)
<223> OTHER INFORMATION: Xaa = G, A, D, R, S or H
<221> NAME/KEY: VARIANT
<222> LOCATION: (10)...(10)
<223> OTHER INFORMATION: Xaa = Y or V

<400> SEQUENCE: 33

Xaa Xaa Xaa Asp Xaa Xaa Xaa Xaa Xaa Xaa Val
1 5 10

<210> SEQ ID NO 34
<211> LENGTH: 11
<212> TYPE: PRT
<213> ORGANISM: Artificial Sequence
<220> FEATURE:
<223> OTHER INFORMATION: Consensus VL CDR3 Antibody Sequence
<221> NAME/KEY: VARIANT
<222> LOCATION: (1)...(1)
<223> OTHER INFORMATION: Xaa = Q or E
<221> NAME/KEY: VARIANT
<222> LOCATION: (2)...(2)
<223> OTHER INFORMATION: Xaa = A, S or V
<221> NAME/KEY: VARIANT
<222> LOCATION: (5)...(5)
<223> OTHER INFORMATION: Xaa = Y or S
<221> NAME/KEY: VARIANT
<222> LOCATION: (7)...(7)
<223> OTHER INFORMATION: Xaa = L, S or P
<221> NAME/KEY: VARIANT
<222> LOCATION: (8)...(8)
<223> OTHER INFORMATION: Xaa = G, S or N
<221> NAME/KEY: VARIANT
<222> LOCATION: (9)...(9)
<223> OTHER INFORMATION: Xaa = A, H, P, R, G or D
<221> NAME/KEY: VARIANT
<222> LOCATION: (10)...(10)
<223> OTHER INFORMATION: Xaa = Y or W

<400> SEQUENCE: 34

Xaa Xaa Tyr Asp Xaa Ser Xaa Xaa Xaa Xaa Val
1 5 10

<210> SEQ ID NO 35
<211> LENGTH: 11
<212> TYPE: PRT
<213> ORGANISM: Artificial Sequence
<220> FEATURE:
<223> OTHER INFORMATION: AX1 VL CDR3 Antibody Sequence

<400> SEQUENCE: 35

Ala Ala Tyr Asp Tyr Ser Leu Gly Gly Tyr Val
1 5 10

<210> SEQ ID NO 36
<211> LENGTH: 33
<212> TYPE: DNA
<213> ORGANISM: Artificial Sequence
<220> FEATURE:
<223> OTHER INFORMATION: AX1 VL CDR3 Antibody Sequence

<400> SEQUENCE: 36
gcggcttacg actattcttt gggcggttac gtg 33

<210> SEQ ID NO 37
<211> LENGTH: 11
<212> TYPE: PRT
<213> ORGANISM: Artificial Sequence
<220> FEATURE:
<223> OTHER INFORMATION: AX9 VL CDR3 Antibody Sequence

<400> SEQUENCE: 37

Gln Val Tyr Asp Ser Ser Pro Asn Ala Tyr Val
1 5 10

<210> SEQ ID NO 38
<211> LENGTH: 33
<212> TYPE: DNA
<213> ORGANISM: Artificial Sequence
<220> FEATURE:
<223> OTHER INFORMATION: AX9 VL CDR3 Antibody Sequence

<400> SEQUENCE: 38
caggtatacg acagctctcc aaacgcttat gtg 33

<210> SEQ ID NO 39
<211> LENGTH: 11
<212> TYPE: PRT
<213> ORGANISM: Artificial Sequence
<220> FEATURE:
<223> OTHER INFORMATION: AX189 VL CDR3 Antibody Sequence

<400> SEQUENCE: 39

Gln Ala Tyr Asp Tyr Ser Leu Ser Gly Tyr Val
1 5 10

<210> SEQ ID NO 40
<211> LENGTH: 33
<212> TYPE: DNA
<213> ORGANISM: Artificial Sequence

```
<220> FEATURE:
<223> OTHER INFORMATION: AX189 VL CDR3 Antibody Sequence

<400> SEQUENCE: 40

caggcttacg actattcttt gagcggttac gtg                                   33


<210> SEQ ID NO 41
<211> LENGTH: 119
<212> TYPE: PRT
<213> ORGANISM: Artificial Sequence
<220> FEATURE:
<223> OTHER INFORMATION: AX1 VH Antibody Sequence

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
            20                  25                  30

Tyr Met His Trp Val Arg Gln Ala Pro Gly Lys Gly Leu Glu Trp Ile
        35                  40                  45

Gly Arg Ile Asn Pro Asp Ser Gly Ser Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Ser Trp Asp Phe Asp Val Trp Gly Gln Gly
            100                 105                 110

Thr Leu Val Thr Val Ser Ser
        115


<210> SEQ ID NO 42
<211> LENGTH: 357
<212> TYPE: DNA
<213> ORGANISM: Artificial Sequence
<220> FEATURE:
<223> OTHER INFORMATION: AX1 VH Antibody Sequence

<400> SEQUENCE: 42

gaagtgcagc tgctggaatc tggtggtggt ctggtgcagc caggtggttc tctgcgtctg      60

tcttgcaagg cctctggttt caccttcact tcttactaca tgcactgggt gcgtcaggca     120

ccaggtaagg gtctggaatg gatcggtcgg atcaacccag attctggtag tactaagtac     180

aacgagaagt tcaagggtcg tgccaccatc tctagagaca actctaagaa caccctgtac     240

ttgcagatga actctctgcg tgccgaggac actgcagtgt actactgcgc ccgtggtggt     300

cgtttatcct gggacttcga cgtctggggt cagggtacgc tggtgactgt ctcgagc        357


<210> SEQ ID NO 43
<211> LENGTH: 121
<212> TYPE: PRT
<213> ORGANISM: Artificial Sequence
<220> FEATURE:
<223> OTHER INFORMATION: AX9 AX189 VH Antibody Sequence

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30
```

```
Trp Met His Trp Val Arg Gln Ala Pro Gly Lys Gly Leu Glu Trp Ile
        35                  40                  45

Gly Arg Ile Asp Pro Tyr Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120


<210> SEQ ID NO 44
<211> LENGTH: 363
<212> TYPE: DNA
<213> ORGANISM: Artificial Sequence
<220> FEATURE:
<223> OTHER INFORMATION: AX9 AX189 VH Antibody Sequence

<400> SEQUENCE: 44

gaagtgcagc tgttggaatc tggtggtggt ctggtgcagc caggtggttc tctgcgtctg      60

tcttgcaagg cctctggtta caccttctct tcttactgga tgcactgggt gcgtcaggca     120

ccaggtaagg gtctggaatg gatcggtcgt atcgacccat ataacggtgg caccaagtac     180

aacgagaagt tcaagggtaa ggccaccatc tctagagaca actctaagaa caccctgtac     240

ttgcagatga actctctgcg tgccgaggac actgcagtgt actactgcgc ccgttatggt     300

tactaccttg gctcttacgc catggactac tggggtcagg gtacgctggt gactgtctcg     360

agc                                                                   363


<210> SEQ ID NO 45
<211> LENGTH: 121
<212> TYPE: PRT
<213> ORGANISM: Artificial Sequence
<220> FEATURE:
<223> OTHER INFORMATION: AX421 VH Antibody Sequence

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asn Glu Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120


<210> SEQ ID NO 46
<211> LENGTH: 121
```

<212> TYPE: PRT
<213> ORGANISM: Artificial Sequence
<220> FEATURE:
<223> OTHER INFORMATION: AX422 VH Antibody Sequence

<400> SEQUENCE: 46

Glu Val Gln Leu Leu Glu Ser Gly Gly Gly Leu Val Gln Pro Gly Gly
1 5 10 15

Ser Leu Arg Leu Ser Cys Lys Ala Ser Gly Tyr Thr Phe Ser Ser Tyr
20 25 30

Trp Met His Trp Val Arg Gln Ala Pro Gly Lys Gly Leu Glu Trp Ile
35 40 45

Gly Arg Ile Asp Pro Tyr Ser Gly Gly Thr Lys Tyr Asn Glu Lys Phe
50 55 60

Lys Gly Lys Ala Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Gly Tyr Tyr Leu Gly Ser Tyr Ala Met Asp Tyr Trp Gly
100 105 110

Gln Gly Thr Leu Val Thr Val Ser Ser
115 120

<210> SEQ ID NO 47
<211> LENGTH: 121
<212> TYPE: PRT
<213> ORGANISM: Artificial Sequence
<220> FEATURE:
<223> OTHER INFORMATION: AX423 VH Antibody Sequence

<400> SEQUENCE: 47

Glu Val Gln Leu Leu Glu Ser Gly Gly Gly Leu Val Gln Pro Gly Gly
1 5 10 15

Ser Leu Arg Leu Ser Cys Lys Ala Ser Gly Tyr Thr Phe Ser Ser Tyr
20 25 30

Trp Met His Trp Val Arg Gln Ala Pro Gly Lys Gly Leu Glu Trp Ile
35 40 45

Gly Arg Ile Asp Pro Tyr Asn Thr Gly Thr Lys Tyr Asn Glu Lys Phe
50 55 60

Lys Gly Lys Ala Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Gly Tyr Tyr Leu Gly Ser Tyr Ala Met Asp Tyr Trp Gly
100 105 110

Gln Gly Thr Leu Val Thr Val Ser Ser
115 120

<210> SEQ ID NO 48
<211> LENGTH: 121
<212> TYPE: PRT
<213> ORGANISM: Artificial Sequence
<220> FEATURE:
<223> OTHER INFORMATION: AX424 VH Antibody Sequence

<400> SEQUENCE: 48

Glu Val Gln Leu Leu Glu Ser Gly Gly Gly Leu Val Gln Pro Gly Gly
1 5 10 15

Ser Leu Arg Leu Ser Cys Lys Ala Ser Gly Tyr Thr Phe Ser Ser Tyr

```
            20                  25                  30

Trp Met His Trp Val Arg Gln Ala Pro Gly Lys Gly Leu Glu Trp Ile
        35                  40                  45

Gly Arg Ile Asp Pro Tyr Thr Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120


<210> SEQ ID NO 49
<211> LENGTH: 121
<212> TYPE: PRT
<213> ORGANISM: Artificial Sequence
<220> FEATURE:
<223> OTHER INFORMATION: AX425 VH Antibody Sequence

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asp Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120


<210> SEQ ID NO 50
<211> LENGTH: 109
<212> TYPE: PRT
<213> ORGANISM: Artificial Sequence
<220> FEATURE:
<223> OTHER INFORMATION: AX1 VL Antibody Sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Ala Ala Tyr Asp Tyr Ser Leu Gly
                85                  90                  95

Gly Tyr Val Phe Gly Asp Gly Thr Lys Val Glu Ile Lys
            100                 105
```

<210> SEQ ID NO 51
<211> LENGTH: 327
<212> TYPE: DNA
<213> ORGANISM: Artificial Sequence
<220> FEATURE:
<223> OTHER INFORMATION: AX1 VL Antibody Sequence

<400> SEQUENCE: 51

```
gacatccaga tgacccagtc tccatcttct ctgtctgcct ctgtgggcga ccgggtgacc     60

atcacctgcc gtgcctctca ggatatctct aggtatctgg cctggtatca gcagaagcca    120

ggtaaggcgc caaagctgct gatctacgcc gcctcttctt tgcagtctgg tgtgccatct    180

cgtttctctg gttctggttc tggcaccgac ttcaccctga ccatctcttc tttgcagcca    240

gaagacttcg ccacctacta ctgcgcggct tacgactatt ctttgggcgg ttacgtgttc    300

ggtgatggta ccaaagtgga gatcaaa                                        327
```

<210> SEQ ID NO 52
<211> LENGTH: 109
<212> TYPE: PRT
<213> ORGANISM: Artificial Sequence
<220> FEATURE:
<223> OTHER INFORMATION: AX1DG VL Antibody Sequence

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala Tyr Asp Tyr Ser Leu Gly
                85                  90                  95

Gly Tyr Val Phe Gly Gly Gly Thr Lys Val Glu Ile Lys
            100                 105
```

<210> SEQ ID NO 53
<211> LENGTH: 109
<212> TYPE: PRT
<213> ORGANISM: Artificial Sequence
<220> FEATURE:
<223> OTHER INFORMATION: AX9 VL Antibody Sequence

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Lys Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Val Tyr Asp Ser Ser Pro Asn
                85                  90                  95

Ala Tyr Val Phe Gly Gly Gly Thr Lys Val Glu Ile Lys
            100                 105


<210> SEQ ID NO 54
<211> LENGTH: 327
<212> TYPE: DNA
<213> ORGANISM: Artificial Sequence
<220> FEATURE:
<223> OTHER INFORMATION: AX9 VL Antibody Sequence

<400> SEQUENCE: 54

gacatccaga tgacccagtc tccatcttct ctgtctgcct ctgtgggcga ccgggtgacc     60

atcacctgcc gtgcctctca ggatgtctct aagtatctgg cctggtatca gcagaagcca    120

ggtaaggcgc caaagctgct gatctacgcc gcctcttctt tgcagtctgg tgtgccatct    180

cgtttctctg gttctggttc tggcaccgac ttcaccctga ccatctcttc tttgcagcca    240

gaagacttcg ccacctacta ctgccaggta tacgacagct ctccaaacgc ttatgtgttc    300

ggtggtggta ccaaagtgga gatcaaa                                        327


<210> SEQ ID NO 55
<211> LENGTH: 109
<212> TYPE: PRT
<213> ORGANISM: Artificial Sequence
<220> FEATURE:
<223> OTHER INFORMATION: AX188 VL Antibody Sequence

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Glu Ala Tyr Asp Tyr Ser Ser Gly
                85                  90                  95

Pro Trp Val Phe Gly Gly Gly Thr Lys Val Glu Ile Lys
            100                 105


<210> SEQ ID NO 56
<211> LENGTH: 109
<212> TYPE: PRT
<213> ORGANISM: Artificial Sequence
<220> FEATURE:
<223> OTHER INFORMATION: AX190 VL Antibody Sequence

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Arg Tyr
            20                  25                  30
```

```
Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Asp Tyr Ser Leu Ser
                85                  90                  95

Asp Tyr Val Phe Gly Gly Gly Thr Lys Val Glu Ile Lys
            100                 105


<210> SEQ ID NO 57
<211> LENGTH: 109
<212> TYPE: PRT
<213> ORGANISM: Artificial Sequence
<220> FEATURE:
<223> OTHER INFORMATION: AX191 VL Antibody Sequence

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Ser Ser
                85                  90                  95

Ala Tyr Val Phe Gly Gly Gly Thr Lys Val Glu Ile Lys
            100                 105


<210> SEQ ID NO 58
<211> LENGTH: 109
<212> TYPE: PRT
<213> ORGANISM: Artificial Sequence
<220> FEATURE:
<223> OTHER INFORMATION: AX192 VL Antibody Sequence

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Val Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Glu Ala Tyr Asp Tyr Ser Leu Gly
                85                  90                  95

Arg Tyr Val Phe Gly Gly Gly Thr Lys Val Glu Ile Lys
            100                 105
```

```
<210> SEQ ID NO 59
<211> LENGTH: 109
<212> TYPE: PRT
<213> ORGANISM: Artificial Sequence
<220> FEATURE:
<223> OTHER INFORMATION: AX193 VL Antibody Sequence

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Glu Ser Tyr Asp Tyr Ser Leu Gly
                85                  90                  95

Arg Tyr Val Phe Gly Gly Gly Thr Lys Val Glu Ile Lys
            100                 105


<210> SEQ ID NO 60
<211> LENGTH: 109
<212> TYPE: PRT
<213> ORGANISM: Artificial Sequence
<220> FEATURE:
<223> OTHER INFORMATION: AX194 VL Antibody Sequence

<400> SEQUENCE: 60

Asp Ile Gln Met Thr Gln Ser Pro Ser Ser Leu Ser Ala Ser Val Gly
1               5                   10                  15

Asp Arg Val Thr Thr Thr Cys Arg Ala Ser Gln Ala Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Gly
                85                  90                  95

Ala Tyr Val Phe Gly Gly Gly Thr Lys Val Glu Ile Lys
            100                 105


<210> SEQ ID NO 61
<211> LENGTH: 109
<212> TYPE: PRT
<213> ORGANISM: Artificial Sequence
<220> FEATURE:
<223> OTHER INFORMATION: AX195 VL Antibody Sequence

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Val Ser Lys Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Gly
                85                  90                  95

Asp Tyr Val Phe Gly Gly Gly Thr Lys Val Glu Ile Lys
            100                 105


<210> SEQ ID NO 62
<211> LENGTH: 109
<212> TYPE: PRT
<213> ORGANISM: Artificial Sequence
<220> FEATURE:
<223> OTHER INFORMATION: AX196 VL Antibody Sequence

<400> SEQUENCE: 62

Asp Ile Gln Ile Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Glu Ser Tyr Asp Tyr Ser Leu Ser
                85                  90                  95

His Tyr Val Phe Gly Gly Gly Thr Lys Val Glu Ile Lys
            100                 105


<210> SEQ ID NO 63
<211> LENGTH: 109
<212> TYPE: PRT
<213> ORGANISM: Artificial Sequence
<220> FEATURE:
<223> OTHER INFORMATION: AX197 VL Antibody Sequence

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Gly
                85                  90                  95

His Tyr Val Phe Gly Gly Gly Thr Lys Val Glu Ile Lys
            100                 105


<210> SEQ ID NO 64
<211> LENGTH: 109
<212> TYPE: PRT
```

<213> ORGANISM: Artificial Sequence
<220> FEATURE:
<223> OTHER INFORMATION: AX198 VL Antibody Sequence

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Val Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Glu Ala Tyr Asp Tyr Ser Leu Gly
                85                  90                  95

Gly Trp Val Phe Gly Gly Gly Thr Lys Val Glu Ile Lys
            100                 105
```

<210> SEQ ID NO 65
<211> LENGTH: 109
<212> TYPE: PRT
<213> ORGANISM: Artificial Sequence
<220> FEATURE:
<223> OTHER INFORMATION: AX199 VL Antibody Sequence

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Asn Tyr
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Gly
                85                  90                  95

Pro Tyr Val Phe Gly Gly Gly Thr Lys Val Glu Ile Lys
            100                 105
```

<210> SEQ ID NO 66
<211> LENGTH: 109
<212> TYPE: PRT
<213> ORGANISM: Artificial Sequence
<220> FEATURE:
<223> OTHER INFORMATION: AX200 VL Antibody Sequence

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Lys Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Glu Ala Tyr Asp Tyr Ser Leu Ser
                85                  90                  95

His Tyr Val Phe Gly Gly Gly Thr Lys Val Glu Ile Lys
            100                 105
```

<210> SEQ ID NO 67
<211> LENGTH: 109
<212> TYPE: PRT
<213> ORGANISM: Artificial Sequence
<220> FEATURE:
<223> OTHER INFORMATION: AX189 VL Antibody Sequence

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Ser
                85                  90                  95

Gly Tyr Val Phe Gly Gly Gly Thr Lys Val Glu Ile Lys
            100                 105
```

<210> SEQ ID NO 68
<211> LENGTH: 327
<212> TYPE: DNA
<213> ORGANISM: Artificial Sequence
<220> FEATURE:
<223> OTHER INFORMATION: AX189 VL Antibody Sequence

<400> SEQUENCE: 68

```
gacatccaga tgacccagtc tccatcttct ctgtctgcct ctgtgggcga ccgggtgacc      60

atcacctgcc gtgcctctca ggatgtctct aggtatctga cctggtatca gcagaagcca     120

ggtaaggcgc caaagctgct gatctacgcc gcctcttctt tgcagtctgg tgtgccatct     180

cgtttctctg gttctggttc tggcaccgac ttcaccctga ccatctcttc tttgcagcca     240

gaagacttcg ccacctacta ctgccaggct tacgactatt ctttgagcgg ttacgtgttc     300

ggtggtggta ccaaagtgga gatcaaa                                          327
```

<210> SEQ ID NO 69
<211> LENGTH: 227
<212> TYPE: PRT
<213> ORGANISM: Artificial Sequence
<220> FEATURE:
<223> OTHER INFORMATION: AX1 FD Chain Antibody Sequence

<400> SEQUENCE: 69

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
            20                  25                  30
```

```
Tyr Met His Trp Val Arg Gln Ala Pro Gly Lys Gly Leu Glu Trp Ile
        35                  40                  45

Gly Arg Ile Asn Pro Asp Ser Gly Ser Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Ser Trp Asp Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225
```

<210> SEQ ID NO 70
<211> LENGTH: 681
<212> TYPE: DNA
<213> ORGANISM: Artificial Sequence
<220> FEATURE:
<223> OTHER INFORMATION: AX1 FD Chain Antibody Sequence

<400> SEQUENCE: 70

```
gaagtgcagc tgctggaatc tggtggtggt ctggtgcagc caggtggttc tctgcgtctg     60

tcttgcaagg cctctggttt caccttcact tcttactaca tgcactgggt gcgtcaggca    120

ccaggtaagg gtctggaatg gatcggtcgg atcaacccag attctggtag tactaagtac    180

aacgagaagt tcaagggtcg tgccaccatc tctagagaca actctaagaa caccctgtac    240

ttgcagatga actctctgcg tgccgaggac actgcagtgt actactgcgc ccgtggtggt    300

cgtttatcct gggacttcga cgtctggggt cagggtacgc tggtgactgt ctcgagcgca    360

agcaccaaag gcccatcggt attccccctg gcaccctcct ccaagagcac ctctgggggc    420

acagcggccc tgggctgcct ggtcaaggac tacttccccg agccggtgac ggtgtcgtgg    480

aactcaggcg ctctgaccag cggcgtgcac accttcccgg ctgtcctaca gtcctcagga    540

ctctactccc tcagcagcgt ggtgactgtg ccctccagca gcttgggcac ccagacctac    600

atctgcaacg tgaatcacaa gcccagcaac actaaggtgg acaagaaagt tgagcccaaa    660

tcttgtgaca aaactcacac a                                              681
```

<210> SEQ ID NO 71
<211> LENGTH: 229
<212> TYPE: PRT
<213> ORGANISM: Artificial Sequence
<220> FEATURE:

<223> OTHER INFORMATION: AX9 AX189 FD Chain Antibody Sequence

<400> SEQUENCE: 71

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr
225
```

<210> SEQ ID NO 72
<211> LENGTH: 687
<212> TYPE: DNA
<213> ORGANISM: Artificial Sequence
<220> FEATURE:
<223> OTHER INFORMATION: AX9 AX189 FD Chain Antibody Sequence

<400> SEQUENCE: 72

```
gaagtgcagc tgttggaatc tggtggtggt ctggtgcagc caggtggttc tctgcgtctg      60

tcttgcaagg cctctggtta caccttctct tcttactgga tgcactgggt gcgtcaggca     120

ccaggtaagg gtctggaatg gatcggtcgt atcgacccat ataacggtgg caccaagtac     180

aacgagaagt tcaagggtaa ggccaccatc tctagagaca actctaagaa caccctgtac     240

ttgcagatga actctctgcg tgccgaggac actgcagtgt actactgcgc ccgttatggt     300

tactaccttg gctcttacgc catggactac tggggtcagg gtacgctggt gactgtctcg     360

agcgcaagca ccaaaggccc atcggtattc cccctggcac cctcctccaa gagcacctct     420

gggggcacag cggccctggg ctgcctggtc aaggactact tccccgagcc ggtgacggtg     480

tcgtggaact caggcgctct gaccagcggc gtgcacacct tcccggctgt cctacagtcc     540

tcaggactct actccctcag cagcgtggtg actgtgccct ccagcagctt gggcacccag     600
```

```
acctacatct gcaacgtgaa tcacaagccc agcaacacta aggtggacaa gaaagttgag    660

cccaaatctt gtgacaaaac tcacaca                                        687


<210> SEQ ID NO 73
<211> LENGTH: 216
<212> TYPE: PRT
<213> ORGANISM: Artificial Sequence
<220> FEATURE:
<223> OTHER INFORMATION: AX1 Fab Light Chain Antibody Sequence

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala Tyr Asp Tyr Ser Leu Gly
                85                  90                  95

Gly Tyr Val Phe Gly Asp Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 74
<211> LENGTH: 648
<212> TYPE: DNA
<213> ORGANISM: Artificial Sequence
<220> FEATURE:
<223> OTHER INFORMATION: AX1 Fab Light Chain Antibody Sequence

<400> SEQUENCE: 74

gacatccaga tgacccagtc tccatcttct ctgtctgcct ctgtgggcga ccgggtgacc     60

atcacctgcc gtgcctctca ggatatctct aggtatctgg cctggtatca gcagaagcca    120

ggtaaggcgc caaagctgct gatctacgcc gcctcttctt tgcagtctgg tgtgccatct    180

cgtttctctg gttctggttc tggcaccgac ttcaccctga ccatctcttc tttgcagcca    240

gaagacttcg ccacctacta ctgcgcggct tacgactatt ctttgggcgg ttacgtgttc    300

ggtgatggta ccaaagtgga gatcaaacgt acggtggctg caccatctgt cttcatcttc    360

ccgccatctg atgagcagtt gaaatctgga actgcctctg ttgtgtgcct gctgaataac    420
```

```
ttctatccca gagaggccaa agtacagtgg aaggtggata acgccctcca atcgggtaac    480

tcccaggaga gtgtcacaga gcaggacagc aaggacagca cctacagcct cagcagcacc    540

ctgacgctga gcaaagcaga ctacgagaaa cacaaagtct acgcctgcga agtcacccat    600

cagggcctga gctcgcccgt cacaaagagc ttcaacaggg gagagtgt                 648


<210> SEQ ID NO 75
<211> LENGTH: 216
<212> TYPE: PRT
<213> ORGANISM: Artificial Sequence
<220> FEATURE:
<223> OTHER INFORMATION: AX9 Fab Light Chain Antibody Sequence

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Lys Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Val Tyr Asp Ser Ser Pro Asn
                85                  90                  95

Ala Tyr Val Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 76
<211> LENGTH: 648
<212> TYPE: DNA
<213> ORGANISM: Artificial Sequence
<220> FEATURE:
<223> OTHER INFORMATION: AX9 Fab Light Chain Antibody Sequence

<400> SEQUENCE: 76

gacatccaga tgacccagtc tccatcttct ctgtctgcct ctgtgggcga ccgggtgacc     60

atcacctgcc gtgcctctca ggatgtctct aagtatctgg cctggtatca gcagaagcca    120

ggtaaggcgc caaagctgct gatctacgcc gcctcttctt tgcagtctgg tgtgccatct    180

cgtttctctg gttctggttc tggcaccgac ttcaccctga ccatctcttc tttgcagcca    240
```

```
gaagacttcg ccacctacta ctgccaggta tacgacagct ctccaaacgc ttatgtgttc    300

ggtggtggta ccaaagtgga gatcaaacgt acggtggctg caccatctgt cttcatcttc    360

ccgccatctg atgagcagtt gaaatctgga actgcctctg ttgtgtgcct gctgaataac    420

ttctatccca gagaggccaa agtacagtgg aaggtggata acgccctcca atcgggtaac    480

tcccaggaga gtgtcacaga gcaggacagc aaggacagca cctacagcct cagcagcacc    540

ctgacgctga gcaaagcaga ctacgagaaa cacaaagtct acgcctgcga agtcacccat    600

cagggcctga gctcgcccgt cacaaagagc ttcaacaggg gagagtgt                 648


<210> SEQ ID NO 77
<211> LENGTH: 216
<212> TYPE: PRT
<213> ORGANISM: Artificial Sequence
<220> FEATURE:
<223> OTHER INFORMATION: AX189 Fab Light Chain Antibody Sequence

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Ser
                85                  90                  95

Gly Tyr Val Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 78
<211> LENGTH: 648
<212> TYPE: DNA
<213> ORGANISM: Artificial Sequence
<220> FEATURE:
<223> OTHER INFORMATION: AX189 Fab Light Chain Antibody Sequence

<400> SEQUENCE: 78

gacatccaga tgacccagtc tccatcttct ctgtctgcct ctgtgggcga ccgggtgacc     60

atcacctgcc gtgcctctca ggatgtctct aggtatctga cctggtatca gcagaagcca    120
```

```
ggtaaggcgc caaagctgct gatctacgcc gcctcttctt tgcagtctgg tgtgccatct    180

cgtttctctg gttctggttc tggcaccgac ttcaccctga ccatctcttc tttgcagcca    240

gaagacttcg ccacctacta ctgccaggct tacgactatt ctttgagcgg ttacgtgttc    300

ggtggtggta ccaaagtgga gatcaaacgt acggtggctg caccatctgt attcatcttc    360

ccgccatctg atgagcagtt gaaatctgga actgcctctg ttgtgtgcct gctgaataac    420

ttctatccca gagaggccaa agtacagtgg aaggtggata acgccctcca atcgggtaac    480

tcccaggaga gtgtcacaga gcaggacagc aaggacagca cctacagcct cagcagcacc    540

ctgacgctga gcaaagcaga ctacgagaaa cacaaagtct acgcctgcga agtcacccat    600

cagggcctga gctcgcccgt cacaaagagc ttcaacaggg gagagtgt                 648
```

<210> SEQ ID NO 79
<211> LENGTH: 445
<212> TYPE: PRT
<213> ORGANISM: Artificial Sequence
<220> FEATURE:
<223> OTHER INFORMATION: AX1 IgG2 Heavy Chain Antibody Sequence

<400> SEQUENCE: 79

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
            20                  25                  30

Tyr Met His Trp Val Arg Gln Ala Pro Gly Lys Gly Leu Glu Trp Ile
        35                  40                  45

Gly Arg Ile Asn Pro Asp Ser Gly Ser Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Ser Trp Asp Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270
```

```
Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 80
<211> LENGTH: 1335
<212> TYPE: DNA
<213> ORGANISM: Artificial Sequence
<220> FEATURE:
<223> OTHER INFORMATION: AX1 IgG2 Heavy Chain Antibody Sequence

<400> SEQUENCE: 80

```
gaagtgcagc tgctggaatc tggtggtggt ctggtgcagc caggtggttc tctgcgtctg     60

tcttgcaagg cctctggttt caccttcact tcttactaca tgcactgggt gcgtcaggca    120

ccaggtaagg gtctggaatg gatcggtcgg atcaacccag attctggtag tactaagtac    180

aacgagaagt tcaagggtcg tgccaccatc tctagagaca actctaagaa caccctgtac    240

ttgcagatga actctctgcg tgccgaggac actgcagtgt actactgcgc ccgtggtggt    300

cgtttatcct gggacttcga cgtctggggt cagggtacgc tggtgactgt ctcgagcgca    360

tccaccaagg gcccatccgt cttccccctg gcgccctgct ccaggagcac ctccgagagc    420

acagccgccc tgggctgcct ggtcaaggac tacttccccg aaccggtgac ggtgtcctgg    480

aactctggcg ccctgacctc tggcgtgcac accttccctg ctgtgctgca atcctctggc    540

ctgtactccc tgtcctctgt ggtgacagtg ccatcctcca acttcggcac ccagacctac    600

acatgcaatg tggaccacaa gccatccaac accaaggtgg acaagacagt ggagcggaag    660

tgctgtgtgg agtgcccccc atgccctgcc ccccctgtgg ctggcccatc tgtgttcctg    720

ttccccccca agcccaagga caccctgatg atctcccgga cccctgaggt gacctgtgtg    780

gtggtggacg tgtcccatga ggaccctgag gtgcagttca actggtatgt ggatggcgtg    840

gaggtgcaca atgccaagac caagccccgg gaggagcagt tcaactccac cttccgggtg    900

gtgtctgtgc tgacagtggt gcaccaggac tggctgaatg gcaaggagta caagtgcaag    960

gtgtccaaca agggcctgcc tgcccccatc gagaagacca tctccaagac caagggccag   1020

ccccgggagc cccaggtgta caccctgccc ccatcccggg aggagatgac caagaaccag   1080
```

```
gtgtccctga cctgcctggt gaagggcttc tacccatccg acattgctgt ggagtgggag   1140

tccaatggcc agcctgagaa caactacaag accacccccc ccatgctgga ctctgatggc   1200

tccttcttcc tgtactccaa gctgacagtg gacaagtccc ggtggcagca gggcaatgtg   1260

ttctcctgct ctgtgatgca tgaggccctg cacaaccact acacccagaa gtccctgtcc   1320

ctgtccccctg gcaag                                                     1335


<210> SEQ ID NO 81
<211> LENGTH: 447
<212> TYPE: PRT
<213> ORGANISM: Artificial Sequence
<220> FEATURE:
<223> OTHER INFORMATION: AX9 AX189 IgG2 Heavy Chain Antibody Sequence

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
```

```
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 82
<211> LENGTH: 1341
<212> TYPE: DNA
<213> ORGANISM: Artificial Sequence
<220> FEATURE:
<223> OTHER INFORMATION: AX9 AX189 IgG2 Heavy Chain Antibody Sequence

<400> SEQUENCE: 82

```
gaagtgcagc tgttggaatc tggtggtggt ctggtgcagc caggtggttc tctgcgtctg     60

tcttgcaagg cctctggtta caccttctct tcttactgga tgcactgggt gcgtcaggca    120

ccaggtaagg gtctggaatg gatcggtcgt atcgacccat ataacggtgg caccaagtac    180

aacgagaagt tcaagggtaa ggccaccatc tctagagaca actctaagaa caccctgtac    240

ttgcagatga actctctgcg tgccgaggac actgcagtgt actactgcgc ccgttatggt    300

tactaccttg gctcttacgc catggactac tggggtcagg gtacgctggt gactgtctcg    360

agcgcatcca ccaagggccc atccgtcttc cccctggcgc cctgctccag gagcacctcc    420

gagagcacag ccgccctggg ctgcctggtc aaggactact tccccgaacc ggtgacggtg    480

tcctggaact ctggcgccct gacctctggc gtgcacacct tccctgctgt gctgcaatcc    540

tctggcctgt actccctgtc ctctgtggtg acagtgccat cctccaactt cggcacccag    600

acctacacat gcaatgtgga ccacaagcca tccaacacca aggtggacaa gacagtggag    660

cggaagtgct gtgtggagtg cccccccatgc cctgcccccc ctgtggctgg cccatctgtg    720

ttcctgttcc cccccaagcc caaggacacc ctgatgatct cccggacccc tgaggtgacc    780

tgtgtggtgg tggacgtgtc ccatgaggac cctgaggtgc agttcaactg gtatgtggat    840

ggcgtggagg tgcacaatgc caagaccaag ccccgggagg agcagttcaa ctccaccttc    900

cgggtggtgt ctgtgctgac agtggtgcac caggactggc tgaatggcaa ggagtacaag    960

tgcaaggtgt ccaacaaggg cctgcctgcc cccatcgaga agaccatctc caagaccaag   1020

ggccagcccc gggagcccca ggtgtacacc ctgcccccat cccgggagga gatgaccaag   1080

aaccaggtgt ccctgacctg cctggtgaag ggcttctacc catccgacat tgctgtggag   1140

tgggagtcca atggccagcc tgagaacaac tacaagacca cccccccat gctggactct   1200

gatggctcct tcttcctgta ctccaagctg acagtggaca agtcccggtg gcagcagggc   1260

aatgtgttct cctgctctgt gatgcatgag gccctgcaca accactacac ccagaagtcc   1320
```

```
ctgtccctgt cccctggcaa g                                             1341

<210> SEQ ID NO 83
<211> LENGTH: 466
<212> TYPE: PRT
<213> ORGANISM: Artificial Sequence
<220> FEATURE:
<223> OTHER INFORMATION: AX9 AX189 IgG2 Heavy Chain Antibody Sequence
      plus leader

<400> SEQUENCE: 83

Met Gly Trp Ser Leu Ile Leu Leu Phe Leu Val Ala Val Ala Thr Arg
1               5                   10                  15

Val Leu Ser Glu Val Gln Leu Leu Glu Ser Gly Gly Gly Leu Val Gln
            20                  25                  30

Pro Gly Gly Ser Leu Arg Leu Ser Cys Lys Ala Ser Gly Tyr Thr Phe
        35                  40                  45

Ser Ser Tyr Trp Met His Trp Val Arg Gln Ala Pro Gly Lys Gly Leu
    50                  55                  60

Glu Trp Ile Gly Arg Ile Asp Pro Tyr Asn Gly Gly Thr Lys Tyr Asn
65                  70                  75                  80

Glu Lys Phe Lys Gly Lys Ala Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Tyr Gly Tyr Tyr Leu Gly Ser Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350
```

```
Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 84
<211> LENGTH: 1398
<212> TYPE: DNA
<213> ORGANISM: Artificial Sequence
<220> FEATURE:
<223> OTHER INFORMATION: AX9 AX189 IgG2 Heavy Chain Antibody Sequence
      plus leader

<400> SEQUENCE: 84

atgggctggt ccctgattct gctgttcctg gtggctgtgg ctaccagggt gctgtctgag      60

gtccaacttt tggagtctgg aggaggactg gtccaacctg gaggctccct gagactgtcc     120

tgtaaggcat ctggctacac cttctcctcc tactggatgc actgggtgag acaggctcct     180

ggcaagggat tggagtggat tggcaggatt gacccataca atggaggcac caaatacaat     240

gagaagttca agggcaaggc taccatcagc agggacaaca gcaagaacac cctctacctc     300

caaatgaact ccctgagggc tgaggacaca gcagtctact actgtgccag atatggctac     360

tacctgggct cctatgctat ggactactgg ggacaaggca ccctggtgac agtgtcctct     420

gctagcacca agggcccatc ggtcttcccc ctggcgccct gctccaggag cacctccgag     480

agcacagcgg ccctgggctg cctggtcaag gactacttcc ccgaaccggt gacggtgtcg     540

tggaactcag gcgctctgac cagcggcgtg cacaccttcc cggctgtcct acagtcctca     600

ggactctact ccctcagcag cgtggtgacc gtgccctcca gcaacttcgg cacccagacc     660

tacacctgca acgtagatca caagcccagc aacaccaagg tggacaagac agttgagcgc     720

aaatgttgtg tcgagtgccc accgtgccca gcaccacctg tggcaggacc gtcagtcttc     780

ctcttccccc caaaacccaa ggacaccctc atgatctccc ggacccctga ggtcacgtgc     840

gtggtggtgg acgtgagcca cgaagacccc gaggtccagt tcaactggta cgtggacggc     900

gtggaggtgc ataatgccaa gacaaagcca cgggaggagc agttcaacag cacgttccgt     960

gtggtcagcg tcctcaccgt cgtgcaccag gactggctga acggcaagga gtacaagtgc    1020

aaggtctcca acaaaggcct cccagccccc atcgagaaaa ccatctccaa aaccaaaggg    1080

cagccccgag aaccacaggt gtacaccctg cccccatccc gggaggagat gaccaagaac    1140

caggtcagcc tgacctgcct ggtcaaaggc ttctacccca gcgacatcgc cgtggagtgg    1200

gagagcaatg ggcagccgga gaacaactac aagaccacac ctcccatgct ggactccgac    1260

ggctccttct tcctctacag caagctcacc gtggacaaga gcaggtggca gcaggggaac    1320
```

gtcttctcat gctccgtgat gcatgaggct ctgcacaacc actacacaca gaagagcctc 1380
tccctgtctc cgggtaaa 1398

<210> SEQ ID NO 85
<211> LENGTH: 216
<212> TYPE: PRT
<213> ORGANISM: Artificial Sequence
<220> FEATURE:
<223> OTHER INFORMATION: AX1 IgG2 Light Chain Antibody Sequence

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala Tyr Asp Tyr Ser Leu Gly
                85                  90                  95

Gly Tyr Val Phe Gly Asp Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 86
<211> LENGTH: 648
<212> TYPE: DNA
<213> ORGANISM: Artificial Sequence
<220> FEATURE:
<223> OTHER INFORMATION: AX1 IgG2 Light Chain Antibody Sequence

<400> SEQUENCE: 86

```
gacatccaga tgacccagtc tccatcttct ctgtctgcct ctgtgggcga ccgggtgacc     60

atcacctgcc gtgcctctca ggatatctct aggtatctgg cctggtatca gcagaagcca    120

ggtaaggcgc caaagctgct gatctacgcc gcctcttctt tgcagtctgg tgtgccatct    180

cgtttctctg gttctggttc tggcaccgac ttcaccctga ccatctcttc tttgcagcca    240

gaagacttcg ccacctacta ctgcgcggct tacgactatt ctttgggcgg ttacgtgttc    300

ggtgatggta ccaaagtgga gatcaaacgt acggtggctg caccatctgt cttcatcttc    360
```

ccgccatctg atgagcagtt gaaatctgga actgcctctg ttgtgtgcct gctgaataac 420
ttctatccca gagaggccaa agtacagtgg aaggtggata acgccctcca atcgggtaac 480
tcccaggaga gtgtcacaga gcaggacagc aaggacagca cctacagcct cagcagcacc 540
ctgacgctga gcaaagcaga ctacgagaaa cacaaagtct acgcctgcga agtcacccat 600
cagggcctga gctcgcccgt cacaaagagc ttcaacaggg gagagtgt 648

<210> SEQ ID NO 87
<211> LENGTH: 216
<212> TYPE: PRT
<213> ORGANISM: Artificial Sequence
<220> FEATURE:
<223> OTHER INFORMATION: AX9 IgG2 Light Chain Antibody Sequence

<400> SEQUENCE: 87

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Lys Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Val Tyr Asp Ser Ser Pro Asn
                85                  90                  95

Ala Tyr Val Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 88
<211> LENGTH: 648
<212> TYPE: DNA
<213> ORGANISM: Artificial Sequence
<220> FEATURE:
<223> OTHER INFORMATION: AX9 IgG2 Light Chain Antibody Sequence

<400> SEQUENCE: 88
gacatccaga tgacccagtc tccatcttct ctgtctgcct ctgtgggcga ccgggtgacc 60
atcacctgcc gtgcctctca ggatgtctct aagtatctgg cctggtatca gcagaagcca 120
ggtaaggcgc caaagctgct gatctacgcc gcctcttctt tgcagtctgg tgtgccatct 180
cgtttctctg gttctggttc tggcaccgac ttcaccctga ccatctcttc tttgcagcca 240

```
gaagacttcg ccacctacta ctgccaggta tacgacagct ctccaaacgc ttatgtgttc    300

ggtggtggta ccaaagtgga gatcaaacgt acggtggctg caccatctgt cttcatcttc    360

ccgccatctg atgagcagtt gaaatctgga actgcctctg ttgtgtgcct gctgaataac    420

ttctatccca gagaggccaa agtacagtgg aaggtggata acgccctcca atcgggtaac    480

tcccaggaga gtgtcacaga gcaggacagc aaggacagca cctacagcct cagcagcacc    540

ctgacgctga gcaaagcaga ctacgagaaa cacaaagtct acgcctgcga agtcacccat    600

cagggcctga gctcgcccgt cacaaagagc ttcaacaggg gagagtgt                 648
```

<210> SEQ ID NO 89
<211> LENGTH: 235
<212> TYPE: PRT
<213> ORGANISM: Artificial Sequence
<220> FEATURE:
<223> OTHER INFORMATION: AX189 IgG2 Light Chain Antibody Sequence

<400> SEQUENCE: 89

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Ser Arg Tyr Leu Thr Trp Tyr Gln Gln Lys Pro Gly Lys Ala Pro Lys
    50                  55                  60

Leu Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Ala Tyr Asp Tyr
            100                 105                 110

Ser Leu Ser Gly Tyr Val Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 90
<211> LENGTH: 705
<212> TYPE: DNA
<213> ORGANISM: Artificial Sequence
<220> FEATURE:
<223> OTHER INFORMATION: AX189 IgG2 Light Chain Antibody Sequence

<400> SEQUENCE: 90

```
atgggctggt cctgtatcat cctgttcctg gtggctacag ccacaggagt gcattctgac     60

atccagatga cccagagccc atcctccctg tctgcctctg tgggagacag ggtgaccatc    120

acttgtaggg caagccagga tgtgagcaga tacctgacct ggtatcaaca gaagcctggc    180

aaggctccaa aactgctgat ttatgctgcc tcctccctcc aatctggagt gccaagcagg    240

ttctctggct ctggctctgg cacagacttc accctgacca tctcctccct ccaacctgag    300

gactttgcca cctactactg tcaggcttat gactactccc tgtctggcta tgtgtttgga    360

ggaggcacca aggtggagat taagcgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705
```

```
<210> SEQ ID NO 91
<211> LENGTH: 4752
<212> TYPE: DNA
<213> ORGANISM: Artificial Sequence
<220> FEATURE:
<223> OTHER INFORMATION: AX1 Antibody Plasmid Sequence

<400> SEQUENCE: 91

gcgcaacgca attaatgtga gttagctcac tcattaggca ccccaggctt tacactttat     60

gcttccggct cgtatgttgt gtggaattgt gagcggataa caatttaccg gttcttgtaa    120

ggaggaatta aaaaatgaaa aagtctttag tcctcaaagc ctccgtagcc gttgctaccc    180

tcgttccgat gctaagcttc gctgacatcc agatgaccca gtctccatct tctctgtctg    240

cctctgtggg cgaccgggtg accatcacct gccgtgcctc tcaggatatc tctaggtatc    300

tggcctggta tcagcagaag ccaggtaagg cgccaaagct gctgatctac gccgcctctt    360

ctttgcagtc tggtgtgcca tctcgtttct ctggttctgg ttctggcacc gacttcaccc    420

tgaccatctc ttctttgcag ccagaagact tcgccaccta ctactgcgcg gcttacgact    480

attctttggg cggttacgtg ttcggtgatg gtaccaaagt ggagatcaaa cgtacggtgg    540

ctgcaccatc tgtcttcatc ttcccgccat ctgatgagca gttgaaatct ggaactgcct    600

ctgttgtgtg cctgctgaat aacttctatc ccagagaggc caaagtacag tggaaggtgg    660

ataacgccct ccaatcgggt aactcccagg agagtgtcac agagcaggac agcaaggaca    720

gcacctacag cctcagcagc accctgacgc tgagcaaagc agactacgag aaacacaaag    780

tctacgcctg cgaagtcacc catcagggcc tgagctcgcc cgtcacaaag agcttcaaca    840

ggggagagtg ttgataaggc gcgccacaat ttcacagtaa ggaggtttaa cttatgaaaa    900

aattattatt cgcaattcct ttagttgttc ctttctattc tcactccgct ggatccgaag    960

tgcagctgct ggaatctggt ggtggtctgg tgcagccagg tggttctctg cgtctgtctt   1020

gcaaggcctc tggtttcacc ttcacttctt actacatgca ctgggtgcgt caggcaccag   1080

gtaagggtct ggaatggatc ggtcggatca acccagattc tggtagtact aagtacaacg   1140

agaagttcaa gggtcgtgcc accatctcta gagacaactc taagaacacc ctgtacttgc   1200

agatgaactc tctgcgtgcc gaggacactg cagtgtacta ctgcgcccgt ggtggtcgtt   1260

tatcctggga cttcgacgtc tggggtcagg gtacgctggt gactgtctcg agcgcaagca   1320
```

```
ccaaaggccc atcggtattc cccctggcac cctcctccaa gagcacctct gggggcacag   1380
cggccctggg ctgcctggtc aaggactact tccccgagcc ggtgacggtg tcgtggaact   1440
caggcgctct gaccagcggc gtgcacacct tcccggctgt cctacagtcc tcaggactct   1500
actccctcag cagcgtggtg actgtgccct ccagcagctt gggcacccag acctacatct   1560
gcaacgtgaa tcacaagccc agcaacacta aggtggacaa gaaagttgag cccaaatctt   1620
gtgacaaaac tcacacagcg gccgcttatc catacgacgt accagactac gcaggaggtc   1680
atcaccatca tcaccatgtc gacagatctg gaggaggtga ggagaagtcc cggctgttgg   1740
agaaggagaa ccgtgaactg gaaaagatca ttgctgagaa agaggagcgt gtctctgaac   1800
tgcgccatca actccagtct gtaggaggtt gttaataagt cgacgtttaa acggtctcca   1860
gcttggctgt tttggcggat gagagaagat tttcagcctg atacagatta aatcagaacg   1920
cagaagcggt ctgataaaac agaatttgcc tggcggcagt agcgcggtgg tcccacctga   1980
ccccatgccg aactcagaag tgaaacgccg tagcgccgat ggtagtgtgg ggtctcccca   2040
tgcgagagta gggaactgcc aggcatcaaa taaaacgaaa ggctcagtcg aaagactggg   2100
cctttacgcg ctcactggcc gtcgttttac aacgtcgtga ctgggaaaac cctggcgtta   2160
cccaacttaa tcgccttgca gcacatcccc ctttcgccag ctggcgtaat agcgaagagg   2220
cccgcaccga tcgcccttcc caacagttgc gcagcctgaa tggcgaatgg gacgcgccct   2280
gtagcggcgc attaagcgcg gcgggtgtgg tggttacgcg cagcgtgacc gctacacttg   2340
ccagcgccct agcgcccgct cctttcgctt tcttcccttc ctttctcgcc acgttcgccg   2400
gctttccccg tcaagctcta aatcgggggc tccctttagg gttccgattt agtgctttac   2460
ggcacctcga ccccaaaaaa cttgattagg gtgatggttc acgtagtggg ccatcgccct   2520
gatagacggt ttttcgccct ttgacgttgg agtccacgtt ctttaatagt ggactcttgt   2580
tccaaactgg aacaacactc aaccctatct cggtctattc ttttgattta taagggattt   2640
tgccgatttc ggcctattgg ttaaaaaatg agctgattta acaaaaattt aacgcgaatt   2700
ttaacaaaat attaacgctt acaatttagg tggcactttt cggggaaatg tgcgcggaac   2760
ccctatttgt ttatttttct aaatacattc aaatatgtat ccgctcatga gacaataacc   2820
ctgataaatg cttcaataat attgaaaaag gaagagtatg agtattcaac atttccgtgt   2880
cgcccttatt cccttttttg cggcattttg ccttcctgtt tttgctcacc cagaaacgct   2940
ggtgaaagta aaagatgctg aagatcagtt gggtgcacga gtgggttaca tcgaactgga   3000
tctcaacagc ggtaagatcc ttgagagttt tcgccccgaa gaacgttttc caatgatgag   3060
cacttttaaa gttctgctat gtggcgcggt attatcccgt attgacgccg ggcaagagca   3120
actcggtcgc cgcatacact attctcagaa tgacttggtt gagtactcac cagtcacaga   3180
aaagcatctt acggatggca tgacagtaag agaattatgc agtgctgcca taaccatgag   3240
tgataacact gcggccaact tacttctgac aacgatcgga ggaccgaagg agctaaccgc   3300
ttttttgcac aacatggggg atcatgtaac tcgccttgat cgttgggaac cggagctgaa   3360
tgaagccata ccaaacgacg agcgtgacac cacgatgcct gtagcaatgg caacaacgtt   3420
gcgcaaacta ttaactggcg aactacttac tctagcttcc cggcaacaat taatagactg   3480
gatggaggcg gataaagttg caggaccact tctgcgctcg gcccttccgg ctggctggtt   3540
tattgctgat aaatctggag ccggtgagcg tgggtctcgc ggtatcattg cagcactggg   3600
gccagatggt aagccctccc gtatcgtagt tatctacacg acggggagtc aggcaactat   3660
ggatgaacga aatagacaga tcgctgagat aggtgcctca ctgattaagc attggtaact   3720
```

```
gtcagaccaa gtttactcat atatacttta gattgattta aaacttcatt tttaatttaa   3780

aaggatctag gtgaagatcc tttttgataa tctcatgacc aaaatccctt aacgtgagtt   3840

ttcgttccac tgagcgtcag accccgtaga aaagatcaaa ggatcttctt gagatccttt   3900

ttttctgcgc gtaatctgct gcttgcaaac aaaaaaacca ccgctaccag cggtggtttg   3960

tttgccggat caagagctac caactctttt tccgaaggta actggcttca gcagagcgca   4020

gataccaaat actgtccttc tagtgtagcc gtagttaggc caccacttca agaactctgt   4080

agcaccgcct acatacctcg ctctgctaat cctgttacca gtggctgctg ccagtggcga   4140

taagtcgtgt cttaccgggt tggactcaag acgatagtta ccggataagg cgcagcggtc   4200

gggctgaacg gggggttcgt gcacacagcc cagcttggag cgaacgacct acaccgaact   4260

gagataccta cagcgtgagc tatgagaaag cgccacgctt cccgaaggga gaaaggcgga   4320

caggtatccg gtaagcggca gggtcggaac aggagagcgc acgagggagc ttccaggggg   4380

aaacgcctgg tatctttata gtcctgtcgg gtttcgccac ctctgacttg agcgtcgatt   4440

tttgtgatgc tcgtcagggg ggcggagcct atggaaaaac gccagcaacg cggccttttt   4500

acggttcctg gccttttgct ggccttttgc tcacatgttc tttcctgcgt tatcccctga   4560

ttctgtggat aaccgtatta ccgcctttga gtgagctgat accgctcgcc gcagccgaac   4620

gaccgagcgc agcgagtcag tgagcgagga agcggaagag cgcccaatac gcaaaccgcc   4680

tctccccgcg cgttggccga ttcattaatg cagctggcac gacaggtttc ccgactggaa   4740

agcgggcagt ga                                                       4752
```

<210> SEQ ID NO 92
<211> LENGTH: 4758
<212> TYPE: DNA
<213> ORGANISM: Artificial Sequence
<220> FEATURE:
<223> OTHER INFORMATION: AX9 Antibody Plasmid Sequence

<400> SEQUENCE: 92

```
gcgcaacgca attaatgtga gttagctcac tcattaggca ccccaggctt tacactttat     60

gcttccggct cgtatgttgt gtggaattgt gagcggataa caatttaccg gttcttgtaa    120

ggaggaatta aaaaatgaaa aagtctttag tcctcaaagc ctccgtagcc gttgctaccc    180

tcgttccgat gctaagcttc gctgacatcc agatgaccca gtctccatct tctctgtctg    240

cctctgtggg cgaccgggtg accatcacct gccgtgcctc tcaggatgtc tctaagtatc    300

tggcctggta tcagcagaag ccaggtaagg cgccaaagct gctgatctac gccgcctctt    360

ctttgcagtc tggtgtgcca tctcgtttct ctggttctgg ttctggcacc gacttcaccc    420

tgaccatctc ttctttgcag ccagaagact tcgccaccta ctactgccag gtatacgaca    480

gctctccaaa cgcttatgtg ttcggtggtg gtaccaaagt ggagatcaaa cgtacggtgg    540

ctgcaccatc tgtcttcatc ttcccgccat ctgatgagca gttgaaatct ggaactgcct    600

ctgttgtgtg cctgctgaat aacttctatc ccagagaggc caaagtacag tggaaggtgg    660

ataacgccct ccaatcgggt aactcccagg agagtgtcac agagcaggac agcaaggaca    720

gcacctacag cctcagcagc accctgacgc tgagcaaagc agactacgag aaacacaaag    780

tctacgcctg cgaagtcacc catcagggcc tgagctcgcc cgtcacaaag agcttcaaca    840

ggggagagtg ttgataaggc gcgccacaat ttcacagtaa ggaggtttaa cttatgaaaa    900

aattattatt cgcaattcct ttagttgttc ctttctattc tcactccgct ggatccgaag    960
```

```
tgcagctgtt ggaatctggt ggtggtctgg tgcagccagg tggttctctg cgtctgtctt   1020
gcaaggcctc tggttacacc ttctcttctt actggatgca ctgggtgcgt caggcaccag   1080
gtaagggtct ggaatggatc ggtcgtatcg acccatataa cggtggcacc aagtacaacg   1140
agaagttcaa gggtaaggcc accatctcta gagacaactc taagaacacc ctgtacttgc   1200
agatgaactc tctgcgtgcc gaggacactg cagtgtacta ctgcgcccgt tatggttact   1260
accttggctc ttacgccatg gactactggg gtcagggtac gctggtgact gtctcgagcg   1320
caagcaccaa aggcccatcg gtattccccc tggcaccctc ctccaagagc acctctgggg   1380
gcacagcggc cctgggctgc ctggtcaagg actacttccc cgagccggtg acggtgtcgt   1440
ggaactcagg cgctctgacc agcggcgtgc acaccttccc ggctgtccta cagtcctcag   1500
gactctactc cctcagcagc gtggtgactg tgccctccag cagcttgggc acccagacct   1560
acatctgcaa cgtgaatcac aagcccagca acactaaggt ggacaagaaa gttgagccca   1620
aatcttgtga caaaactcac acagcggccg cttatccata cgacgtacca gactacgcag   1680
gaggtcatca ccatcatcac catgtcgaca gatctggagg aggtgaggag aagtcccggc   1740
tgttggagaa ggagaaccgt gaactggaaa agatcattgc tgagaaagag gagcgtgtct   1800
ctgaactgcg ccatcaactc cagtctgtag gaggttgtta ataagtcgac gtttaaacgg   1860
tctccagctt ggctgttttg gcggatgaga gaagattttc agcctgatac agattaaatc   1920
agaacgcaga agcggtctga taaaacagaa tttgcctggc ggcagtagcg cggtggtccc   1980
acctgacccc atgccgaact cagaagtgaa acgccgtagc gccgatggta gtgtggggtc   2040
tccccatgcg agagtaggga actgccaggc atcaaataaa acgaaaggct cagtcgaaag   2100
actgggcctt tacgcgctca ctggccgtcg ttttacaacg tcgtgactgg gaaaaccctg   2160
gcgttaccca acttaatcgc cttgcagcac atcccccttt cgccagctgg cgtaatagcg   2220
aagaggcccg caccgatcgc ccttcccaac agttgcgcag cctgaatggc gaatgggacg   2280
cgccctgtag cggcgcatta agcgcggcgg gtgtggtggt tacgcgcagc gtgaccgcta   2340
cacttgccag cgccctagcg cccgctcctt tcgctttctt cccttccttt ctcgccacgt   2400
tcgccggctt tccccgtcaa gctctaaatc gggggctccc tttagggttc cgatttagtg   2460
ctttacggca cctcgacccc aaaaaacttg attagggtga tggttcacgt agtgggccat   2520
cgccctgata gacggttttt cgccctttga cgttggagtc cacgttcttt aatagtggac   2580
tcttgttcca aactggaaca acactcaacc ctatctcggt ctattctttt gatttataag   2640
ggattttgcc gatttcggcc tattggttaa aaaatgagct gatttaacaa aaatttaacg   2700
cgaattttaa caaaatatta acgcttacaa tttaggtggc acttttcggg gaaatgtgcg   2760
cggaacccct atttgtttat ttttctaaat acattcaaat atgtatccgc tcatgagaca   2820
ataaccctga taaatgcttc aataatattg aaaaaggaag agtatgagta ttcaacattt   2880
ccgtgtcgcc cttattccct tttttgcggc attttgcctt cctgtttttg ctcacccaga   2940
aacgctggtg aaagtaaaag atgctgaaga tcagttgggt gcacgagtgg gttacatcga   3000
actggatctc aacagcggta agatccttga gagttttcgc cccgaagaac gttttccaat   3060
gatgagcact tttaaagttc tgctatgtgg cgcggtatta tcccgtattg acgccgggca   3120
agagcaactc ggtcgccgca tacactattc tcagaatgac ttggttgagt actcaccagt   3180
cacagaaaag catcttacgg atggcatgac agtaagagaa ttatgcagtg ctgccataac   3240
catgagtgat aacactgcgg ccaacttact tctgacaacg atcggaggac cgaaggagct   3300
aaccgctttt ttgcacaaca tgggggatca tgtaactcgc cttgatcgtt gggaaccgga   3360
```

```
gctgaatgaa gccataccaa acgacgagcg tgacaccacg atgcctgtag caatggcaac   3420

aacgttgcgc aaactattaa ctggcgaact acttactcta gcttcccggc aacaattaat   3480

agactggatg gaggcggata aagttgcagg accacttctg cgctcggccc ttccggctgg   3540

ctggtttatt gctgataaat ctggagccgg tgagcgtggg tctcgcggta tcattgcagc   3600

actggggcca gatggtaagc cctcccgtat cgtagttatc tacacgacgg ggagtcaggc   3660

aactatggat gaacgaaata gacagatcgc tgagataggt gcctcactga ttaagcattg   3720

gtaactgtca gaccaagttt actcatatat actttagatt gatttaaaac ttcattttta   3780

atttaaaagg atctaggtga agatcctttt tgataatctc atgaccaaaa tcccttaacg   3840

tgagttttcg ttccactgag cgtcagaccc cgtagaaaag atcaaaggat cttcttgaga   3900

tccttttttt ctgcgcgtaa tctgctgctt gcaaacaaaa aaaccaccgc taccagcggt   3960

ggtttgtttg ccggatcaag agctaccaac tctttttccg aaggtaactg gcttcagcag   4020

agcgcagata ccaaatactg tccttctagt gtagccgtag ttaggccacc acttcaagaa   4080

ctctgtagca ccgcctacat acctcgctct gctaatcctg ttaccagtgg ctgctgccag   4140

tggcgataag tcgtgtctta ccgggttgga ctcaagacga tagttaccgg ataaggcgca   4200

gcggtcgggc tgaacggggg gttcgtgcac acagcccagc ttggagcgaa cgacctacac   4260

cgaactgaga tacctacagc gtgagctatg agaaagcgcc acgcttcccg aagggagaaa   4320

ggcggacagg tatccggtaa gcggcagggt cggaacagga gagcgcacga gggagcttcc   4380

agggggaaac gcctggtatc tttatagtcc tgtcgggttt cgccacctct gacttgagcg   4440

tcgatttttg tgatgctcgt caggggggcg gagcctatgg aaaaacgcca gcaacgcggc   4500

ctttttacgg ttcctggcct tttgctggcc ttttgctcac atgttctttc ctgcgttatc   4560

ccctgattct gtggataacc gtattaccgc ctttgagtga gctgataccg ctcgccgcag   4620

ccgaacgacc gagcgcagcg agtcagtgag cgaggaagcg gaagagcgcc caatacgcaa   4680

accgcctctc cccgcgcgtt ggccgattca ttaatgcagc tggcacgaca ggtttcccga   4740

ctggaaagcg ggcagtga                                                 4758
```

```
<210> SEQ ID NO 93
<211> LENGTH: 4534
<212> TYPE: DNA
<213> ORGANISM: Artificial Sequence
<220> FEATURE:
<223> OTHER INFORMATION: AX189 Antibody Plasmid Sequence

<400> SEQUENCE: 93
```

```
gcgcaacgca attaatgtga gttagctcac tcattaggca ccccaggctt tacactttat     60

gcttccggct cgtatgttgt gtggaattgt gagcggataa caatttaccg gttcttgtaa    120

ggaggaatta aaaaatgaaa aagtctttag tcctcaaagc ctccgtagcc gttgctaccc    180

tcgttccgat gctaagcttc gctgacatcc agatgaccca gtctccatct tctctgtctg    240

cctctgtggg cgaccgggtg accatcacct gccgtgcctc tcaggatgtc tctaggtatc    300

tgacctggta tcagcagaag ccaggtaagg cgccaaagct gctgatctac gccgcctctt    360

ctttgcagtc tggtgtgcca tctcgtttct ctggttctgg ttctggcacc gacttcaccc    420

tgaccatctc ttctttgcag ccagaagact tcgccaccta ctactgccag gcttacgact    480

attctttgag cggttacgtg ttcggtggtg gtaccaaagt ggagatcaaa cgtacggtgg    540

ctgcaccatc tgtattcatc ttcccgccat ctgatgagca gttgaaatct ggaactgcct    600
```

```
ctgttgtgtg cctgctgaat aacttctatc ccagagaggc caaagtacag tggaaggtgg    660
ataacgccct ccaatcgggt aactcccagg agagtgtcac agagcaggac agcaaggaca    720
gcacctacag cctcagcagc accctgacgc tgagcaaagc agactacgag aaacacaaag    780
tctacgcctg cgaagtcacc catcagggcc tgagctcgcc cgtcacaaag agcttcaaca    840
ggggagagtg ttaatgatgt accggcgcgc cacaatttca cagtaaggag gtttaactta    900
tgaaaaaatt attattcgca attcctttag ttgttccttt ctattctcac tccgctggat    960
ccgaagtgca gctgttggaa tctggtggtg gtctggtgca gccaggtggt tctctgcgtc   1020
tgtcttgcaa ggcctctggt tacaccttct cttcttactg gatgcactgg gtgcgtcagg   1080
caccaggtaa gggtctggaa tggatcggtc gtatcgaccc atataacggt ggcaccaagt   1140
acaacgagaa gttcaagggt aaggccacca tctctagaga caactctaag aacaccctgt   1200
acttgcagat gaactctctg cgtgccgagg acactgcagt gtactactgc gcccgttatg   1260
gttactacct tggctcttac gccatggact actggggtca gggtacgctg gtgactgtct   1320
cgagcgcaag caccaaaggc ccatcggtat tccccctggc accctcctcc aagagcacct   1380
ctgggggcac agcggccctg ggctgcctgg tcaaggacta cttccccgag ccggtgacgg   1440
tgtcgtggaa ctcaggcgct ctgaccagcg gcgtgcacac cttcccggct gtcctacagt   1500
cctcaggact ctactccctc agcagcgtgg tgactgtgcc ctccagcagc ttgggcaccc   1560
agacctacat ctgcaacgtg aatcacaagc ccagcaacac taaggtggac aagaaagttg   1620
agcccaaatc ttgtgacaaa actcacacag cggccgctta tccatacgac gtaccagact   1680
acgcaggagg tcatcaccat catcaccatt agagatctgg aggaggtgag gagaagtccc   1740
ggctgttgga gaaggagaac cgtgaactgg aaaagatcat tgctgagaaa gaggagcgtg   1800
tctctgaact gcgccatcaa ctccagtctg taggaggttg ttaataagtc gacctcgacc   1860
aattcgccct atagtgagtc gtattacgcg cgctcactgg ccgtcgtttt acaacgtcgt   1920
gactgggaaa accctggcgt tacccaactt aatcgccttg cagcacatcc ccctttcgcc   1980
agctggcgta atagcgaaga ggcccgcacc gatcgccctt cccaacagtt gcgcagcctg   2040
aatggcgaat gggacgcgcc ctgtagcggc gcattaagcg cggcgggtgt ggtggttacg   2100
cgcagcgtga ccgctacact tgccagcgcc ctagcgcccg ctcctttcgc tttcttccct   2160
tcctttctcg ccacgttcgc cggctttccc cgtcaagctc taaatcgggg gctcccttta   2220
gggttccgat ttagtgcttt acggcacctc gaccccaaaa aacttgatta gggtgatggt   2280
tcacgtagtg ggccatcgcc ctgatagacg gtttttcgcc ctttgacgtt ggagtccacg   2340
ttctttaata gtggactctt gttccaaact ggaacaacac tcaaccctat ctcggtctat   2400
tcttttgatt tataagggat tttgccgatt tcggcctatt ggttaaaaaa tgagctgatt   2460
taacaaaaat ttaacgcgaa ttttaacaaa atattaacgc ttacaattta ggtggcactt   2520
ttcggggaaa tgtgcgcgga acccctattt gtttattttt ctaaatacat tcaaatatgt   2580
atccgctcat gagacaataa ccctgataaa tgcttcaata atattgaaaa aggaagagta   2640
tgagtattca acatttccgt gtcgccctta ttcccttttt tgcggcattt tgccttcctg   2700
tttttgctca cccagaaacg ctggtgaaag taaaagatgc tgaagatcag ttgggtgcac   2760
gagtgggtta catcgaactg gatctcaaca gcggtaagat ccttgagagt tttcgccccg   2820
aagaacgttt tccaatgatg agcactttta aagttctgct atgtggcgcg gtattatccc   2880
gtattgacgc cgggcaagag caactcggtc gccgcataca ctattctcag aatgacttgg   2940
ttgagtactc accagtcaca gaaaagcatc ttacggatgg catgacagta agagaattat   3000
```

```
gcagtgctgc cataaccatg agtgataaca ctgcggccaa cttacttctg acaacgatcg   3060

gaggaccgaa ggagctaacc gcttttttgc acaacatggg ggatcatgta actcgccttg   3120

atcgttggga accggagctg aatgaagcca taccaaacga cgagcgtgac accacgatgc   3180

ctgtagcaat ggcaacaacg ttgcgcaaac tattaactgg cgaactactt actctagctt   3240

cccggcaaca attaatagac tggatggagg cggataaagt tgcaggacca cttctgcgct   3300

cggcccttcc ggctggctgg tttattgctg ataaatctgg agccggtgag cgtgggtctc   3360

gcggtatcat tgcagcactg gggccagatg gtaagccctc ccgtatcgta gttatctaca   3420

cgacggggag tcaggcaact atggatgaac gaaatagaca gatcgctgag ataggtgcct   3480

cactgattaa gcattggtaa ctgtcagacc aagtttactc atatatactt tagattgatt   3540

taaaacttca tttttaattt aaaaggatct aggtgaagat cctttttgat aatctcatga   3600

ccaaaatccc ttaacgtgag ttttcgttcc actgagcgtc agaccccgta gaaaagatca   3660

aaggatcttc ttgagatcct ttttttctgc gcgtaatctg ctgcttgcaa acaaaaaaac   3720

caccgctacc agcggtggtt tgtttgccgg atcaagagct accaactctt tttccgaagg   3780

taactggctt cagcagagcg cagataccaa atactgtcct tctagtgtag ccgtagttag   3840

gccaccactt caagaactct gtagcaccgc ctacatacct cgctctgcta atcctgttac   3900

cagtggctgc tgccagtggc gataagtcgt gtcttaccgg gttggactca agacgatagt   3960

taccggataa ggcgcagcgg tcgggctgaa cggggggttc gtgcacacag cccagcttgg   4020

agcgaacgac ctacaccgaa ctgagatacc tacagcgtga gctatgagaa agcgccacgc   4080

ttcccgaagg gagaaaggcg gacaggtatc cggtaagcgg cagggtcgga acaggagagc   4140

gcacgaggga gcttccaggg ggaaacgcct ggtatcttta tagtcctgtc gggtttcgcc   4200

acctctgact tgagcgtcga tttttgtgat gctcgtcagg ggggcggagc ctatggaaaa   4260

acgccagcaa cgcggccttt ttacggttcc tggccttttg ctggcctttt gctcacatgt   4320

tctttcctgc gttatcccct gattctgtgg ataaccgtat taccgccttt gagtgagctg   4380

ataccgctcg ccgcagccga acgaccgagc gcagcgagtc agtgagcgag gaagcggaag   4440

agcgcccaat acgcaaaccg cctctccccg cgcgttggcc gattcattaa tgcagctggc   4500

acgacaggtt tcccgactgg aaagcgggca gtga                                4534
```

<210> SEQ ID NO 94
<211> LENGTH: 22
<212> TYPE: PRT
<213> ORGANISM: Artificial Sequence
<220> FEATURE:
<223> OTHER INFORMATION: Antibody Heavy Chain Framework Sequence

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys
            20
```

<210> SEQ ID NO 95
<211> LENGTH: 8
<212> TYPE: PRT
<213> ORGANISM: Artificial Sequence
<220> FEATURE:
<223> OTHER INFORMATION: Antibody Heavy Chain Framework Sequence

<400> SEQUENCE: 95

Gln Ala Pro Gly Lys Gly Leu Glu
1 5

<210> SEQ ID NO 96
<211> LENGTH: 26
<212> TYPE: PRT
<213> ORGANISM: Artificial Sequence
<220> FEATURE:
<223> OTHER INFORMATION: Antibody Heavy Chain Framework Sequence

<400> SEQUENCE: 96

Ile Ser Arg Asp Asn Ser Lys Asn Thr Leu Tyr Leu Gln Met Asn Ser
1 5 10 15

Leu Arg Ala Glu Asp Thr Ala Val Tyr Tyr
20 25

<210> SEQ ID NO 97
<211> LENGTH: 8
<212> TYPE: PRT
<213> ORGANISM: Artificial Sequence
<220> FEATURE:
<223> OTHER INFORMATION: Antibody Heavy Chain Framework Sequence

<400> SEQUENCE: 97

Gly Thr Leu Val Thr Val Ser Ser
1 5

<210> SEQ ID NO 98
<211> LENGTH: 23
<212> TYPE: PRT
<213> ORGANISM: Artificial Sequence
<220> FEATURE:
<223> OTHER INFORMATION: Antibody Light Chain Framework Sequence

<400> SEQUENCE: 98

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 99
<211> LENGTH: 15
<212> TYPE: PRT
<213> ORGANISM: Artificial Sequence
<220> FEATURE:
<223> OTHER INFORMATION: Antibody Light Chain Framework Sequence

<400> SEQUENCE: 99

Trp Tyr Gln Gln Lys Pro Gly Lys Ala Pro Lys Leu Leu Ile Tyr
1 5 10 15

<210> SEQ ID NO 100
<211> LENGTH: 32
<212> TYPE: PRT
<213> ORGANISM: Artificial Sequence
<220> FEATURE:
<223> OTHER INFORMATION: Antibody Light Chain Framework Sequence

<400> SEQUENCE: 100

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 101

```
<211> LENGTH: 10
<212> TYPE: PRT
<213> ORGANISM: Artificial Sequence
<220> FEATURE:
<223> OTHER INFORMATION: Antibody Light Chain Framework Sequence

<400> SEQUENCE: 101

Phe Gly Asp Gly Thr Lys Val Glu Ile Lys
1               5                   10


<210> SEQ ID NO 102
<211> LENGTH: 10
<212> TYPE: PRT
<213> ORGANISM: Artificial Sequence
<220> FEATURE:
<223> OTHER INFORMATION: Antibody Light Chain Framework Sequence

<400> SEQUENCE: 102

Phe Gly Gly Gly Thr Lys Val Glu Ile Lys
1               5                   10


<210> SEQ ID NO 103
<211> LENGTH: 6
<212> TYPE: PRT
<213> ORGANISM: Artificial Sequence
<220> FEATURE:
<223> OTHER INFORMATION: PCSK9 internal processing site

<400> SEQUENCE: 103

Ser Ser Val Phe Ala Gln
1               5


<210> SEQ ID NO 104
<211> LENGTH: 6
<212> TYPE: PRT
<213> ORGANISM: Artificial Sequence
<220> FEATURE:
<223> OTHER INFORMATION: PCSK9 internal processing site

<400> SEQUENCE: 104

Ser Ile Pro Trp Asn Leu
1               5


<210> SEQ ID NO 105
<211> LENGTH: 4
<212> TYPE: PRT
<213> ORGANISM: Artificial Sequence
<220> FEATURE:
<223> OTHER INFORMATION: Epitope sequence

<400> SEQUENCE: 105

Pro Trp Asn Leu
1


<210> SEQ ID NO 106
<211> LENGTH: 22
<212> TYPE: PRT
<213> ORGANISM: Artificial Sequence
<220> FEATURE:
<223> OTHER INFORMATION: Epitope sequence

<400> SEQUENCE: 106

Pro Ala Ser Ala Pro Glu Val Ile Thr Val Gly Ala Thr Asn Ala Gln
1               5                   10                  15

Asp Gln Pro Val Thr Leu
            20
```

<210> SEQ ID NO 107
<211> LENGTH: 13
<212> TYPE: PRT
<213> ORGANISM: Artificial Sequence
<220> FEATURE:
<223> OTHER INFORMATION: Epitope sequence

<400> SEQUENCE: 107

Arg Leu Ile His Phe Ser Ala Lys Asp Val Ile Asn Glu
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Epitope sequence

<400> SEQUENCE: 108

Phe Pro Glu Asp Gln Arg Val Leu Thr Pro Asn Leu
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Epitope sequence

<400> SEQUENCE: 109

Val Gly Ala Thr Asn Ala Gln Asp Gln Pro Val Thr Leu
1               5                   10

<210> SEQ ID NO 110
<211> LENGTH: 8
<212> TYPE: PRT
<213> ORGANISM: Artificial Sequence
<220> FEATURE:
<223> OTHER INFORMATION: Epitope sequence

<400> SEQUENCE: 110

Ser Ala Lys Asp Val Ile Asn Glu
1               5

<210> SEQ ID NO 111
<211> LENGTH: 5
<212> TYPE: PRT
<213> ORGANISM: Artificial Sequence
<220> FEATURE:
<223> OTHER INFORMATION: Epitope sequence

<400> SEQUENCE: 111

Phe Pro Glu Asp Gln
1               5

<210> SEQ ID NO 112
<211> LENGTH: 14
<212> TYPE: PRT
<213> ORGANISM: Artificial Sequence
<220> FEATURE:
<223> OTHER INFORMATION: Epitope sequence

<400> SEQUENCE: 112

Thr Asn Ala Gln Asp Gln Pro Val Thr Leu Gly Thr Leu Gly
1               5                   10

```
<210> SEQ ID NO 113
<211> LENGTH: 10
<212> TYPE: PRT
<213> ORGANISM: Artificial Sequence
<220> FEATURE:
<223> OTHER INFORMATION: Epitope sequence

<400> SEQUENCE: 113

Asp Val Ile Asn Glu Ala Trp Phe Pro Glu
1               5                   10


<210> SEQ ID NO 114
<211> LENGTH: 11
<212> TYPE: PRT
<213> ORGANISM: Artificial Sequence
<220> FEATURE:
<223> OTHER INFORMATION: Epitope sequence

<400> SEQUENCE: 114

Phe Glu Asn Val Pro Glu Glu Asp Gly Thr Arg
1               5                   10


<210> SEQ ID NO 115
<211> LENGTH: 6
<212> TYPE: PRT
<213> ORGANISM: Artificial Sequence
<220> FEATURE:
<223> OTHER INFORMATION: Epitope sequence

<400> SEQUENCE: 115

Gln Ala Ser Lys Cys Asp
1               5


<210> SEQ ID NO 116
<211> LENGTH: 9
<212> TYPE: PRT
<213> ORGANISM: Artificial Sequence
<220> FEATURE:
<223> OTHER INFORMATION: Epitope sequence

<400> SEQUENCE: 116

Arg Val Leu Asn Cys Gln Gly Lys Gly
1               5


<210> SEQ ID NO 117
<211> LENGTH: 330
<212> TYPE: PRT
<213> ORGANISM: Artificial Sequence
<220> FEATURE:
<223> OTHER INFORMATION: Sequence containing FC domain of IgG1

<400> SEQUENCE: 117

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 118
<211> LENGTH: 326
<212> TYPE: PRT
<213> ORGANISM: Artificial Sequence
<220> FEATURE:
<223> OTHER INFORMATION: Sequence containing FC domain of IgG2

<400> SEQUENCE: 118

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125
```

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 119
<211> LENGTH: 327
<212> TYPE: PRT
<213> ORGANISM: Artificial Sequence
<220> FEATURE:
<223> OTHER INFORMATION: Sequence containing FC domain of IgG4

<400> SEQUENCE: 119

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 120
<211> LENGTH: 326
<212> TYPE: PRT
<213> ORGANISM: Artificial Sequence
<220> FEATURE:
<223> OTHER INFORMATION: Sequence containing FC domain of IgG2m4

<400> SEQUENCE: 120

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190
```

```
Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 121
<211> LENGTH: 21
<212> TYPE: PRT
<213> ORGANISM: Artificial Sequence
<220> FEATURE:
<223> OTHER INFORMATION: PCSK9 fragment

<400> SEQUENCE: 121

Ala Leu Arg Ser Glu Glu Asp Gly Leu Ala Glu Ala Pro Glu His Gly
1               5                   10                  15

Thr Thr Ala Thr Phe
            20


<210> SEQ ID NO 122
<211> LENGTH: 7
<212> TYPE: PRT
<213> ORGANISM: Artificial Sequence
<220> FEATURE:
<223> OTHER INFORMATION: PCSK9 fragment

<400> SEQUENCE: 122

Arg Ser Glu Glu Asp Gly Leu
1               5


<210> SEQ ID NO 123
<211> LENGTH: 19
<212> TYPE: PRT
<213> ORGANISM: Artificial Sequence
<220> FEATURE:
<223> OTHER INFORMATION: PCSK9 fragment

<400> SEQUENCE: 123

Arg Ser Glu Glu Asp Gly Leu Ala Glu Ala Pro Glu His Gly Thr Thr
1               5                   10                  15

Ala Thr Phe


<210> SEQ ID NO 124
<211> LENGTH: 24
<212> TYPE: PRT
<213> ORGANISM: Artificial Sequence
<220> FEATURE:
<223> OTHER INFORMATION: PCSK9 fragment
```

<400> SEQUENCE: 124

```
Ala Pro Glu His Gly Thr Thr Ala Thr Phe His Arg Cys Ala Lys Asp
1               5                   10                  15

Pro Trp Arg Leu Pro Gly Thr Tyr
            20
```

<210> SEQ ID NO 125
<211> LENGTH: 13
<212> TYPE: PRT
<213> ORGANISM: Artificial Sequence
<220> FEATURE:
<223> OTHER INFORMATION: PCSK9 fragment

<400> SEQUENCE: 125

```
Arg Cys Ala Lys Asp Pro Trp Arg Leu Pro Gly Thr Tyr
1               5                   10
```

<210> SEQ ID NO 126
<211> LENGTH: 38
<212> TYPE: PRT
<213> ORGANISM: Artificial Sequence
<220> FEATURE:
<223> OTHER INFORMATION: PCSK9 fragment

<400> SEQUENCE: 126

```
Glu Thr His Leu Ser Gln Ser Glu Arg Thr Ala Arg Arg Leu Gln Ala
1               5                   10                  15

Gln Ala Ala Arg Arg Gly Tyr Leu Thr Lys Ile Leu His Val Phe His
            20                  25                  30

Gly Leu Leu Pro Gly Phe
        35
```

<210> SEQ ID NO 127
<211> LENGTH: 39
<212> TYPE: PRT
<213> ORGANISM: Artificial Sequence
<220> FEATURE:
<223> OTHER INFORMATION: PCSK9 fragment

<400> SEQUENCE: 127

```
Glu Thr His Leu Ser Gln Ser Glu Arg Thr Ala Arg Arg Leu Gln Ala
1               5                   10                  15

Gln Ala Ala Arg Arg Gly Tyr Leu Thr Lys Ile Leu His Val Phe His
            20                  25                  30

Gly Leu Leu Pro Gly Phe Leu
        35
```

<210> SEQ ID NO 128
<211> LENGTH: 13
<212> TYPE: PRT
<213> ORGANISM: Artificial Sequence
<220> FEATURE:
<223> OTHER INFORMATION: PCSK9 fragment

<400> SEQUENCE: 128

```
Ile Leu His Val Phe His Gly Leu Leu Pro Gly Phe Leu
1               5                   10
```

<210> SEQ ID NO 129
<211> LENGTH: 5
<212> TYPE: PRT
<213> ORGANISM: Artificial Sequence
<220> FEATURE:
<223> OTHER INFORMATION: PCSK9 fragment

<400> SEQUENCE: 129

Met Ser Gly Asp Leu
1 5

<210> SEQ ID NO 130
<211> LENGTH: 7
<212> TYPE: PRT
<213> ORGANISM: Artificial Sequence
<220> FEATURE:
<223> OTHER INFORMATION: PCSK9 fragment

<400> SEQUENCE: 130

Met Ser Gly Asp Leu Leu Glu
1 5

<210> SEQ ID NO 131
<211> LENGTH: 8
<212> TYPE: PRT
<213> ORGANISM: Artificial Sequence
<220> FEATURE:
<223> OTHER INFORMATION: PCSK9 fragment

<400> SEQUENCE: 131

Leu Lys Leu Pro His Val Asp Tyr
1 5

<210> SEQ ID NO 132
<211> LENGTH: 7
<212> TYPE: PRT
<213> ORGANISM: Artificial Sequence
<220> FEATURE:
<223> OTHER INFORMATION: PCSK9 fragment

<400> SEQUENCE: 132

Lys Leu Pro His Val Asp Tyr
1 5

<210> SEQ ID NO 133
<211> LENGTH: 19
<212> TYPE: PRT
<213> ORGANISM: Artificial Sequence
<220> FEATURE:
<223> OTHER INFORMATION: PCSK9 fragment

<400> SEQUENCE: 133

Ile Thr Pro Pro Arg Tyr Arg Ala Asp Glu Tyr Gln Pro Pro Asp Gly
1 5 10 15

Gly Ser Leu

<210> SEQ ID NO 134
<211> LENGTH: 21
<212> TYPE: PRT
<213> ORGANISM: Artificial Sequence
<220> FEATURE:
<223> OTHER INFORMATION: PCSK9 fragment

<400> SEQUENCE: 134

Ile Thr Pro Pro Arg Tyr Arg Ala Asp Glu Tyr Gln Pro Pro Asp Gly
1 5 10 15

Gly Ser Leu Val Glu
20

<210> SEQ ID NO 135
<211> LENGTH: 14

```
<212> TYPE: PRT
<213> ORGANISM: Artificial Sequence
<220> FEATURE:
<223> OTHER INFORMATION: PCSK9 fragment

<400> SEQUENCE: 135

Thr Ser Ile Gln Ser Asp His Arg Glu Ile Glu Gly Arg Val
1               5                   10


<210> SEQ ID NO 136
<211> LENGTH: 17
<212> TYPE: PRT
<213> ORGANISM: Artificial Sequence
<220> FEATURE:
<223> OTHER INFORMATION: PCSK9 fragment

<400> SEQUENCE: 136

Ile Gln Ser Asp His Arg Glu Ile Glu Gly Arg Val Met Val Thr Asp
1               5                   10                  15

Phe


<210> SEQ ID NO 137
<211> LENGTH: 23
<212> TYPE: PRT
<213> ORGANISM: Artificial Sequence
<220> FEATURE:
<223> OTHER INFORMATION: PCSK9 fragment

<400> SEQUENCE: 137

Val Pro Glu Glu Asp Gly Thr Arg Phe His Arg Gln Ala Ser Lys Cys
1               5                   10                  15

Asp Ser His Gly Thr His Leu
            20


<210> SEQ ID NO 138
<211> LENGTH: 40
<212> TYPE: PRT
<213> ORGANISM: Artificial Sequence
<220> FEATURE:
<223> OTHER INFORMATION: PCSK9 fragment

<400> SEQUENCE: 138

Val Pro Glu Glu Asp Gly Thr Arg Phe His Arg Gln Ala Ser Lys Cys
1               5                   10                  15

Asp Ser His Gly Thr His Leu Ala Gly Val Val Ser Gly Arg Asp Ala
            20                  25                  30

Gly Val Ala Lys Gly Ala Ser Met
        35                  40


<210> SEQ ID NO 139
<211> LENGTH: 15
<212> TYPE: PRT
<213> ORGANISM: Artificial Sequence
<220> FEATURE:
<223> OTHER INFORMATION: PCSK9 fragment

<400> SEQUENCE: 139

Val Val Ser Gly Arg Asp Ala Gly Val Ala Lys Gly Ala Ser Met
1               5                   10                  15


<210> SEQ ID NO 140
<211> LENGTH: 16
<212> TYPE: PRT
<213> ORGANISM: Artificial Sequence
<220> FEATURE:
```

```
<223> OTHER INFORMATION: PCSK9 fragment

<400> SEQUENCE: 140

Leu Arg Val Leu Asn Cys Gln Gly Lys Gly Thr Val Ser Gly Thr Leu
1               5                   10                  15


<210> SEQ ID NO 141
<211> LENGTH: 16
<212> TYPE: PRT
<213> ORGANISM: Artificial Sequence
<220> FEATURE:
<223> OTHER INFORMATION: PCSK9 fragment

<400> SEQUENCE: 141

Ile Arg Lys Ser Gln Leu Val Gln Pro Val Gly Pro Leu Val Val Leu
1               5                   10                  15


<210> SEQ ID NO 142
<211> LENGTH: 15
<212> TYPE: PRT
<213> ORGANISM: Artificial Sequence
<220> FEATURE:
<223> OTHER INFORMATION: PCSK9 fragment

<400> SEQUENCE: 142

Arg Lys Ser Gln Leu Val Gln Pro Val Gly Pro Leu Val Val Leu
1               5                   10                  15


<210> SEQ ID NO 143
<211> LENGTH: 8
<212> TYPE: PRT
<213> ORGANISM: Artificial Sequence
<220> FEATURE:
<223> OTHER INFORMATION: PCSK9 fragment

<400> SEQUENCE: 143

Leu Leu Pro Leu Ala Gly Gly Tyr
1               5


<210> SEQ ID NO 144
<211> LENGTH: 11
<212> TYPE: PRT
<213> ORGANISM: Artificial Sequence
<220> FEATURE:
<223> OTHER INFORMATION: PCSK9 fragment

<400> SEQUENCE: 144

Leu Ala Gly Gly Tyr Ser Arg Val Leu Asn Ala
1               5                   10


<210> SEQ ID NO 145
<211> LENGTH: 13
<212> TYPE: PRT
<213> ORGANISM: Artificial Sequence
<220> FEATURE:
<223> OTHER INFORMATION: PCSK9 fragment

<400> SEQUENCE: 145

Leu Ala Gly Gly Tyr Ser Arg Val Leu Asn Ala Ala Cys
1               5                   10


<210> SEQ ID NO 146
<211> LENGTH: 8
<212> TYPE: PRT
<213> ORGANISM: Artificial Sequence
<220> FEATURE:
<223> OTHER INFORMATION: PCSK9 fragment
```

<400> SEQUENCE: 146

Leu Ala Arg Ala Gly Val Val Leu
1 5

<210> SEQ ID NO 147
<211> LENGTH: 5
<212> TYPE: PRT
<213> ORGANISM: Artificial Sequence
<220> FEATURE:
<223> OTHER INFORMATION: PCSK9 fragment

<400> SEQUENCE: 147

Ala Gly Val Val Leu
1 5

<210> SEQ ID NO 148
<211> LENGTH: 5
<212> TYPE: PRT
<213> ORGANISM: Artificial Sequence
<220> FEATURE:
<223> OTHER INFORMATION: PCSK9 fragment

<400> SEQUENCE: 148

Ala Ala Gly Asn Phe
1 5

<210> SEQ ID NO 149
<211> LENGTH: 5
<212> TYPE: PRT
<213> ORGANISM: Artificial Sequence
<220> FEATURE:
<223> OTHER INFORMATION: PCSK9 fragment

<400> SEQUENCE: 149

Asp Asp Ala Cys Leu
1 5

<210> SEQ ID NO 150
<211> LENGTH: 7
<212> TYPE: PRT
<213> ORGANISM: Artificial Sequence
<220> FEATURE:
<223> OTHER INFORMATION: PCSK9 fragment

<400> SEQUENCE: 150

Pro Ala Ser Ala Pro Glu Val
1 5

<210> SEQ ID NO 151
<211> LENGTH: 8
<212> TYPE: PRT
<213> ORGANISM: Artificial Sequence
<220> FEATURE:
<223> OTHER INFORMATION: PCSK9 fragment

<400> SEQUENCE: 151

Leu Gly Thr Asn Phe Gly Arg Cys
1 5

<210> SEQ ID NO 152
<211> LENGTH: 7
<212> TYPE: PRT
<213> ORGANISM: Artificial Sequence
<220> FEATURE:
<223> OTHER INFORMATION: PCSK9 fragment

<400> SEQUENCE: 152

Leu Phe Ala Pro Gly Glu Asp
1 5

<210> SEQ ID NO 153
<211> LENGTH: 15
<212> TYPE: PRT
<213> ORGANISM: Artificial Sequence
<220> FEATURE:
<223> OTHER INFORMATION: PCSK9 fragment

<400> SEQUENCE: 153

Pro Gly Glu Asp Ile Ile Gly Ala Ser Ser Asp Cys Ser Thr Cys
1 5 10 15

<210> SEQ ID NO 154
<211> LENGTH: 9
<212> TYPE: PRT
<213> ORGANISM: Artificial Sequence
<220> FEATURE:
<223> OTHER INFORMATION: PCSK9 fragment

<400> SEQUENCE: 154

Gly Ala Ser Ser Asp Cys Ser Thr Cys
1 5

<210> SEQ ID NO 155
<211> LENGTH: 15
<212> TYPE: PRT
<213> ORGANISM: Artificial Sequence
<220> FEATURE:
<223> OTHER INFORMATION: PCSK9 fragment

<400> SEQUENCE: 155

Gln Ser Gly Thr Ser Gln Ala Ala Ala His Val Ala Gly Ile Ala
1 5 10 15

<210> SEQ ID NO 156
<211> LENGTH: 8
<212> TYPE: PRT
<213> ORGANISM: Artificial Sequence
<220> FEATURE:
<223> OTHER INFORMATION: PCSK9 fragment

<400> SEQUENCE: 156

Ser Ala Glu Pro Glu Leu Thr Leu
1 5

<210> SEQ ID NO 157
<211> LENGTH: 7
<212> TYPE: PRT
<213> ORGANISM: Artificial Sequence
<220> FEATURE:
<223> OTHER INFORMATION: PCSK9 fragment

<400> SEQUENCE: 157

Ala Glu Pro Glu Leu Thr Leu
1 5

<210> SEQ ID NO 158
<211> LENGTH: 8
<212> TYPE: PRT
<213> ORGANISM: Artificial Sequence
<220> FEATURE:
<223> OTHER INFORMATION: PCSK9 fragment

<400> SEQUENCE: 158

Leu Arg Gln Arg Leu Ile His Phe
1 5

<210> SEQ ID NO 159
<211> LENGTH: 16
<212> TYPE: PRT
<213> ORGANISM: Artificial Sequence
<220> FEATURE:
<223> OTHER INFORMATION: PCSK9 fragment

<400> SEQUENCE: 159

Leu Arg Gln Arg Leu Ile His Phe Ser Ala Lys Asp Val Ile Asn Glu
1 5 10 15

<210> SEQ ID NO 160
<211> LENGTH: 5
<212> TYPE: PRT
<213> ORGANISM: Artificial Sequence
<220> FEATURE:
<223> OTHER INFORMATION: PCSK9 fragment

<400> SEQUENCE: 160

Arg Leu Ile His Phe
1 5

<210> SEQ ID NO 161
<211> LENGTH: 6
<212> TYPE: PRT
<213> ORGANISM: Artificial Sequence
<220> FEATURE:
<223> OTHER INFORMATION: PCSK9 fragment

<400> SEQUENCE: 161

Val Leu Thr Pro Asn Leu
1 5

<210> SEQ ID NO 162
<211> LENGTH: 5
<212> TYPE: PRT
<213> ORGANISM: Artificial Sequence
<220> FEATURE:
<223> OTHER INFORMATION: PCSK9 fragment

<400> SEQUENCE: 162

Leu Thr Pro Asn Leu
1 5

<210> SEQ ID NO 163
<211> LENGTH: 13
<212> TYPE: PRT
<213> ORGANISM: Artificial Sequence
<220> FEATURE:
<223> OTHER INFORMATION: PCSK9 fragment

<400> SEQUENCE: 163

Ala Leu Pro Pro Ser Thr His Gly Ala Gly Trp Gln Leu
1 5 10

<210> SEQ ID NO 164
<211> LENGTH: 21
<212> TYPE: PRT
<213> ORGANISM: Artificial Sequence
<220> FEATURE:
<223> OTHER INFORMATION: PCSK9 fragment

<400> SEQUENCE: 164

```
Met Gly Thr Arg Val His Cys His Gln Gln Gly His Val Leu Thr Gly
1               5                   10                  15

Cys Ser Ser His Trp
            20


<210> SEQ ID NO 165
<211> LENGTH: 18
<212> TYPE: PRT
<213> ORGANISM: Artificial Sequence
<220> FEATURE:
<223> OTHER INFORMATION: PCSK9 fragment

<400> SEQUENCE: 165

Arg Val His Cys His Gln Gln Gly His Val Leu Thr Gly Cys Ser Ser
1               5                   10                  15

His Trp


<210> SEQ ID NO 166
<211> LENGTH: 23
<212> TYPE: PRT
<213> ORGANISM: Artificial Sequence
<220> FEATURE:
<223> OTHER INFORMATION: Epitope Sequence

<400> SEQUENCE: 166

Glu Arg Ile Thr Pro Pro Arg Tyr Arg Ala Asp Glu Tyr Gln Pro Pro
1               5                   10                  15

Asp Gly Gly Ser Leu Val Glu
            20


<210> SEQ ID NO 167
<211> LENGTH: 692
<212> TYPE: PRT
<213> ORGANISM: Homo Sapiens
<220> FEATURE:
<223> OTHER INFORMATION: Human PCSK9

<400> SEQUENCE: 167

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175
```

```
Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590
```

```
Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690


<210> SEQ ID NO 168
<211> LENGTH: 80
<212> TYPE: PRT
<213> ORGANISM: Artificial Sequence
<220> FEATURE:
<223> OTHER INFORMATION: EGF_AB peptide

<400> SEQUENCE: 168

Asp Lys Val Cys Asn Met Ala Arg Asp Cys Arg Asp Trp Ser Asp Glu
1               5                   10                  15

Pro Ile Lys Glu Cys Gly Thr Asn Glu Cys Leu Asp Asn Asn Gly Gly
            20                  25                  30

Cys Ser His Val Cys Asn Asp Leu Lys Ile Gly Tyr Glu Cys Leu Cys
        35                  40                  45

Pro Asp Gly Phe Gln Leu Val Ala Gln Arg Arg Cys Glu Asp Ile Asp
    50                  55                  60

Glu Cys Gln Asp Pro Asp Thr Cys Ser Gln Leu Cys Val Asn Leu Glu
65                  70                  75                  80


<210> SEQ ID NO 169
<211> LENGTH: 10
<212> TYPE: PRT
<213> ORGANISM: Artificial Sequence
<220> FEATURE:
<223> OTHER INFORMATION: AX9 AX189 VH CDR1

<400> SEQUENCE: 169

Gly Tyr Thr Phe Ser Ser Tyr Trp Met His
1               5                   10


<210> SEQ ID NO 170
<211> LENGTH: 30
<212> TYPE: DNA
<213> ORGANISM: Artificial Sequence
<220> FEATURE:
<223> OTHER INFORMATION: AX9 AX189 VH CDR1

<400> SEQUENCE: 170

ggttacacct tctcttctta ctggatgcac                                        30


<210> SEQ ID NO 171
<211> LENGTH: 17
<212> TYPE: PRT
<213> ORGANISM: Artificial Sequence
<220> FEATURE:
<223> OTHER INFORMATION: AX9 AX189 VH CDR2
```

-continued

```
<400> SEQUENCE: 171

Arg Ile Asp Pro Tyr Asn Gly Gly Thr Lys Tyr Asn Glu Lys Phe Lys
1               5                   10                  15

Gly


<210> SEQ ID NO 172
<211> LENGTH: 51
<212> TYPE: DNA
<213> ORGANISM: Artificial Sequence
<220> FEATURE:
<223> OTHER INFORMATION: AX9 AX189 VH CDR2

<400> SEQUENCE: 172

cgtatcgacc catataacgg tggcaccaag tacaacgaga agttcaacac c            51


<210> SEQ ID NO 173
<211> LENGTH: 12
<212> TYPE: PRT
<213> ORGANISM: Artificial Sequence
<220> FEATURE:
<223> OTHER INFORMATION: AX9 AX189 VH CDR3

<400> SEQUENCE: 173

Tyr Gly Tyr Tyr Leu Gly Ser Tyr Ala Met Asp Tyr
1               5                   10


<210> SEQ ID NO 174
<211> LENGTH: 36
<212> TYPE: DNA
<213> ORGANISM: Artificial Sequence
<220> FEATURE:
<223> OTHER INFORMATION: AX9 AX189 VH CDR3

<400> SEQUENCE: 174

tatggttact accttggctc ttacgccatg gactac                             36
```